United States Patent
Walker et al.

(10) Patent No.: US 6,803,378 B2
(45) Date of Patent: Oct. 12, 2004

(54) HIV INTEGRASE INHIBITORS

(75) Inventors: Michael A. Walker, Durham, CT (US); Timothy D. Johnson, Durham, NC (US); Nicholas A. Meanwell, East Hampton, CT (US); Jacque Banville, St. Hubert (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 28 days.

(21) Appl. No.: 10/254,365

(22) Filed: Sep. 25, 2002

(65) Prior Publication Data

US 2003/0181490 A1 Sep. 25, 2003

Related U.S. Application Data

(63) Continuation of application No. 09/883,902, filed on Jun. 18, 2001, now abandoned.
(60) Provisional application No. 60/211,900, filed on Jun. 16, 2000.

(51) Int. Cl.$^7$ .................. C07D 317/00; C07D 415/00; A61K 31/42; A61K 31/36
(52) U.S. Cl. ............... 514/357; 514/325; 514/443; 514/471; 514/532; 514/533; 514/534; 514/563; 546/269.1; 546/273.4; 546/273.7; 546/335; 546/336; 546/337; 549/51; 549/52; 549/58; 549/60; 549/730; 549/296; 549/304; 560/24; 560/26; 560/32; 560/157; 560/160; 560/174; 560/205; 560/225; 562/555; 564/164; 564/165
(58) Field of Search .................. 598/83, 902; 548/298, 548/304, 230; 564/164, 165; 560/24, 26, 32, 57, 160, 194, 215, 225; 562/555; 546/293.7, 335, 338, 337; 549/51, 52, 5, 8, 60; 514/359, 375, 443, 476, 532, 533, 554, 563

(56) References Cited

PUBLICATIONS

Charles C.J. Carpenter, et al., "Antiretroviral Therapy in Adults", JAMA 2000, vol. 283, No. 3, p. 381–391 (Jan. 19, 2000).

Nouri Nemati, et al., "Design and Discovery of HIV–1 Integrase Inhibitors", Drug Disc. Today, vol. 2, No. 11, p. 487–498 (Nov.1997).

Frank J. Palella, et al., "Declining Morbidity and Mortality among Patients with Advanced Human Immunodeficiency Virus Infection", New Engl. J. Med., vol. 338, No. 13, p. 853–860 (Mar. 26, 1998).

Regine Riess, et al., "Evaluation of Protecting Groups for 3–Hydroxyisoxazoles—Short Access to 3–Alkoxyisoxazole–5–carbaldehydes and 3–Hydroxyisoxazole–5–carbaldehyde, the Putative Toxic Metabolite of Muscimole", *Eur. J. Org. Chem.*, p. 473–479 (1998).

*Primary Examiner*—Rita Desai
*Assistant Examiner*—Raymond Covington
(74) *Attorney, Agent, or Firm*—James Epperson; Scott A. McNeil; David M. Morse

(57) ABSTRACT

Novel diketoacid compounds of Formula I are provided which are useful as HIV integrase inhibitors and for the treatment of AIDS or ARC.

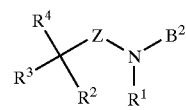

8 Claims, No Drawings

HIV INTEGRASE INHIBITORS

RELATED APPLICATIONS

This is a non-provisional application which claims the benefit of U.S. Provisional Application No. 60/211,900 filed Jun. 16, 2000. This application is a continuation of Ser No. 09/883,902, filed Jun. 18, 2001 now abandoned.

BACKGROUND

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavaridine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Further, J.; Satten, G. A.; Aschman, D. J.; Holmberg, S. D. N. *Engl. J. Med.* 1998, 338, 853).

Unfortunately, not all patients are responsive and a large number fail this therapy. In fact, approximately 30–50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic-pharmacological barriers to exposure provides fertile ground for resistance to emerge. More disturbing are recent findings which suggest that low-level replication continues even when viral plasma levels have dropped below detectable levels (<50 copies/ml) (Carpenter, C. C. J.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S. G.; Richman, D. D.; Saag, M. S.; Schecter, M.; Schoolery, R. T.; Thompson, M. A.; Vella, S.; Yeni, P. G.; Volberding, P. A. *JAMA* 2000, 283, 381). Clearly there is a need for new antiviral agents, preferably targeting other viral enzymes to reduce the rate of resistance and suppress viral replication even further.

HIV expresses three enzymes, reverse transcriptase, an apartyl protease and integrase, all of which are potential antiviral targets for the development of drugs for the treatment of AIDS. However, integrase stands out as being the only viral enzyme not targeted by current therapy. The integrase enzyme is responsible for insertion of the viral cDNA into the host cell genome, which is critical step in the viral life cycle. There are a number of discrete steps involved in this process including processing of the viral cDNA by removal of two bases from each 3'-terminus and joining of the recessed ends to the host DNA. Studies have shown that in the absence of a functional integrase enzyme HIV is not infectious. Therefore, an inhibitor of integrase would be useful as a therapy for AIDS and HIV infection.

A number of inhibitors of the enzyme have been reported. These include, nucleotide-based inhibitors, known DNA binders, catechols and hydrazide containing derivatives (Nemati, N.; Sundar, S.; Pommier, Y., *Drug Disc. Today*, 1997, 2, 487). However, no clinically active compound has resulted from these leads.

Thus, what is needed is a clinically effective inhibitor of the HIV integrase enzyme.

SUMMARY OF THE INVENTION

The present invention relates to compounds of Formula I, or pharmaceutically acceptable salts or solvates thereof.

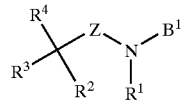

Formula I

In Formula I, $R^1$ is $C_1$–$C_4$ alkyl, carbocyclic radical, heterocyclic radical, aryl-$C_1$–$C_2$ alkylene, aryloxy-$C_1$–$C_2$ alkylene, alkoxy-CC(O)—, wherein $R^1$ is optionally substituted from 1–3 times with halo, $C_1$–$C_2$ alkyl or $C_1$–$C_2$ alkoxy, or $R^1$ is H;

$R^2$ is H or $C_1$–$C_4$ alkyl;

$R^3$ is H, $C_1$–$C_4$ alkyl or phenyl-$C_0$–$C_2$ alkylene which is optionally substituted with 1–3 $R^5$;

$R^4$ is carbocyclic radical, heterocyclic radical, aryloxy, aryl-$C_1$–$C_4$ alkylene, aryl-cyclopropylene, aryl-NHC(O)—, wherein $R^4$ is optionally substituted with 1–3 $R^5$, provided that, when $R^1$, $R^2$ and $R^3$ are each H, R4 is not unsubstituted phenyl, o-methoxy phenyl or naphthalen-1-yl;

each $R^5$ is independently selected from H, halo, $C_1$–$C_4$ alkyl, $C_1$–$C_4$ alkenyl, $C_1$–$C_4$ haloalkyl, $C_1$–$C_4$ alkoxy, $R^6$-phenyl, $R^6$-phenoxy, $R^6$-benzyl, $R^6$-benzyloxy, $NH_2C(O)$—, alkyl-NHC(O)—, wherein $R^6$ is H, halo, Z is a bond or a substituted or unsubstituted $C_1$–$C_4$ alkylene group;

$B^1$ is selected from the group consisting of

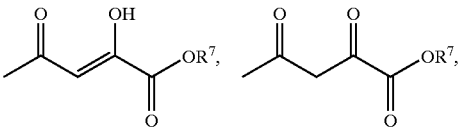

-continued

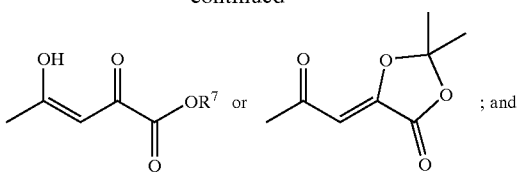

$R^7$ is H or $C_1$–$C_4$ alkyl.

The present invention also relates to a method of inhibiting HIV integrase by administering to a patient an effective amount of a compound of Structural Formula Ia, or a pharmaceutically salt, solvate or prodrug thereof.

Formula Ia

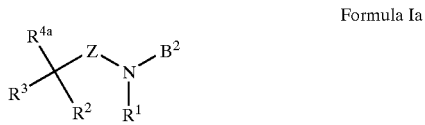

In Formula Ia, Z, $R^1$, $R^2$, $R^3$, $R^5$, $R^6$ and $R^7$ are as defined for Formula I, whereas $R^{4a}$ is carbocylic radical, heterocyclic radical, aryloxy, aryl-$C_1$–$C_4$ alkylene, arylcyclopropylene, aryl-NHC(O)—, wherein $R^{4a}$ is optionally substituted with 1–3 $R^5$; and wherein $B^2$ is

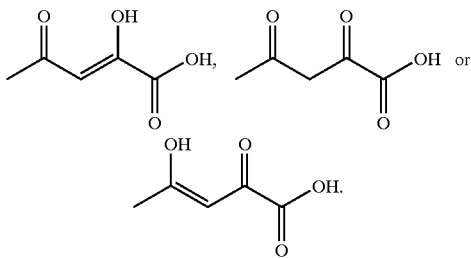

The present invention further relates to a method of treating a patients infected by the HIV virus, or of treating AIDS or ARC, by administering to the patient an effective amount of a compound of Structural Formula Ia, or a pharmaceutically salt, solvate or prodrug thereof.

Another embodiment includes a pharmaceutical composition, useful for inhibiting HIV integrase, or for treating patients infected with the HIV virus, or suffering from AIDS or ARC, which comprises a therapeutically effective amount of one or more of the compounds of Formula Ia, including pharmaceutically acceptable salts, solvates or prodrugs thereof, and a pharmaceutically acceptable carrier.

DETAILED DESCRIPTION OF THE INVENTION

In the present invention, unless otherwise specified the following definitions apply.

The numbers in the subscript after the symbol "C" define the number of carbon atoms a particular group can contain. For example, "$C_1$–$C_6$" means a substituent containing from one to six carbon atoms.

As used herein, the term "alkyl" means a saturated, straight chain or branched monovalent hydrocarbon radical having the stated number of carbon atoms. Examples of such alkyl radicals include methyl, ethyl, n-propyl, isopropyl, n-butyl, isobutyl, sec-butyl, t-butyl and, where indicated, higher homologs and isomers such as n-pentyl, n-hexyl, 2-methylpentyl and the like. Haloalkyl refers to an alkyl radical that is substituted with one or more halo radicals, such as trifluoromethyl.

The term "alkenyl" means a partially-saturated, straight chain or branched monovalent hydrocarbon radical having the stated number of carbon atoms and is typified by groups such as vinyl, crotonyl and isopentyl.

The term "alkylene" means a bivalent straight chain alkyl radical having the stated number of carbon atoms such as methylene, 1,2-ethanediyl, 1,3-propanediyl and 1,4-butanediyl.

A preferred substituent for Z, when Z is a substituted $C_1$–$C_4$ alkylene group, is a hydroxyl group.

The term "alkoxy" means any of methoxy, ethoxy, n-propoxy, isopropoxy and the like.

"Halo" means chloro, bromo, iodo or fluoro radicals.

The term "carbocyclic radical" refers to radicals derived from monocyclic or polycyclic, saturated or unsaturated, 3–16 membered organic nucleus whose ring forming atoms are solely carbon atoms. Typical carbocyclic radicals include aryl, and fused carbocyclic ring systems.

"Aryl" means aromatic hydrocarbon having from six to ten carbon atoms; examples include phenyl and naphthyl, indenyl, azulenyl, fluorenyl and anthracenyl.

"Fused carbocyclic ring system" means an aromatic or non-aromatic, 5–8 membered ring which is optionally fused with one or more 5–6 membered rings. These fused 5–6 membered rings include aromatic groups, such as phenyl, 1-naphthyl, 2-naphthyl, indenyl, azulenyl, fluorenyl and anthracenyl, and non-aromatic rings such as cyclopentyl, cyclohexyl and cycloheptyl. Fused ring systems include, for example, dibenzoannulene, naphthylene, tetrahydronaphthylene and indanylene.

The term "heterocyclic radical" refers to radicals derived from monocyclic or polycyclic, saturated or unsaturated, heterocyclic nuclei having 5–16 ring atoms and containing 1 to 3 heteroatoms selected from the group consisting of nitrogen, oxygen or sulfur. Typical heterocyclic radicals include heteroaryl, heterocycloalkyl and fused heterocylic ring systems.

"Heteroaryl" means a five- or six-membered aromatic ring containing at least one and up to four non-carbon atoms selected from oxygen, sulfur and nitrogen. Examples of heteroaryl, as defined for $R_1$, include 2-furyl, 3-furyl, 2-pyridyl, 3-pyridyl, 4-pyridyl, pyrazinyl, 2-thienyl, 3-thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, 1,3,5-triazinyl and 1,3,5-trithianyl. Examples of a heteroaryl group, as defined for $R_4$, include thienyl, thiazolyl, pyradazinyl, pyrimidinyl, pyrrolyl and oxazolyl.

In a preferred embodiment, examples of a heteroaryl group, as defined for $R_1$, include 2-furyl, 3-furyl, 2-pyridyl, 3-pyridyl, 4-pyridyl and pyrazinyl.

"Fused heterocyclic ring system" means an aromatic or non-aromatic, 5–8 membered ring which is optionally fused with one or more 5–6 membered rings. These fused 5–6 membered rings include aromatic groups, such as phenyl, 1-napthyl, 2-naphthyl, indenyl, azulenyl, fluorenyl and anthracenyl, and non-aromatic rings such as cyclopentyl, cyclohexyl, piperidinyl, piperazinyl, pyrrolyl and tetrahydofuryl. Examples of fused ring systems include: benzo[1,3] dioxolyl, benzo[b]thiophenyl, indolizinyl, indolyl, isoindolyl, 3H-indolyl, indolinyl, benzo[b]furanyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl.

In a preferred embodiment, compounds of the present invention that are useful in treating AIDS have the structure of Formula II, shown below.

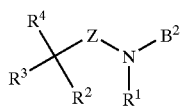

Formula II

In Formula II, $R^1$, $R^2$, $R^3$, $R^4$, $R^5$, $R^6$ and Z are as defined for Formula I while $B^2$ is as defined in Formula Ia.

In yet another embodiment of the present inventions, compounds having the structure of Formula III, as follows, are preferred chemical intermediates from which compounds, or pharmaceutically acceptable salts, solvates or prodrugs, useful for the treatment of AIDS are formed. Even more preferentially, the compounds of Formula III are useful, themselves, as prodrugs and can be administered as a prodrug to a patient as a compound or in a pharmaceutical formulation.

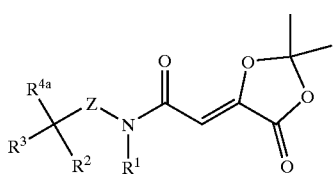

Formula III

In Formula III, $R^1$, $R^2$, $R^3$, $R^{4a}$, $R^5$, $R^6$ and Z are as defined for Formula Ia.

In a more preferred embodiment, compounds of the present invention have the structure of Formula V, shown below.

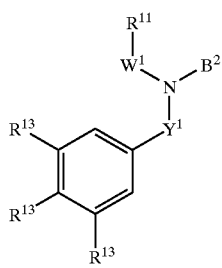

Formula V wherein:

$W^1$ is a bond or a $C_1$–$C_4$ alkylene group;
$R^{11}$ is aryl, aryloxy, aryl-cyclopropylene, heteroaryl, heteroaryloxy, wherein $R^{11}$ is optionally substituted from 1–3 times with halo, $C_1$–$C_2$ alkyl or $C_1$–$C_2$ alkoxy, or wherein $R^{11}$ is H;
$Y^1$ is a bond, $C_1$–$C_3$ alkylene or —O—$C_1$–$C_2$ alkylene; each $R^{13}$ is independently selected from H, halo, $N_2O$, $C_1$–$C_4$ alkyl, $C_1$–$C_2$ alkoxy, $C_1$–$C_2$ haloalkyl, phenyl, phenoxy, benzyl, benzyloxy, p-halophenyl, p-halobenzyl, p-halophenoxy and p-halobenzyloxy; and $B^2$ is as defined in for Formula Ia.

In an even more preferred embodiment, compounds of the present invention have the structure of Formula VI, shown below.

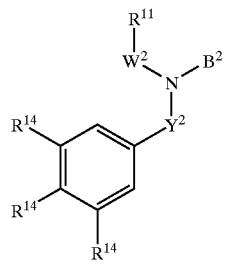

Formula VI wherein:

$W^2$ is $C_1$–$C_3$ alkylene;
$R^{11}$ is aryl, aryloxy, aryl-cyclopropylene, heteroaryl, heteroaryloxy, wherein $R^{11}$ is optionally substituted from 1–3 times with halo, $C_1$–$C_2$ alkyl or $C_1$–$C_2$ alkoxy, or $R^{11}$ is H;
$Y^2$ is a bond, $C_1$–$C_3$ alkylene;
each $R^{14}$ is independently selected from H, halo, $C_1$–$C_2$ alkyl $C_1$–$C_2$ alkoxy, $C_1$–$C_2$ haloalkyl; and $B^2$ is as defined for Formula Ia.

In an alternate embodiment, compounds of the present invention have the structure of Formula VII, shown below.

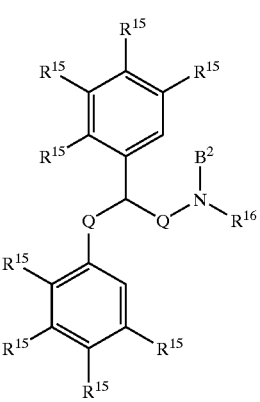

Formula VII wherein:

each Q is a bond or a methylene group;
each $R^{15}$ is independently selected from H, halo, $NO_2$, $C_1$–$C_4$ alkyl, $C_1$–$C_2$ alkoxy, $C_1$–$C_2$ haloalkyl and CONHCH$_3$;
$R^{16}$ is H or $C_1$–$C_2$ alkyl; and $B^2$ is as defined for Formula Ia.

By virtue of its acidic moiety, where applicable, a compound of Formula I forms salts by the addition of a pharmaceutically acceptable base. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino acids such as lysine, arginine and N-methylglutamine. These salts may be prepared by methods known to those skilled in the art.

Salts of an amine group may also comprise quaternary ammonium salts in which the amino nitrogen carries a suitable organic group such as an alkyl, alkenyl, alkynyl or aralkyl moiety.

Compounds of Formula I, which are substituted with a basic group, may exist as salts formed through acid addition. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Certain compounds of Formula I, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

This invention also encompasses pharmaceutically acceptable prodrugs of the compounds of Formula I. Prodrugs are derivatives of the compounds of the invention which have chemically or metabolically cleavable groups and become, by solvolysis or under physiological conditions, the compounds of the invention which are pharmaceutically active in vivo.

A prodrug of a compound of Formula Ia may be formed in a conventional manner with a functional group of the compounds such as with an amino, hydroxy or carboxy group. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or (alkoxycarbonyl)oxy)alkyl esters. Examples of prodrugs of compounds of the present invention include the compounds described in Examples 143–146 as well as the ester chemical intermediates from which the compounds of Examples 1–57 were formed.

In a preferred embodiment, the prodrugs of the present invention comprise compounds of Formula III, examples of which are further provided in the exemplification.

In addition, a compound of Structural Formula I, or a salt, solvate or prodrug thereof, may exhibit polymorphism. The present invention also encompasses any such polymorphic form.

Certain compounds of Structural Formula I may contain one or more chiral centers and exist in different optically active forms. When compounds of Structural Formula I contain one chiral center, the compounds exist in two enantiomeric forms. The present invention includes both enantiomers and mixtures of enantiomers such as racemic mixtures. The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of Structural Formula I may also exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

The compounds of this invention can also exist as tautomers; therefore the present invention also includes all tautomeric forms.

The compounds of Formula Ia are useful in the inhibition of HIV integrase, the prevention or treatment of infection by the human immunodeficiency virus and the treatment of consequent pathological conditions such as AIDS or ARC. The treatment involves administering to a patient, in need of such treatment, a compound of Formula Ia, or a pharmaceutically acceptable salt, solvate or prodrug thereof, or a pharmaceutical composition comprising a pharmaceutical carrier and a therapeutically effective amount of a compound of the present invention, or a pharmaceutically acceptable salt, solvate or prodrug therefor.

It will be appreciated by those skilled in the art that reference herein to treatment extends to prophylaxis as well as the treatment of established infections or symptoms. This includes initiating treatment pre- and post-exposure to the virus. In addition, the present invention can be administered in conjunction with other anti-HIV agents, immunomodulators, antiinfectives and/or vaccines.

The compounds of the present invention are also useful in the preparation and execution of screening assays for antiviral compounds. Further, the compounds of the present invention are useful in establishing or determining the binding site of other antiviral compounds to HIV integrase, for example, by competitive inhibition.

The compounds of the present invention may be administered orally, parenterally (including subcutaneous injections, intravenous, intramuscular, intrasternal injection or infusion techniques), by inhalation spray or rectally, in dosage unit formulations containing conventional non-toxic pharmaceutically acceptable carriers, adjuvants and vehicles.

This invention also provides a pharmaceutical composition for use in the above-described therapeutic method. A pharmaceutical composition of the present invention comprises an effective amount of a compound of Formula I in association with a pharmaceutically acceptable carrier, excipient or diluent.

The active ingredient in such formulations comprises from 0.1 percent to 99.9 percent by weight of the formulation. By "pharmaceutically acceptable' it is meant that the carrier, diluent or excipient must be compatible with the other ingredients of the formulation and not deleterious to the recipient thereof.

The present pharmaceutical compositions are prepared by known procedures using well-known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like.

The compounds can be administered by a variety of routes including oral, intranasally, rectal, transdermal, subcutaneous, intravenous, intramuscular and intranasal.

When administered orally, these compositions are prepared according to techniques well-known in the art of pharmaceutical formulation. For oral administration, the compound is typically formulated with excipients such as binders, fillers, lubricants, extenders, diluents, disintegration agents and the like as are known in the art.

For parenteral administration, the compound is formulated in pharmaceutically acceptable non-toxic, parenterally-acceptable diluents or solvents, such as mannitol, 1,3-butanediol, water, 5 percent dextrose, Ringer's solution or isotonic sodium chloride solution, or suitable dispersing or wetting and suspending agents, such as sterile, bland, fixed oils, including synthetic mono- or diglycerides, and fatty acids, including oleic acid.

A compound of the present invention, or a salt or solvate thereof, can be formulated in unit dosage formulations comprising a dose between about 0.1 mg and about 1000 mg, or more, according to the particular treatment involved. An example of a unit dosage formulation comprises 5 mg of a compound of the present invention in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds of the present invention can also be administered to humans in a dosage range of 1 to 100 mg/kg body weight in divided doses. One preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the route of administration, the age, body weight, general health, sex, diet, mode and time of administration, rate of excretion, drug combination, the severity of the particular condition, and the host undergoing therapy.

General methods useful for the synthesis of compounds embodied in this invention are shown below. The preparations shown below are disclosed for the purpose of illustration and are not meant to be interpreted as limiting the processes to make the compounds by any other methods.

It will be appreciated by those skilled in the art that a number of methods are available for the preparation of the compounds of the present invention as provided by Structural Formula I. A compound of Structural Formula I may be prepared by processes which include processes known in the chemical art for the production of structurally analogous compounds or by a novel process described herein. A process for the preparation of a compound of Structural Formula I (or a pharmaceutically acceptable salt thereof) and novel intermediates for the manufacture of a compound of Formula I, as defined above, provide further features of the invention and are illustrated by the following procedures in which the meanings of the generic radicals are as defined above, unless otherwise specified. It will be recognized that it may be preferred or necessary to prepare a compound of Formula I in which a functional group is protected using a conventional protecting group then to remove the protecting group to provide the compound of Formula I.

Thus, there is provided a process for preparing a compound of Formula I (or a pharmaceutically acceptable salt thereof) as provided in any of the above descriptions which is selected from any of those described in the examples, including the following. As shown below in Scheme I, in one method an appropriately substituted methyl-carbonyl, such as a methyl ketone, acetylamide or acetylhydrazide, is condensed with oxalic acid ester under basic conditions to form a diketobutyric acid of the present invention. A representative procedure has been described by Gramain (Gramian, J.-F.; Remuson, R., Vallee D. *J. Org. Chem.* 1985, 50, 710). A variety of bases can be used to effect this reaction including LDA, LiHMDS, tBuOK, NaOMe, NaOEt, NaH or MeOCO$_2$MgOMe. In addition there a number of oxalic acid derivatives that have been disclosed which may be useful in the formation of the diketobutyric acid group (de las Heras, M. A.; Vaquerao, J. J.; García-Navio, J. L.; Alvarez-Builla, J. *J. Org. Chem.* 1996, 61, 9009). This method is generally applicable to the compounds embodied by Formula I.

Exemplification

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (d) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). Examples of solvents employed for taking NMR spectra are acetone-d$_6$ (deuterated acetone), DMSO-d₆ (perdeuterodimethylsulfoxide), D₂O (deuterated water), CDCl₃ (deuterochloroform) and other conventional deuterated solvents such as deuterated methanol.

The abbreviations used herein are conventional abbreviations widely employed in the art. Some of which are: calcd (calculated); DMSO (dimethylsulfoxide); EtOAc (ethyl acetate); HPLC (high-pressure liquid chromatography); LC/MS (liquid chromatography, mass spectroscopy); LDA (lithium diisopropyl amide); LiHMDS (lithium bis(trimethylsilyl)amide); SiO₂ (silica gel); THF (tetrahydrofuran), Me (methyl), Et (ethyl), Ph (phenyl), tBuOK (potassium tert-butoxide), NaOMe (sodium methoxide), and NaOEt (sodium ethoxide).

Many compounds were analysed using the following LC/MS conditions:

Column: Luna 5μ C-8, 4.6×30 mm

Solvents: Solvent A: 10% CH₃CN-90% H₂O, 5 mM NH₄OAc Solvent B: 90% CH₃CN-10% H₂O, 5 mM NH₄OAc Gradient: 100% solvent A/0% solvent B to 0% solvent A/100% solvent B Gradient time: 2 minutes, hold time 1 minute.

Flow rate: 4 ml/min.

Detector wavelength: 220 nm.

Spectrometry (MS) data were determined with a Micromass ZMD Platform for LC in electrospray mode.

The compounds and chemical intermediates of the present invention, described in the following examples, were prepared according to the following methods.

Method I

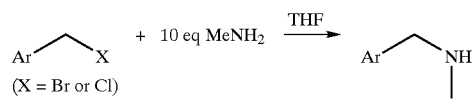

(X = Br or Cl)

Aryl halide (4.6 mmol) was dissolved in 1 mL of THF and 23 mL of 2M MeNH₂ in THF added. The resulting mixture was allowed to stir overnight resulting in a suspension. This was filtered and the solvent removed under vacuum to yield crude amine, which was taken on to the next step without further purification. This method can also be utilized with compounds similar to the aryl halide starting material.

Method II

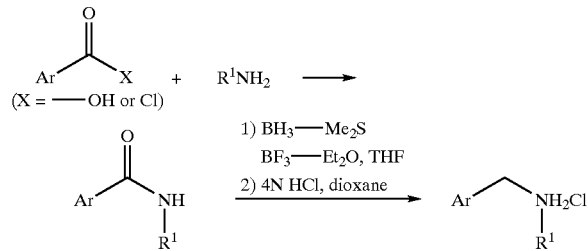

Step 1:

Substituted benzoic acid (50 mmol) and 1-hydroxybenzotriazolehydrate (50 mmol) were combined in a round bottom flask and dissolved in 25 mL of DMF. To this solution was added amine (50 mmol) in THF and triethylamine (150 mmol) followed by HBTU [O-(1H-benzotriazol-1-yl)-N,N,N',N'-tetramethyluronium hexafluorophosphate] (75 mmol). The reaction was allowed to proceed overnight after which, H₂O was added and the resulting solution extracted with ethyl acetate. The organic layer was separated, washed with H₂O, dried over Na₂SO₄, filtered and solvent removed. The crude product was isolated by flash column chromatography (SiO₂, Hexanes/ethyl acetate)

Alternatively, to a solution of amine (139 mmol), 140 mL of 1N NaOH and 130 mL of methylene chloride was added substituted benzoyl chloride (139 mmol). The resulting mixture was stirred 1 h, after which time the organic layer was separated, washed with H₂O and dried over Na₂SO₄. After filtration the solvent was removed and the product carried on to the next step without further purification. This method can also be utilized with compounds similar to the substituted benzoic acid starting material.

Step 2:

The resultant amide (123 mmol) was dissolved in 180 mL of THF. 5.51 mL of BF₃.Et₂O was added and the resulting solution heated to reflux for 15 min. The reaction was then cooled to −20–40° C. and BH₃.DMS added with a dropping funnel over 10 min. The reaction vessel was then fitted with a distillation condenser, then heated to reflux and solvent removed over 20 min. The distillation condenser was replaced with reflux condenser and the solution heated to 110° C. for 2 h. After cooling to room temp 75 mL of 6N HCl was added and then the resulting mixture heated to reflux for 1 h. The solution was then allowed to cool to room temp and 200 mL of 6 N NaOH was slowly added. The resulting mixture was extracted with Et₂O and the organic layer was washed with satd NaCl (aq.), dried over Na₂SO₄, filtered and the solvent removed under vacuum. The resulting oil was dissolved in Et₂O and 30 mL of 4N HCl (dioxane) added to form a precipitate.

Alternatively, a solution of the amide (13.2 mmol) in tetrahydrofuran (75 ml) was treated with lithium aluminum hydride (1.0 g, 26.3 mmol) and the resulting mixture was heated under reflux for 1 h. The cooled mixture was hydrolyzed by the successive addition of water (1 ml), 15% sodium hydroxide solution (1 ml) and water (3 ml). The solid formed was filtered and the filtrate was concentrated under reduce pressure. Chromatography of the residue on silica gel (elution dichloromethane/methanol) gave the pure product.

Method III

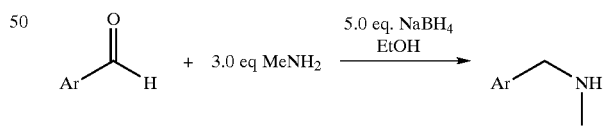

Aryl aldehyde (2.6 mmol) and 3.9 mL of 2 M methyl amine in THF were dissolved in 0.5 mL of EtOH followed by the addition of NaBH₄ (13 mmol). The resulting mixture was stirred overnight, after which it was filtered and the filtrate acidified with 10% H₂SO₄ (aq.). This was washed with Et₂O then neutralized with 10 N NaOH. The resulting mixture was extracted with Et₂O, the organic layer separated and washed with satd NaCl, dried over Na₂SO₄, filtered and the solvent removed under vacuum to yield pure amine. This method can also be utilized with compounds similar to the aryl aldehyde starting material.

Method IV

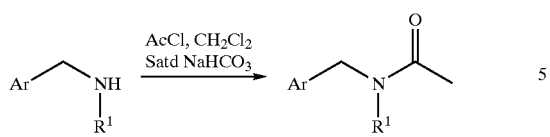

To a solution of amine (7.3 mmol) in a 1:1 mixture of 50 mL of CH$_2$Cl$_2$ and Satd NaHCO$_3$ (aq.) was added AcCl (14.7 mmol). The resulting mixture was stirred overnight after which the organic layer was separated, dried over Na$_2$SO$_4$, filtered and solvent removed to yield pure product. This method can also be utilized with amine compounds similar to the above-identified starting material.

Method V

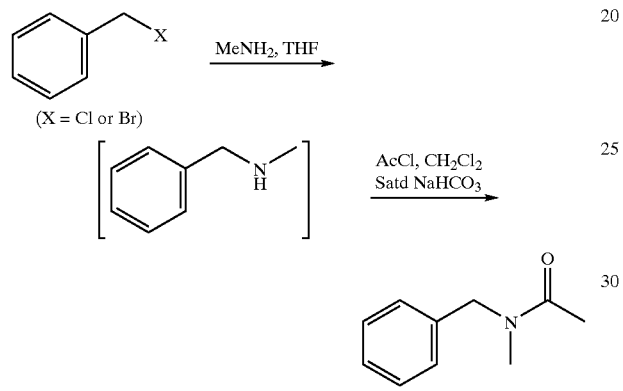

Step 1:
Benzyl halide (6.67 mmol) was dissolved in 5 ml of THF. To this was added 5 ml of 40% (aq.) methylamine and the resulting mixture stirred 15 min. The reaction mixture was transferred to a separatory funnel, diluted with 100 ml H$_2$O and extracted with 100 ml of ethyl acetate. The organic solution was washed with brine, dried over Na$_2$SO$_4$ then filtered and the solvent removed. The crude product was purified by column chromatography (SiO$_2$, 2–10% EtOH/ CH$_2$Cl$_2$). This method can also be utilized with compounds similar to the benzyl halide starting material.

Step 2:
The intermediate amine (4.6 mmol) synthesized above was dissolved in 30 ml CH$_2$Cl$_2$. Satd. (aq.) NaHCO$_3$ was added followed by CH$_3$COCl (5.0 mmol) and the resulting mixture stirred for 1 h. The organic layer was separated, washed with brine dried over Na$_2$SO$_4$ then filtered and the solvent removed to yield pure product.

Method VI

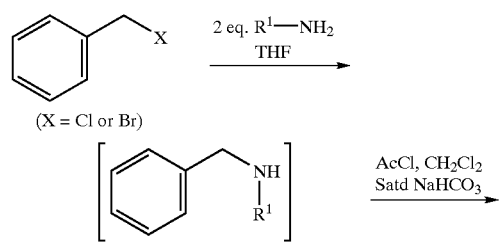

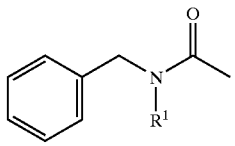

Step 1:
Benzyl halide (11.1 mmol) was dissolved in 11 mL of THF, to which was added R$_3$NH$_2$ (22.1 mmol). The resulting reaction was stirred for 2 h during which a white precipitate forms. The solid was filtered and washed with THF. Solvent was removed from the THF solution under vacuum. This method can also be utilized with compounds similar to the benzyl halide starting material.

Step 2:
The product of step 1 was dissolved in 75 mL of methylene chloride, to which 75 mL of satd NaCO$_3$ (aq.) was added followed by acetyl chloride (22.1 mmol). The mixture was stirred for 2 hours. The organic layer was separated, washed with satd NaCl, dried over Na$_2$SO$_4$, filtered and the solvent removed under vacuum to yield crude product. The product was purified by flash column chromatography (SiO$_2$, EtOAc/Hexanes).

Method VII

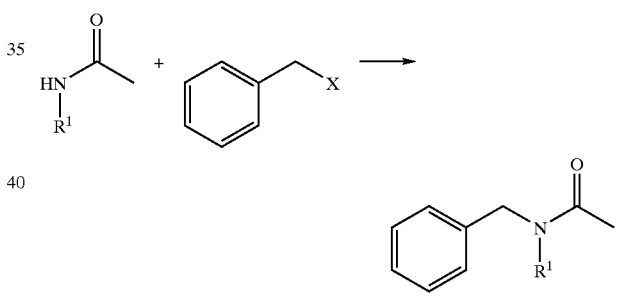

Sodium hydride (60% in mineral oil) (27.5 mmol) was measured into a round bottom flask and triturated with hexanes. To this was added N-alkylacetamide (13.8 mmol) dissolved in 34 mL of toluene. To the resulting suspension was added benzyl halide (6.9 mmol) and the reaction mixture stirred overnight. The mixture was then filtered and the solvent removed under vacuum. The product was purified by flash column chromatography (SiO$_2$, EtOH/methylene chloride). This method can also be utilized with compounds similar to the N-alkylacetamide starting material.

Method VIII

A solution of amine (7.63 mmol), as in Method IV, in a mixture of pyridine (10 ml) and acetic anhydride was stirred at 22° C. for 2 h. The excess reagents were evaporated in vacuo and the residue was filtered on a silica gel pad (elution toluene-ethyl acetate) to give pure product.

Method IX

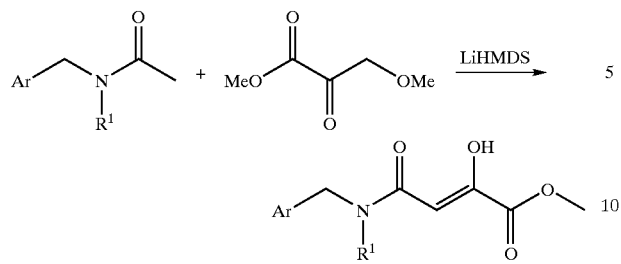

Acetyl amide (9.92 mmol) was dissolved in 20 ml of anhydrous THF under an $N_2$ atmosphere then cooled to $-78°$ C. To this was added 30 ml of 1M LiHMDS (lithium bis(trimethylsilyl)amide) and the reaction mixture stirred for 20 min. at which point dimethyl oxalate (14.9 mmol) dissolved in 8 ml of THF was added. The reaction was allowed to continue at $-78°$ C. for 20 min. then warmed to 0° C. and stirred an additional 45 min. 1 N HCl was added and the resulting mixture extracted with EtOAc. The organic solution was washed with brine, dried over $Na_2SO_4$ then filtered and the solvent removed. The crude product was purified by reverse phase preparative HPLC ($C_{18}$, MeOH/$H_2O$ (0.1% TFA)-gradient), flash column chromatography ($SiO_2$, Hexanes/EtOAc) or carried onto the next step without further purification.

Alternatively, acetyl amide (54 mmol) and dimethyl oxalate (81 mmol) were dissolved in 54 mL of THF and cooled to 0° C. To this solution was added 108 mL of 1N LiHMDS (THF) dropwise via an addition funnel. The resulting mixture was stirred at 0° C. for 1 h, after which the reaction was quenched with 1N HCl. The solution was extracted with methylene chloride, the organic layer separated, dried over $Na_2SO_4$, filtered and the solvent removed under vacuum to yield crude product. The compound was purified by flash chromatography ($SiO_2$, Hexanes/ethyl acetate).

This method can also be utilized with compounds similar to the acetyl amide starting material.

Method X

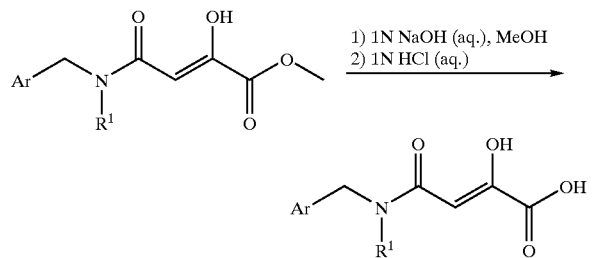

To a solution of methyl ester (0.33 mmol) dissolved in 0.4 ml of MeOH was added 0.4 ml of 1N NaOH. After stirring for 1 h, 0.4 ml of 1N HCL was added and the resulting mixture extracted with EtOAc. The organic layer was washed with brine, dried over $Na_2SO_4$ then filtered and the solvent removed under vacuum. The crude product was purified by reverse phase preparative HPLC (C18, MeOH/$H_2O$ (0.1% TFA)). This method can also be utilized with compounds similar to the above-identified starting material.

Method XI

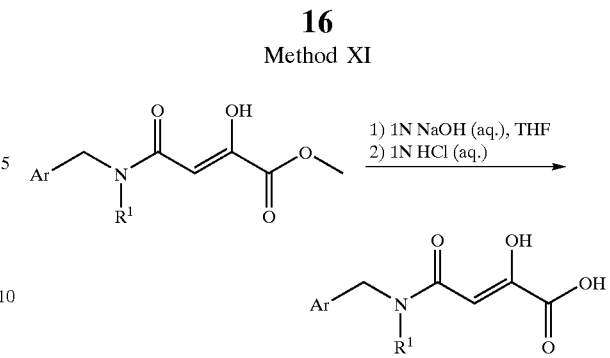

The methyl ester (5.5 mmol) was suspended in 16.5 mL of 1N NaOH (aq.) with rapid stirring. To this was added THF, dropwise until all the solid had dissolved. After stirring the resulting solution an additional 20 min., it was transferred to a separatory funnel, washed with $CH_2Cl_2$, acidified with 1 N HCl and the product extracted with EtOAc. The organic layer was dried over $Na_2SO_4$, filtered and the solvent removed to yield crude product. The crude product could be purified by preparative HPLC ($C_{18}$, MeOH/$H_2O$, 0.1% TFA). This method can also be utilized with methyl ester compounds similar to the above-identified starting material.

Method XII

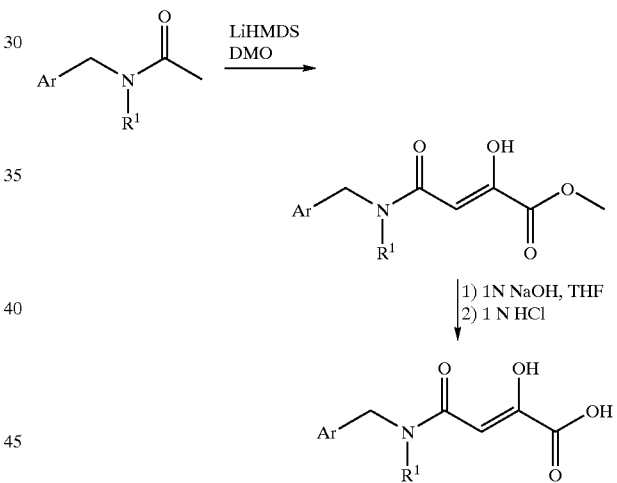

Acetyl amide (2.0 mmol) was dissolved in 10 mL of THF and the resulting solution cooled to $-78°$ C., after which 4.0 mL of 1N LiHMDS (in THF) was added. The resulting solution was allowed to stir for 20 min. Dimethyloxalate (0.36 grams, 3.0 mmol), dissolved in 2 mL of THF was then added and the reaction stirred for 3 h at $-78°$ C. The reaction was warmed to 0° C. and stirred an additional 20 min. before being quenched with 1 N HCl. The mixture was extracted with EtOAc, and the organic layer dried over $MgSO_4$. The solution was filtered and solvent removed to yield the crude methyl ester. The crude ester was either taken on to the next step crude or purified by preparative HPLC ($C_{18}$, MeOH/$H_2O$-0.1% TFA)

The intermediate methyl ester was dissolved in a 1:1 mixture of 1N NaOH and THF and stirred for 2 h. THF was then removed under vacuum and the solution acidified with 1 N HCl. Solvent was then removed under vacuum to yield crude product, which was purified by preparative HPLC ($C_{18}$, MeOH/$H_2O$-0.1% TFA).

This method can also be utilized with compounds similar to the acetyl amide starting material.

Method XIII
Preparation of (Z)-2,2-Dimethyl-5-(carboxymethylene)-1,3-dioxolane-4-one (IV)

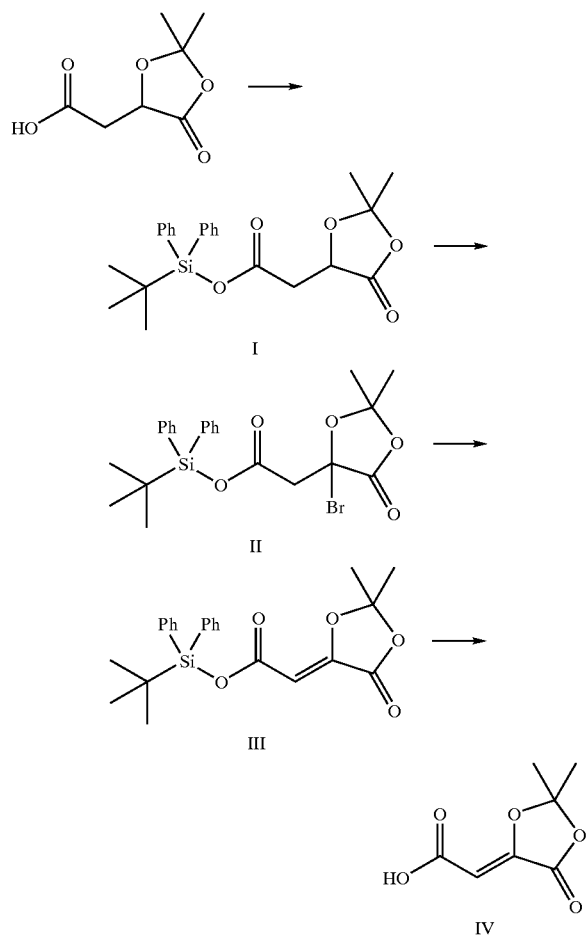

Step 1: Preparation of (S)-(+)-2,2-Dimethyl-5-oxo-1,3-dioxolane-4-acetic Acid, tert-butyldiphenylsilyl ester (I):

A solution of (S)-(+)-2,2-dimethyl-5-oxo-1,3-dioxolane-4-acetic acid (2.08 g, 11.9 mmol), which was derived from L-malic acid by means known in the art, in dry dichloromethane (20 ml) was treated with triethylamine (1.83 ml, 13.1 mmol) followed by a solution of t-butylchlorodiphenylsilane (3.44 g, 12.5 mmol) in dichloromethane (5 ml) added dropwise over 5 minutes. After 3 hours at 22° C., the reaction mixture was diluted with toluene (250 ml) washed with water, saturated sodium bicarbonate, brine and dried over magnesium sulfate. Evaporation of the solvent under reduced pressure and chromatography of the residue on silica gel (4×12 cm) using a mixture of toluene and ethyl acetate (0–2%) as eluent gave 4.90 g (99%) of the title material as a clear oil. $^1$H NMR (400 MHz, CDCl$_3$) δ: 1.13 (s, 9), 1.58 (s, 3), 3.05 (m, 2), 4.79 (dd, 1, J=4, 7), 7.4–7.8 (m, 10).

Step 2: Preparation of 4-Bromo-2,2-dimethyl-5-oxo-1,3-dioxolane-4-acetic acid, tert-butyldiphenylsilyl ester (II):

A solution of (S)-(+)-2,2-dimethyl-5-oxo-1,3-dioxolane-4-acetic acid, tert-butyldiphenylsilyl ester (21.65 g, 52.4 mmol) in carbon tetrachloride (160 ml) was treated with N-bromosuccinimide (9.35 g, 52.4 mmol) and 2,2'-azobisisobutyronitrile (200 mg) and the resulting mixture was heated under reflux (bath temperature 85° C.) while irradiating with a 500 watt lamp. After 10 minutes, the reaction mixture was cooled and the succinimide was filtered. The solvent was evaporated under vacuum to give the title bromide as a light yellow oil (~26 g) which was used immediately for the next step. $^1$H NMR (400 MHz, CDCl$_3$) δ: 1.12 (s, 9), 1.41 (s, 3), 1.80 (s, 3), 3.80 (m, 2), 7.3–7.7 (m, 10).

Step 3: Preparation of (Z)-2,2-Dimethyl-5-(tert-butyldiphenylsilyloxycarbonyl-methylene)-1,3-dioxolan-4-one (III):

A solution of 4-bromo-2,2-dimethyl-5-oxo-1,3-dioxolane-4-acetic acid, tert-butyldiphenylsilyl ester (~26 g, 52.4 mmol) in dry tetrahydrofuran (160 ml) was cooled to 0° C. and treated dropwise over 5 minutes with 1,8-diazabicyclo [5,4,0] undec-7-ene (12.7 g, 78.8 mmol) and the resulting mixture was stirred at 5° C. for 1.5 hour. The solid formed was filtered and washed with a small amount of tetrahydrofuran. The filtrate was used as such for the next step.

Alternatively, the reaction mixture can be diluted with toluene, washed with water, saturated sodium bicarbonate, brine and dried (magnesium sulfate). Evaporation of the solvent gave an oil which was chromatographed on silica gel using a mixture of toluene and ethyl acetate (0–2%) as eluent. The title ester was obtained as an oil in 30–50% yield. $^1$NMR (400 MHz, CDCl$_3$) δ: 1.16 (s, 9), 1.76 (s, 6), 5.97 (s, 1), 7.4–7.8 (m, 10)

Step 4: Preparation of (Z)-2,2-dimethyl-5-(carboxymethylene)-1,3-dioxolan-4-one (IV) from pure (III):

A solution of pure (Z)-2,2 dimethyl-5-(t-butyldiphenylsilyloxycarbonylmethylene)-1,3-dioxolan-4-one (2.80 g, 6.82 mmol) in tetrahydrofuran (40 ml) was treated at 22° C. with acetic acid (2 ml) followed by 6.8 ml of a 1 M solution of tetrabutylammonium fluoride in tetrahydrofuran. After 15 minutes at 22° C., the reaction mixture was diluted with ethyl acetate, washed with water, brine and dried (magnesium sulfate). The solvent was concentrated under reduced pressure and the residue was triturated with toluene to give 1.00 g (85%) of the title compound as a white crystalline material: mp 203–204° C. (dec.). IR (KBr) v max (cm $^{-1}$): 1805, 1707 and 1662. $^1$H NMR (400 MHz, CDCl$_3$) δ: 1.78 (s, 6), 5.89 (s, 1). Anal. calcd for $C_7H_8O_5$: C, 48.84; H, 4.68. found: C, 48.84; H, 4.65.

Preparation of (Z)-2,2-dimethyl-5-(carboxymethylene)-1,3-dioxolan-4-one (IV) from crude (III):

A solution of the crude (Z)-2,2-dimethyl-5-(tert-butyldiphenylsilyloxycarbonyl methylene)-1,3-dioxolan-4-one (52.4 mmol) in tetrahydrofuran (200 ml) was treated with acetic acid (13 ml) followed with 50 ml of a 1 M solution of tetrabutylammonium fluoride in tetrahydrofuran. After 15 minutes at 22° C., the reaction mixture was filtered and the filtrate was concentrated in vacuo. Trituration of the residue with toluene gave 6.3 g (70% for three steps) of the title material as a white solid (>95% pure by $^1$HNMR)

Method XIV

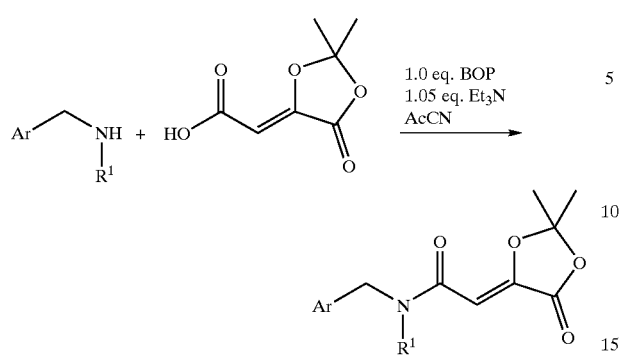

A solution of (Z)-2,2-dimethyl -5-(carboxymethylene)-1,3-dioxolan-4-one (0.214 g, 1.24 mmol) and amine (1.24 mmol) in acetonitrile (15 ml) was treated at 22° C. with benzotriazol-1-yloxytris(dimethylamino)phosphonium hexafluorophosphate (BOP) (0.550 g, 1.24 mmol) followed by triethylamine (0.18 ml, 1.29 mmol). After 2 hours, the reaction mixture was diluted with ethyl acetate, washed with water, saturated sodium bicarbonate, brine and dried (magnesium sulfate). Evaporation of the solvent and chromatography of the residue on silica gel (elution toluene-ethyl acetate) gave amide as an oil or solid. This method can also be utilized with amine compounds similar to the above-identified starting material.

Method XV

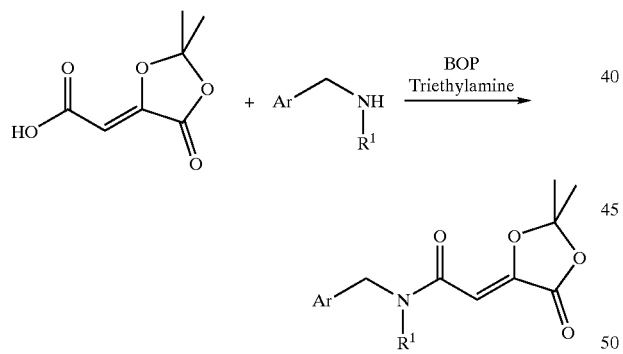

The amine (0.1 mmol) was treated with 0.5 ml of a 0.3M stock solution of benzotriazole-1-yl-oxy-tris-(dimethylamino)-phosphonium hexafluorophosphate (BOP®) (1.5 eq) and triethylamine (1.5 equivalent) in dichloromethane followed by 0.5 ml of a 0.2 M solution of (Z)-2,2-dimethyl-5-(carboxymethylene)-1,3-dioxolan-4-one (1 eq) in a mixture of dichloromethane-N,N-dimethylformamide (10: 1). After 16 h at 22° C., the mixtures were purified using a Shimadzu automated preparative HPLC system (Primesphere C-8, 5μ, 21×100 mm, H$_2$O 5 mM NH$_4$OAc-acetonitrile). This method can also be utilized with compounds similar to the amine starting material.

Method XVI

Preparation of (Z)-2,2-Dimethyl-5-(carboxymethylene)-1,3-dioxolane-4-one (IV)

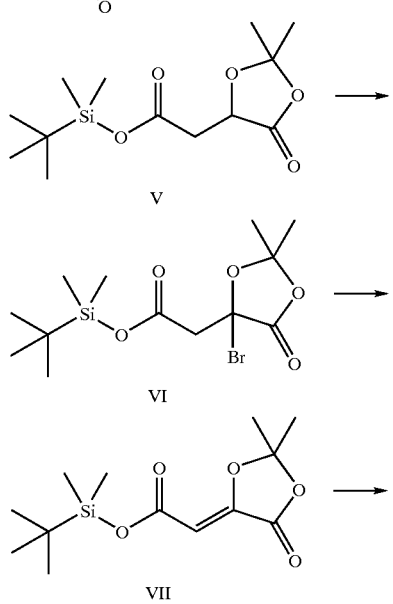

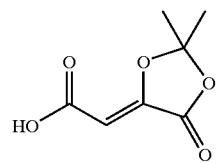

Step 1: Preparation of (+)-2,2-Dimethyl-5-oxo-1,3-dioxolane-4-acetic acid, tert-butyldimethylsilyl ester (V):

A solution of (S)-(+)-2,2-dimethyl-5-oxo-1,3-dioxolane-4-acetic acid (13.20 g, 75.8 mmol), which was derived from L-malic acid by means known in the art, in N,N-dimethylformamide (25 ml) was treated at 22° C. with imidazole (10.56 g, 0.155 mmol) followed by tert-butyldimethylsilyl chloride (12.0 g, 79.6 mmol) and the resulting mixture was stirred at 22° C. for 18 h. The reaction mixture was then diluted with toluene (500 ml), washed with water (×3), saturated sodium bicarbonate and brine. After drying (magnesium sulfate), the solvent was evaporated under reduced pressure to give an oil. Distillation under vacuum gave 20.9 g (96%) of the title material as a clear oil: Bp 80–90° C./0.1 torr (bulb to bulb distillation, air bath temperature). $^1$H NMR (400 MHz, CDCl$_3$) δ: 0.33 (s, 3), 0.36 (s, 3), 1.00 (s, 9), 1.11 (s, 3), 1.37 (s, 3), 2.72 (m, 2), 4.35 (dd, 1, J=4, 6).

Step 2: Preparation of 4-Bromo-2,2-dimethyl-5-oxo-1,3-dioxolane-4-acetic acid, tertbutyldimethylsilyl ester (VI):

A solution of (S)-(+)-2,2-dimethyl-5-oxo-1,3-dioxolane-4-acetic acid, t-butyldimethylsilyl ester (20.9 g, 72.4 mmol) in carbon tetrachloride (200 ml) was treated with N-bromosuccinimide (14.18 g, 79.6 mmol) and 2,2'-azobisisobutyronitrile (0.30 g) and the resulting mixture was heated under reflux while irradiating with a 500 W lamp.

After ~5 min., a mild exothermic reaction was observed and the mixture was heated for an additional 5 min. The reaction mixture was then cooled in an ice bath and the floating succinimide was filtered and washed with a small amount of carbon tetrachloride. The filtrate was used immediately as such for the next step. $^1$H NMR (400 MHz, CDCl$_3$) δ: 0.27 (s, 3), 0.28 (s, 3), 0.94 (s, 9), 1.66 (s, 3), 1.84 (s, 3), 3.62 (m, 2).

Step 3: Preparation of (Z)-2,2-Dimethyl-5-(tert-butyldimethylsilyloxycarbonyl-methylene)-1,3-dioxolane-4-one (VII):

The solution of crude 4-bromo-2,2-dimethyl-5-oxo-1,3-dioxolane-4-acetic acid, tert-butyldimethylsilyl ester (72.4 mmol) in carbon tetrachloride (~220 ml) was cooled to 0–5° C. and treated dropwise over 10 min. and under good stirring with a solution of 1,8-diazabcyclo 5,4,0 undec-7-ene (12.1 g, 79.6 mmol) in dry tetrahydrofuran (125 ml). A heavy precipitate was formed which gradually became a granular solid. After 1 h, the solid obtained was filtered and washed with a small amount of tetrahydrofuran. The filtrate was concentrated under reduced pressure to give a light orange oil which was used as such for the next step.

Step 4: Preparation of (Z)-2,2-Dimethyl-5-(carboxymethylene)-1,3-dioxolan-4-one (V):

The crude (Z)-2,2-dimethyl-5-(tert-butyldimethylsilyloxycarbonylmethylene)-1,3-dioxolan-4-one (72.4 mmol) in tetrahydrofuran (50 ml) was treated at 22° C. with acetic acid (13 ml, 0.227 mmol) followed by 73 ml (73.0 mmol) of a 1M solution of tetrabutylammonium fluoride in tetrahydrofuran. After 1 h at 22° C., the reaction mixture was diluted with ethyl acetate (500 ml), washed with water, brine and dried (anhydrous magnesium sulfate). Evaporation of the solvent under reduced pressure and trituration of the residual solid with toluene (50 ml) gave 7.70 g (62% for 3 steps) of the title Z-isomer as a white crystalline solid. Concentration of the mother liquors yielded another 0.2 g of a 75:25 mixture of Z and E isomers. Z-Isomer; $^1$H NMR (400 MHz, CDCl$_3$) δ: 1.78 (s, 3), 5.89 (s, 1). E-Isomer: $^1$H NMR (400 MHz, CDCl$_3$) δ: 1.80 (s, 3), 6.03 (s, 1).

Preparation of (Z)-2,2-Dimethyl-5-(chlorocarbonylmethylene)-1,3-dioxolan-4-one (VIII):

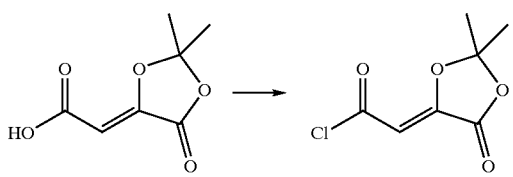

A mixture of (Z)-2,2-dimethyl-5-(carboxymethylene)-1,3-dioxolan-4-one (0.50 g, 2.9 mmol) in dry dichloromethane (10 ml) was treated at 22° C. with oxalyl chloride (0.5 ml, 5.8 mmol) followed by a trace (capillary) of N,N-dimethylformamide. After 1 h at 22° C., the clear solution was concentrated in vacuo to give 0.55 g (quantitative) of the title acid chloride as a white crystalline solid.

Method XVII

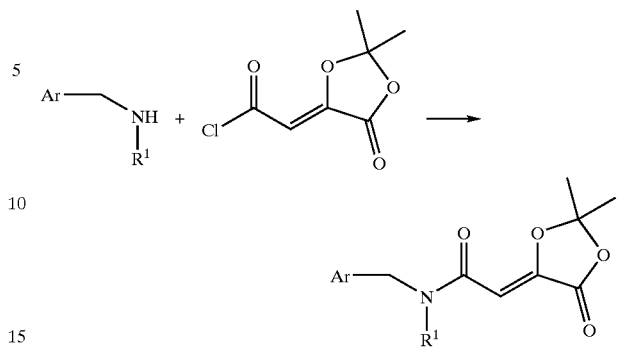

(Z)-2,2-Dimethyl-5-(chlorocarbonylmethylene)-1,3-dioxolane (1.3 mmol) was dissolved in 5 mL of THF. To this was added an amine (1.5 mmol) followed by Et$_3$N (2.6 mmol). The resulting slurry was stirred for 2 h then filtered. The mother liquor was isolate, and the solvent removed under vacuum to yield crude product which was purified by flash column chromatography (SiO$_2$, CH$_2$Cl$_2$/EtOH). This method can also be utilized with amine compounds similar to the above-identified starting material.

Method XVIII

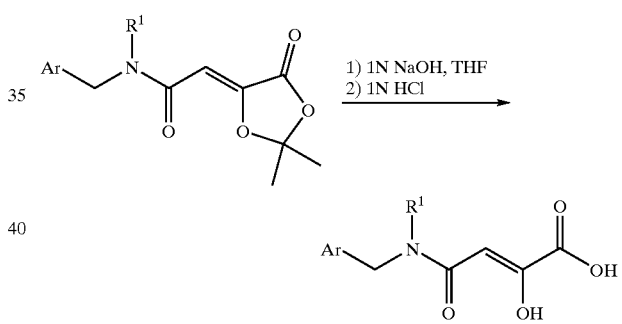

A solution of dioxolane (0.62 mmol) in tetrahydrofuran (5 ml) was treated with 1 ml of 1 M aqueous sodium hydroxide and the resulting clear solution was stirred at 22° C. for 30 minutes. The reaction mixture was then acidified with 2 N hydrochloric acid and diluted with ethyl acetate. The organic phase was washed with brine, dried (magnesium sulfate) and evaporated under reduced pressure. This method can also be utilized with dioxolane compounds similar to the above-identified starting material.

Method XIX

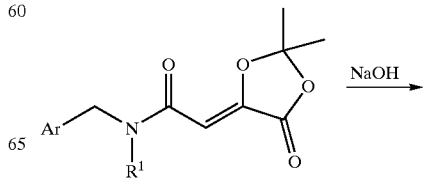

-continued

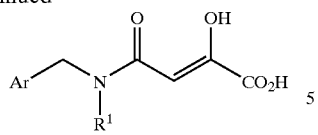

Dioxolane(~0.05 mmol) in a mixture of tetrahydrofuran (0.5 ml) and water (0.3 ml) was treated at 22° C. with 0.15 ml of 1 M aqueous sodium hydroxide and the resulting mixture was stirred for 1.5 h. The reaction mixture was then quenched by the addition of 0.3 ml of 1M trifluoroacetic acid in acetonitrile and filtered on a Varian Bond Elute C-18 cartridge (1.5 g) using water and then water-acetonitrile (1:1) as eluent.

If not commercially available, a necessary starting material for the preparation of a compound of Formula I may be prepared by a procedure which is selected from standard techniques of organic chemistry including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention. This method can also be utilized with dioxolane compounds similar to the above-identified starting material.

Method XX

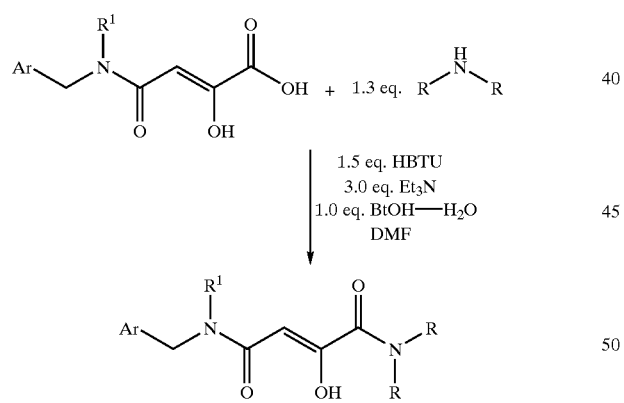

To a solution of dioxobutyric acid (0.58 mmol), 1-hydroxybenzotriazole hydrate (BtOH.H$_2$O) (0.58 mmol), amine (0.75 mmol) and O-(1H-benzotriazol-1-yl)-N,N,N', N'-tetramethyluronium hexafluorophosphate (HBTU) (0.88 mmol) in 4 mL of DMF was added Et$_3$N (1.72 mmol). The resulting mixture was stirred overnight, then diluted with EtOAc, washed H$_2$O and dried over MgSO$_4$. After filtration the solvent was removed under vacuum to yield crude product which was purified by preparative HPLC (C$_{18}$, MeOH/H$_2$O-0.1% TFA). This method can also be utilized with compounds similar to the dioxobutyric acid starting material.

EXAMPLE 1

Intermediate 1A

Methyl 4-(4-fluorobenzyloxy)-benzoate

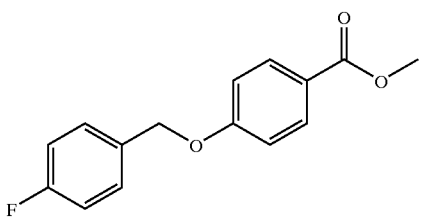

A mixture of methyl p-hydroxybenzoate (4.38 g, 28.8 mmol), p-fluorobenzyl chloride (5.0 g, 34.6 mmol) and anhydrous potassium carbonate (10 g) in acetone (250 ml) was heated under reflux for 24 h. The solid was then filtered and the filtrate was evaporated under reduced pressure. Crystallization of the residue from hexane gave 7.20 g (96%) of the title ester as white plates: mp 93–94° C. $^1$HNMR 400 MHz (CDCl$_3$) δ (ppm): 3.9 (3H, s, OCH$_3$), 5.1 (2H, s, CH$_2$), 7.0 (2H, d, J=8.8 Hz, aromatics), 7.11 (2H, m, aromatics), 7.43 (2 H, m, aromatics), 8.02 (2H, d, J=8.8 Hz, aromatics). Anal. Calcd for C$_{15}$H$_{13}$FO$_3$: C, 69.22; H, 5.03. Found: C, 68.89; H, 4.69.

Intermediate 1B 4-(4-Fluorobenzyloxy)-benzoic acid

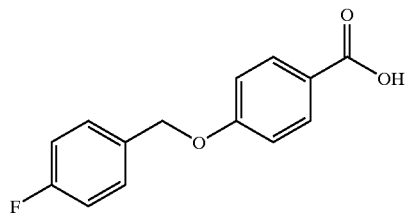

A mixture of Intermediate 1A (7.2 g, 27.6 mmol) in 80% aqueous ethanol (100 ml) was treated with sodium hydroxide (3.5 g) and the resulting mixture was heated at 50° C. for 2 h. The solvent was evaporated under reduced pressure and the residual solid was diluted with water and acidified with concentrated hydrochloric acid (20 ml). Filtration of the resulting solid and crystallization from ethyl acetate gave 6.05 g (89%) of the title acid as white plates: mp 213–215° C. $^1$HNMR 400 MHz (CDCl$_3$) δ (ppm): 5.16 (2H, s, CH$_2$), 7.1 (2H, d, J=8.9 Hz, aromatics), 7.24 (2 H, m, aromatics), 7.53 (2 H, m, aromatics), 7.9 (2H, d, J=0.9 Hz, aromatics) and 12.7 (1H, s, OH). Anal. Calcd for C$_{14}$H$_{11}$FO$_3$: C, 68.29; H, 4.50. Found: C, 68.30; H, 4.41.

Intermediate 1C

4-(4-Fluorobenzyloxy)-N-methyl-benzylamine

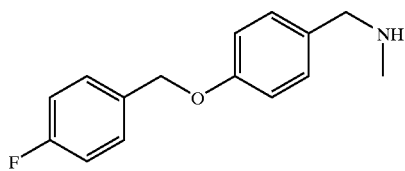

Intermediate 1C was prepared from Intermediate 1B using Method II, step 2. $^1$HNMR 400 MHz (CDCl$_3$) δ (ppm): 2.47 (3H, s, NCH$_3$), 3.72 (2H, s, NCH$_2$), 5.03 (2H, s, OCH$_2$), 6.95 (2H, d, J=8.6 Hz, aromatics), 7.09 (2H, m, aromatics), 7.27 (2H, d, J=8.6 Hz, aromatics) 7.42 (2H, m, aromatics). HRMS (ESI$^+$) calculated for C$_{15}$H$_{17}$FNO [M+H]: 246.1294: found: 246.1285.

Intermediate 1D

N-{4-(4-Fluorobenzyloxy)-benzyl}-N-methylacetamide

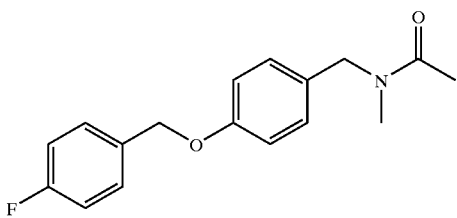

Intermediate 1D was prepared from Intermediate 1C using Method VIII. Solid: mp 82–83° C. (ethyl acetate-hexane). $^1$HNMR 400 MHz (CDCl$_3$) δ (ppm): mixture of rotamers; 2.16 and 2.19 (3H, 2 s, COCH$_3$), 2.93 and 2.94 (3H, 2 s, NCH$_3$), 4.48 and 4.54 (2H, 2 s, NCH$_2$), 5.03 and 5.04 (2H, 2 s, OCH$_2$), 6.95–7.44 (8H, m, aromatics). Anal. Calcd for C$_{17}$H$_{18}$FNO$_2$: C, 71.06; H, 6.31; N, 4.87. Found: C, 70.99; H, 6.23; N, 4.74.

Intermediate 1E

3-{[4-(4-Fluoro-benzyloxy)-benzyl]-methyl-carbamoyl}-2-hydroxy-acrylic acid methyl ester

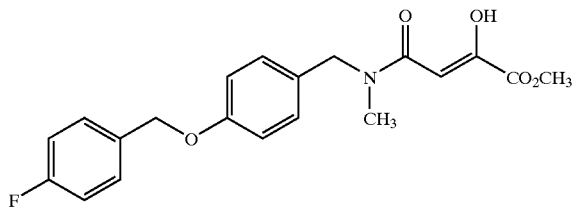

Intermediate 1E was prepared from Intermediate 1D using Method IX. $^1$HNMR 400 MHz (CDCl$_3$) δ (ppm): mixture of rotamers; 3.01 (3H, s, NCH$_3$), 3.89 and 3.92 (3H, 2 s, OCH$_3$), 4.54 and 4.60 (2H, 2 s, NCH$_2$), 5.03 (2H, s, OCH$_2$), 6.31 and 6.38 (1H, 2 s, CH), 6.94–7.44 (8H, m, aromatics). HRMS (MAB N$_2$) calculated for C$_{20}$H$_{20}$FNO$_5$ [M$^+$]: 373.1314: found: 373.1320.

Compound 1

3-{[4-(4-Fluoro-benzyloxy)-benzyl]-methyl-carbamoyl}-2-hydroxy-acrylic acid

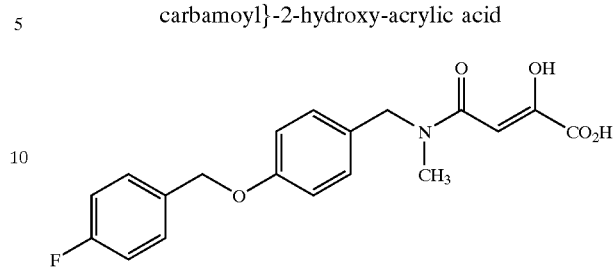

Compound 1 was prepared from Intermediate 1E using Method XI. $^1$HNMR 400 MHz (CDCl$_3$) δ (ppm): mixture of rotamers; 2.93 and 2.94 (3H, 2 s, NCH$_3$), 4.45 and 4.52 (2H, 2 s, NCH$_2$), 4.94 (2H, s, OCH$_2$), 6.27 and 6.35 (1H, 2 s, CH), 6.85–7.35 (8 H, m, aromatics). HRMS (MAB N$_2$) calculated for C$_{19}$H$_{18}$FNO$_5$ [M$^+$]: 359.1157: found: 359.1167, δ 0.5 ppm.

EXAMPLE 2

Intermediate 2A

3-{1-Hydroxy-1-(4-fluorophenyl)-methyl}-N-methyl-benzamide

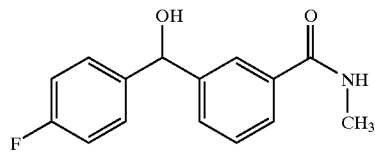

A solution of 3-bromo-N-methylbenzamide (3.48 g, 16.25 mmol) in dry tetrahydrofuran (100 ml) was cooled to −78° C. and treated dropwise over 10 min. with 13 ml (32.5 mmol) of a 2.5 M solution of n-butyllithium in hexane. After 15 min. at −78° C., a solution of 4-fluorobenzaldehyde (2.5 g, 20.1 mmol) in tetrahydrofuran (10 ml) was added dropwise over 10 min. and the resulting mixture was stirred for another 45 min at the same temperature. The temperature was then allowed to reach −20° C. and the mixture was quenched by the addition of saturated ammonium chloride. The reaction mixture was then extracted with ethyl acetate and the organic layer was washed with 0.1N hydrochloric acid, saturated sodium bicarbonate, brine and dried (magnesium sulfate). Evaporation of the solvent and crystallization of the residue from ethyl acetate gave 1.60 g (38%) of the title compound as a white solid: mp: 138–139° C. $^1$HNMR 400 MHz (CDCl$_3$) δ (ppm): 3.0 and 3.01 (3H, 2 s, NCH$_3$), 5.88 (1H, s, CH), 6.19 (1H, broad, NH), 7.03 (2H, m, aromatics), 7.36 (2H, m, aromatics), 7.41 (1H, t, J=7.6 Hz, aromatic), 7.49 (1H, d, J=7.6 Hz, aromatic), 7.66 (1H, d, J=7.6 Hz, aromatic), 7.79 (1H, s, aromatic). Anal. Calcd for C$_{15}$H$_{14}$FNO$_2$: C, 69.49; H, 5.44; N, 5.40. Found: C, 69.41; H, 5.41; N, 5.63.

Intermediate 2B 3-(4-Fluorobenzyl)-N-methyl-benzamide

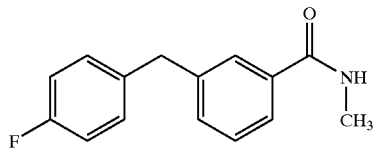

A solution of Intermediate 2A (1.0 g, 3.85 mmol) in ethyl acetate (150 ml) and acetic acid (1 ml) was hydrogenated over 0.5 g of 10% palladium on activated carbon and under 45 psi of hydrogen for 24 h. After filtration the solvent was evaporated under reduce pressure. Crystallization of the residue from a mixture of ethyl acetate and hexane gave 0.778 g of the title amide as white needles: mp 93–94° C. $^1$HNMR 400 MHz (CDCl$_3$) δ (ppm): 3.02 and 3.03 (3H, 2 s, NCH$_3$), 4.01 (2H, s, CH$_2$), 6.12 (1H, broad, NH), 7.0 (2H, m, aromatics), 7.14 (2H, m, aromatics), 7.32 (1H, d, J=7.6 Hz, aromatic), 7.37 (1H, t, J=7.6 Hz, aromatic), 7.59 (1H, d, J=7.6 Hz, aromatic), 7.62 (1H, s, aromatic). Anal. Calcd for C$_{15}$H$_{14}$FNO: C, 74.06; H, 5.80; N, 5.76. Found: C, 73.74; H, 5.87; N, 5.74.

Intermediate 2C 3-(4-Fluorobenzyl)-N-methyl-benzylamine

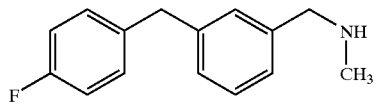

Intermediate 2C was prepared from Intermediate 2B using Method II, step 2. $^1$HNMR 400 MHz (C$_6$D$_6$) δ (ppm): 2.3 (3H, s, NCH$_3$), 3.59 (2H, s, CH$_2$), 3.76 (2H, s, CH$_2$), 6.85–7.25 (8H, m, aromatics). MS (ESI$^+$) (m/z): 230 (M+H).

Intermediate 2D

N-{3-(4-Fluorobenzyl)-benzyl}-N-methylacetamide

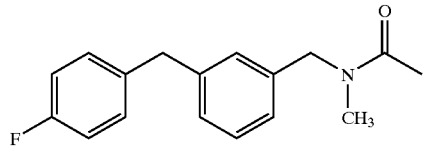

Intermediate 2D was prepared from Intermediate 2C using Method VIII. $^1$HNMR 400 MHz (CDCl$_3$) δ (ppm): mixture of rotamers; 2.16 and 2.17 (3H, 2 s, COCH$_3$), 2.92 and 2.94 (3H, 2 s, NCH$_3$), 3.95 and 3.97 (2H, 2 s, CH$_2$), 4.51 and 4.57 (2H, s, NCH$_2$), 6.96–7.31 (8H, m, aromatics). MS (ESI$^+$) (m/z): 272 (M+H). Anal. Calcd for C$_{17}$H$_{18}$FNO: C, 75.25; H, 6.69; N, 5.16. Found: C, 74.99; H, 6.75; N, 5.08.

Intermediate 2E

3-{[3-(4-Fluoro-benzyl)-benzyl]-methyl-carbamoyl}-2-hydroxy-acrylic acid methyl ester

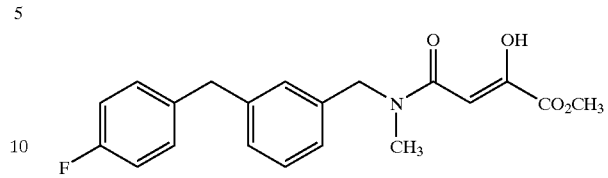

Intermediate 2E was prepared from Intermediate 2D using Method IX. $^1$HNMR 400 MHz (CDCl$_3$) δ (ppm): mixture of rotamers; 3.01 and 3.02 (3H, 2 s, NCH$_3$), 3.88, 3.92 and 3.96 (5H, 3 s, CH$_2$ and OCH$_3$), 4.58 and 4.64 (2H, 2 s, NCH$_2$), 6.32 (1H, s, CH), 6.97–7.54 (8 H, m, aromatics). HRMS (MAB N$_2$) calculated for C$_{20}$H$_{20}$FNO$_4$ [M$^+$]: 357.1376: found: 357.1375.

Compound 2

3-{[3-(4-Fluoro-benzyl)-benzyl]-methyl-carbamoyl}-2-hydroxy-acrylic acid

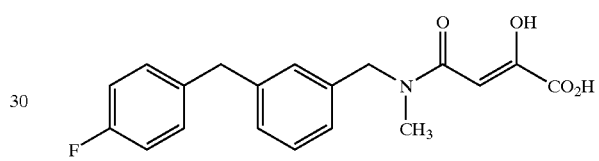

Compound 2 was prepared from Intermediate 2E using Method XI. $^1$HNMR 400 MHz (CDCl$_3$) δ (ppm): mixture of rotamers; 3.02 and 3.04 (3H, 2 s, NCH$_3$), 3.76 (2H, s, CH$_2$), 4.56 and 4.64 (2H, 2 s, NCH$_2$), 6.37 (1H, s, CH), 6.96–7.33 (8 H, m, aromatics). HRMS (MAB N$_2$) calculated for C$_{19}$H$_{18}$FNO$_4$ [M$^+$]: 343.12198: found: 343.12234, δ –1.0 ppm.

EXAMPLE 3

Intermediate 3A

Methyl 3-(4-fluorobenzyloxy)-benzoate

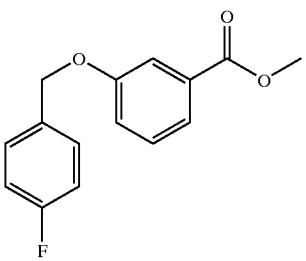

Reaction of methyl 3-hydroxybenzoate with p-fluorobenzyl chloride as described in the preparation of Intermediate 1A gave the title ester as white prisms: mp 58–59° C. (hexane). $^1$HNMR 400 MHz (CDCl$_3$) δ (ppm): 3.94 (3H, s, OCH$_3$), 5.1 (2H, s, OCH$_2$), 7.09–7.69 (8H, m, aromatics). Anal. Calcd for C$_{15}$H$_{13}$FO$_3$: C, 69.22; H, 5.03. Found: C, 69.08; H, 4.97.

Intermediate 3B 3-(4-Fluorobenzyloxy)-benzoic acid

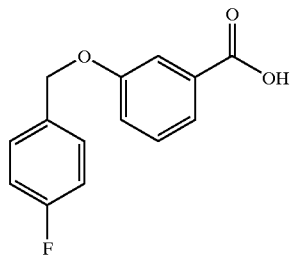

Saponification of methyl 3-(4-fluorobenzyloxy)-benzoate as described in the preparation of Intermediate 1B gave the title acid as white needles: mp 145–146° C. (ethyl acetate). $^1$HNMR 400 MHz (CDCl$_3$) δ (ppm): 5.11 (2H, s, OCH$_2$), 7.12 (2H, m, aromatics), 7.24 (1 H, m, aromatics), 7.45 (3 H, m, aromatics), 7.75 (2H, m, aromatics). Anal. Calcd for C$_{14}$H$_{11}$FO$_3$: C, 68.29; H, 4.50. Found: C, 68.39; H, 4.43.

Intermediate 3C 3-(4-Fluorobenzyloxy)-N-methyl-benzylamine

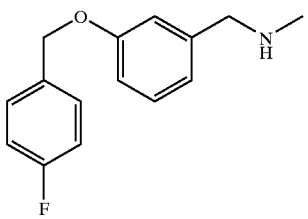

Intermediate 3C was prepare from Intermediate 3B using Method II, step 2. $^1$HNMR 400 MHz (CDCl$_3$) δ (ppm): 2.48 (3H, s, NCH$_3$), 3.72 (2H, s, NCH$_2$), 5.05 (2H, s, OCH$_2$), 6.9–7.45 (8H, m, aromatics). MS (ESI$^+$) (m/z): 246 (M+H).

Intermediate 3D

N-{3-(4-Fluorobenzyloxy)-benzyl}-N-methylacetamide

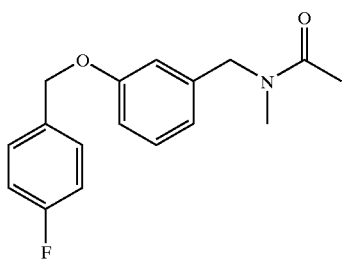

Intermediate 3D was prepared from Intermediate 3C using Method VIII. $^1$HNMR 400 MHz (CDCl$_3$) δ (ppm): mixture of rotamers; 2.15 and 2.16 (3H, 2 s, COCH$_3$), 2.91 and 2.94 (3H, 2 s, NCH$_3$), 4.49 and 4.55 (2H, 2 s, NCH$_2$), 5.01 (2H, s, OCH$_2$), 6.75;7.42 (8H, m, aromatics). MS (ESI$^+$) (m/z): 288 (M+H).

Intermediate 3E

3-{[3-(4-Fluoro-benzyloxy)-benzyl]-methyl-carbamoyl}-2-hydroxy-acrylic acid methyl ester

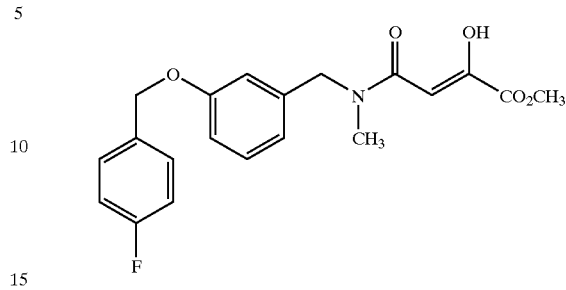

Intermediate 3E was prepared from Intermediate 3D using Method IX. $^1$HNMR 400 MHz (CDCl$_3$) δ (ppm): mixture of rotamers; 2.99 and 3.01 (3H, 2 s, NCH$_3$), 3.86 and 3.9 (3H, 2 s, OCH$_3$), 4.55 and 4.62 (2H, 2 s, NCH$_2$), 5.01 (2H, s, OCH$_2$), 6.29 (1H, s, CH), 6.7–7.41 (8 H, m, aromatics). HRMS (MAB N$_2$) calculated for C$_{20}$H$_{20}$FNO$_5$ [M$^+$]: 373.1325: found: 373.1326.

Compound 3

3-{[3-(4-Fluoro-benzyloxy)-benzyl]-methyl-carbamoyl}-2-hydroxy-acrylic acid

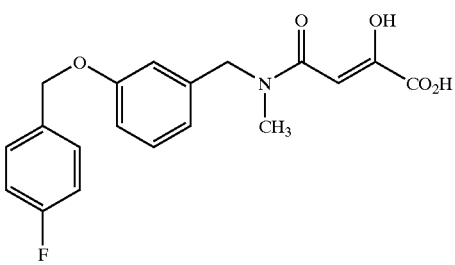

Compound 3 was prepared from Intermediate 3E using Method XI. $^1$HNMR 400 MHz (CDCl$_3$) δ (ppm): mixture of rotamers; 3.02 and 3.05 (3H, 2 s, NCH$_3$), 4.58 and 4.65 (2H, 2 s, NCH$_2$), 5.03 (2H, s, OCH$_2$), 6.38 (1H, s, CH), 6.79–7.43 (8 H, m, aromatics). HRMS (MAB N$_2$) calculated for C$_{19}$H$_{18}$FNO$_5$ [M$^+$]: 359.1169: found 359.1170, δ –0.2 ppm.

EXAMPLE 4

Intermediate 4A

[Bis-(4-chloro-phenyl)-methyl]-methyl-amine

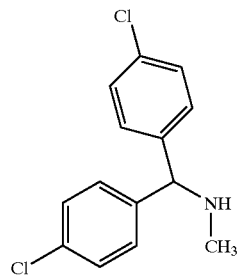

A solution of 4,4'-dichlorobenzhydryl chloride (3.22 g, 11.85 mmol) in a 1.85 M solution of methylamine in tetrahydrofuran (40 ml) was heated at 125° C. in a pressure vessel for 24 h. The cooled reaction mixture was diluted with ethyl acetate, washed with sodium carbonate, brine and dried (magnesium sulfate). Evaporation of the solvent and chromatography of the residue on silica gel (elution toluene-ethyl acetate 8:2) gave 2.12 g (67%) of the title amine as a clear oil. $^1$HNMR 400 MHz (CDCl$_3$) δ (ppm): 2.57 (3H, s, NCH$_3$), 4.85 (1H, s, CH benzhydryl), 7.0–7.53 (8H, m, aromatics). MS (ESI$^+$) (m/z): 266 (M+H).

Intermediate 4B

N-[Bis-(4-chloro-phenyl)-methyl]-N-methyl-acetamide

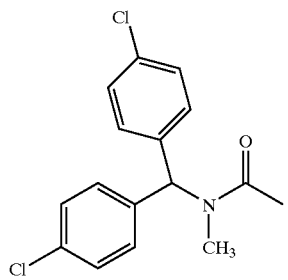

Intermediate 4B was prepared from Intermediate 4A using Method VIII. $^1$HNMR 400 MHz (CDCl$_3$) δ (ppm): mixture of rotamers; 2.17 (3H, s, COCH$_3$), 2.66 and 2.75 (3H, 2 s, NCH$_3$), 6.13 (1H, s, CH benzhydryl), 7.06 and 7.3 (2×4H, m, aromatics).

Intermediate 4C

3-{[Bis-(4-chloro-phenyl)-methyl]-methyl-carbamoyl}-2-hydroxy-acrylic acid methyl ester

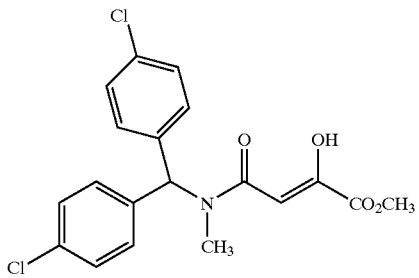

Intermediate 4C was prepared from Intermediate 4B using Method IX. $^1$HNMR 400 MHz (CDCl$_3$) δ (ppm): mixture of rotamers; 2.79 and 2.89 (3H, 2 s, NCH$_3$), 3.88 and 3.92 (3H, 2 s, OCH$_3$), 6.31, 6.33 and 6.35 (2H, 3 s, CH benzhydryl and CH), 7.28 (4 H, m, aromatics), 7.37 (4 H, m, aromatics). HRMS (ESI$^+$) calculated for C$_{19}$H$_{19}$Cl$_2$NO$_4$ [M+H$^+$]: 394.0613: found 394.0609.

Compound 4

3-{[Bis-(4-chloro-phenyl)-methyl]-methyl-carbamoyl}-2-hydroxy-acrylic acid

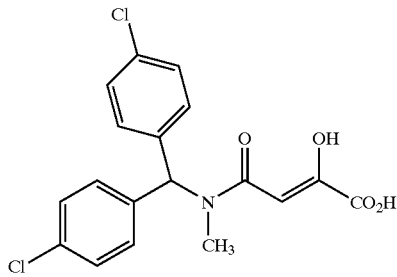

Compound 4 was prepared from Intermediate 4C using Method XI. $^1$HNMR 400 MHz (CDCl$_3$) δ (ppm): mixture of rotamers; 2.80 and 2.89 (3H, 2 s, NCH$_3$), 6.31, 6.37 and 6.41 (2H, 3 s, CH benzhydryl and CH), 7.06–7.17 and 7.32–7.43 (8H, m, aromatics). HRMS (MAB N$_2$) calculated for C$_{18}$H$_{15}$Cl$_2$NO$_4$ [M$^+$]: 379.0378: found 379.0374, δ1.1 ppm.

EXAMPLE 5

Intermediate 5A

[Bis-(4-fluoro-phenyl)-methyl]-methyl-amine

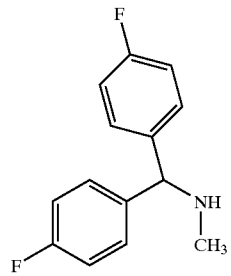

A mixture of 4,4'-difluorobenzophenone (2.18 g, 10.0 mmol) in anhydrous ethanol (15 ml) was treated successively with titanium (IV) isopropoxide (5.9 ml, 20.0 mmol), methylamine hydrochloride (1.35 g, 20.0 mmol) and triethylamine (2.8 ml, 20.0 mmol). The resulting mixture was stirred at 22° C. for 18 h and then treated with sodium borohydride (0.57 g, 15.0 mmol). After 6 h at 22° C., the reaction mixture was quenched by the addition of 2N aqueous ammonia (30 ml) and the resulting precipitate was filtered and washed with dichloromethane. The organic layer was collected and extracted with 1N hydrochloric acid. The aqueous phase was then treated with 2N aqueous sodium hydroxide (pH 11) and extracted twice with dichloromethane. The combined extracts were dried (magnesium sulfate) and concentrated. Distillation of the residue in vacuo gave 2.12 g (91%) of the title amine as a clear oil: bp 85–90° C./0.2 torr, (bulb to bulb distillation, air bath temperature). $^1$HNMR 400 MHz (CDCl$_3$) δ (ppm): 2.40 (3H, s, NCH$_3$), 4.68 (1H, s, CH benzhydryl), 7.0 (4H, m, aromatics), 7.35 (4H, m, aromatics). Anal. Calcd for C$_{14}$H$_{13}$F$_2$N: C, 72.09; H, 5.62; N, 6.0. Found: C, 71.76; H, 5.76; N, 5.84.

Intermediate 5B

N-[Bis-(4-fluoro-phenyl)-methyl]-N-methyl-acetamide

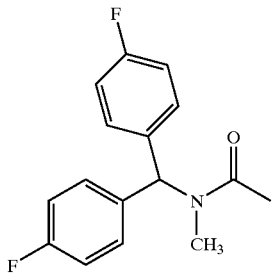

Intermediate 5B was prepared from Intermediate 5A using Method VIII. Solid: mp 99–100° C. (ethyl acetate-hexane). ¹HNMR 400 MHz (CDCl₃) δ (ppm): mixture of rotamers; 2.20 and 2.21 (3H, 2 s, COCH₃), 2.70 and 2.78 (3H, 2 s, NCH₃), 6.18 (1H, s, CH benzhydryl), 7.0–7.25 (8H, m, aromatics). Anal. Calcd for $C_{16}H_{15}F_2NO$: C, 69.81; H, 5.49; N, 5.09. Found: C, 69.52; H, 5.47, N, 5.01.

Intermediate 5C

3-{[Bis-(4-fluoro-phenyl)-methyl]-methyl-carbamoyl}-2-hydroxy-acrylic acid methyl ester

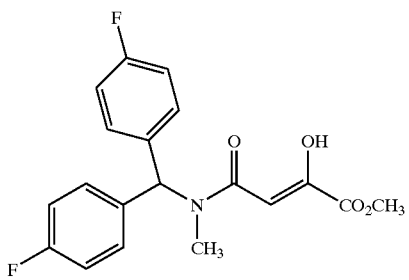

Intermediate 5C was prepared from Intermediate 5B using Method IX. ¹HNMR 400 MHz (CDCl₃) δ (ppm): mixture of rotamers; 2.79 and 2.89 (3H, 2 s, NCH₃), 3.88 and 3.92 (3H, 2 s, OCH₃), 6.33 and 6.35 (2H, 2 s, CH benzhydryl and CH), 7–7.2 (8H, m, aromatics). MS (ESI⁺) (m/z): 362 (M+H).

Compound 5

3-{[Bis-(4-fluoro-phenyl)-methyl]-methyl-carbamoyl}-2-hydroxy-acrylic acid

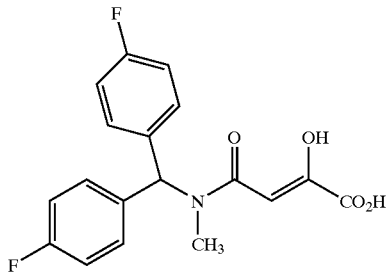

Compound 5 was prepared from Intermediate 5C using Method XI. ¹HNMR 400 MHz (CDCl₃) δ (ppm): mixture of rotamers; 2.82 and 2.91 (3H, 2 s, NCH₃), 6.36 and 6.41 (1H, 2 s, CH), 6.43 (1H, s, CH benzhydryl),7.1–7.4 (8H, m, aromatics). HRMS (MAB N₂) calculated for $C_{18}H_{15}F_2NO_4$ [M⁺]: 347.0969: found: 349.0960, δ 2.6 ppm.

EXAMPLE 6

Intermediate 6A

N-[Bis-(4-methoxy-phenyl)-methyl]-N-methyl-acetamide

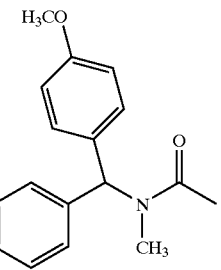

Intermediate 6A was prepared from bis-(4-methoxy-phenyl)-methyl]-methyl-amine (Cymerman-Craig, et al. Aust. J. Chem. 1955, 8, 385) using Method VIII. ¹HNMR 400 MHz (CDCl₃) δ (ppm): mixture of rotamers; 2.19 and 2.21 (3H, 2 s, COCH₃), 2.70 and 2.78 (3H, 2 s, NCH₃), 3.81 and 3.82 (3H, 2 s, OCH₃), 6.13 (1H, s, CH benzhydryl), 6.87 and 7.08 (2×4H, m, aromatics). Anal. Calcd for $C_{18}H_{21}NO_3$: C, 72.22; H, 7.07; N, 4.68. Found: C, 71.99; H, 6.88; N, 4.65.

Intermediate 6B

3-{[Bis-(4-methoxy-phenyl)-methyl]-methyl-carbamoyl}-2-hydroxy-acrylic acid methyl ester

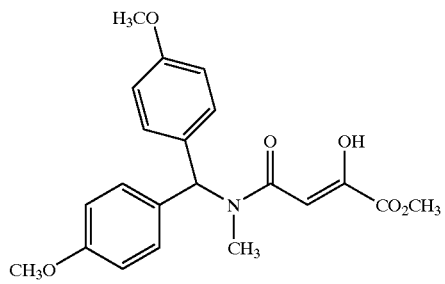

Intermediate 6B was prepared from Intermediate 6A using Method IX. ¹HNMR 400 MHz (CDCl₃) δ (ppm): mixture of rotamers; 2.79 and 2.89 (3H, 2 s, NCH₃), 3.84, 3.85, 3.87 and 3.92 (9H, 4 s, OCH₃), 6.30, 6.34 and 6.37 (2H, 3 s, CH benzhydryl and CH), 6.9–6.93 (4H, m, aromatics), 7.08–7.14 (4H, m, aromatics). HRMS (ESI⁺) calculated for $C_{21}H_{24}NO_6$ [M+H⁺]: 386.16037: found: 386.15890.

Compound 6

3-{[Bis-(4-methoxy-phenyl)-methyl]-methyl-carbamoyl}-2-hydroxy-acrylic acid

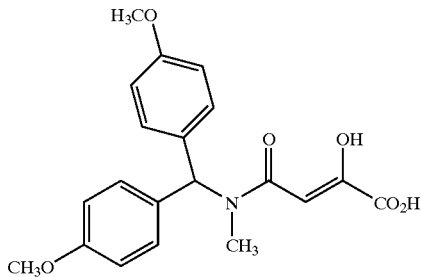

Compound 6 was prepared from Intermediate 6B using Method XI. $^1$HNMR 400 MHz (CDCl$_3$) δ (ppm): mixture of rotamers; 2.75 and 2.83 (3H, 2 s, NCH$_3$), 3.77, and 3.78 (6H, 2 s, OCH$_3$), 6.23, 6.33 and 6.36 (2H, 3 s, CH benzhydryl and CH), 6.83–6.86 (4H, m, aromatics), 6.88–7.06 (4H, m, aromatics). HRMS (ESI$^-$) calculated for C$_{20}$H$_{20}$NO$_6$ [M–H]$^-$: 370.12906: found: 370.13003, δ –2.6 ppm.

EXAMPLE 7

Intermediate 7A 3-(Benzhydryl-methyl-carbamoyl)-2-hydroxy-acrylic acid methyl ester

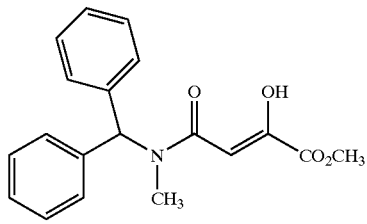

Intermediate 7A was prepared from N-Bis-(phenyl)-methyl]-N-methyl-acetamide from using Method IX. $^1$HNMR 400 MHz (CDCl$_3$) δ (ppm): mixture of rotamers; 2.67 and 2.83 (3H, 2 s, NCH$_3$), 3.79 and 3.83 (3H, 2 s, OCH$_3$), 6.28 (1H, s, CH benzhydryl), 6.3 and 6.31 (1H, 2 s, CH), 7–7.4 (10 H, m, aromatics).

Compound 7

3-(Benzhydryl-methyl-carbamoyl)-2-hydroxy-acrylic acid

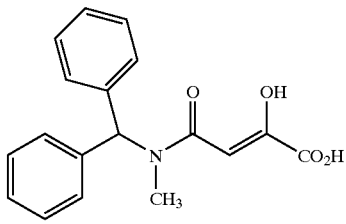

Compound 7 was prepared from Intermediate 7A using Method XI. $^1$HNMR 400 MHz (CDCl$_3$) δ (ppm): mixture of rotamers; 2.82 and 2.91 (3H, 2 s, NCH$_3$), 6.41 (1H, s, CH benzhydryl), 6.37 and 6.43 (1H, 2 s, CH), 7.1–7.4 (10 H, m, aromatics). HRMS (MAB N$_2$) calculated for C$_{18}$H$_{17}$NO$_4$ [M$^+$]: 311.1157: found: 311.1154, δ 1 ppm.

EXAMPLE 8

Intermediate 8A 2,2-Bis-(4-fluoro-phenyl)-N-methyl-acetamide

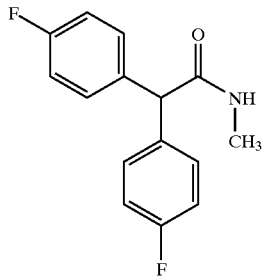

A mixture of bis-(4-fluorophenyl)-acetic acid (8.07 g, 32.5 mmol) (prepared using the procedure of Takahashi, Y. et al., Chem. Lett., 1985, 1733.), in dichloromethane (30 ml) was treated at 22° C. with oxalyl chloride (5.5 ml, 65.0 mmol) and a drop of N,N-dimethylformamide. After 18 h at 22° C., the solvent and excess reagent were evaporated under reduce pressure. The residual oil was then dissolved in dry tetrahydrofuran (10 ml) and added dropwise and under good stirring to a cold (0–5° C.) mixture of methylamine hydrochloride (10.9 g, 0.16 mol), sodium hydroxide (6 g) in water (50 ml) and tetrahydrofuran (100 ml). After 1 h at 22° C., the reaction mixture was diluted with ethyl acetate, washed successively with water, 1N hydrochloric acid, saturated sodium bicarbonate, brine and dried (magnesium sulfate). Evaporation of the solvent and crystallization of the residue in ethyl acetate gave 7.75 g (91%) of the title material as white needles: mp 179–180° C. $^1$HNMR 400 MHz (CDCl$_3$) δ (ppm): 2.86 (3H d, J=5.1 Hz, NCH$_3$), 4.87 (1H, s, CH) 5.65 (1H, broad, NH), 7.04 and 7.23 (2×4H, 2 m, aromatics). Anal. Calcd for C$_{15}$H$_{13}$F$_2$NO: C, 68.96; H, 5.02; N, 5.36. Found: C, 68.88; H, 4.49; N, 5.75.

Intermediate 8B

[2,2-Bis-(4-fluoro-phenyl)-ethyl]-methyl-amine

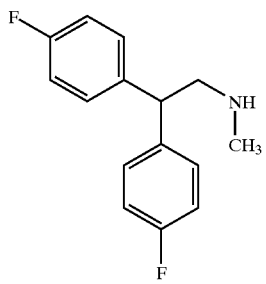

A mixture of Intermediate 8A (8.68 g, 33.2 mmol) in tetrahydrofuran (50 ml) was treated with boron trifluoride diethyl etherate (4.2 ml, 33.2 mmol) and heated under reflux for 15 min. The resulting homogeneous solution was cooled at 22° C. and treated with borane-methyl sulfide complex (4.5 ml, 4.5 mmol) added dropwise over 5 min. The solution was then heated under reflux for 30 min. The tetrahydrofuran was then distilled and the residue was maintained at 110°

C. for another hour. The cooled mixture was then treated dropwise with 6N hydrochloric acid (15 ml) and heated under reflux for 1 h. The mixture was cooled to 0–5° C. and 6N sodium hydroxide solution (30 ml) was added. The aqueous mixture was extracted with ether (4×), the combined extracts were dried (anhydrous sodium carbonate) and concentrated under reduce pressure. Distillation of the residue in vacuo gave 7.66 g (93%) of the title amine as a clear oil: bp 90–105° C./0.2 torr (bulb to bulb distillation, air bath temperature). $^1$HNMR 400 MHz ($C_6D_6$) δ (ppm): 2.27 (3H, s, $NCH_3$), 2.93 (2H, d, J=7.6 Hz, $CH_2$), 3.96 (1H, t, J=7.6 Hz, CH) and 6.91 (8H, m, aromatics). MS (ESI$^+$) (m/z): 248 (M+H) Anal. Calcd for $C_{15}H_{15}F_2N \cdot 0.25H_2O$: C, 71.55; H, 6.21; N, 5.56. Found: C, 71.67; H, 5.86; N, 5.59.

Intermediate 8C

N-[2,2-Bis-(4-fluoro-phenyl)-ethyl]-N-methyl-acetamide

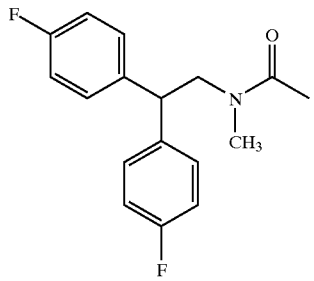

Intermediate 8C was prepared from Intermediate 8B using Method VIII. $^1$HNMR 400 MHz (CDCl$_3$) δ (ppm): mixture of rotamers; 1.72 and 2.01 (3H, 2 s, COCH$_3$), 2.71 and 2.87 (3H, 2 s, NCH$_3$), 3.88 and 3.95 (2H, 2d, J=7.6 Hz and J=8.0 Hz, CH$_2$), 4.31 and 4.40 (1H, 2t, J=7.6 Hz and J=8.0 Hz, CH), 6.98;7.25 (8H, m, aromatics). MS (ESI$^+$) (m/z): 290 (M+H).

Intermediate 8D

3-{[2,2-Bis-(4-fluoro-phenyl)-ethyl]-methyl-carbamoyl}-2-hydroxy-acrylic acid methyl ester

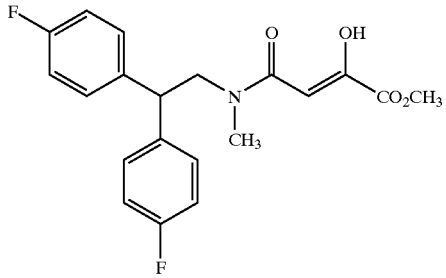

Intermediate 8D was prepared from Intermediate 8C using Method IX. $^1$HNMR 400 MHz (CDCl$_3$) δ (ppm):

mixture of rotamers; 2.78 and 2.84 (3H, 2 s, NCH$_3$), 3.88 and 3.90 (3H, 2 s, OCH$_3$), 3.96 and 4.03 (2H, 2d, J=8 Hz, CH$_2$), 4.23 and 4.42 (1H, 2t, J=8.0 Hz, CH), 5.95 and 6.14 (1H, 2 s, CH), 7.0–7.24 (8H, m, aromatics). MS (ESI$^+$) (m/z): 376 (M+H).

Compound 8

3-{[2,2-Bis-(4-fluoro-phenyl)-ethyl]-methyl-carbamoyl}-2-hydroxy-acrylic acid

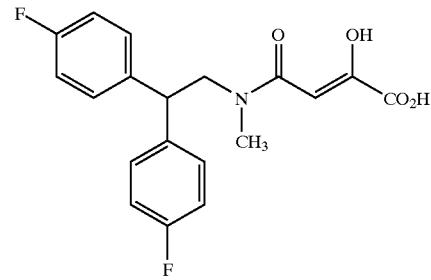

Compound 8 was prepared from Intermediate 8D using Method XI. $^1$HNMR 400 MHz (CDCl$_3$) δ (ppm): mixture of rotamers; 2.77 and 2.84 (3H, 2 s, NCH$_3$), 3.94 and 4.02 (2H, 2 d, J=8.1 Hz and J=8.2 Hz, CH$_2$), 4.21 and 4.40 (1H, 2t, J=8.1 Hz and J=8.2 Hz, CH), 6.0 and 6.18 (1H, 2 s, CH), 6.98–7.25 (8H, m, aromatics). HRMS (ESI$^-$) calculated for $C_{19}H_{16}F_2NO_4$ [M−H]$^-$: 360.1036: found: 360.1049, δ −0.5 ppm.

EXAMPLE 9

Intermediate 9A 2,2-Bis-(4-chlorophenyl)-N-methyl-ethylamine

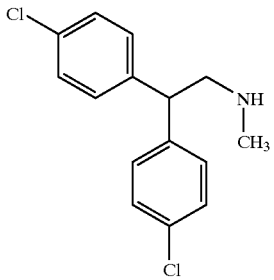

Intermediate 9A was prepared from 2,2-bis-(4-chlorophenyl)-N-methylacetamide using Method II, step II. $^1$HNMR 400 MHz (C$_6$D$_6$) δ (ppm): 2.26 (3H, s, NCH$_3$), 2.89 (2H, d, J=7.1 Hz, CH$_2$), 3.87 (1H, t, J=7.1 Hz, CH), 6.86 (4H, d, J=8.3 Hz, aromatics) and 7.19 (4H, d, J=8.3 Hz, aromatics).

Intermediate 9B

N-{2,2-Bis-(4-chlorophenyl)-ethyl}-N-methylacetamide

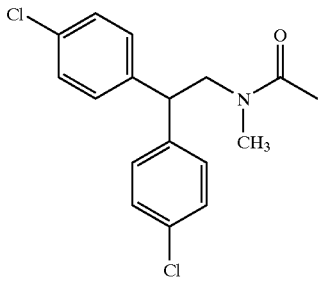

Intermediate 9B was prepared from Intermediate 9A using Method VIII. Solid: mp 103–104° C. (ethyl acetate-hexane). $^1$HNMR 400 MHz (CDCl$_3$) δ (ppm): mixture of rotamers; 1.92 (3H, s, COCH$_3$), 2.63 and 2.78 (3H, 2 s, NCH$_3$), 3.79 and 3.85 (2H, 2d, J=7.6 Hz and J=8.0 Hz, CH$_2$), 4.10 and 4.30 (1H, 2t, J=7.6 Hz and J=8.0 Hz, CH), 7.03–7.25 (8H, m, aromatics). Anal. Calcd for C$_{17}$H$_{17}$Cl$_2$NO: C, 63.37; H, 5.32; N, 4.35. Found: C, 63.09; H, 5.34; N, 4.29. MS (ESI$^+$) (m/z): 322 (M+H).

Intermediate 9C

3-{[2,2-Bis-(4-chloro-phenyl)-ethyl]-methyl-carbamoyl}-2-hydroxy-acrylic acid methyl ester

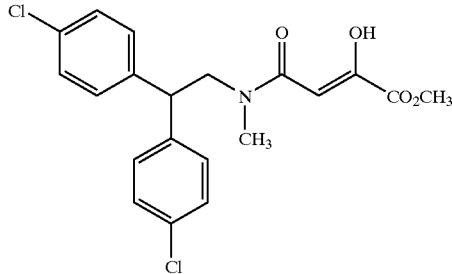

Intermediate 9C was prepared from Intermediate 9B using Method IX. $^1$HNMR 400 MHz (CDCl$_3$) δ (ppm): mixture of rotamers; 2.81 and 2.88 (3H, 2 s, NCH$_3$), 3.92 and 3.93 (3H, 2 s, OCH$_3$), 3.99 and 4.06 (2H, 2d, J=7.6 Hz and J=8.1 Hz, CH$_2$), 4.23 and 4.45 (1H, 2t, J=7.6 Hz and J=8.1 Hz, CH), 5.95 and 6.17 (1H, 2 s, CH), 7.16–7.37 (8H, m, aromatics). MS (ESI$^+$) (m/z): 408 (M+H).

Compound 9

3-{[2,2-Bis-(4-chloro-phenyl)-ethyl]-methyl-carbamoyl}-2-hydroxy-acrylic acid

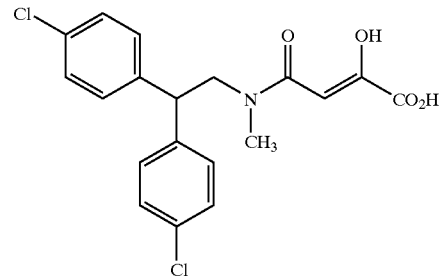

Compound 9 was prepared from Intermediate 9C using Method XI. $^1$HNMR 400 MHz (CDCl$_3$) δ (ppm): mixture of rotamers; 2.78 and 2.84 (3H, 2 s, NCH$_3$), 3.95 and 4.02 (2H, 2 d, J=8.1 Hz and J=8.3 Hz, CH$_2$), 4.18 and 4.38 (1H, 2t, J=8.1 Hz and J=8.3 Hz, CH), 6.0 and 6.2 (1H, 2 s, CH), 7.1–7.31 (8H, m, aromatics). HRMS (ESI$^-$) calculated for C$_{19}$H$_{16}$Cl$_2$NO$_4$ [M–H]$^-$: 392.0456: found: 392.0475, δ –4.8 ppm.

EXAMPLE 10

Intermediate 10A

N-(2-Chloro-benzyl)-N-methyl-acetamide

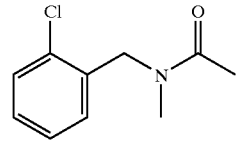

2-Chlorobenzyl bromide (1.37 g, 6.67 mmol) was dissolved in 5 ml of THF. To this was added 5 ml of 40% (aq.) methylamine and the resulting mixture stirred 15 min. The reaction mixture was transferred to a separatory funnel, diluted with 100 ml H$_2$O and extracted with 100 ml of ethyl acetate. The organic solution was washed with brine, dried over Na$_2$SO$_4$ then filtered and the solvent removed to yield 1.21 g oil. The crude product was purified by column chromatography (5×6.5 cm SiO$_2$, 2–10% EtOH/CH$_2$Cl$_2$) to yield 710 mg (68% yield) oil. LC/MS (M+H) calcd for C$_8$H$_{11}$ClN: 156.06; found: 155.99.

The amine (710 mg, 4.6 mmol) synthesized above was dissolved in 30 ml CH$_2$Cl$_2$. Satd. (aq.) NaHCO$_3$ was added followed by CH$_3$COCl (0.36 ml, 5.0 mmol) and the resulting mixture stirred for 1 h. The organic layer was separated, washed with brine dried over Na$_2$SO$_4$ then filtered and the solvent removed to yield 900 mg (>99% yield) oil as a pure product. LC/MS (M+H) calcd for C$_{10}$H$_{13}$ClNO: 198.06; found: 198.02. $^1$H NMR and $^{13}$C NMR show a mixture of rotamers at room temperature. $^1$H NMR (500 MHz, CDCl$_3$) δ: 2.10 (s), 2.19 (s), 2.97 (s), 4.59 (s), 4.73 (S), 7.10–7.41 (overlapping m, 4). $^{13}$C NMR (125 MHz, CDCl$_3$) δ: 21.33, 21.82, 34.06, 36.03, 48.06, 52.22, 126.79, 127.10, 127.36, 128.54, 128.83, 129.10, 129.57, 129.91, 132.84, 133.59, 133.96, 134.67, 170.99, 171.41. LC/MS (M+H) calcd for C$_{10}$H$_{13}$ClNO: 198.06; found: 198.02. Anal calcd for C$_{10}$H$_{12}$ClNO: C, 60.76; H, 6.11; N, 7.08; Cl, 17.93. found: C, 60.53; H, 6.15; N, 7.04; Cl, 17.81.

Intermediate 10B

3-[(2-Chloro-benzyl)-methyl-carbamoyl]-2-hydroxy-acrylic acid methyl ester

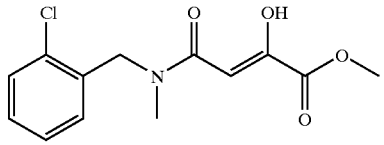

Intermediate 10A (1.96 g, 9.92 mmol) was dissolved in 20 ml of anhydrous THF under an $N_2$ atmosphere then cooled to $-78°$ C. To this was added 30 ml of 1M LiHMDS (lithium bis(trimethylsilyl)amide) and the reaction mixture stirred for 20 min. at which point dimethyl oxalate (1.76 g, 14.9 mmol) dissolved in 8 ml of THF was added. The reaction was allowed to continue at $-78°$ C. for 20 min. then warmed to $0°$ C. and stirred an additional 45 min. 1 N HCl was added and the resulting mixture extracted with EtOAc. The organic solution was washed with brine, dried over $Na_2SO_4$ then filtered and the solvent removed to yield 2.80 g oil. The crude product was purified by reverse phase preparative HPLC ($C_{18}$, MeOH/$H_2O$ (0.1% TFA)-gradient) to yield 382 mg (14% yield) oil. LC/MS (M+H) calcd for $C_{13}H_{15}NO_4Cl$: 284.06; found 284.01. $^1H$ NMR shows a mixture of rotamers at room temperature. $^1H$ NMR (500 MHz, $CDCl_3$) δ: 3.06 (s), 3.07 (s), 3.85 (s), 3.91 (s), 4.68 (s), 4.81 (s), 6.19 (s), 6.34 (s), 7.07–7.44 (overlapping m, 4).

Compound 10

3-[(2-Chloro-benzyl)-methyl-carbamoyl]-2-hydroxy-acrylic acid

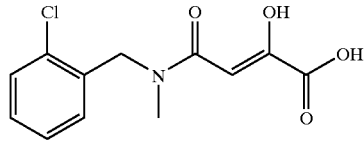

Compound 10 was prepared from Intermediate 10B using Method X. More specifically, to a solution of Intermediate 10B (95 mg, 0.33 mmol) dissolved in 0.4 ml of MeOH was added 0.4 ml of 1N NaOH. After stirring for 1 h, 0.4 ml of 1N HCL was added and the resulting mixture extracted with EtOAc. The organic layer was washed with brine, dried over $Na_2SO_4$ then filtered and the solvent removed to yield 100 mg oil. The crude product was purified by reverse phase preparative HPLC ($C_{18}$, MeOH/$H_2O$ (0.1% TFA)) to yield 47 mg (52% yield) solid. mp=84–86° C. LC/MS (M+H) calcd for $C_{12}H_{13}ClNO_4$: 270.05; found: 269.96. HRMS (M+H) calcd for $C_{12}H_{13}ClNO_4$: 270.0533; found: 270.0534. $^1H$ NMR and $^{13}C$ NMR show a mixture of rotamers at room temperature. $^1H$ NMR (500 MHz, $CDCl_3$) δ: 3.08 (s), 4.69 (s), 4.82 (s), 6.27 (s), 6.41 (s), 7.06–7.45 (overlapping m, 4). $^{13}C$ NMR (125 MHz, $CDCl_3$) δ: 34.00, 35.36, 48.34, 51.18, 93.44, 127.20, 127.33, 127.48, 128.97, 129.10, 129.35, 129.83, 130.08, 132.70, 133.02, 133.33, 133.62, 159.11, 159.22, 164.65, 164.73, 171.21, 171.60.

EXAMPLE 11

Intermediate 11A

N,N-bis-(4-fluoro-benzyl)-acetamide

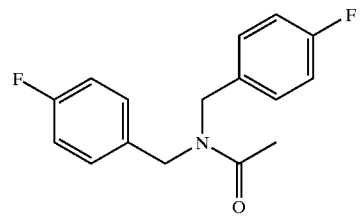

To 4-flourobenzylamine (1.17 g, 9.4 mmol) dissolved in 5 mL of THF was added 4-fluorobenzyl-bromide (0.88 g, 4.7 mmol) dropwise. The reaction was stirred overnight resulting in the formation of a white solid. After filtering off the solid solvent was removed to yield 1.08 g crude di-(4-fluorobenzyl) amine. To this was added 19 mL of $CH_2Cl_2$ and 19 mL of saturated (aq.) $NaHCO_3$. Acetyl chloride (0.67 mL, 9.4 mmol) was added to the rapidly stirring mixture and the reaction allowed to proceed overnight. The mixture was diluted with $CH_2Cl_2$, transferred to a separatory funnel. The organic layer was separated, washed with satd (aq.) NaCl, dried over $Na_2SO_4$ and the solvent removed to yield 1.01 g oil. The product was purified by column chromatography (4×7 cm $SiO_2$, 20–40% EtOAc/Hexanes) to yield 603 mg (55% yield) oil. LC/MS (M+H) calcd for $C_{14}H_{14}NF_2$: 276.12, found: 276.13. HRMS (M+H) calcd for $C_{14}H_{14}NF_2$: 276.1200, found: 276.1192. Anal calcd for $C_{16}H_{15}F_2NO$: C, 69.80; H, 5.49; N, 5.08; found: C, 59.53; H, 5.41; N, 5.06. $^1H$ NMR (500 MHz, DMSO) δ: 2.10 (s, 3), 4.45 (s, 2), 4.49 (s, 2), 7.18–7.27 (m, 8). $^{13}C$ NMR (125 MHz, DMSO) δ; 21.34, 47.04, 50.04, 114.90, 115.07, 115.27, 115.45, 128.51, 128.58, 129.57, 129.64, 133.32, 133.34, 133.86, 133.89, 160.25, 160.33, 162.17, 162.27, 170.22.

Intermediate 11B

3-[Bis-(4-fluoro-benzyl)-carbamoyl]-2-hydroxy-acrylic acid methyl ester

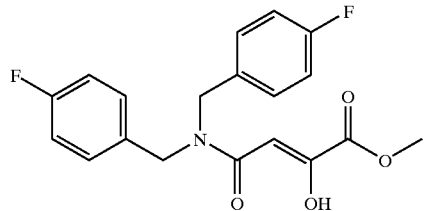

Intermediate 11B was prepared from Intermediate 11A by the same method that Intermediate 10B was prepared from Intermediate 10A. Solid, mp=117–118° C. LC/MS (M+H) calcd for $C_{19}H_{18}F_2NO_4$: 362.11, found: 362.03. HRMS (M+H) calcd for $C_{19}H_{18}F_2NO_4$: 362.1204, found: 362.1187. Anal. calcd for $C_{19}H_{17}NO_4F_2$: C, 63.15; H, 4.74; N, 3.87. found: C, 62.97; H, 4.72; N, 3.81. $^1H$ NMR (500 MHz, $CDCl_3$) δ: 3.87 (s, 3), 4.46 (s, 2), 4.58 (s, 2), 6.32 (s, 1), 7.00–7.26 (m, 8). $^{13}C$ NMR (125 MHz, $CDCl_3$) δ: 47.34, 49.35, 53.03, 93.34, 115.56, 115.83, 116.00, 116.18, 128.45, 128.52, 130.03, 130.10, 131.09, 131.93, 131.96, 160.29, 161.44, 161.51, 163.10, 163.41, 163.47, 171.36.

Compound 11

3-[Bis-(4-fluoro-benzyl)-carbamoyl]-2-hydroxy-acrylic acid

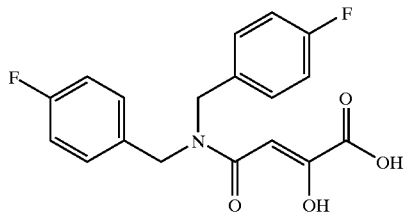

Compound 11 was prepared from Intermediate 11B by Method XI. Solid mp>147° C. (decomposition). LC/MS (M+H) calcd for $C_{18}H_{16}F_2NO_4$: 348.10, found 347.98. HRMS (M−H) calcd for $C_{18}H_{14}F_2NO_4$: 346.089, found 346.088. $^1$H NMR (500 MHz, DMSO) δ: 4.61 (s, 2), 4.67 (s, 2), 6.25 (s, 1), 7.12–7.35 (overlapping m). $^{13}$C NMR (125 MHz, DMSO) δ: 47.94, 49.49, 93.27, 115.11, 115.28, 115.38, 115.55, 128.46, 128.52, 129.88, 129.94, 132.76, 132.78, 132.93, 132.96, 10.35, 163.27, 171.25.

EXAMPLE 12

Intermediate 12A: N-(2-bromo-benzyl)-N-methyl-acetamide

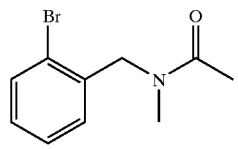

Intermediate 12A was prepared from ortho-bromobenzyl bromide by Method V. Anal calcd for $C_{10}H_{12}BrNO$: C, 49.60; H, 4.99; N, 5.78; Br, 33.00; found: C, 49.40; H, 4.95; N, 5.75; Br, 32.98. LC/MS (M+H) calcd for $C_{10}H_{13}BrNO$: 242.02; found: 243.96. $^1$H NMR shows a mixture of rotamers at room temperature. $^1$H NMR (500 MHz, CDCl$_3$) δ: 2.09 (s), 2.19 (s), 2.98 (s), 2.99 (s), 4.55 (s), 4.71 (s), 7.08–7.60 (overlapping m, 4). $^1$H NMR (300 MHz, DMSO, T=393 K) δ: 2.06 (s, 3), 2.92 (s, 3), 4.58 (s, 2), 7.21 (m, 2), 7.37 (m, 1), 7.60 (d, 1, J=8).

Intermediate 12B

3-[(2-Bromo-benzyl)-methyl-carbamoyl]-2-hydroxy-acrylic acid methyl ester

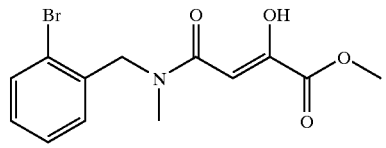

Intermediate 12B was prepared from Intermediate 12A using Method IX. $^1$H NMR shows a mixture of rotamers at room temperature. $^1$H NMR (500 MHz, CDCl$_3$) δ: 3.06 (s), 3.07 (s), 3.85 (s), 3.91 (s), 4.65 (s), 4.79 (s), 7.17–7.35 (overlapping m, 4).

Compound 12

3-[(2-Bromo-benzyl)-methyl-carbamoyl]-2-hydroxy-acrylic acid

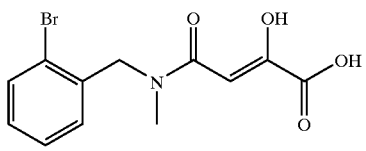

Compound 12 was prepared from Intermediate 12B using Method X. HRMS (M+H) calcd for $C_{12}H_{13}BrNO_4$: 314.0028; found: 314.0023. $^1$H NMR and $^{13}$C NMR show a mixture of rotamers at room temperature. $^1$H NMR (500 MHz, CDCl$_3$) δ: 3.08 (s, 3), 4.66 (s), 4.80 (s), 6.25 (s), 6.42 (s), 7.04–7.63 (overlapping m, 4). $^{13}$C NMR (125 MHz, CDCl$_3$) δ: 34.09, 35.37, 50.85, 53.70, 93.21, 122.84, 123.59, 127.17, 127.97, 128.11, 128.77, 129.38, 129.63, 133.17, 133.40, 134.13, 134.82, 159.00, 159.14, 171.22, 171.64.

EXAMPLE 13

Intermediate 13A

N-benzyl-N-phenethyl-acetamide

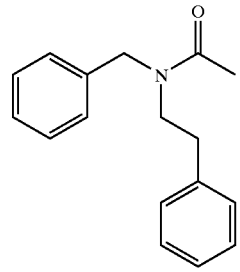

N-benzyl-2-phenethylamine (2.2 g, 10 mmol) was dissolved in 7 mL of CH$_2$Cl$_2$. To this was added 7 mL of satd (aq.) NaHCO$_3$ followed by acetyl chloride (0.88 g, 11 mmol) and the resulting mixture stirred for 40 min. The organic layer was separated, dried over Na$_2$SO$_4$ filtered and the solvent removed to yield 2.60 g (100%) oil. LC/MS (M+H) calcd for $C_{17}H_{20}NO$: 254.15; found: 254.07. $^1$H NMR and $^{13}$C NMR show a mixture of rotamers at room temperature. $^1$H NMR (500 MHz, CDCl$_3$), δ: 2.04 (br s), 2.14 (br s), 2.81 (br m), 2.87 (br m), 3.44 (br m), 3.58 (br m), 4.36 (s), 4.62 (s), 7.11–7.36 (overlapping m, 10). $^{13}$C NMR (125 MHz, CDCl$_3$) δ: 21.19, 21.80, 33.99, 34.87, 48.18, 48.28, 49.49, 52.75, 126.34, 126.81, 127.44, 127.65, 128.18, 128.52, 128.64, 128.73, 128.80, 128.85, 128.94, 136.74, 137.56, 138.17, 139.24, 170.81, 171.07.

Intermediate 13B 3-(Benzyl-phenethyl-carbamoyl)-2-hydroxy-acrylic acid methyl ester

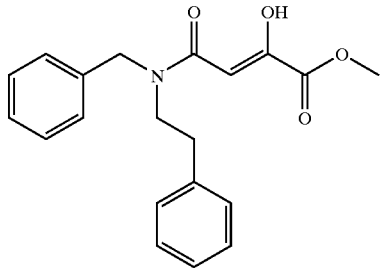

Intermediate 13B was prepared from Intermediate 13A using Method IX. LC/MS (M+H) calcd for $C_{20}H_{22}NO_4$: 340.03; found: 340.15. $^1$H NMR and $^{13}$C NMR show a mixture of rotamers at room temperature. $^1$H NMR (500 MHz, CDCl$_3$) δ: 2.84 (t, J=7), 2.90 (t, J=7), 3.52 (t, J=7), 3.63 (t, J=7), 3.86 (s), 3.90 (s), 4.41(s), 4.56 (s), 6.22 (s), 6.26 (s), 7.13–7.37 (overlapping m, 10). $^{13}$C NMR (125 MHz, CDCl$_3$) δ: 33.94, 35.38, 48.40, 48.94, 51.84, 52.97, 93.72, 126.62, 126.65, 126.97, 127.81, 128.02, 128.05, 128.67, 128.77, 128.83, 128.90, 129.03, 135.84, 136.56, 137.64, 138.64, 159.52, 159.80, 163.31, 170.88, 171.28.

Compound 13

3-(Benzyl-phenethyl-carbamoyl)-2-hydroxy-acrylic acid

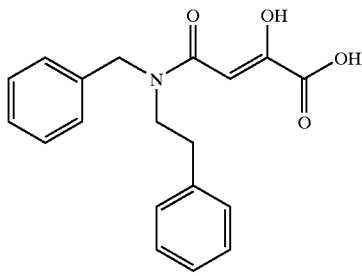

Compound 13 was prepared from Intermediate 13B using Method X. LC/MS (M+H) calcd for $C_{19}H_{20}NO_4$: 326.14; found: 326.01. HRMS (M−H) calcd for $C_{19}H_{18}NO_4$: 324.1236; found: 324.1234. $^1$H NMR and $^{13}$C NMR show a mixture of rotamers at room temperature. $^1$H NMR (500 MHz, CDCl$_3$) δ: 2.85 (t, J=7), 2.90 (t, J=7), 3.54 (t, J=7), 3.65 (t, J=7), 4.41 (s), 4.56 (s), 6.26 (s), 6.33 (s), 7.11–7.40 (overlapping m, 10). $^{13}$C NMR (125 MHz, CDCl$_3$) δ: 33.91, 35.30, 48.59, 49.05, 49.10, 51.97, 93.76, 93.86, 126.69, 128.09, 128.28, 128.72, 128.78, 128.80, 128.88, 128.97, 129.09, 135.55, 136.29, 137.45, 138.49, 158.84, 159.27, 165.08, 165.15, 170.85, 171.26.

EXAMPLE 14

Intermediate 14A

N,N-dibenzyl-acetamide

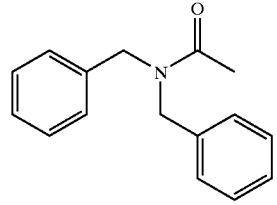

Intermediate 14A was prepared from dibenzylamine by the same method as Intermediate 12A. LC/MS (M+H) calcd for $C_{16}H_{18}NO$: 240.14; found: 240.03. $^1$H NMR (500 MHz, CDCl$_3$) δ: 3.23 (s, 3), 4.47 (s, 2), 4.61 (s, 2), 7.16–7.39 (overlapping m, 10). $^{13}$C NMR (125 MHz, CDCl$_3$) δ: 21.70, 48.02, 50.78, 126.42, 127.46, 127.68, 128.34, 128.63, 129.01, 136.41, 137.31, 171.22.

Intermediate 14B

3-Dibenzylcarbamoyl-2-hydroxy-acrylic acid methyl ester

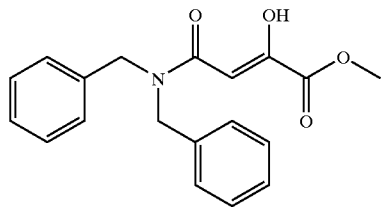

Intermediate 14B was prepared from Intermediate 14A using Method IX. LC/MS (M+H) calcd for $C_{19}H_{20}NO_4$: 326.14; found: 326.01. $^1$H NMR (500 MHz, CDCl$_3$) δ: 3.87 (s, 3), 4.51 (s, 2), 4.64 (s, 2), 6.36 (s, 1), 7.17–7.40 (overlapping m, 10). $^{13}$C NMR (125 MHz, CDCl$_3$) δ: 48.02, 49.95, 53.00, 93.62, 126.78, 127.85, 128.08, 128.13, 128.25, 128.77, 128.85, 129.00, 129.10, 135.50, 136.24, 160.05, 163.22, 171.43.

Compound 14

3-Dibenzylcarbamoyl-2-hydroxy-acrylic acid

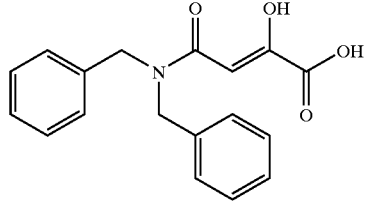

Compound 14 was prepared from Intermediate 14B using Method X. LC/MS (M+H) calcd for $C_{18}H_{18}NO_4$: 312.12; found: 312.07. HRMS (M−H) calcd for $C_{18}H_{16}NO_4$: 310.1079; found: 310.1075. $^1$H NMR (500 MHz, CDCl$_3$) δ: 4.52 (s, 2), 4.66 (s, 2), 6.43 (s, 1), 7.16–7.43 (overlapping m, 10). $^{13}$C NMR (125 MHz, CDCl$_3$) δ: 48.30, 50.07, 93.24, 126.77, 127.98, 128.20, 128.27, 128.90, 129.15, 135.12, 135.90, 159.35, 164.50, 171.43.

EXAMPLE 15

Intermediate 15A

N-(5-Chloro-benzo[b]thiophen-3-ylmethyl)-N-methyl-acetamide

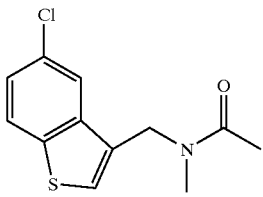

Intermediate 15A was prepared from 3-(bromomethyl)-5-chlorobenzothiophene by Method V. LC/MS (M+H) calcd for $C_{12}H_{13}NOClS$: 254.04; found: 253.92. $^1$H NMR and $^{13}$C NMR show a mixture of rotamers at room temperature. $^1$H NMR (500 MHz, CDCl$_3$) δ: 2.17 (s, 3), 2.93 (s), 3.05 (s), 4.70 (s), 4.79 (s), 7.22–7.88 (overlapping m, 5). $^{13}$C NMR (125 MHz, CDCl$_3$) δ: 1.26, 21.92, 34.17, 35.27, 44.22, 49.43, 120.77, 122.04, 123.76, 124.18, 125.16, 125.42, 126.79, 131.85, 138.66, 139.30, 170.78.

Intermediate 15B

3-[(5-Chloro-benzo[b]thiophen-3-ylmethyl)-methyl-carbamoyl]-2-hydroxy-acrylic acid methyl ester

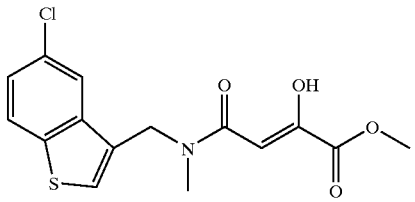

Intermediate 15B was prepared from Intermediate 15A using Method IX. LC/MS (M+H) calcd for $C_{15}H_{15}NO_4ClS$: 340.04; found: 339.89. HRMS (M+H) calcd for $C_{15}H_{15}NO_4ClS$: 340.0410; found: 340.0410. $^1$H NMR shows a mixture of rotamers at room temperature. $^1$H NMR (500 MHz, CDCl$_3$) δ: 3.03 (s), 3.13 (s), 3.85 (s), 3.90, 4.77 (s), 4.87 (s), 6.28 (s), 6.30 (s), 7.23–7.86 (overlapping m, 4).

Compound 15

3-[(5-Chloro-benzo[b]thiophen-3-ylmethyl)-methyl-carbamoyl]-2-hydroxy-acrylic acid

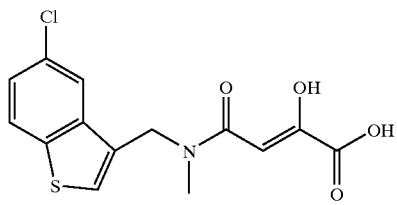

Compound 15 was prepared from Intermediate 15B using Method X. LC/MS (M+H) calcd for $C_{14}H_{13}NO_4ClS$: 326.03; found: 326.08. HRMS (M−H) calcd for $C_{14}H_{11}NO_4ClS$: 324.0097; found: 324.0104. $^1$H NMR and $^{13}$C NMR show a mixture of rotamers at room temperature. $^1$H NMR (500 MHz, DMSO) δ: 3.05 (s), 4.85 (s), 4.97 (s), 6.27 (s), 6.30 (s), 7.41–8.07 (overlapping m). $^{13}$C NMR (125 MHz, CDCl$_3$) δ: 33.68, 34.46, 43.62, 47.54, 93.00, 93.32, 121.33, 121.38, 121.61, 124.55, 124.64, 124.71, 125.55, 128.15, 129.41, 129.52, 130.79, 131.21, 138.37, 138.45, 138.99, 139.05, 160.02, 160.12, 163.38, 163.45, 170.50, 171.05.

EXAMPLE 16

Intermediate 16A

N-(4-fluoro-benzyl)-N-methyl-acetamide

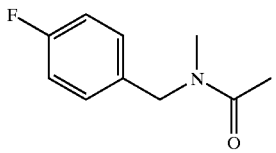

Intermediate 16A was prepared from 4-fluorobenzyl bromide by Method IV. LC/MS (M+H) calcd for $C_{10}H_{13}FNO$: 182.09; found: 182.10. HRMS (M+H) calcd for $C_{10}H_{14}NFNO$; 182.0891; found: 182.0979. $^1$H NMR (500 MHz, DMSO) δ: 2.04 (s), 2.05 (s), 2.77 (s), 2.90 (s), 4.46 (s), 4.53 (s), 7.13–7.28 (m, 4). $^{13}$C NMR (125 MHz, DMSO) δ: 21.16, 21.47, 32.85, 35.24, 48.81, 52.40, 114.97, 115.14, 115.30, 115.47, 128.52, 128.59, 129.38, 129.44, 133.58, 133.60, 134.01, 134.03, 160.23, 160.33, 162.16, 162.26, 169.70, 169.84.

Intermediate 16B

3-[(4-Fluoro-benzyl)-methyl-carbamoyl]-2-hydroxy-acrylic acid methyl ester

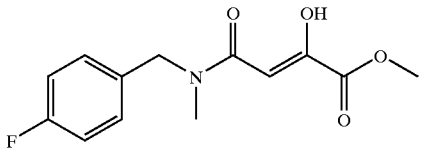

Intermediate 16B was prepared from Intermediate 16A using Method IX. HRMS (M+H) calcd for $C_{13}H_{15}NO_4F$: 268.0985; found: 268.0983. Anal calcd for $C_{13}H_{14}NO_4F$: C, 58.42; H, 5.28; N, 5.24. found: C, 58.48; H, 5.21; N, 5.26. $^1$H NMR and $^{13}$C NMR show a mixture of rotamers at room temperature. LC/MS (M+H) calcd for $C_{13}H_{15}FNO_4$: 268.09, found: 268.15. $^1$H NMR (500 MHz, CDCl$_3$) δ: 3.00 (s, 3), 3.86 (s), 3.89 (s), 4.55 (s), 4.61 (s), 6.29 (s) 6.31, 7.00–7.24 (overlapping m, 4). $^{13}$C NMR δ: 33.43, 34.79, 49.97, 52.63, 52.97, 93.27, 93.55, 115.63, 115.80, 115.95, 116.13, 128.36, 128.42, 129.71, 129.78, 131.32, 132.03, 159.70, 161.40, 163.25, 163.35, 170.93, 171.16.

Compound 16

3-[(4-Fluoro-benzyl)-methyl-carbamoyl]-2-hydroxy-acrylic acid

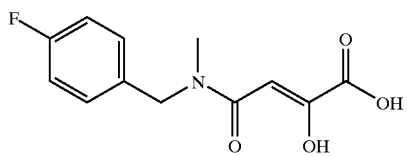

Compound 16 was prepared from Intermediate 16B using Method XI. HRMS (M−H) calcd for $C_{12}H_{11}NO_4F$: 252.0672; found: 252.0666. Anal calcd for $C_{12}H_{12}NO_4F$: C, 56.91; H, 4.77; N, 5.53. found: C, 57.22; H, 4.78; N, 5.56. LC/MS (M+H) calcd for $C_{12}H_{13}FNO_4$: 254.08, found: 254.05. $^1$H NMR shows a mixture of rotamers at room temperature. $^1$H NMR (500 MHz, CDCl$_3$) δ 3.02 (s, 3), 4.57 (s), 4.63 (s), 6.36 (s), 6.39, 7.02–7.26 (overlapping m, 4).

EXAMPLE 17

Intermediate 17A: N-benzyl-N-methyl-acetamide

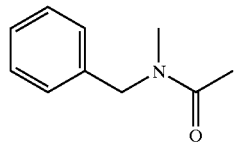

Intermediate 17A was prepared from N-methyl-benzylamine using Method IV. $^1$H NMR and $^{13}$C NMR show a mixture of rotamers at room temperature. $^1$H NMR (500 MHz, CDCl$_3$) δ: 2.20 (s), 2.95 (s), 2.97 (s), 4.56 (s), 4.62 (s), 7.19–7.41 (overlapping m). $^{13}$C NMR (125 MHz, CDCl$_3$) δ: 21.42, 21.80, 33.82, 35.58, 50.68, 54.29, 126.33, 127.41, 127.70, 128.07, 128.63, 128.99, 136.46, 137.26, 170.88, 171.19.

Intermediate 17B 3-(Benzyl-methyl-carbamoyl)-2-hydroxy-acrylic acid methyl ester

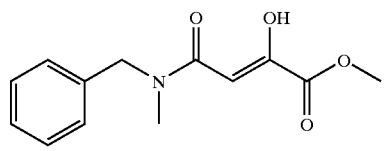

Intermediate 17B was prepared from Intermediate 17A using Method IX. $^1$H NMR shows a mixture of rotamers at room temperature. $^1$H NMR (500 MHz, CDCl$_3$) δ: 3.02 (s), 3.86 (s), 3.90 (s), 4.60 (s), 4.66 (s), 6.31 (s), 6.34 (s), 7.18–7.40 (overlapping m).

Compound 17

3-(Benzyl-methyl-carbamoyl)-2-hydroxy-acrylic acid

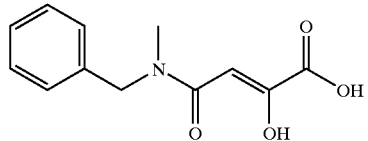

Compound 17 was prepared from Intermediate 17B using Method X. HRMS (M−H) calcd for $C_{12}H_{12}NO_4$: 234.0766; found: 234.0765. $^1$H NMR shows a mixture of rotamers at room temperature. $^1$H NMR (500 MHz, CDCl$_3$) δ: 3.02 (s), 3.04 (s), 4.59 (s), 4.67 (s), 6.36 (s), 6.40 (s), 7.17–7.39 (overlapping m).

EXAMPLE 18

Intermediate 18A

N-(2-Chloro-benzyl)-N-[2-(4-fluoro-phenyl)-ethyl]-acetamide

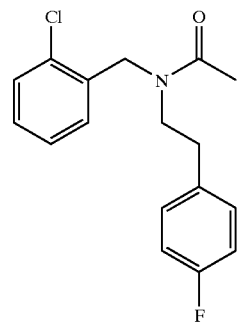

Intermediate 18A was prepared from 2(-4-fluorophenyl)-ethylamine and 2-chlorobenzylbromide using Method VI. LC/MS (M+H) calcd for $C_{17}H_{18}ClFNO$: 306.10; found: 306.00. $^1$H NMR shows a mixture of rotamers at room temperature. $^1$H NMR (500 MHz, CDCl$_3$) δ: 2.05(s), 2.10 (s), 2.84(m), 3.44(m), 3.55(m), 4.46(s), 4.77(s), 6.99(m), 7.13(m), 7.22(m), 7.38(m).

Intermediate 18B

3-{2-Chloro-benzyl)-[2-(4-fluoro-phenyl)-ethyl]-carbamoyl}-2-hydroxy-acrylic acid methyl ester

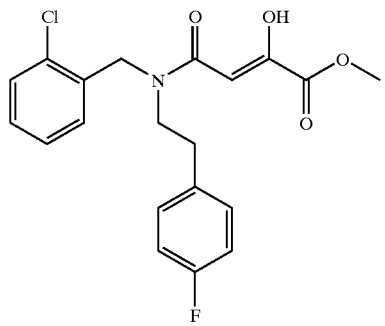

Intermediate 18B was prepared from Intermediate 18A using Method IX. HRMS (M+H) calcd for $C_{20}H_{20}NO_4ClF$:

392.1065; found: 392.1053. Anal calcd for C₂₀H₁₉NO₄ClF: C, 61.30; H, 4.88; N, 3.57. found: C, 61.33; H, 4.86; N, 3.50. ¹H NMR and ¹³C NMR show a mixture of rotamers at room temperature. ¹H NMR (500 MHz, CDCl₃) δ: 2.87(m), 3.53(m), 3.60(m), 3.85(s), 3.91(s), 4.53(s), 4.74(s), 6.14(s), 6.20(s), 6.97–7.42(overlapping m). ¹³C NMR (125 MHz, CDCl₃) δ: 33.12, 34.62, 46.17, 48.55, 49.36, 49.52, 52.98, 53.01, 93.43, 115.41, 115.58, 115.68, 115.85, 127.36, 127.41, 127.44, 129.10, 129.26, 129.39, 129.73, 129.98, 130.21, 130.27, 130.33, 132.96, 133.19, 133.59, 133.98, 159.71, 160.04, 160.77, 160.95, 162.72, 162.91, 163.20, 171.08, 171.64.

Compound 18

3-{(2-Chloro-benzyl)-[2-(4-fluoro-phenyl)-ethyl]-carbamoyl}-2-hydroxy-acrylic acid

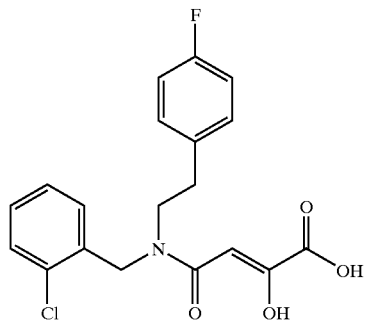

Compound 18 was prepared from Intermediate 18B using Method X. HRMS (M–H) calcd for C₁₉H₁₆NO₄ClF: 376.0752; found: 376.0761. ¹H NMR and ¹³C NMR show a mixture of rotamers at room temperature. ¹H NMR (500 MHz, CDCl₃) δ: 2.87(m), 3.53(dd, J=7, 7), 3.62(dd, J=7, 9), 4.55(s), 4.75(s), 6.23(s), 6.27(s), 6.97–7.43 (overlapping m). ¹³C NMR (125 MHz, CDCl₃) δ: 33.07, 34.53, 46.32, 48.67, 49.40, 49.61, 93.27, 115.46, 115.63, 115.75, 115.92, 127.40, 127.44, 129.25, 129.42, 129.45, 129.80, 130.08, 130.20, 130.27, 130.29, 130.35, 132.82, 133.02, 133.64, 133.67, 158.90, 159.30, 160.80, 160.99, 162.75, 162.95, 171.06, 171.61.

EXAMPLE 19

Intermediate 19A

N-(2-Chlorobenzyl)-N-(4-fluorobenzyl)-acetamide

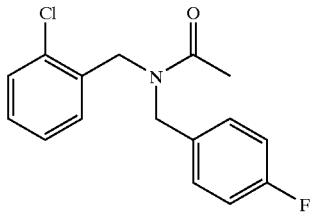

Intermediate 19A was prepared from 2-chlorobenzylamine and 4-fluorobenzylbromide using Method VI. LCMS (M+H) calcd for C₁₆H₁₆FNO: 292.08; found: 292.01. ¹H NMR and ¹³C NMR show a mixture of rotamers at room temperature. ¹H NMR (500 MHz, CDCl₃) δ: 2.15(s), 2.24(s), 4.47(s), 4.51(s), 4.56(s), 4.73(s), 6.97–7.40 (overlapping m, 8). ¹³C NMR (125 MHz, CDCl₃) δ: 21.52, 21.62, 45.86, 48.04, 49.09, 50.93, 115.40, 115.57, 115.82, 115.99, 126.92, 127.10, 127.33, 127.97, 128.04, 128.70, 128.93, 129.50, 129.58, 129.98, 130.02, 130.09, 131.99, 132.02, 132.91, 132.93, 132.99, 133.65, 133.67, 134.54, 161.30, 163.25, 171.29, 171.52.

Intermediate 19B

3-[(2-Chloro-benzyl)-(4-fluoro-benzyl)-carbamoyl]-2-hydroxy-acrylic acid methyl ester

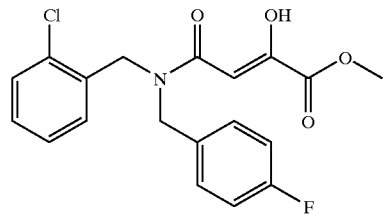

Intermediate 19B was prepared from Intermediate 19A using Method IX. HRMS (M+H) calcd for C₁₉H₁₈ClFNO₄: 378.0908; found: 378.0908. ¹H NMR and ¹³C NMR show a mixture of rotamers at room temperature. ¹H NMR (500 MHz, CDCl₃) δ: 3.85(s), 3.88(s), 4.53(s), 4.60(s), 4.61(s), 4.78(s), 6.19(s), 6.37(s), 7.00–7.42 (overlapping m). ¹³C NMR (125 MHz, CDCl₃) δ: 45.88, 48.06, 48.08, 50.07, 53.00, 53.04, 53.45, 93.29, 93.36, 115.63, 115.80, 115.92, 116.10, 127.29, 127.41, 128.42, 128.48, 129.09, 129.24, 129.26, 129.77, 130.03, 130.07, 130.14, 131.16, 131.92, 132.81, 133.05, 133.58, 133.66, 160.29, 160.31, 161.47, 163.05, 163.11, 163.43, 171.62, 171.80.

Compound 19

3-[(2-Chloro-benzyl)-(4-fluoro-benzyl)-carbamoyl]-2-hydroxy-acrylic acid

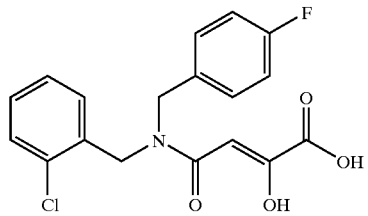

Compound 19 was prepared from Intermediate 19B using Method X. HRMS (M–H) calcd for C₁₈H₁₄NO₄ClF: 362.0595; found: 362.0604. ¹H NMR and ¹³C NMR show a mixture of rotamers at room temperature. ¹H NMR (500 MHz, CDCl₃) δ: 4.54(s), 4.60(s), 4.62(s), 4.79(s), 6.27(s), 6.44(s), 7.01–7.42 (overlapping m). ¹³C NMR (125 MHz, CDCl₃) δ: 46.09, 48.17, 48.27, 50.15, 93.43, 93.56, 115.70, 115.87, 116.00, 116.17, 127.26, 127.32, 127.44, 128.42, 128.49, 129.23, 129.30, 129.40, 129.83, 130.11, 130.18, 130.86, 130.88, 131.61, 131.63, 132.48, 133.08, 133.29, 133.69, 159.29, 159.35, 161.53, 164.31, 171.55, 171.71.

EXAMPLE 20

Intermediate 20A

N-(5-Chloro-benzo[b]thiophen-3-ylmethyl)-N-[2-(4-fluoro-phenyl)-ethyl]-acetamide

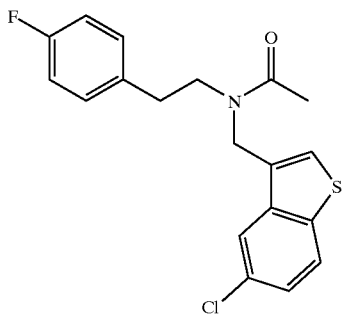

Intermediate 20A was prepared from 2-(4-fluoro-phenyl)-ethylamine and 3-bromomethyl-5-chloro-benzo{b}thiophene using Method VI. HRMS (M+H) calcd for $C_{19}H_{18}NOClFS$: 362.0782; found: 362.0776. $^1$H NMR and $^{13}$C NMR show a mixture of rotamers at room temperature. $^1$H NMR (500 MHz, CDCl$_3$) δ: 2.05 (s), 2.16 (s), 2.73 (t, J=8), 2.87 (t, J=8), 3.42 (t, J=8), 3.63 (t, J=8), 4.52 (s), 4.79 (s), 6.96–7.82 (overlapping m). $^{13}$C NMR (125 MHz, CDCl$_3$) δ: 21.37, 21.68, 33.40, 34.23, 41.90, 47.94, 48.48, 49.26, 115.31, 115.47, 115.65, 115.82, 120.74, 121.88, 123.86, 124.19, 124.42, 125.22, 125.45, 126.84, 130.14, 130.20, 130.22, 130.28, 130.90, 130.96, 131.22, 132.01, 133.68, 133.71, 134.58, 134.60, 138.27, 138.64, 139.18, 139.31, 160.85, 162.80, 170.58, 170.94.

Intermediate 20B

3-{(5-Chloro-benzo[b]thiophen-3-ylmethyl)-[2-(4-fluoro-phenyl)-ethyl]-carbamoyl}-2-hydroxy-acrylic acid methyl ester

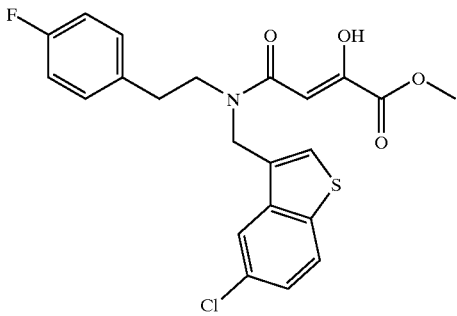

Intermediate 20B was prepared from Intermediate 20A using Method IX. HRMS (M+H) calcd for $C_{22}H_{19}NO_4SFCl$: 448.0786; found: 448.0777. Anal calcd for $C_{22}H_{18}NO_4SFCl$: C, 58.99; H, 4.27; N, 3.12. found: C, 59.36; H, 4.22; N, 3.08. $^1$H NMR and $^{13}$C NMR show a Mixture of rotamers at room temperature. $^1$H NMR (500 MHz, CDCl$_3$) δ: 2.75(t, J=7), 2.90(dd, J=8, 8), 3.51(t, J=7), 3.68(dd, J=8, 8), 3.84(s), 3.91(s), 4.57(s), 4.75(s), 6.18(s), 6.21(s), 6.97–7.80 (overlapping m). $^{13}$C NMR (125 MHz, CDCl$_3$) δ: 33.34, 34.68, 42.60, 46.91, 48.65, 53.01, 53.04, 93.33, 93.64, 115.48, 115.65, 115.69, 115.75, 115.86, 115.92, 120.76, 121.67, 123.97, 124.22, 125.40, 125.56, 127.35, 130.21, 130.28, 130.91, 131.04, 131.12, 133.19, 134.03, 138.16, 138.65, 139.03, 139.11, 159.82, 160.18, 160.96, 162.92, 163.09, 163.18, 170.83, 171.40.

Compound 20

3-{(5-Chloro-benzo[b]thiophen-3-ylmethyl)-[2-(4-fluoro-phenyl)-ethyl]-carbamoyl}-2-hydroxy-acrylic acid

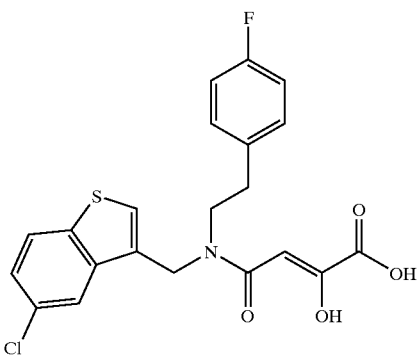

Compound 20 was prepared from Intermediate 20B using Method X. HRMS (M−H) calcd $C_{21}H_{16}NO_4SClF$: 432.0473; found: 432,0485. $^1$H NMR shows a mixture of rotamers at room temperature. $^1$H NMR (500 MHz, CDCl$_3$) δ: 2.75(t, J=7), 2.90(dd, J 7, 7), 3.52(t, J=7), 3.69(dd, J=7), 4.59(s), 4.76(s), 6.26(s), 6.30(s), 6.98–7.81(overlapping m).

EXAMPLE 21

Intermediate 21A

N-(2-Chloro-benzyl)-N-[2-(4-fluoro-phenyl)-ethyl]-acetamide

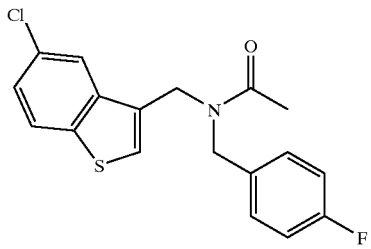

Intermediate 21A was prepared from 4-fluorobenzylamine and 5-chloro-3-bromomethyl-benzo[b]thiophene using Method VI. HRMS (M+H) calcd $C_{18}H_{16}ClFNOS$: 348.0652; found: 348.0619. $^1$H NMR and $^{13}$C NMR show a mixture of rotamers at room temperature. $^1$H NMR (500 MHz, CDCl$_3$) δ: 2.24(s), 4.41(s), 4.59(s), 4.65(s), 4.79(s), 6.98–7.33(overlapping m), 7.54(m), 7.74–7.82(overlapping m). $^{13}$C NMR (125 MHz, CDCl$_3$) δ: 21.56, 21.81, 41.35, 46.25, 47.94, 49.95, 115.47, 115.64, 115.93, 116.10, 120.79, 122.00, 123.77, 124.16, 124.37, 125.18, 125.45, 127.30, 127.95, 128.02, 129.98, 130.04, 130.77, 130.92, 131.58, 131.74, 131.77, 133.06, 138.33, 138.60, 139.20, 139.35, 161.32, 163.28, 170.93, 171.15.

Intermediate 21B

3-[(5-Chloro-benzo[b]thiophen-3-ylmethyl)-(4-fluoro-benzyl)-carbamoyl]-2-hydroxy-acrylic acid methyl ester

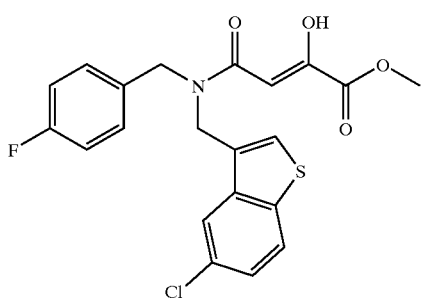

Intermediate 21B was prepared from Intermediate 21A using Method IX. HRMS (M+H) calcd for $C_{21}H_{18}NO_4SFCl$: 434.0629; found: 434.0626. Anal. calcd for $C_{21}H_{17}NO_4SFCl$: C, 58.13; H, 3.94; N, 3.22. found: C, 58.42; H, 3.95; N, 3.02. $^1H$ NMR and $^{13}C$ NMR show a mixture of rotamers at room temperature. $^1H$ NMR (500 MHz, CDCl$_3$) δ:3.85(s), 3.88(s), 4.49(s), 4.66(s), 4.69(s), 4.84(s), 6.28(s), 6.34(s), 7.01–7.81(overlapping m). $^{13}C$ NMR (125 MHz, CDCl$_3$) δ: 41.50, 45.21, 47.98, 49.17, 53.04, 53.06, 93.25, 93.40, 115.73, 115.90, 116.01, 116.18, 120.81, 121.76, 123.88, 124.19, 125.35, 125.56, 127.74, 128.35, 128.42, 129.79, 129.99, 130.05, 130.43, 130.93, 130.96, 131.03, 131.07, 131.98, 138.22, 138.62, 139.09, 139.12, 160.42, 160.45, 161.50, 162.99, 163.07, 163.46, 171.31, 171.53.

Compound 21

3-[(5-Chloro-benzo[b]thiophen-3-ylmethyl)]-(4-fluoro-benzyl)-carbamoyl]-2-hydroxy-acrylic acid

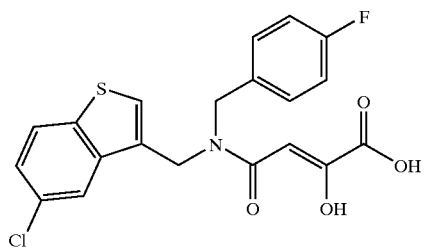

Compound 21 was prepared from Compound 21B using Method X. HRMS (M–H) calcd for $C_{20}H_{14}NO_4SClF$: 418.0316; found: 418.0323. $^1H$ NMR shows a mixture of rotamers at room temperature. $^1H$ NMR (500 MHz, CDCl$_3$) δ: 4.50(s), 4.67(s), 4.74(s), 4.85(s), 6.36(s), 6.41(s), 7.01–7.83 (overlapping m).

EXAMPLE 22

Intermediate 22A

N-[2-(4-Fluoro-phenyl)-ethyl]-N-methyl-acetamide

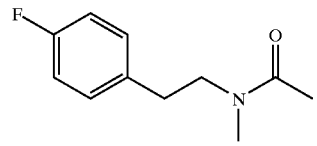

2-(4-Fluoro-phenyl)-ethylamine (1.3 g, 9.33 mmol) was dissolved in 37 mL of CH$_2$Cl$_2$. To this was added 37 mL of satd NaHCO$_3$ follwed by acetyl chloride (2.1 mL, 30.9 mmol). The resulting mixture was stirred 6 hours. The organic layer was separated, washed with satd NaCl, dried over Na$_2$SO$_4$, and the solvent removed under vacuum to yield 280 mg of N-[2-(fluoro-phenyl)-ethyl]-acetamide.

N-[2-(fluoro-phenyl)-ethyl]-acetamide (270 mg, 1.5 mmol) was dissolved in 7.5 mL of toluene to this was added 120 mg of 60% NaH (mineral oil) and MeI (0.12 mL, 1,95 mmol). The resulting mixture was stirred overnight. The solution was diluted with EtOAc, washed with satd NaCl, dried over Na$_2$SO$_4$ and the solvent removed under vacuum. The crude product was purified by flash column chromatography (SiO$_2$, CH$_2$Cl$_2$/EtOH) to yield 230 mg (79% yield) of N-[2-(4-fluoro-phenyl)-ethyl]-N-methyl-acetamide. HRMS (M+H) calcd for $C_{11}H_{15}FNO$: 196.1138; found: 196.1137. $^1H$ NMR shows a mixture of rotamers at room temperature. $^1H$ NMR (500 MHz, CDCl$_3$) δ: 1.85 (s), 2.06 (s), 2.81 (m), 2.88 (s), 2.93 (s), 3.48 (m), 3.55 (m), 6.96–7.18 (overlapping m).

Intermediate 22B

3-{[2-(4-Fluoro-phenyl)-ethyl]-methyl-carbamoyl}-2-hydroxy-acrylic acid methyl ester

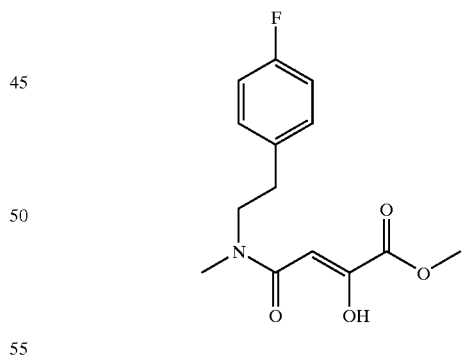

Intermediate 22B was prepared from Intermediate 22A using Method IX. HRMS (M+H) calcd for $C_{14}H_{17}NO_4F$: 282.1142; found: 282.1135. $^1H$ NMR and $^{13}C$ NMR show a mixture of rotamers at room temperature. $^1H$ NMR (500 MHz, CDCl$_3$) δ: 2.87(m), 2.95(s), 3.57(t, J=7), 3.63(dd, J=7, 7), 3.87(s), 3.88(s), 6.05(s), 6.20(s), 6.98(m), 7.15(m). $^{13}C$ NMR (125 MHz, CDCl$_3$) δ: 32.90, 34.02, 34.31, 36.18, 49.96, 51.76, 52.91, 52.94, 93.42, 93.60, 115.40, 115.57, 115.68, 115.85, 130.17, 130.24, 130.31, 133.25, 134.16, 134.19, 159.06, 159.48, 160.74, 160.95, 162.69, 162.90, 163.31, 163.37, 170.74.

Compound 22

3-{[2-(4-Fluoro-phenyl)-ethyl]-methyl-carbamoyl}-2-hydroxy-acrylic acid

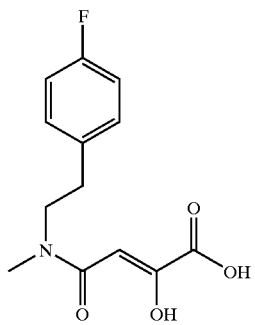

Compound 22 was prepared from Intermediate 22A using Method XI. HRMS (M−H) calcd for $C_{13}H_{13}NO_4F$: 266.0829; found: 266.0823. $^1$H NMR and $^{13}$C NMR show a mixture of rotamers at room temperature. $^1$H NMR (500 MHz, CDCl$_3$) δ: 2.89(m), 2.97(s), 2.98(s), 3.59(t, J=7), 3.65(dd, J=7, 7), 6.13(s), 6.27(s), 6.99(m), 7.14(m). $^{13}$C NMR (125 MHz, CDCl$_3$) δ: 32.86, 34.20, 36.26, 50.14, 51.88, 93.33, 115.46, 115.63, 115.75, 115.92, 130.17, 130.24, 130.33, 133.032, 133.96, 158.43, 159.11, 165.03, 170.72.

EXAMPLE 23

Intermediate 23A

N-(4-Fluoro-benzyl)-N-(1-phenyl-ethyl)-acetamide

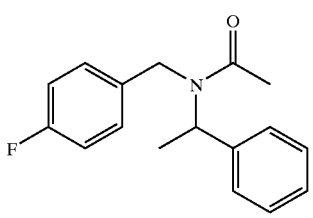

Intermediate 23A was prepared from 4-fluorobenzylamine and (1-bromo-ethyl)-benzene using Method VI. HRMS (M+H) calcd for $C_{17}H_{19}FNO$: 272.1451; found: 272.1454. $^1$H NMR and $^{13}$C NMR show a mixture of rotamers at room temperature. $^1$H NMR (500 MHz, CDCl$_3$) δ: 1.42(d, J=7), 1.49(d, J=7), 2.05(s), 2.29(s), 3.99(d, J=15), 4.18(d, J=18), 4.37(d, J=18), 4.80(d, J=15), 5.17(m), 6.18 (m), 6.86–7.35 (overlapping m). $^{13}$C NMR (125 MHz, CDCl$_3$) δ: 16.96, 19.00, 22.17, 22.52, 114.85, 115.02, 115.42, 115.59, 126.72, 127.43, 127.49, 127.55, 127.62, 127.73, 128.52, 128.79, 129.10, 129.17, 133.91, 135.03, 140.33, 140.82, 160.69, 162.79, 171.31, 171.75.

Intermediate 23B

3-[(4-Fluoro-benzyl)-(1-phenyl-ethyl)-carbamoyl]-2-hydroxy-acrylic acid methyl ester

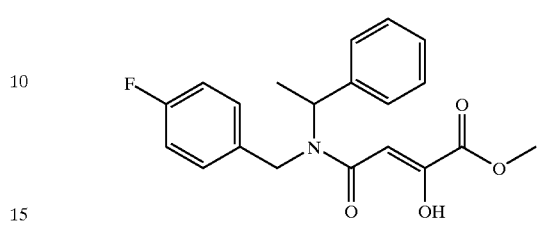

Intermediate 23B was prepared from Intermediate 23A using Method IX. HRMS (M+H) calcd for $C_{20}H_{21}NO_4F$: 358.1454; found: 358.1456. $^1$H NMR and $^{13}$C NMR show a mixture of rotamers at room temperature. $^1$H NMR (500 MHz, CDCl$_3$) δ: 1.46(d, J=7), 1.55(d, J=7), 3.82(s), 3.89(s), 4.12(d, J=16), 4.24(d, J=18), 4.45(d, J=18), 4.77(d, J=16), 5.33(q, J=7), 6.08(s), 6.15(q, J=7), 6.90–7.36 (overlapping m). $^{13}$C NMR (125 MHz, CDCl$_3$) δ: 17.00, 18.65, 45.74, 46.45, 51.73, 52.90, 52.98, 55.85, 93.75, 94.71, 115.12, 115.30, 115.57, 115.75, 127.02, 127.59, 127.65, 127.71, 127.93, 128.14, 128.68, 128.87, 129.00, 129.07, 132.97, 133.00, 133.78, 139.16, 139.71, 159.90, 160.11, 161.04, 162.99, 163.15, 163.32, 171.55, 171.86.

Compound 23

3-[(4-Fluoro-benzyl)-(1-phenyl-ethyl)-carbamoyl]-2-hydroxy-acrylic acid

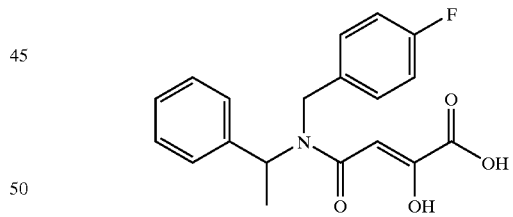

Compound 23 was prepared from Intermediate 23B using Method XI. HRMS (M−H) calcd for $C_{19}H_{17}NO_4F$: 342.1142; found: 342.1148. $^1$H NMR and $^{13}$C NMR show a mixture of rotamers at room temperature. $^1$H NMR (500 MHz, CDCl$_3$) δ: 1.48(d, J=7), 1.54(d, J=7), 4.16(d, J=15), 4.25(d, J=18), 4.45(d, J=18), 4.76(d, J=15), 5.32(q, J=7), 6.13(s), 6.54(s), 6.85–7.36 (overlapping m). $^{13}$C NMR (125 MHz, CDCl$_3$) δ: 16.98, 18.63, 45.82, 46.54, 52.05, 56.07, 93.81, 94.94, 115.20, 115.37, 115.67, 115.84, 127.02, 127.60, 127.68, 128.07, 128.27, 128.75, 128.94, 129.04, 129.11, 132.61, 132.64, 133.42, 138.84, 139.40, 159.05, 159.37, 161.07, 163.03, 164.83, 171.46, 171.76.

EXAMPLE 24

Intermediate 24A

N-(4-Chloro-benzyl)-N-(4-fluoro-benzyl)-acetamide

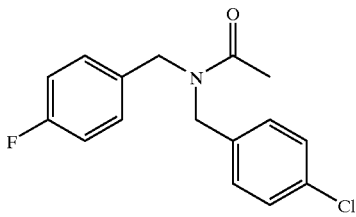

Intermediate 24A was prepared from 4-fluorobenzylamine and 4-chlorobenzylchloride using Method VI. HRMS (M+H) calcd for $C_{16}H_{16}ClFNO$: 292.0905; found: 292.0904. $^1$H NMR and $^{13}$C NMR show a mixture of rotamers at room temperature. $^1$H NMR (500 MHz, CDCl$_3$) δ: 2.19(s), 2.21(s), 4.40(s), 4.53(s), 6.98–7.35 (overlapping m). $^{13}$C NMR (125 MHz, CDCl$_3$) δ: 21.70, 47.31, 50.25, 115.43, 115.60, 115.92, 116.09, 127.78, 128.07, 128.13, 128.80, 129.22, 129.71, 130.02, 130.09, 131.81, 132.89, 133.36, 133.62, 134.78, 135.72, 161.29, 163.24, 171.02.

Intermediate 24B

3-[(4-Chloro-benzyl)-(4-fluoro-benzyl)-carbamoyl]-2-hydroxy-acrylic acid methyl ester

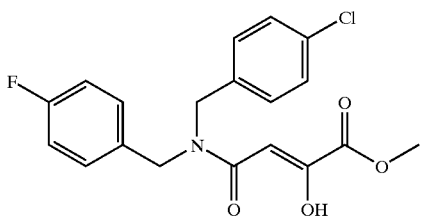

Intermediate 24B was prepared from Intermediate 24A using Method IX. HRMS (M+H) calcd for $C_{19}H_{18}NO_4ClF$: 378.0908; found: 378.0910. $^1$H NMR and $^{13}$C NMR show a mixture of rotamers at room temperature. $^1$H NMR (500 MHz, CDCl$_3$) δ: 3.86(s), 3.87(s), 4.46(s), 4.57(s), 4.58(s), 6.29(s), 6.33(s), 7.00–7.35 (overlapping m). $^{13}$C NMR (125 MHz, CDCl$_3$) δ: 47.42, 47.49, 49.41, 49.47, 53.01, 93.26, 115.68, 115.85, 116.02, 116.19, 128.09, 128.47, 128.54, 129.01, 129.31, 129.65, 130.04, 130.11, 130.99, 131.02, 131.87, 131.89, 133.80, 133.90, 134.04, 134.67, 160.36, 161.47, 161.54, 163.05, 163.43, 163.50, 171.41.

Compound 24

3-[(4-Chloro-benzyl)-(4-fluoro-benzyl)-carbamoyl]-2-hydroxy-acrylic acid

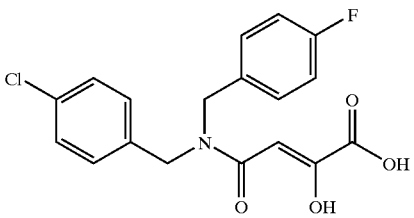

Compound 24 was prepared from Intermediate 24B using Method X. HRMS (M–H) calcd for $C_{18}H_{14}NO_4ClF$: 362.0595; found: 362.0606. $^1$H NMR shows a mixture of rotamers at room temperature. $^1$H NMR (500 MHz, CDCl$_3$) δ: 4.45(s), 4.56(s), 6.31(s), 6.35(s), 6.99–7.35 (overlapping m).

EXAMPLE 25

Intermediate 25A

N-(2,4-difluoro-benzyl)-N-(4-fluoro-benzyl)-acetamide

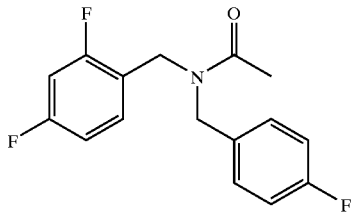

Intermediate 25A was prepared from 4-fluorobenzyl amine and 2,4-difluorobenzylbromide using Method VI. HRMS (M+H) calcd for $C_{16}H_{15}F_3NO$: 294.1106; found: 294.1105. $^1$H NMR shows a mixture of rotamers at room temperature. $^1$H NMR (500 MHz, CDCl$_3$) δ: 2.14(s), 2.17(s), 4.39(s), 4.42(s), 4.46(s), 4.51(s), 6.69–7.30 (overlapping m).

Intermediate 25B

3-[(2,4-Difluoro-benzyl)-(4-fluoro-benzyl)-carbamoyl]-2-hydroxy-acrylic acid methyl ester

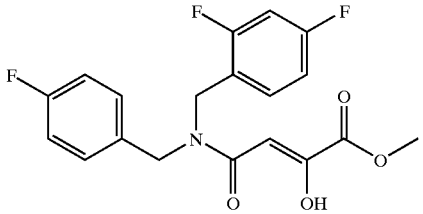

Intermediate 25B was prepared from Intermediate 25A using Method IX. HRMS (M+H) calcd for $C_{19}H_{17}NO_4F_3$: 380.1110; found: 380.1100. $^1$H NMR shows a mixture of rotamers at room temperature. $^1$H NMR (500 MHz, CDCl$_3$) δ: 3.87(s), 3.88(s), 4.51(s), 4.52(s), 4.59(s), 4.62(s), 6.33(s), 6.77–7.40 (overlapping m).

Compound 25

3-[(2,4-Difluoro-benzyl)-(4-fluoro-benzyl)-carbamoyl]-2-hydroxy-acrylic acid

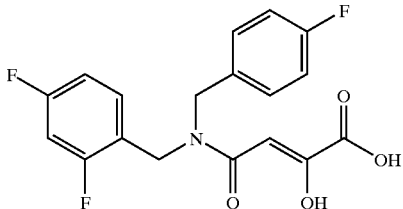

Compound 25 was prepared from Intermediate 25B using Method X. HRMS (M−H) calcd for $C_{18}H_{13}NO_4F_3$: 364.0800; found: 364.0800. $^1$H NMR shows a mixture of rotamers at room temperature. $^1$H NMR (500 MHz, CDCl$_3$) δ: 4.47(s), 4.48(s), 4.55(s), 4.58(s), 6.32(s), 6.73–7.34 (overlapping m).

EXAMPLE 26

Intermediate 26A

N-(3,5-difluoro-benzyl)-N-(4-fluoro-benzyl)-acetamide

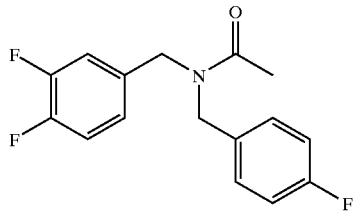

Intermediate 26A was prepared from 4-fluorobenzylamine and 3,4-difluorobenzylamine using Method VI. HRMS (M+H) calcd for $C_{16}H_{14}F_3NO$: 294.1106; found: 294.1103. $^1$H NMR shows a mixture of rotamers at room temperature. $^1$H NMR (500 MHz, CDCl$_3$) δ: 2.11(s), 2.13(s), 4.32(s), 4.35(s), 4.40(s), 4.44(s), 678–7.21 (overlapping m).

Intermediate 26B

3-[(3,4-Difluoro-benzyl)-(4-fluoro-benzyl)-carbamoyl]-2-hydroxy-acrylic acid methyl ester

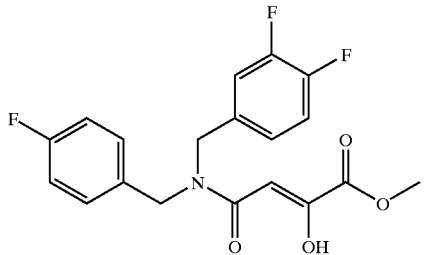

Intermediate 26B was prepared from Intermediate 25A using Method IX. HRMS (M+H) calcd for $C_{19}H_{17}NO_4F_3$: 380.1110; found: 38.01116. $^1$H NMR and $^{13}$C NMR show a mixture of rotamers at room temperature. $^1$H NMR (500 MHz, CDCl$_3$) δ: 3.88(s), 4.45(s), 4.48(s), 4.55(s), 4.59(s), 6.26(s), 6.34(s), 6.89–7.26 (overlapping m). $^{13}$C NMR(125 MHz, CDCl$_3$) δ: 47.24, 47.54, 49.07, 49.60, 53.08, 93.06, 93.16, 115.75, 115.87, 115.91, 116.08, 116.26, 117.22, 117.36, 117.52, 117.66, 117.99, 118.13, 122.61, 124.30, 124.33, 128.46, 128.52, 130.05, 130.12, 130.85, 131.72, 132.44, 133.22, 160.45, 160.50, 161.51, 161.57, 163.02, 163.47, 163.54, 171.39, 171.43.

Compound 26

3-[(3,4-Difluoro-benzyl)-(4-fluoro-benzyl)-carbamoyl]-2-hydroxy-acrylic acid

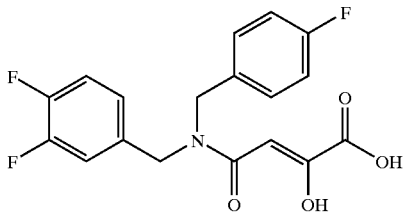

Compound 26 was prepared from Intermediate 26B using Method X. HRMS (M−H) calcd for $C_{18}H_{13}NO_4F_3$: 364.0800; found 364.0792. $^1$H NMR shows a mixture of rotamers at room temperature. $^1$H NMR (500 MHz, CDCl$_3$) δ: 4.43(s), 4.46(s), 4.53(s), 4.61(s), 6.27(s), 6.35(s), 6.86–7.26 (overlapping m).

EXAMPLE 27

Intermediate 27A

N-tert-Butyl-N-(4-fluoro-benzyl)-acetamide

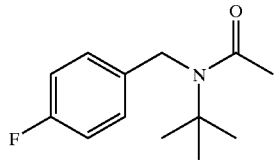

Intermediate 27A was prepared from tert-butylamine and 4-fluorobenzyl bromide using Method VI. HRMS (M+H) calcd for $C_{13}H_{19}FNO$: 224.1451; found: 224.1456. $^1$H NMR (500 MHz, CDCl$_3$) δ: 1.41 (s, 9), 2.08 (s, 3), 4.55 (s, 2), 7.04 (m, 2), 7.17 (m, 2). $^{13}$C NMR (125 MHz, CDCl$_3$) δ: 25.06, 28.78, 49.17, 57.71, 115.61, 115.78, 127.04, 127.10, 134.97, 134.99, 160.97, 162.82, 172.16.

Intermediate 27B

3-[tert-Butyl-(4-fluoro-benzyl)-carbamoyl]-2-hydroxy-acrylic acid methyl ester

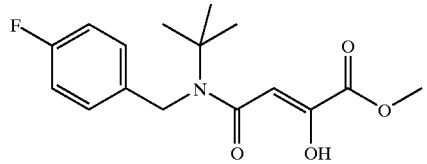

Intermediate 27B was prepared from Intermediate 27A using Method IX. HRMS (M+H) calcd for $C_{16}H_{21}NO_4F$:

310.1455; found 310.1454. Anal. calcd for $C_{16}H_{20}NO_4F$: C, 62.12; H, 6.51; N, 4.52. found: C, 62.31; H, 6.71; N, 4.52. $^1$H NMR (500 MHz, CDCl$_3$) δ: 1.47(s, 9), 3.2(s, 3), 4.62(s, 2), 6.20(s, 1), 7.06(dd, 2, J=9, 9), 7.16(dd, 2, J=5, 9). $^{13}$C NMR (125 MHz, CDCl$_3$) δ: 28.74, 48.27, 52.86, 58.85, 96.31, 115.81, 115.99, 116.61, 127.32, 127.38, 134.00, 159.61, 161.07, 163.02, 163.46, 173.36.

Compound 27

3-[tert-Butyl-(4-fluoro-benzyl)-carbamoyl]-2-hydroxy-acrylic acid

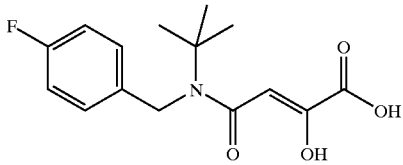

Compound 27 was prepared from Intermediate 27B using Method XI. HRMS (M–H) calcd for $C_{15}H_{17}NO_4F$: 294.1142; found: 294.1144. $^1$H NMR (500 MHz, CDCl$_3$) δ: 1.47(s, 9), 4.62(s, 2), 6.12(br s, 1), 7.04(m, 2), 7.14(m, 2). $^{13}$C NMR (125 MHz, CDCl$_3$) δ: 28.68, 48.34, 59.15, 96.45, 115.86, 116.03, 127.28, 127.35, 133.64, 159.01, 161.09, 163.05, 165.61, 173.28.

EXAMPLE 28

Intermediate 28A

N-(3-Chloro-benzyl)-N-4-fluoro-benzyl)-acetamide

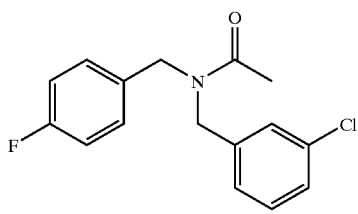

Intermediate 28A was prepared from 4-fluorobenzylamine and 3-chlorobenzylchloride using Method VI. HRMS (M+H) calcd for $C_{16}H_{16}ClFNO$: 292.0905; found: 292.0902. $^1$H NMR and $^{13}$C NMR show a mixture of rotamers at room temperature. $^1$H NMR (500 MHz, CDCl$_3$) δ: 2.19(s), 2.23(s), 4.41(s), 4.55(s), 6.97–7.38 (overlapping m). $^{13}$C NMR (125 MHz, CDCl$_3$) δ: 21.67, 47.50, 50.37, 115.44, 115.61, 115.92, 116.09, 124.47, 126.41, 126.52, 127.72, 128.00, 128.07, 128.14, 128.22, 129.92, 130.04, 130.11, 130.34, 131.77, 131.80, 132.88, 132.90, 134.56, 135.13, 138.49, 139.29, 161.31, 163.26, 171.05.

Intermediate 28B

3-[(3-Chloro-benzyl)-(4-fluoro-benzyl)-carbamoyl]-2-hydroxy-acrylic acid methyl ester

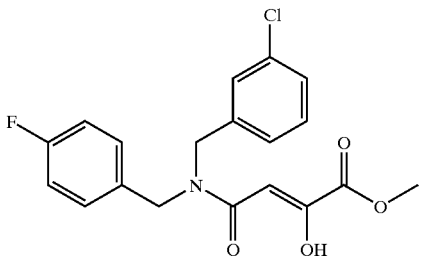

Intermediate 28B was prepared from Intermediate 28A using Method IX. HRMS (M+H) calcd for $C_{19}H_{18}NO_4FCl$: 378.0908; found: 378.0903. $^1$H NMR and $^{13}$C NMR show a mixture of rotamers at room temperature. $^1$H NMR (500 MHz, CDCl$_3$) δ: 3.87(s), 3.88(s), 4.47(s), 4.48(s), 4.59 (s), 4.60(s), 6.28(s), 6.35(s), 7.01–7.31 (overlapping m). $^{13}$C NMR (125 MHz, CDCl$_3$) δ: 47.57, 47.59, 49.49, 49.60, 53.05, 93.23, 93.24, 115.70, 115.87, 116.04, 116.21, 124.78, 126.33, 126.82, 128.12, 128.20, 128.38, 128.49, 128.55, 130.07, 130.14, 130.44, 130.94, 130.96, 131.83, 131.85, 134.77, 135.16, 137.52, 138.22, 160.38, 160.39, 161.49, 161.55, 163.05, 163.08, 163.45, 163.51, 171.44.

Compound 28

3-[(3-Chloro-benzyl)-(4-fluoro-benzyl)-carbamoyl]-2-hydroxy-acrylic acid

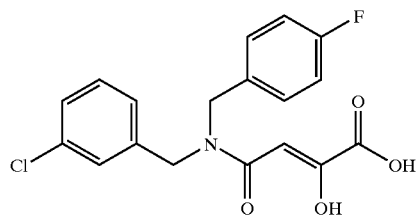

Compound 28 was prepared from Intermediate 28B using Method X. HRMS (M+H) calcd for $C_{18}H_{16}NO_4ClF$: 364.0752; found: 364.0758. $^1$H NMR and $^{13}$C NMR show a mixture of rotamers at room temperature. $^1$H NMR (500 MHz, CDCl$_3$) δ: 4.48(s), 4.49(s), 4.60(s), 4.61(s), 6.35(s), 6.42(s), 7.02–7.34 (overlapping m). $^{13}$C NMR (125 MHz, CDCl$_3$) δ: 47.49, 49.57, 49.70, 93.57, 115.76, 115.94, 116.11, 116.28, 124.77, 126.35, 126.80, 128.23, 128.49, 128.57, 130.11, 130.18, 130.49, 134.81, 135.21, 137.23, 137.94, 159.45, 164.76, 171.34.

EXAMPLE 29

Intermediate 29A

N-(4-Fluoro-benzyl)-N-isopropyl-acetamide

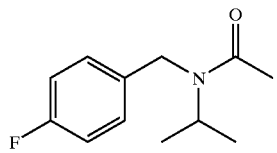

Intermediate 29A was prepared from 4-fluorobenzylbromide and isopropylamine using Method VI. HRMS (M+H) calcd for $C_{12}H_{17}FNO$: 210.1294; found: 210.1293. $^1H$ NMR and $^{13}C$ NMR show a mixture of rotamers at room temperature. $^1H$ NMR (500 MHz, CDCl$_3$) δ: 1.08 (d, J=7), 1.13(d, J=7), 2.00(s), 2.23(s), 4.12(p, J=7), 4.42(s), 4.49(s), 4.86(p, J=7), 6.93(m), 7.05(m), 7.19(m). $^{13}C$ NMR (125 MHz, CDCl$_3$) δ: 20.33, 21.51, 22.03, 22.59, 43.05, 45.51, 46.31, 49.79, 114.99, 115.16, 115.57, 115.74, 127.33, 128.64, 134.17, 135.42, 160.71, 160.93, 162.65, 162.89, 170.70, 171.36.

Intermediate 29B

3-[(4-Fluoro-benzyl)-isopropyl-carbamoyl]-2-hydroxy-acrylic acid methyl ester

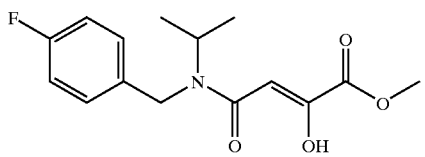

Intermediate 29B was prepared from Intermediate 29A using Method IX. HRMS (M+H) calcd for $C_{15}H_{19}NO_4F$: 296.1298; found: 296.1299. $^1H$ NMR and $^{13}C$ NMR show a mixture of rotamers at room temperature. $^1H$ NMR (500 MHz, CDCl$_3$) δ: 1.14(d, J=7), 1.19(d, J=7), 3.81(s), 3.90(s), 4.28(heptet, J=7), 4.49(s), 4.59(s), 4.84(heptet, J=7), 6.03(s), 6.40(s), 6.97–7.22 (overlapping m). $^{13}C$ NMR (125 MHz, CDCl$_3$) δ: 20.23, 21.51, 43.51, 45.55, 46.04, 49.13, 52.88, 52.99, 93.54, 94.71, 115.32, 115.49, 115.75, 115.92, 127.57, 127.64, 128.50, 128.57, 133.14, 134.11, 159.74, 159.95, 160.90, 161.13, 162.85, 163.09, 163.25, 163.46, 171.08, 171.65.

Compound 29

3-[(4-Fluoro-benzyl)-isopropyl-carbamoyl]-2-hydroxy-acrylic acid

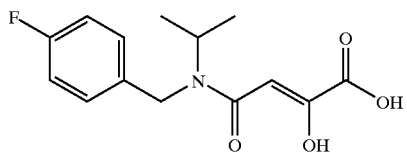

Compound 29 was prepared from Intermediate 29B using Method XI. HRMS (M−H) calcd $C_{14}H_{15}NO_4F$: 280.9851; found: 280.988. $^1H$ NMR shows a mixture of rotamers at room temperature. $^1H$ NMR (500 MHz, CDCl$_3$) δ: 1.16(d, J=7), 1.20(d, J=7), 4.28(heptet, J=7), 4.51(s), 4.61(s), 4.82(heptet, J=7), 6.10(s), 6.47(s), 7.03(m), 7.15(m), 7.21(m).

EXAMPLE 30

Intermediate 30A

N-Methyl-N-(4-methyl-benzyl)-acetamide

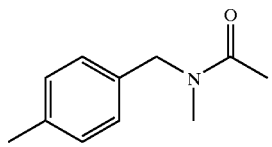

Intermediate 30A was prepared from N-(4-methyl-benzyl)-acetamide and methyl iodide using Method VII. HRMS (M+H) calcd for $C_{11}H_{16}NO$: 178.1232; found: 178.1230. $^1H$ NMR and $^{13}C$ NMR show a mixture of rotamers at room temperature. $^1H$ NMR (500 MHz, CDCl$_3$) δ: 2.14 (s), 2.15 (s), 2.33 (s), 2.35 (s), 2.90 (s), 2.92 (s), 4.48 (s), 4.54 (s), 7.05–7.18 (overlapping m). $^{13}C$ NMR (125 MHz, CDCl$_3$) δ: 21.07, 21.12, 21.46, 21.68, 33.68, 35.44, 50.33, 54.05, 126.32, 128.10, 129.27, 129.63, 133.44, 134.30, 137.04, 137.41, 170.74, 171.08.

Intermediate 30B

2-Hydroxy-3-[methyl-(4-methyl-benzyl)-carbamoyl]-acrylic acid methyl ester

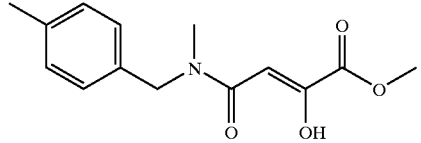

Intermediate 30B was prepared from Intermediate 30A using Method IX. HRMS (M+H) calcd for $C_{14}H_{18}NO_4$: 264.1236; found: 264.1243. Anal calcd for $C_{14}H_{17}NO_4$: C, 63.96; H, 6.50; N, 5.32. found: C, 63.57; H, 6.50; N, 5.28. $^1H$ NMR and $^{13}C$ NMR show a mixture of rotamers at room temperature. $^1H$ NMR (500 MHz, CDCl$_3$) δ:2.34 (s), 2.99 (s), 3.86 (s), 3.89 (s), 4.54 (s), 4.61 (s), 6.29 (s), 6.34 (s), 7.06–7.18 (overlapping m). $^{13}C$ NMR (125 MHz, CDCl$_3$) δ: 21.12, 33.47, 34.75, 50.37, 52.91, 53.09, 93.56, 93.66, 126.65, 128.00, 129.48, 129.71, 132.51, 133.16, 137.53, 137.86, 159.59, 163.35, 170.87, 171.19.

Compound 30

2-Hydroxy-3-[methyl-(4-methyl-benzyl)-carbamoyl]-acrylic acid

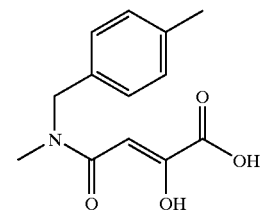

Compound 30 was prepared from Intermediate 30B using Method XI. HRMS (M−H) calcd for $C_{13}H_{14}NO_4$: 248.0923;

found: 248.0926. ¹H NMR and ¹³C NMR show a mixture of rotamers at room temperature. ¹H NMR (500 MHz, CDCl₃) δ: 2.34 (s), 3.01 (s), 3.02 (s), 4.55 (s), 4.62 (s), 6.36 (s), 6.42 (s), 7.06–7.18 (overlapping m). ¹³C NMR (125 MHz, CDCl₃) δ: 21.13, 33.72, 34.85, 50.58, 53.23, 93.67, 93.74, 126.69, 128.03, 129.54, 129.77, 132.20, 132.83, 137.68, 138.00, 158.90, 159.111, 165.36, 170.80, 171.08.

EXAMPLE 31

Intermediate 31A

N-(4-Methoxy-benzyl)-N-methyl-acetamide

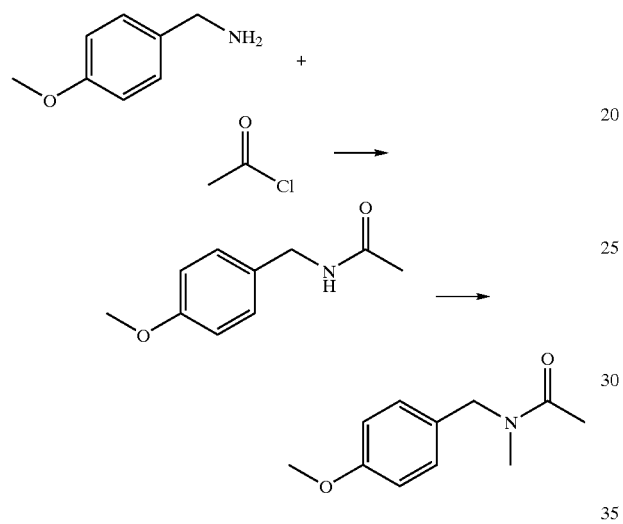

4-Methoxybenzyl amine (3.8 grams, 27.8 mmol) was dissolved in 100 mL of methylene chloride, to this was added 100 mL of satd NaHCO₃ (aq.) followed by acetyl chloride (3.0 mL, 41.7 mmol). After stirring 1 h, an additional 41.7 mmol of acetyl chloride was added and the resulting mixture stirred overnight. The organic layer was separated, washed with satd NaCl (aq.), dried over Na₂SO₄, filtered and solvent removed under vacuum. Crude N-(4-methoxybenzyl)-acetamide was purified by flash column chromatography (SiO₂, 2% EtOH in methylene chloride) 1.75 grams (35% yield) as a white solid.

Sodium hydride (60% in mineral oil) (1.11 grams, 27.4 mmol) was measured into a round bottom flask and triturated with hexanes. To this was added pure N-(4-methoxybenzyl)-acetamide (1.23 grams, 6.9 mmol) followed by iodomethane (1.95 grams, 13.7 mmol)and the resulting mixture stirred overnight. The reaction was filtered and the solvent removed under vacuum. The crude product was purified by flash column chromatography (SiO₂, 2% EtOH in methylene chloride) to yield 1.2 grams of a colorless oil. HRMS (M+H) calcd for C₁₁H₁₆NO₂: 194.1181; found: 194.1177. ¹H NMR and ¹³C NMR show a mixture of rotamers at room temperature. ¹H NMR (500 MHz, CDCl₃) δ: 2.13 (s), 2.15 (s), 2.89 (s), 2.90 (s), 3.78 (s), 3.80 (s), 4.45 (s), 4.50 (s), 6.86 (m), 7.08 (d, J=9), 7.17 (d, J=9). ¹³C NMR (125 MHz, CDCl₃) δ: 21.50, 21.91, 33.49, 35.33, 49.95, 53.72, 55.28, 113.95, 114.32, 127.66, 128.46, 129.44, 129.52, 158.95, 159.13, 170.63, 170.91.

Intermediate 31B 2-Hydroxy-3-[(4-methoxy-benzyl)-methyl-carbamoyl]-acrylic acid methyl ester

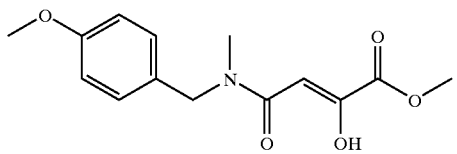

Intermediate 31B was prepared from Intermediate 31A using Method IX. HRMS (M+H) calcd for C₁₄H₁₈NO₅: 280.1185; found: 280.1188. ¹H NMR and ¹³C NMR show a mixture of rotamers at room temperature. ¹H NMR (500 MHz, CDCl₃) δ: 2.98 (s), 3.80 (s), 3.89 (s), 3.90 (s), 4.52 (s), 4.58 (s), 6.28 (s), 6.36 (s), 6.88 (m), 7.10 (d, J=8), 7.18 (d, J=8). ¹³C NMR (125 MHz, CDCl₃) δ: 33.30, 34.62, 50.03, 52.77, 52.91, 55.32, 93.53, 93.69, 114.18, 114.42, 127.49, 128.05, 128.28, 129.44, 159.27, 159.42, 159.57, 163.35, 170.80, 171.08.

Compound 31

2-Hydroxy-3-[(4-methoxy-benzyl)-methyl-carbamoyl]-acrylic acid

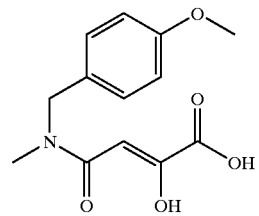

Compound 31 was prepared from Intermediate 31B using Method XI. HRMS (M–H) calcd for C₁₃H₁₄NO₅: 264.0872; found: 264.0874. ¹H NMR and ¹³C NMR show a mixture of rotamers at room temperature. ¹H NMR (500 MHz, CDCl₃) δ: 2.99 (s), 3.00 (s), 3.80 (s), 4.52 (s) 4.59 (s), 6.34 (s), 6.43 (s), 6.89 (m), 7.10 (d, J=8), 7.19 (d, J=8). ¹³C NMR (125 MHz, CDCl₃) δ: 33.52, 34.71, 50.25, 52.90, 55.35, 93.45, 114.25, 114.38, 114.49, 127.19, 127.95, 128.12, 129.48, 129.70, 159.03, 159.21, 159.32, 159.48, 164.89, 170.77, 171.01.

EXAMPLE 32

Intermediate 32A

N-Ethyl-N-(4-fluoro-benzyl)-acetamide

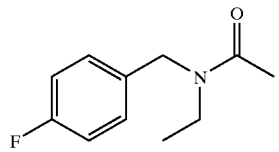

Intermediate 32A was prepared from 4-fluorobenzylbromide and N-ethylacetamide using Method VII. HRMS (M+H) calcd C₁₁H₁₅FNO: 196.1138; found: 196.1137. ¹H NMR and ¹³C NMR show a mixture of rotamers at room temperature. ¹H NMR (500 MHz, CDCl₃)

δ: 1.11 (m), 2.10 (s), 2.17 (s), 3.25 (q, J=7), 3.40 (q, J=7), 4.48 (s), 4.54 (s), 6.97–7.26 (overlapping m). $^{13}$C NMR (125 MHz, CDCl$_3$) δ: 12.67, 13.61, 21.29, 21.79, 40.70, 42.46, 47.12, 50.89, 115.28, 115.44, 115.74, 115.91, 127.87, 127.94, 129.65, 129.71, 132.64, 132.67, 133.66, 133.69, 161.15, 163.10, 170.43, 170.61.

Intermediate 32B

3-[Ethyl-(4-fluoro-benzyl)-carbamoyl]-2-hydroxy-acrylic acid methyl ester

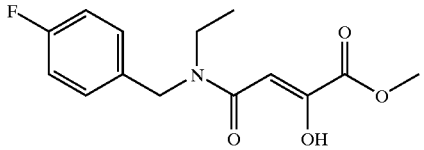

Intermediate 32B was prepared from Intermediate 32A using Method IX. HRMS (M+H) calcd for $C_{14}H_{17}NO_4F$: 282.1142; found 282.1134. $^1$H NMR and $^{13}$C NMR show a mixture of rotamers at room temperature. $^1$H NMR (500 MHz, CDCl$_3$) δ: 1.18 (overlapping m), 3.35 (q, J=7), 3.46 (q, J=7), 3.85 (s), 3.89 (s), 4.54 (s), 4.60 (s), 6.22 (s), 6.26 (s), 6.99–7.25 (overlapping m). $^{13}$C NMR (125 MHz, CDCl$_3$) δ: 12.62, 14.00, 41.06, 42.16, 47.70, 50.10, 52.92, 52.96, 93.55, 93.59, 115.55, 115.72, 115.88, 116.05, 128.24, 128.31, 129.67, 129.73, 132.63, 159.80, 161.35, 163.31, 163.34, 170.60, 170.98.

Compound 32

3-[Ethyl-(4-fluoro-benzyl)-carbamoyl]-2-hydroxy-acrylic acid

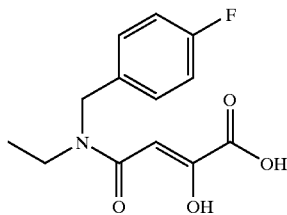

Compound 32 was prepared from Intermediate 32B using Method XI. HRMS (M−H) calcd for $C_{13}H_{13}NO_4$: 266.0829; found: 266.0829,1 $^1$H NMR and $^{13}$C NMR show a mixture of rotamers at room temperature. $^1$H NMR (500 MHz, CDCl$_3$) δ: 1.19 (overlapping m), 3.36 (q, J=7), 3.47 (q, J=7), 4.55 (s), 4.61 (s), 6.30 (s), 6.33 (s), 7.03 (m), 7.16 (m), 7.25 (m). $^{13}$C NMR (125 MHz, CDCl$_3$) δ: 12.58, 13.96, 41.32, 42.31, 47.91, 50.22, 93.46, 115.63, 115.80, 115.96, 116.13, 128.29, 128.35, 129.71, 129.78, 131.45, 132.28, 132.31, 159.331, 159.39, 163.37, 164.90, 170.58, 170.97.

EXAMPLE 33

Intermediate 33A

N-(3-Methoxy-benzyl)-N-methyl-acetamide

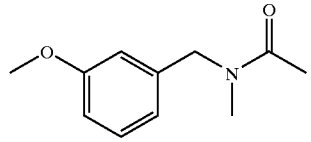

Intermediate 33A was prepared from N-methylacetamide and 3-methoxybenzylbromide using Method VII. HRMS (M+H) calcd for $C_{11}H_{16}NO_2$: 194.1181; found: 194.1180. $^1$H NMR and $^{13}$C NMR show a mixture of rotamers at room temperature. $^1$H NMR (500 MHz, CDCl$_3$) δ: 2.13 (s), 2.14 (s), 2.91 (s), 2.93 (s), 3.78 (s), 3.79 (s), 4.48 (s), 4.55 (s), 6.69–6.83 (overlapping m), 7.21–7.29 (overlapping m).

Intermediate 33B

2-Hydroxy-3-[(3-methoxy-benzyl)-methyl-carbamoyl]-acrylic acid methyl ester

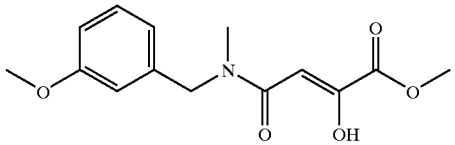

Intermediate 33B was prepared from Intermediate 33A using Method IX. HRMS (M+H) calcd for $C_{14}H_{18}NO_5$: 280.1185; found 280.1183. $^1$H NMR and $^{13}$C NMR show a mixture of rotamers at room temperature. $^1$H NMR (500 MHz, CDCl$_3$) δ: 3.01 (s), 3.79 (s), 3.85 (s), 3.89 (s), 4.55 (s), 4.62 (s), 6.30 (s), 6.31 (s), 6.70–6.85 (overlapping m), 7.29 (m). $^{13}$C NMR (125 MHz, CDCl$_3$) δ: 33.62, 34.89, 50.58, 52.93, 53.22, 55.27, 93.46, 93.59, 112.57, 113.02, 113.67, 118.81, 120.19, 129.84, 130.17, 137.24, 137.81, 159.65, 160.01, 160.19, 163.32, 170.95, 171.28.

Compound 33

2-Hydroxy-3-[(3-methoxy-benzyl)-methyl-carbamoyl]-acrylic acid

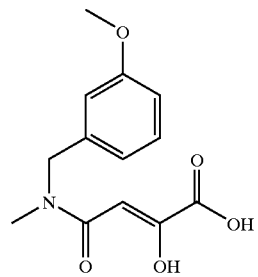

Compound 33 was prepared from Intermediate 33B using Method XI. HRMS (M−H) calcd for $C_{13}H_{14}NO_5$: 264.0872; found: 264.0868. $^1$H NMR and $^{13}$C NMR show a mixture of rotamers at room temperature. $^1$H NMR (500 MHz, CDCl$_3$) δ: 3.02 (s), 3.03 (s), 3.80 (s), 4.56 (s), 4.63 (s) 6.36 (s), 6.38

(s), 6.70–6.85 (overlapping m), 7.26 (m). $^{13}$C NMR (125 MHz, CDCl$_3$) δ: 33.82, 34.98, 50.75, 53.33, 55.30, 93.55, 112.62, 113.08, 113.14, 113.36, 113.73, 114.76, 118.86, 120.22, 122.03, 129.90, 130.28, 136.97, 137.54, 159.21, 159.39, 159.99, 160.06, 165.18, 170.96, 171.25.

EXAMPLE 34

Intermediate 34A

N-Biphenyl-3-ylmethyl-N-methyl-acetamide

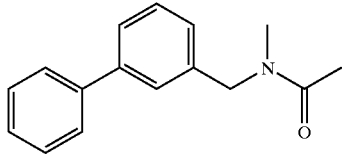

C-Biphenyl-3-yl-methylamine (700 mg, 3.8 mmol) was dissolved in 38 mL of CH$_2$Cl$_2$. To this was added 38 mL of satd NaHCO$_3$ (aq) followed by acetyl chloride (1.41 mL 19,8 mmol). The resulting mixture was stirred 45 min. The organic layer was separated, washed with satd NaCl, dried over Na$_2$SO$_4$, filtered and solvent removed under vacuum to yield 1.1 grams of N-biphenyl-3-ylmethyl-acetamide.

N-biphenyl-3-ylmethyl-acetamide (860 mg, 3.8 mmol) was dissolved in 10 mL of toluene. To this was added 611 mg of 60% NaH (mineral oil) and MeI (0.48 mL, 7.6 mmol). The resulting mixture was stirred overnight then filtered. The solvent was removed under vacuum to yield 980 mg (108% yield) of N-biphenyl-3-ylmethyl-N-methyl-acetamide. HRMS ((M+H) calcd for C$_{16}$H$_{18}$N): 240.1389; found: 240.1398. $^1$H NMR and $^{13}$C NMR show a mixture of rotamers at room temperature. $^1$H NMR (500 MHz, CDCl$_3$) δ: 2.17 (s), 2.19 (s), 2.96 (s), 2.99 (s), 4.60 (s), 4.66 (s), 7.15–7.60 (overlapping m). $^{13}$C NMR (125 MHz, CDCl$_3$) δ: 21.55, 21.91, 33.84, 35.61, 50.66, 54.33, 125.05, 125.16, 126.25, 126.55, 126.85, 127.00, 127.20, 127.23, 127.42, 127.65, 128.79, 128.90, 129.06, 129.45, 137.19, 137.95, 140.65, 140.95, 141.64, 142.12, 170.79, 171.08.

Intermediate 34B 3-(Biphenyl-3-ylmethyl-methyl-carbamoyl)-2-hydroxy-acrylic acid methyl ester

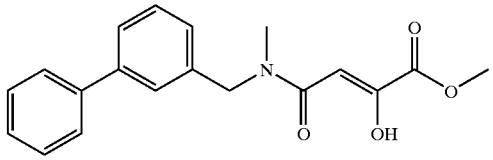

Intermediate 34B was prepared from Intermediate 34A using Method IX. HRMS (M+H) calcd for C$_{19}$H$_{20}$NO$_4$: 326.1392; found: 326.1398. $^1$H NMR and $^{13}$C NMR show a mixture of rotamers at room temperature. $^1$H NMR (500 MHz, CDCl$_3$) δ: 3.04 (s), 3.06 (s), 3.87 (s), 3.90 (s), 4.65 (s), 4.73 (s), 6.33 (s), 6.38 (s), 7.16–7.59 (overlapping m). $^{13}$C NMR (125 MHz, CDCl$_3$) δ: 33.68, 34.95, 50.69, 52.95, 53.34, 93.48, 93.65, 125.40, 125.44, 126.66, 126.76, 126.87, 126.93, 127.20, 127.57, 127.72, 128.88, 128.94, 129.31, 129.58, 136.22, 136.82, 140.53, 140.73, 141.88, 142.17, 159.69, 163.32, 171.01, 171.33.

Compound 34

3-(Biphenyl-3-ylmethyl-methyl-carbamoyl)-2-hydroxy-acrylic acid

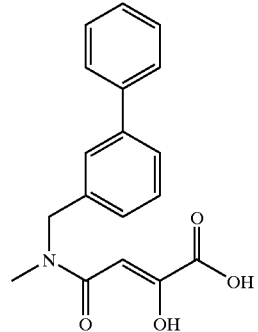

Compound 34 was prepared from Intermediate 34B using Method X. HRMS (M+H) calcd for C$_{18}$H$_{18}$NO$_4$: 312.1236; found: 312.1250. $^1$H NMR shows a mixture of rotamers at room temperature. $^1$H NMR (500 MHz, CDCl$_3$) δ: 3.05 (s), 3.08 (s), 4.65 (s), 4.73 (s), 6.39 (s), 6.46 (s), 7.15–7.59 (overlapping m).

EXAMPLE 35

Intermediate 35A

N-(2,4-Dimethoxy-benzyl)-N-(4-fluoro-benzyl)-acetamide

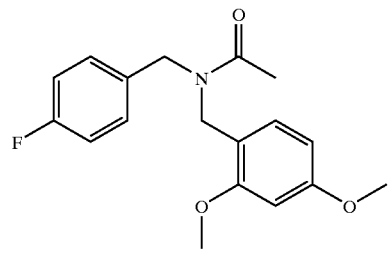

Intermediate 35A was prepared from (2,4-dimethoxybenzyl)-(4-fluoro-benzyl)-amine using Method IV. HRMS (M+H) calcd for C$_{18}$H$_{21}$FNO$_3$: 318.1506; found: 318.1505. $^1$H NMR and $^{13}$C NMR show a mixture of rotamers at room temperature. $^1$H NMR (500 MHz, CDCl$_3$) δ: 2.14 (s), 2.22 (s), 3.71 (s), 3.77 (s), 3.79 (s), 3.81 (s), 4.34 (s), 4.46 (s), 4.51 (s), 4.55 (s), 6.45 (m), 6.92–7.22 (overlapping m). $^{13}$C NMR (125 MHz, CDCl$_3$) δ: 21.61, 21.82, 42.89, 46.56, 47.10, 50.86, 55.19, 55.46, 98.30, 98.68, 103.87, 104.25, 115.16, 115.33, 115.56, 115.73, 116.50, 117.85, 127.83, 127.90, 128.29, 129.79, 129.85, 131.00, 132.97, 133.53, 133.55, 158.35, 158.58, 160.34, 160.66, 161.09, 163.03, 171.11, 171.46.

Intermediate 35B

3-[(2,4-Dimethoxy-benzyl)-(4-fluoro-benzyl)-carbamoyl]-2-hydroxy-acrylic acid methyl ester

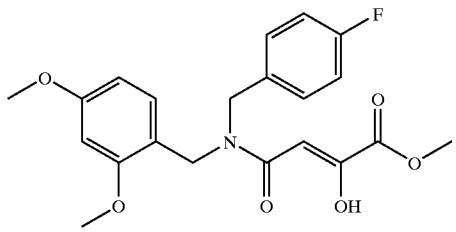

Intermediate 35B was prepared from Intermediate 35A using Method IX. HRMS (M+H) calcd for $C_{21}H_{23}NO_6F$: 404.1510; found: 404.1514. $^1H$ NMR and $^{13}C$ NMR show a mixture of rotamers at room temperature. $^1H$ NMR (500 MHz, CDCl$_3$) δ: 3.73 (s), 3.78 (s), 3.80 (s), 3.81 (s), 3.85 (s), 3.87 (s), 4.42 (s), 4.53 (s), 4.58 (s), 4.60 (s), 6.27 (s), 6.42 (s), 6.45 (s), 6.94–7.23 (overlapping m). $^{13}C$ NMR (125 MHz, CDCl$_3$) δ: 43.10, 45.55, 47.29, 49.88, 52.91, 55.20, 55.26, 55.46, 93.77, 94.39, 98.43, 98.68, 104.09, 104.36, 115.44, 115.61, 115.67, 115.76, 115.84, 116.66, 128.26, 128.32, 128.86, 129.80, 129.86, 131.02, 132.05, 132.50, 132.52, 158.37, 158.60, 159.40, 159.83, 160.70, 160.94, 161.28, 163.24, 163.31, 163.41, 171.36, 171.46.

Compound 35

3-[(2,4-Dimethoxy-benzyl)-(4-fluoro-benzyl)-carbamoyl]-2-hydroxy-acrylic acid

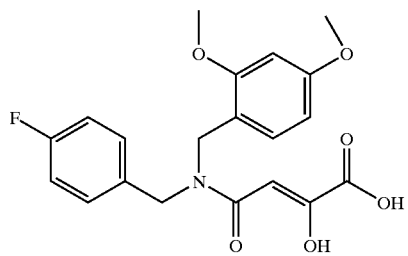

Compound 35 was prepared from Intermediate 35B using Method XI. HRMS (M+H) calcd for $C_{20}H_{21}NO_6F$: 390.1353; found: 390.1362.

EXAMPLE 36

Intermediate 36A

N-(4-Benzyloxy-benzyl)-N-methyl-acetamide

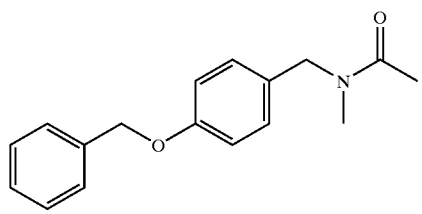

Intermediate 36A was prepared from 4-benzyloxy-benzylchloride using Method VI. HRMS (M+H) calcd for $C_{17}H_{20}NO_2$: 270.1494; found: 270.1491. $^1H$ NMR and $^{13}C$ NMR show a mixture of rotamers at room temperature. $^1H$ NMR (500 MHz, CDCl$_3$) δ: 2.14 (s), 2.16 (s), 2.90 (s), 2.92 (s), 4.46 (s0, 4.52 (s), 5.05 (s), 5.07 (s), 6.92–7.44 (overlapping m). $^{13}C$ NMR (125 MHz, CDCl$_3$) δ: 21.52, 21.93, 33.52, 35.37, 49.98, 53.73, 70.06, 70.13, 114.92, 115.29, 127.49, 127.53, 127.62, 127.68, 127.99, 128.07, 128.61, 128.65, 128.67, 128.80, 129.46, 129.85, 136.84, 137.00, 158.19, 158.35, 170.62, 170.89.

Compound 36

3-[(4-Benzyloxy-benzyl)-methyl-carbamoyl]-2-hydroxy-acrylic acid

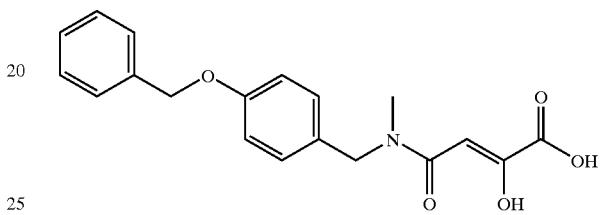

Compound 36 was prepared from Intermediate 36A using Method XII. HRMS (M+H) calcd for $C_{19}H_{20}NO_5$: 342.1342; found: 342.1352. $^1H$ NMR and $^{13}C$ NMR show a mixture of rotamers at room temperature. $^1H$ NMR (500 MHz, CDCl$_3$) 2.90 (s), 4.43 (s), 4.50 (s) 4.97 (s), 6.21 (s), 6.29 (s), 6.87–7.35 (overlapping m). $^{13}C$ NMR (125 MHz, CDCl$_3$) δ: 33.42, 34.62, 49.91, 52.66, 69.99, 93.20, 93.34, 115.03, 115.25, 127.45, 127.89, 127.98, 128.08, 128.57, 128.66, 129.34, 136.73, 136.82, 158.32, 158.47, 160.24, 164.44, 170.99, 171.24.

EXAMPLE 37

Intermediate 37A

N-Methyl-N-(3-trifluoromethyl-benzyl)-acetamide

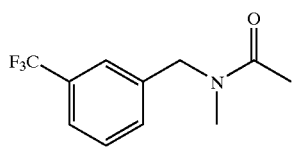

Intermediate 37A was prepared from 3-trifluorobenzyl bromide using Method VII. HRMS (M+H) calcd for $C_{11}H_{13}F_3NO$: 232.0949; found: 232.0945. $^1H$ NMR and $^{13}C$ NMR show a mixture of rotamers at room temperature. $^1H$ NMR (500 MHz, CDCl$_3$) δ: 2.14 (s), 2.17 (s), 2.94 (s), 4.58 (s), 4.62 (s), 7.37–7.55 (overlapping m). $^{13}C$ NMR (125 MHz, CDCl$_3$) δ: 21.44, 21.77, 33.76, 35.71, 122.97. 123.12, 123.15, 124.23, 124.26, 124.29, 124.56, 124.59, 124.62, 124.64, 125.13, 129.15, 129.53, 129.58, 130.55, 130.81, 131.07, 131.34, 131.59., 137.78, 138.48, 170.91, 170.95.

Intermediate 37B

2-Hydroxy-3-[methyl-(3-trifluoromethyl-benzyl)-carbamoyl]-acrylic acid methyl ester

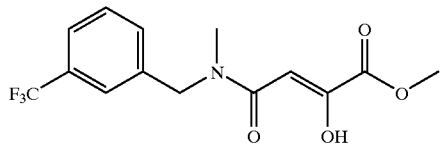

Intermediate 37B was prepared from Intermediate 37A using Method IX. HRMS (M+H) calcd for $C_{14}H_{15}NO_4F_3$: 318.0953; found: 318.0948. $^1$H NMR and $^{13}$C NMR show a mixture of rotamers at room temperature. $^1$H NMR (500 MHz, CDCl$_3$) δ: 3.02 (s), 3.03 (s), 3.84 (s), 3.88 (s), 4.64 (s), 4.70 (s), 6.27 (s), 6.31 (s), 7.36–7.59 (overlapping m). $^{13}$C NMR (125 MHz, CDCl$_3$) δ: 33.65, 35.05, 50.34, 52.87, 52.97, 93.04, 93.42, 122.86, 123.46, 123.49, 124.55, 124.58, 124.61, 124.64, 124.68, 124.71, 125.02, 129.41, 129.74, 129.81, 130.78, 131.03, 131.25, 131.36, 131.55, 131.62, 136.79, 137.39, 159.82, 159.93, 163.12, 163.17, 171.14, 171.35.

Compound 37

2-Hydroxy-3-[methyl-(3-trifluoromethyl-benzyl)-carbamoyl]-acrylic acid

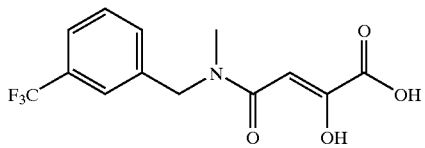

Compound 37 was prepared from Intermediate 37B using Method X. Anal Calcd for $C_{13}H_{12}NO_4F_3$: C, 51.49; H, 3.98; N, 4.62. found: C, 51.72; H, 3.76; N, 4.39. $^1$H NMR and $^{13}$C NMR show a mixture of rotamers at room temperature. $^1$H NMR (500 MHz, CDCl$_3$) δ: 3.05 (s), 4.66 (s), 4.72 (s), 6.36 (s), 6.39 (s), 7.36–7.61 (overlapping m). $^{13}$C NMR (125 MHz, CDCl$_3$) δ: 33.85, 35.14, 50.53, 52.98, 93.32, 93.72, 122.83, 123.51, 124.65, 124.68, 124.82, 124.85, 124.99, 125.14, 129.48, 129.81, 131.13, 131.27, 131.39, 136.44, 137.07, 159.04, 159.17, 165.05, 165.13, 171.04, 171.26.

EXAMPLE 38

Intermediate 38A

N-(2-Fluoro-benzyl)-N-methyl-acetamide

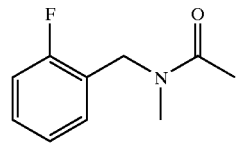

Intermediate 38A was prepared from 2-fluoro-benzyl bromide using Method VII. HRMS (M+H) calcd for $C_{10}H_{13}FNO$: 182.0981; found: 182.0982. $^1$H NMR shows a mixture of rotamers at room temperature. $^1$H NMR (500 MHz, CDCl$_3$) δ: 2.14 (s), 2.16 (s), 2.94 (s), 2.97 (s), 4.56 (s), 4.64 (s), 7.01–7.31 (overlapping m).

Intermediate 38B

3-[(2-Fluoro-benzyl)-methyl-carbamoyl]-2-hydroxy-acrylic acid methyl ester

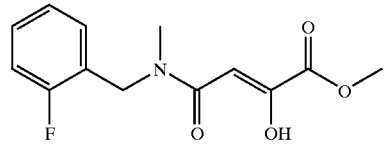

Intermediate 38B was prepared from Intermediate 38A using Method IX. HRMS (M+H) calcd for $C_{13}H_{15}NO_4F$: 268.0985; found: 268.0992. $^1$H NMR and $^{13}$C NMR show a mixture of rotamers at room temperature. $^1$H NMR (500 MHz, CDCl$_3$) δ: 3.02 (s), 3.05 (s), 3.84 (s), 3.87 (s), 4.62 (s), 4.70 (s), 6.28 (s), 6.32 (s), 7.03–7.30 (overlapping m). $^{13}$C NMR (125 MHz, CDCl$_3$) δ: 33.55, 35.21, 44.27, 44.30, 47.24, 47.28, 93.40, 93.57, 115.40, 115.57, 115.70, 115.87, 122.66, 122.77, 123.15, 123.27, 124.53, 124.55, 124.65, 124.68, 128.26, 128.29, 129.53, 129.60, 129.84, 129.91, 130.34, 130.37, 159.59, 159.65, 160.07, 161.61, 162.03, 163.24, 171.11, 171.34.

Compound 38

3-[(2-Fluoro-benzyl)-methyl-carbamoyl]-2-hydroxy-acrylic acid:

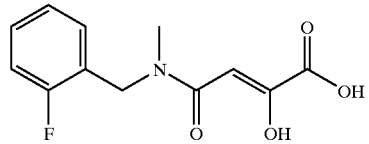

Compound 38 was prepared from Intermediate 38B using Method XI. HRMS (M+H) calcd for $C_{12}H_{13}NO_4F$: 254.0829; found: 254.0833. $^1$H NMR and $^{13}$C NMR show a mixture of rotamers at room temperature. $^1$H NMR (500 MHz, CDCl$_3$) δ: 3.04 (s), 3.07 (s), 4.64 (s), 4.72 (s), 6.36 (s), 6.41 (s), 7.05–7.20 (overlapping m), 7.31 (m). $^{13}$C NMR (125 MHz, CDCl$_3$) δ: 33.75, 35.29, 44.84, 44.51, 47.43, 47.46, 93.81, 93.85, 115.46, 115.64, 115.78, 115.95, 122.39, 122.51, 122.90, 123.02, 124.58, 124.60, 124.71, 124.73, 128.40, 128.43, 129.67, 129.74, 130.00, 130.06, 130.40, 130.43, 158.92, 159.03, 159.68, 160.08, 161.64, 162.04, 165.48, 171.03, 171.23

EXAMPLE 39

Intermediate 39A

N-Biphenyl-2-ylmethyl-N-methyl-acetamide

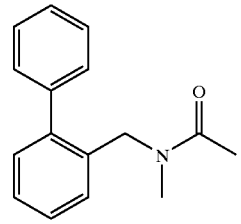

Intermediate 39A was prepared from C-Biphenyl-2-yl-methylamine using the same Method as Intermediate 34A. LCMS (M+H) calcd for $C_{16}H_{18}NO$: 240.1; found: 240.1

Intermediate 39B 3-(Biphenyl-2-ylmethyl-methyl-carbamoyl)-2-hydroxy-acrylic acid methyl ester

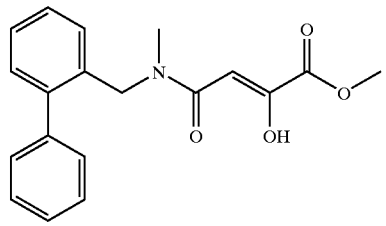

Intermediate 39B was prepared from Intermediate 39A using Method IX. HRMS (M+H) calcd for $C_{19}H_{20}NO_4$: 326.1392; found: 326.1396. $^1$H NMR and $^{13}$C NMR show a mixture of rotamers at room temperature. $^1$H NMR (500 MHz, CDCl$_3$) δ: 2.80 (s), 2.90 (s), 3.86 (s), 3.89 (s), 3.92 (s), 4.51 (s), 4.68 (s), 6.12 (s), 6.21 (s), 7.18–7.46 (overlapping m). $^{13}$C NMR (125 MHz, CDCl$_3$) δ: 33.53, 34.76, 48.13, 51.34, 52.88, 52.94, 53.67, 93.48, 93.52, 126.43, 127.41, 127.47, 127.55, 127.62, 127.81, 127.96, 128.13, 128.39., 128.62, 128.92, 129.05, 130.30, 130.49, 132.90, 133.29, 140.09, 140.44, 141.70, 142.05, 159.32, 159.49, 163.28, 163.36, 170.96, 171.25.

Compound 39

3-(Biphenyl-2-ylmethyl-methyl-carbamoyl)-2-hydroxy-acrylic acid

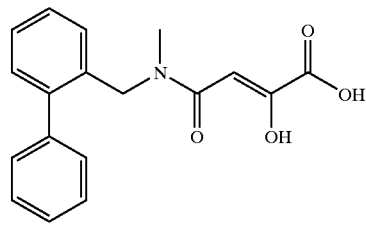

Compound 39 was prepared from Intermediate 39B using Method XI. HRMS (M−H) calcd for $C_{18}H_{16}NO_4$: 310.1079; found: 310.1074. $^1$H NMR and $^{13}$C NMR show a mixture of rotamers at room temperature. $^1$H NMR (500 MHz, CDCl$_3$) δ: 2.80 (s), 2.91 (s), 4.52 (s), 4.69 (s), 6.16 (s), 6.27 (s), 7.18–7.45 (overlapping m). $^{13}$C NMR (125 MHz, CDCl$_3$) δ: 33.70, 34.82, 48.33, 51.50, 93.51, 93.79, 126.58, 127.45, 127.61, 127.66, 127.94, 128.01, 128.15, 128.43, 128.68, 128.90, 129.03, 130.36, 130.56, 132.63, 133.02, 140.01, 140.38, 141.80, 142.09, 158.63, 159.02, 165.27, 170.88, 171.11.

EXAMPLE 40

Intermediate 40A

N-(3-Fluoro-benzyl)-N-methyl-acetamide

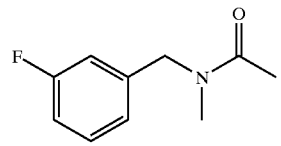

Intermediate 40A was prepared from 3-fluorobenzoyl chloride using Methods II and IV. HRMS (M+H) calcd for $C_{10}H_{13}FNO$: 182.0981; found: 182.0982. $^1$H NMR and $^{13}$C NMR show a mixture of rotamers at room temperature. $^1$H NMR (500 MHz, CDCl$_3$) δ: 2.07 (s), 2.10 (s), 2.87 (s), 2.88 (s), 4.45 (s), 4.51 (s), 6.80–7.28 (overlapping m). $^{13}$C NMR (125 MHz, CDCl$_3$) δ: 21.68, 22.06, 34.08, 35.95, 50.49, 50.50, 54.08, 54.09, 113.47, 113.64, 114.45, 114.62, 114.81, 114.91, 114.98, 115.08, 122.08, 122.10, 123.76, 123.79, 130.34, 130.41, 130.85, 130.91, 139.60, 139.66, 140.26, 140.32, 162.33, 162.57, 164.29, 164.54, 171.08, 171.24.

Intermediate 40B

3-[(3-Fluoro-benzyl)-methyl-carbamoyl]-2-hydroxy-acrylic acid methyl ester

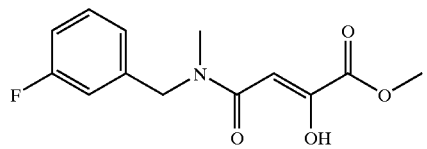

Intermediate 40A was prepared from Intermediate 40A using Method IX. HRMS (M+H) calcd for $C_{13}H_{15}NO_4F$: 268.0985; found: 268.0987. $^1$H NMR and $^{13}$C NMR show a mixture of rotamers at room temperature. $^1$H NMR (500 MHz, CDCl$_3$) δ: 3.03 (s), 3.86 (s), 3.90 (s), 4.58 (s), 4.65 (s), 6.27 (s), 6.31 (s), 6.99 (m), 7.31 (m). $^{13}$C NMR (125 MHz, CDCl$_3$) δ: 33.68, 35.02, 50.26, 52.82, 52.99, 93.19, 93.46, 113.54, 113.72, 114.68, 114.85, 115.00, 115.17, 122.14, 123.44, 123.46, 130.36, 130.42, 130.72, 130.79, 138.80, 138.85, 159.78, 162.10, 163.24, 164.07, 171.05, 171.30.

Compound 40

3-[(3-Fluoro-benzyl)-methyl-carbamoyl]-2-hydroxy-acrylic acid

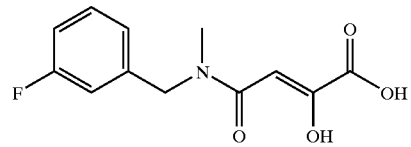

Compound 40 was prepared from Intermediate 40B using Method XI. HRMS (M−H) calcd for $C_{12}H_{11}NO_4F$: 252.0672.; found: 252.0668. $^1$H NMR and $^{13}$C NMR show a mixture of rotamers at room temperature. $^1$H NMR (500 MHz, CDCl$_3$) δ: 3.04 (s), 4.59 (s), 4.65 (s), 6.35 (s), 6.38 (s), 6.87–7.03 (overlapping m), 7.33 (m). $^{13}$C NMR (125 MHz, CDCl$_3$) δ: 33.90, 35.11, 50.43, 52.94, 93.61, 93.84, 113.55, 113.73, 114.73, 114.78, 114.90, 114.95, 115.10, 115.26, 122.19, 123.49, 130.42, 130.48, 130.80, 130.68, 137.99, 138.50, 138.56, 159.06, 162.09, 162.24, 164.06, 165.46, 170.94, 171.20.

EXAMPLE 41

Intermediate 41A

N-(4-Fluoro-naphthalen-1-ylmethyl)-N-methyl-acetamide

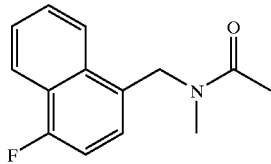

Intermediate 41A was prepared from 4-fluoro-naphthalene-1-carboxylic acid using Methods II and IV. HRMS (M+H) calcd for C$_{14}$H$_{15}$FNO: 232.1138; found: 232.1135. $^1$H NMR and $^{13}$C NMR show a mixture of rotamers at room temperature. $^1$H NMR (500 MHz, CDCl$_3$) δ: 2.13 (s), 2.17 (s), 2.82 (s), 3.04 (s), 4.94 (s), 5.01 (s), 7.06–8.19 (overlapping m). $^{13}$C NMR (125 MHz, CDCl$_3$) δ: 21.29, 22.07, 34.26, 34.80, 47.99, 51.78, 108.43, 108.59, 108.90, 109.06, 121.10, 121.15, 121.67, 121.71, 122.04, 122.06, 122.49, 122.56, 124.04, 124.13, 124.15, 126.32, 126.33, 126.44, 126.97, 127.03, 127.14, 127.17, 127.53, 127.57, 128.65, 128.68, 131.88, 132.96, 133.00, 157.52, 157.81, 159.53, 159.81, 170.55, 171.58.

Intermediate 41B

3-[(4-Fluoro-naphthalen-1-ylmethyl)-methyl-carbamoyl]-2-hydroxy-acrylic acid methyl ester

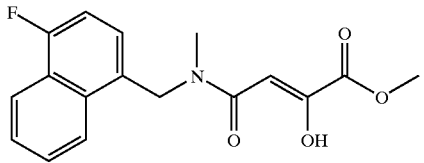

Intermediate 41B was prepared from Intermediate 41A using Method IX. HRMS (M+H) calcd for C$_{17}$H$_{17}$NO$_4$F: 318.1142; found: 318.1144. $^1$H NMR and $^{13}$C NMR show a mixture of rotamers at room temperature. $^1$H NMR (500 MHz, CDCl$_3$) δ: 2.93 (s), 3.09 (s), 3.81 (s), 3.90 (s), 5.02 (s), 5.09 (s), 6.22 (s), 6.30 (s) 7.11 (m), 7.28 (m), 7.6 (m), 7.85 (d, J=8), 8.05 (m), 8.16 (m), 8.19 (m). $^{13}$C NMR (125 MHz, CDCl$_3$) δ: 33.90, 34.09, 47.95, 50.85, 52.93, 52.99, 93.31, 93.76, 108.56, 108.72, 108.92, 109.08, 121.32, 121.36, 121.74, 121.78, 122.10, 123.33, 123.40, 123.60, 123.62, 124.11, 124.43, 126.51, 126.57, 126.99, 127.06, 127.37, 127.41, 127.76, 127.80, 132.80, 132.84, 158.02, 159.75, 159.88, 160.03, 163.19, 163.29, 170.73, 171.76.

Compound 41

3-[(4-Fluoro-naphthalen-1-ylmethyl)-methyl-carbamoyl]-2-hydroxy-acrylic acid

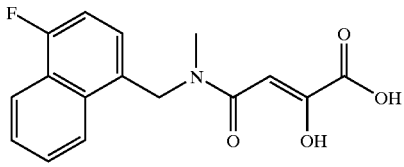

Compound 41 was prepared from Intermediate 41B using Method XI. HRMS (M–H) calcd for C$_{16}$H$_{14}$NO$_4$F: 302.0829; found: 302.0821. $^1$H NMR shows a mixture of rotamers at room temperature. $^1$H NMR (500 MHz, CDCl$_3$) δ: 3.00 (s), 3.04 (s), 5.08 (s), 5.20 (s), 6.17 (s), 6.31 (s), 7.11 (m), 7.33 (m), 7.40 (m), 7.69 (m), 8.12 (m).

EXAMPLE 42

Intermediate 42A

N-(4-Fluoro-benzyl)-N-(2-methoxy-ethyl)-acetamide

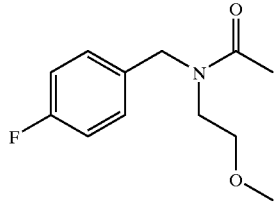

Intermediate 42A was prepared from 4-fluorobenzylamine and 1-bromo-2-methoxy ethane using Method VI. HRMS (M+H) calcd for C$_{12}$H$_{17}$FNO$_2$: 226.1243; found: 226.1244. $^1$H NMR and $^{13}$C NMR show a mixture of rotamers at room temperature. $^1$H NMR (500 MHz, CDCl$_3$) δ: 2.17 (s), 2.24 (s), 3.30 (s), 3.31 (s), 3.43 (s), 3.55 (s), 4.63 (s), 4.64 (s), 6.98–7.23 (overlapping m). $^{13}$C NMR (125 MHz, CDCl$_3$) δ: 21.25, 21.32, 46.08, 47.87, 48.46, 52.91, 58.85, 59.10, 70.25, 71.05, 115.40, 115.57, 115.82, 115.99, 127.92, 127.98, 129.73, 129.80, 132.09, 132.12, 132.96, 132.98, 158.91, 159.23, 161.26, 161.28, 163.22, 163.24, 172.34, 172.61.

Intermediate 42B

3-[(4-Fluoro-benzyl)-(2-methoxy-ethyl)-carbamoyl]-2-hydroxy-acrylic acid methyl ester

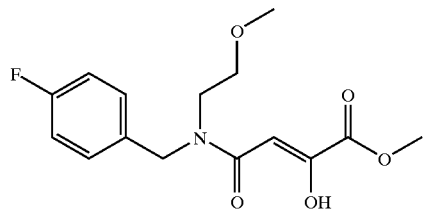

Intermediate 42B was prepared from Intermediate 42A using Method IX. HRMS (M+H) calcd for C$_{15}$H$_{19}$NO$_5$F: 312.1247; found: 312.1256. $^1$H NMR and $^{13}$C NMR show a mixture of rotamers at room temperature. $^1$H NMR (500

MHz, CDCl₃) δ:3.32 (s), 3.58 (m), 3.85 (s), 3.89 (s), 4.67 (s), 4.69 (s), 6.25 (s), 6.31 (s), 7.03 (m), 7.15 (m), 7.24 (m). $^{13}$C NMR (125 MHz, CDCl₃) δ: 45.84, 46.90, 48.87, 51.79, 52.97, 58.95, 59.16, 70.81, 70.89, 93.64, 93.89, 115.53, 115.70, 115.82, 115.99, 128.27, 128.33, 129.70, 129.77, 131.84, 131.86, 132.54, 132.56, 159.54, 159.83, 161.34, 161.38, 163.21, 163.29, 163.34, 171.17, 171.43.

Compound 42

3-[(4-Fluoro-benzyl)-(2-methoxy-ethyl)-carbamoyl]-2-hydroxy-acrylic acid

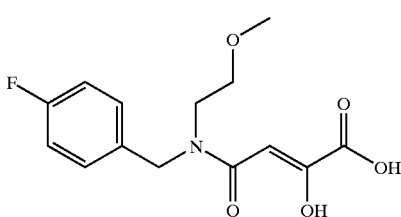

Compound 42 was prepared from Intermediate 42B using Method XI. HRMS (M−H) calcd for C₁₄H₁₅NO₅F: 296.0934; found: 296.0940. $^1$H NMR shows a mixture of rotamers at room temperature. $^1$H NMR (500 MHz, CDCl₃) δ: 3.22 (s), 3.45 (m), 3.57 (m), 4.64 (s), 4.73 (s), 6.17 (s), 6.32 (s), 7.15–7.33 (overlapping m).

EXAMPLE 43

Intermediate 43A

N-(4-Fluoro-benzyl)-N-(3-phenyl-propyl)-acetamide

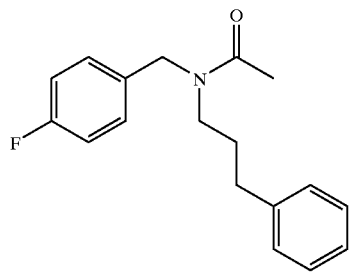

4-Fluorobenzylamine (11.4 g, 91 mmol) was dissolved in 910 mL of CH₂Cl₂. To this was added 910 mL of satd NaHCO₃ followed by acetyl chloride (23.4 mL, 329 mmol) stir 1 h. The organic layer was separated, washed with satd NaCl, dried over Na₂SO₄, filtered and solvent removed to yield 8.4 grams of N-(4-fluoro-benzyl)-acetamide.

N-(4-fluoro-benzyl)-acetamide (697 mg, 4.17 mmol) was suspended in toluene and treated with 668 mg of 60% NaH (mineral oil) followed by (3-bromopropyl)-benzene (1.27 mL, 8.34 mmol) and the resulting mixture stirred overnight. The mixture was filtered and the solvent removed. The crude product was purified by preparative HPLC (C₁₈, MeOH/H₂O-0.1% TFA) to yield 221 mg (19% yield) N-(4-Fluoro-benzyl)-N-(3-phenyl-propyl)-acetamide. HRMS (M+H) calcd for C₁₈H₂₁FNO: 286.1607; found: 286.1603. $^1$H NMR and $^{13}$C NMR show a mixture of rotamers at room temperature. $^1$H NMR (500 MHz, CDCl₃) δ: 1.89 (m), 2.11 (s), 2.16 (s), 2.60 (t, J=7), 3.19 (dd, J=8, 8), 3.41 (dd, J=8, 8), 4.46 (s), 4.54 (s), 6.96–7.32 (overlapping m). $^{13}$C NMR (125 MHz, CDCl₃) δ: 20.67, 21.21, 28.71, 29.53, 32.77, 33.14, 46.21, 47.25, 48.04, 51.60, 115.48, 115.65, 115.95, 116.12, 116.22, 126.04, 126.44, 128.01, 128.07, 128.28, 128.46, 128.68, 129.94, 130.01, 131.57, 131.59, 132.61, 132.64, 140.32, 141.19, 158.96, 159.28, 161.32, 161.37, 163.28, 163.34, 172.14, 172.46.

Intermediate 43B

3-[(4-Fluoro-benzyl)-(3-phenyl-propyl)-carbamoyl]-2-hydroxy-acrylic acid methyl ester

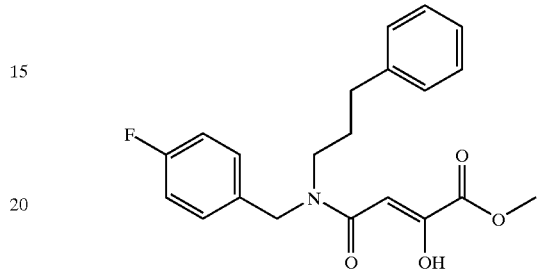

Intermediate 43B was prepared from Intermediate 43A using Method IX. HRMS (M+H) calcd for C₂₁H₂₃NO₄F: 372.1611; found: 372.1618. $^1$H NMR and $^{13}$C NMR show a mixture of rotamers at room temperature. $^1$H NMR (500 MHz, CDCl₃) δ:1.92 (m), 2.62 (t, J=7), 3.26 (dd, J=8, 8), 3.44 (dd, J=8, 8), 3.86 (s), 3.89 (s), 4.50 (s), 4.57 (s), 6.17 (s), 6.24 (s), 6.97–7.33 (overlapping m). $^{13}$C NMR (125 MHz, CDCl₃) δ: 28.91, 29.89, 32.75, 33.18, 45.90, 46.63, 48.08, 50.58, 52.99, 93.57, 115.56, 115.73, 115.90, 116.08, 126.11, 126.37, 128.27, 128.32, 128.39, 128.50, 128.68, 129.80, 129.87, 131.59, 131.62, 132.43, 132.46, 140.30, 141.07, 159.78, 159.86, 161.35, 161.44, 163.27, 163.31, 163.40, 170.78, 171.20.

Compound 43

3-[(4-Fluoro-benzyl)-(3-phenyl-propyl)-carbamoyl]-2-hydroxy-acrylic acid

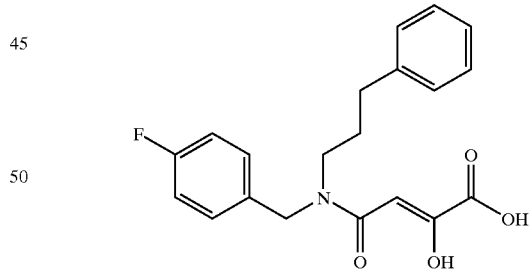

Compound 43 was prepared from Intermediate 43B using Method XI. HRMS (M−H) calcd for C₂₀H₁₉NO₄F: 356.1298; found: 356.1305. $^1$H NMR and $^{13}$C NMR show a mixture of rotamers at room temperature. $^1$H NMR (500 MHz, CDCl₃) δ: 1.91 (m), 2.64 (m), 3.26 (dd, J=8, 8), 3.45 (dd, J=7, 7). 4.53 (s), 4.57 (s), 6.24 (s), 6.31 (s), 6.97–7.32 (overlapping m). $^{13}$C NMR (125 MHz, CDCl₃) δ 28.84, 29.88, 32.71, 33.14, 46.08, 46.70, 48.26, 50.68, 93.54, 93.66, 115.62, 115.79, 115.98, 116.15, 126.16, 126.46, 128.24, 128.27, 128.36, 128.42, 128.52, 128.74, 128.83, 129.85, 129.92, 131.29, 132.15, 132.17, 140.15, 140.96, 159.14, 159.31, 161.41, 163.37, 165.03, 170.70, 171.16.

EXAMPLE 44

Intermediate 44A

N-Isopropyl-N-(3-phenyl)-acetamide

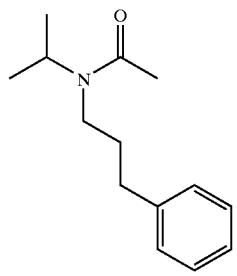

Intermediate 44A was prepared from (3-bromo-propyl)-benzene and isopropyl amine using Method VI. $^1$H NMR shows a mixture of rotamers at room temperature. $^1$H NMR (500 MHz, CDCl$_3$) δ: 1.09 (d, J=7), 1.13 (d, J=7), 1.90 (m), 1.98 (s), 2.10 (s), 2.64 (t, J=7), 3.12 (m), 3.19 (m), 3.96 (heptet, J=7), 4.65 (heptet, J=7), 7.16–7.32 (overlapping m).

Intermediate 44B

2-Hydroxy-3-[isopropyl-(3-phenyl-propyl)-carbamoyl]-acrylic acid methyl ester

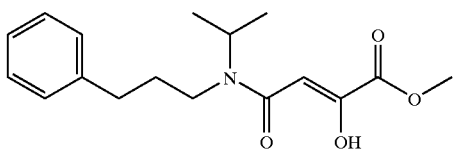

Intermediate 44A was prepared from Intermediate 44B using Method IX. HRMS (M+H) calcd for $C_{17}H_{24}NO_4$: 306.1705; found: 306.1699. $^1$H NMR and $^{13}$C NMR show a mixture of rotamers at room temperature. $^1$H NMR (500 MHz, CDCl$_3$) δ: 1.13 (d, J=7), 1.18 (d, J=7), 1.94 (m), 2.67 (m), 3.18 (m), 3.29 (m), 3.88 (s), 4.14 (septet, J=7), 4.70 (septet, J=7), 6.06 (s), 6.29 (s), 7.14–7.33 overlapping m). $^{13}$CNMR (125 MHz, CDCl$_3$) 20.30, 21.27, 30.84, 32.34, 33.21, 33.61, 40.96, 42.39, 45.50, 48.58, 52.89, 93.60, 94.52, 126.02, 126.34, 126.61, 128.28, 128.34, 128.44, 128.52, 128.67, 128.74, 139.47, 140.40, 141.30, 142.04, 159.39, 159.58, 163.50, 163.65, 170.38, 170.46.

Compound 44

2-Hydroxy-3-[isopropyl-(3-phenyl-propyl)-carbamoyl]-acrylic acid

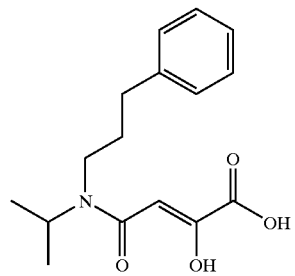

Compound 44 was prepared from Intermediate 44B using Method XI. HRMS (M+H) calcd for $C_{16}H_{22}NO_4$: 292.1549; found: 292.1550. $^1$H NMR and $^{13}$C NMR show a mixture of rotamers at room temperature. $^1$H NMR (500 MHz, CDCl$_3$) δ: 1.14 (d, J=7), 1.19 (d, J=7), 1.96 (m), 2.67 (m), 3.18 (m), 3.30 (m), 4.14 (heptet, J=7), 4.70 (heptet, J=7), 6.11 (s), 6.35 (s), 7.16–7.34 (overlapping m). $^{13}$C NMR (125 MHz, CDCl$_3$) δ: 20.28, 20.80, 21.20, 30.75, 32.28, 33.16, 33.57, 41.14, 42.47, 45.83, 48.79, 93.15, 94.40, 117.13, 126.08, 126.42, 128.27, 128.33, 128.47, 128.74, 140.24, 141.84, 159.15, 159.57, 165.66, 165.77, 170.41, 177.45.

EXAMPLE 45

Intermediate 45A

N-(4-Chloro-benzyl)-N-methyl-acetamide

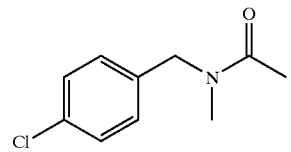

Intermediate 45A was synthesized from 4-chlorobenzylamine using the same procedure as Intermediate 34A. HRMS (M+H) calcd for $C_{10}H_{13}ClNO$: 198.0686; found: 198.0686. $^1$H NMR and $^{13}$C NMR show a mixture of rotamers at room temperature. $^1$H NMR (500 MHz, CDCl$_3$) δ: 2.13 (s), 2.14 (s), 2.90 (s), 2.91 (s) 4.84 (s), 4.53 (s), 7.09–7.34 (overlapping m). $^{13}$C NMR (125 MHz, CDCl$_3$) δ: 21.46, 21.84, 33.70, 35.58, 50.04, 53.67, 127.69, 128.75, 129.16, 129.43, 133.18, 133.51, 135.09, 135.94, 170.78, 170.93.

Intermediate 45B

3-[(4-Chloro-benzyl)-methyl-carbamoyl]-2-hydroxy-acrylic acid methyl ester

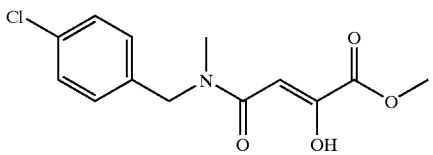

Intermediate 45A was prepared from Intermediate 45A using Method IX. HRMS (M+H) calcd for $C_{13}H_{15}NO_4Cl$:

284.0690; found: 284.0696. ¹H NMR and ¹³C NMR show a mixture of rotamers at room temperature. ¹H NMR (500 MHz, CDCl₃) δ: 3.01 (s) 3.87 (s), 3.90 (s), 4.56 (s), 4,62 (s), 6.29 (s), 7.12–7.31 (overlapping m). ¹³C NMR (125 MHz, CDCl₃) δ: 33.57, 34.90, 50.08, 52.70, 53.00, 93.21, 93.49, 117.03, 117.12, 128.01, 129.00, 129.29, 129.37, 133.70, 134.08, 134.78, 159.75, 163.24, 170.99.

Compound 45

3-[(4-Chloro-benzyl)-methyl-carbamoyl]-2-hydroxy-acrylic acid

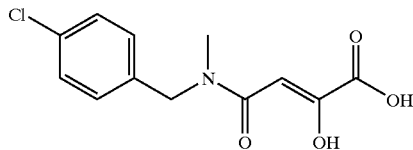

Compound 45 was prepared from Intermediate 45B using Method XI. HRMS (M+H) calcd for $C_{12}H_{13}NO_4Cl$: 270.0533; found: 270.0536. ¹H NMR shows a mixture of rotamers at room temperature. ¹H NMR (500 MHz, CDCl₃) δ: 3.02 (s), 4.56 (s), 4.63 (s), 6.36 (s), 7.11–7.36 (overlapping m).

EXAMPLE 46

Intermediate 46A

N-[3-(4-Fluoro-phenyl)-propyl]-N-methyl-acetamide

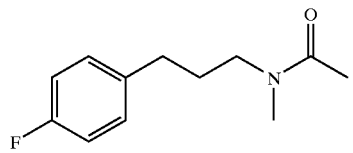

Intermediate 46A was prepared from 3-(4-fluoro-phenyl)-propionic acid using Method II and IV. HRMS (M+H) calcd for $C_{12}H_{16}FNO$: 210.1294; found: 210.1292. ¹H NMR and ¹³C NMR show a mixture of rotamers at room temperature. ¹H NMR (500 MHz, CDCl₃) δ: 1.83 (m), 2.00 (s), 2.05 (s), 2.58 (m), 2.90 (s), 2.94 (s), 3.26 (dd, J=7, 7), 3.39 (dd, J=7, 7), 6.96 (m), 7.12 (m). ¹³C NMR (125 MHz, CDCl₃) δ: 21.19, 21.96, 28.96, 29.87, 32.02, 32.36, 33.17, 36.09, 47.15, 50.08, 115.00, 115.17, 115.28, 115.45, 129.55, 129.59, 129.61, 129.65, 136.40, 137.28, 160.30, 160.46, 162.24, 162.40, 170.37, 170.54.

Intermediate 46B

3-{[3-(4-Fluoro-phenyl)-propyl]-methyl-carbamoyl}-2-hydroxy-acrylic acid methyl ester

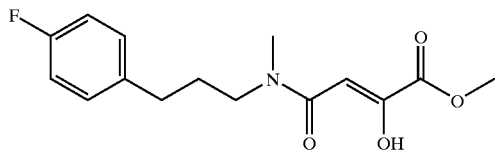

Intermediate 46B was prepared from Intermediate 45A using Method IX. HRMS (M+H) calcd for $C_{15}H_{19}NO_4F$: 296.1298; found: 296.1302. ¹H NMR and ¹³C NMR show a mixture of rotamers at room temperature. ¹H NMR (500 MHz, CDCl₃) δ: 1.89 (m), 2.60 (m), 2.98 (s), 3.02 (s), 3.33 (m), 3.45 (m), 3.86 (s), 6.09 (s), 6.20 (s), 6.96 (m), 7.12 (m). ¹³C NMR (125 MHz, CDCl₃) δ: 28.85, 29.88, 31.83, 32.28, 33.54, 35.35, 47.30, 49.25, 52.88, 93.36, 93.64, 115.11, 115.27, 115.32, 115.49, 129.59, 129.65, 136.03, 136.05, 136.80, 136.82, 159.29, 159.39, 160.38, 160.50, 162.32, 162.44, 163.33, 163.36, 170.62, 170.74.

Compound 46

3-{[3-(4-Fluoro-phenyl)-propyl]-methyl-carbamoyl}-2-hydroxy-acrylic acid

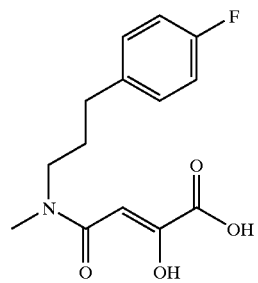

Compound 46 was prepared from Intermediate 46B using Method XI. HRMS (M+H) calcd for $C_{14}H_{17}NO_4F$: 282.1142; found: 282.1148. ¹H NMR and ¹³C NMR show a mixture of rotamers at room temperature. ¹H NMR (500 MHz, CDCl₃) δ: 1.85–1.96 (overlapping m), 2.61 (m), 3.01 (s), 3.04 (s), 3.36 (dd, J=7, 7), 3.47 (dd, J=7, 7), 6.20 (s), 6.28 (s), 6.96 (m), 7.13 (m). ¹³C NMR (125 MHz, CDCl₃) δ: 28.80, 29.89, 31.84, 32.26, 33.81, 35.49, 44.81, 47.55, 49.49, 93.54, 93.64, 115.15, 115.32, 115.38, 115.55, 129.58, 129.64, 135.95, 136.70, 142.04, 158.81, 159.02, 160.41, 160.54, 162.35, 162.48, 165.43, 170.54, 171.68.

EXAMPLE 47

Intermediate 47A

N-(4-Fluoro-benzyl)-N-(2-phenoxy-ethyl)-acetamide

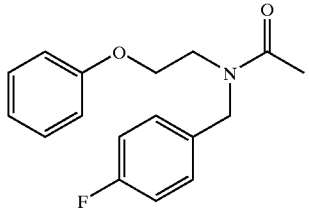

Intermediate 47A was prepared from (2-chloro-ethoxy)-benzene and 4-fluorobenzyl amine using Method VI. ¹H NMR and ¹³C NMR show a mixture of rotamers at room temperature. ¹H NMR (500 MHz, CDCl₃) δ: 2.13 (s), 2.29 (s), 3.64 (t, J=5), 3.73 (t, J=5), 4.02 (t, J=5), 4.17 (t, J=5), 4.67 (s), 4.69 (s), 6.82–7.30 (overlapping m). ¹³C NMR (125 MHz, CDCl₃) δ: 21.77, 21.81, 45.73, 47.12, 48.00, 53.17, 65.35, 66.50, 114.34, 115.38, 115.56, 115.79, 115.96, 120.99, 121.42, 128.03, 128.09, 129.55, 129.63, 129.67, 129.74, 132.60, 132.62, 133.38, 133.41, 158.14, 158.46, 161.20, 161.26, 163.15, 163.21, 171.26, 171.32.

87

Intermediate 47B

3-[(4-Fluoro-benzyl)-(2-phenoxy-ethyl)-carbamoyl]-2-hydroxy-acrylic acid methyl ester

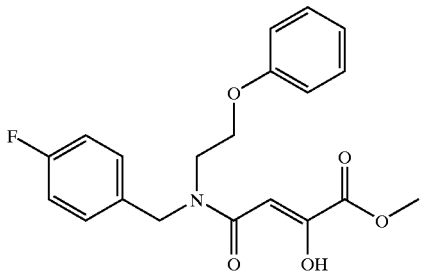

Intermediate 47B was prepared from Intermediate 47A using Method IX. HRMS (M+H) calcd for $C_{20}H_{21}NO_5F$: 374.1404; found: 374.1412. $^1$H NMR (500 MHz, CDCl$_3$) δ: 3.71 (t, J=5), 3.80 (t, J=5), 3.85 (s), 3,90 (s), 4.12 (t, J=5), 4.20 (t, J=50, 4.76 (s), 6.27 (s), 6.44 (s), 6.86 (m), 6.99 (m), 7.17 (m), 7.29 (m). $^{13}$C NMR (125 MHz, CDCl$_3$) δ: 45.82, 46.37, 48.85, 52.23, 53.00, 53.01, 65.74, 66.14, 93.55, 93.94, 114.33, 115.65, 115.82, 115.91, 116.08, 117.05, 117.11, 121.24, 121.53, 128.41, 128.47, 129.61, 129.66, 129.79, 129.85, 131.70, 131.72, 132.35, 132.37, 157.95, 158.23, 159.68, 159.99, 161.41, 161.45, 163.11, 163.25, 163.36, 163.41, 171.37, 171.60.

Compound 47

3-{(4-Fluoro-benzyl)-[2-(4-fluoro-phenoxy)-ethyl]-carbamoyl}-2-hydroxy-acrylic acid

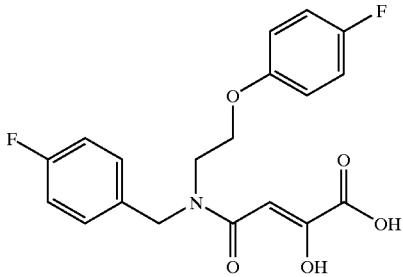

Compound 47 was prepared from Intermediate 47B using Method XI. HRMS (M+H) calcd for $C_{19}H_{18}NO_5F_2$: 378.1153; found: 378.1151. $^1$H NMR shows a mixture of rotamers at room temperature. $^1$H NMR (500 MHz, CDCl$_3$) δ: 3.71 (m), 3.83 (m), 4.04 (m), 4.12 (m), 4.75 (s), 4.76 (s), 6.34 (s), 6.51 (s), 6.75–7.27 (overlapping m).

88

EXAMPLE 48

Intermediate 48A

N-(3-Bromo-4-fluoro-benzyl)-N-methyl-acetamide

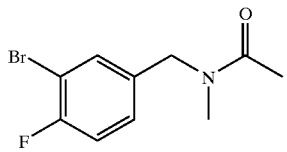

Intermediate 48A was prepared from 3-bromo-4-fluoro-benzoic acid using Methods II and IV. HRMS (M+H) calcd for $C_{10}H_{12}BrFNO$: 260.0086; found: 260.0085. $^1$H NMR and $^{13}$C NMR show a mixture of rotamers at room temperature. $^1$H NMR (500 MHz, CDCl$_3$) δ: 2.13 (s), 2.14 (s), 2.91 (s0, 2.92 (s), 4.47 (s), 4.50 (s), 7.03–7.43 (overlapping m). $^{13}$C NMR (125 MHz, CDCl$_3$) δ: 21.44, 21.80, 33.68, 35.65, 49.61, 53.13, 99.71, 109.05, 109.21, 109.84, 116.45, 116.63, 116.90, 117.07, 126.81, 126.87, 128.64, 128.70, 131.38, 132.96, 134.03, 134.91, 134.94, 157.43, 157.55, 159.39, 159.52, 170.86.

Intermediate 48B

3-[(3-Bromo-4-fluoro-benzyl)-methyl-carbamoyl]-2-hydroxy-acrylic acid methyl ester

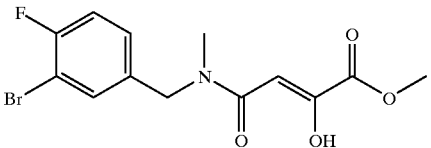

Intermediate 48B was prepared from Intermediate 48A using Method IX. HRMS (M+H) calcd for $C_{13}H_{14}NO_4FBr$: 346.0090; found: 346.0092. $^1$H NMR and $^{13}$C NMR show a mixture of rotamers at room temperature. $^1$H NMR (500 MHz, CDCl$_3$) δ: 3.01 (s), 3.02 (s), 3.70 (s), 3.89 (s), 4.54 (s), 4.59 (s), 6.26 (s), 6.29 (s), 7.10 (m), 7.19 (m), 7.36 (m), 7.44 (m). $^{13}$C NMR (125 MHz, CDCl$_3$) δ: 33.55, 34.95, 49.60, 52.13, 53.01, 92.98, 93.43, 109.32, 109.48, 109.78, 109.95, 116.72, 116.89, 117.04, 117.08, 117.72, 117.21, 127.14, 127.20, 128.62, 128.68, 131.74, 133.02, 133.80, 133.84, 157.68, 159.65, 159.82, 159.97, 163.17, 171.02, 171.21.

Compound 48

3-[(3-Bromo-4-fluoro-benzyl)-methyl-carbamoyl]-2-hydroxy-acrylic acid

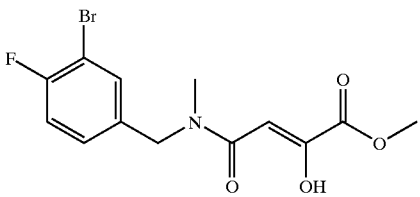

Compound 48 was prepared from Intermediate 48B using Method XI. HRMS (M−H) calcd for $C_{12}H_{10}NO_4BrF$: 329.9777; found: 329.9784. $^1$H NMR and $^{13}$C NMR show a mixture of rotamers at room temperature. $^1$H NMR (500 MHz, CDCl$_3$) δ: 3.03 (s), 3.04 (s), 4.55 (s), 4.60 (s), 6.34 (s), 6.36 (s), 7.10 (m), 7.18 (m), 7.37 (m), 7.45 (m). $^{13}$C NMR (125 MHz, CDCl$_3$) δ: 33.75, 35.04, 49.78, 52.23, 93.29, 93.75, 109.38, 109.55, 116.77, 116.95, 117.28, 127.26, 128.66, 128.72, 131.78, 132.76, 133.07, 133.51, 133.54, 157.75, 159.05, 159.72, 165.10, 170.92, 171.12.

EXAMPLE 49

Intermediate 49A

N-(4-Fluoro-benzyl)-N-[2-(4-fluoro-phenoxy)-ethyl]-acetamide

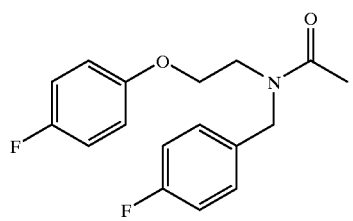

Intermediate 49A was prepared from 1-(2-Bromo-ethoxy)-4-fluoro-benzene and 4-fluorobenzylamine using Method VI. HRMS (M+H) calcd for $C_{17}H_{18}F_2NO$: 306.1351; found: 306.1298. $^1$H NMR and $^{13}$C NMR show a mixture of rotamers at room temperature. $^1$H NMR (500 MHz, CDCl$_3$) δ: 2.13 (s), 2.28 (s), 3.63 (t, J=5), 3.71 (t, J=5), 3.96 (t, J=5), 4.11 (t, J=5), 6.74–7.24 (overlapping m). $^{13}$C NMR (125 MHz, CDCl$_3$) δ: 21.75, 21.80, 45.78, 47.15, 48.04, 53.18, 66.11, 67.07, 115.24, 115.31, 115.35, 115.41, 115.56, 115.79, 115.81, 115.92, 115.98, 116.10, 127.98, 128.05, 129.64, 129.70, 132.52, 132.54, 133.35, 133.37, 154.28, 154.59, 154.60, 156.39, 156.61, 158.28, 158.52, 161.20, 161.27, 163.16, 163.23, 171.24, 171.35.

Intermediate 49B

3-{(4-Fluoro-benzyl)-[2-(4-fluoro-phenoxy)-ethyl]-carbamoyl}-2-hydroxy-acrylic acid methyl ester

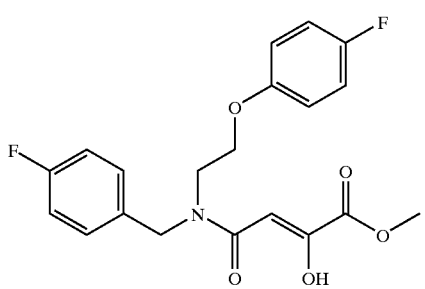

Intermediate 49B was prepared from Intermediate 49A sing Method IX. HRMS (M+H) calcd for $C_{20}H_{20}NO_5F$: 392.1310; found: 392.1319. Anal calcd for $C_{20}H_{19}NO_5F$: C, 61.38; H, 4.89; N, 3.57. found: C, 61.28; H, 4.82; N, 3.50. $^1$H NMR and $^{13}$C NMR show a mixture of rotamers at room temperature. $^1$H NMR (500 MHz, CDCl$_3$) δ: 3.70 (t, J=5), 3.80 (t, J=5), 3.85 (s), 3.90 (s), 4.03 (t, J=5), 4.15 (t J=5), 4.74 (s), 4.75 (s), 6.28 (s), 6.42 (s), 6.78 (m), 6.95–7.07 (overlapping m), 7.24 (m), 7.26 (m). $^{13}$C NMR (125 MHz, CDCl$_3$) δ: 45.88, 46.39, 48.87, 52.25, 53.01, 53.03, 66.43, 66.77, 93.50, 93.88, 115.292, 115.36, 115.43, 115.66, 115.83, 115.87, 115.93, 115.95, 116.06, 116.11, 116.14, 128.36, 128.43, 129.75, 129.82, 131.63, 132.32, 154.08, 154.36, 156.52, 158.42, 158.58, 159.71, 160.04, 161.47, 163.08, 163.24, 163.38, 163.43, 171.37, 171.63.

Compound 49

3-[(4-Fluoro-benzyl)-(2-phenoxy-ethyl)-carbamoyl]-2-hydroxy-acrylic acid

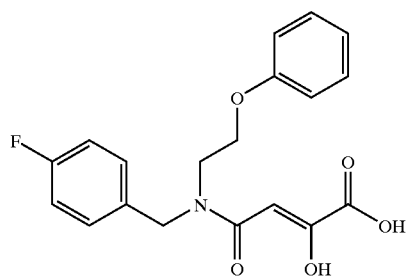

Compound 49 was prepared from Intermediate 49B using Method XI. HRMS (M−H) calcd for $C_{19}H_{17}NO_5F$: 358.1091; found: 358.1098. $^1$H NMR and $^{13}$C NMR show a mixture of rotamers at room temperature. $^1$H NMR (500 MHz, CDCl$_3$) δ: 3.72 (m), 3.82 (m), 4.09 (m), 4.21 (m), 6.35 (s), 6.53 (s), 6.86 (m), 7.04 (overlapping m), 7.17 (m), 7.27 (m). $^{13}$C NMR (125 MHz, CDCl$_3$) δ: 45.97, 46.48, 49.05, 52.33, 65.72, 66.04, 93.74, 94.14, 114.33, 115.71, 115.89, 115.99, 116.16, 121.31, 121.60, 128.43, 128.50, 129.63, 129.68, 129.76, 129.83, 129.89, 131.40, 132.05, 157.88, 158.17, 158.81, 159.15, 161.46, 161.50, 163.42, 163.47, 164.65, 164.77, 171.32, 171.52.

EXAMPLE 50

Intermediate 50A

N-[1-(4-Fluoro-phenyl)-ethyl]-N-methyl-acetamide

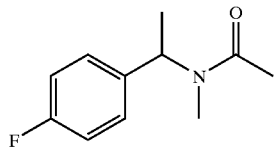

Intermediate 50A was prepared 1-(4-fluoro-phenyl)-ethyl amine using the same method as Intermediate 34A. HRMS (M+H) calcd for $C_{11}H_{15}FNO$: 196.1138; found: 196.1139. $^1$H NMR and $^{13}$C NMR show a mixture of rotamers at room temperature. $^1$H NMR (500 MHz, CDCl$_3$) δ: 1.44 (d, J=7), 1.57 (d, J=7), 2.11 (s), 2.22 (s), 2.63 (s), 5.05 (q, J=7), 6.02

(q, J=7), 7.00 (overlapping m), 7.23 (overlapping m). $^{13}$C NMR (125 MHz, CDCl$_3$) δ: 15.76, 17.72, 21.75, 22.31, 27.57, 30.05, 49.40, 55.15, 115.14, 115.31, 115.51, 115.69, 128.11, 128.86, 135.96, 136.46, 160.98, 161.09, 162.933, 163.06, 170.42, 170.63.

Intermediate 50B

3-{[1-(4-Fluoro-phenyl)-ethyl]-methyl-carbamoyl}-2-hydroxy-acrylic acid methyl ester

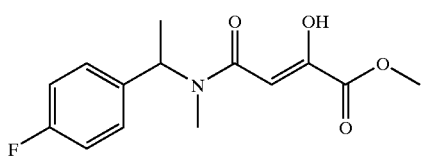

Intermediate 50B was prepared from Intermediate 50A using Method IX. HRMS (M+H) calcd for C$_{14}$H$_{17}$NO$_4$F: 282.1142; found: 282.1141. $^1$H NMR and $^{13}$C NMR show a mixture of rotamers at room temperature. $^1$H NMR (500 MHz, CDCl$_3$) δ: 1.52 (d, J=7), 1.63 (d, J=7), 2.71 (s), 2.72 (s), 3.89 (s), 5.24 (q, J=7), 6.03 (q, J=7), 6.24 (s), 6.45 (s), 7.04 (m), 7.26 (m). $^{13}$C NMR (125 MHz, CDCl$_3$) δ: 15.81, 17.56, 27.69, 29.47, 49.73, 52.97, 54.19, 93.10, 94.04, 115.45, 115.62, 115.70, 115.87, 128.41, 128.47, 128.91, 128.97, 135.34, 135.37, 159.63, 159.96, 161.22, 163.18, 163.34, 163.43, 170.75.

Compound 50

3-{[1-(4-Fluoro-phenyl)-ethyl]-methyl-carbamoyl}-2-hydroxy-acrylic acid

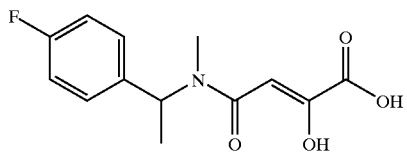

Compound 50 was prepared from Intermediate 50B using Method XI. HRMS (M–H) calcd for C$_{13}$H$_{13}$NO$_4$F: 266.0829; found: 266.0835. $^1$H NMR and $^{13}$C NMR show a mixture of rotamers at room temperature. $^1$H NMR (500 MHz, CDCl$_3$) δ: 1.53 (d, J=7), 1.64 (d, J=7), 2.74 (s), 5.25 (q, J=7), 6.02 (q, J=7), 6.31 (s), 6.52 (s), 7.05 (m), 7.21–7.27 (overlapping m). $^{13}$C NMR (125 MHz, CDCl$_3$) δ: 15.81, 17.54, 27.94, 29.56, 50.09, 54.42, 93.04, 94.09, 115.52, 115.69, 115.77, 115.90, 115.94, 128.43, 128.50, 128.93, 128.99, 134.59, 135.04, 135.07, 159.08, 159.49, 161.28, 163.24, 165.22, 170.66, 170.71.

EXAMPLE 51

Intermediate 51A 2-(2,2-Dimethyl-5-oxo-[1,3]dioxolan-4-ylidene)-N-(4-fluoro-benzyl)-N-[3-(2-fluoro-phenyl)-propyl]-acetamide

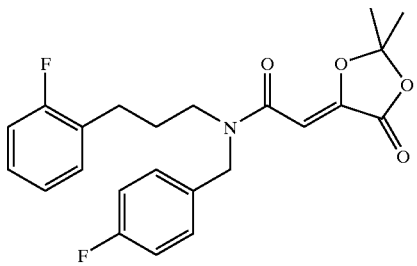

Intermediate 51A was prepared from 4-(Fluoro-benzyl)-[3-(2-fluoro-phenyl)-propyl]-amine hydrochloride using Method XIV. MS (M+H) calcd for C$_{23}$H$_{24}$F$_2$NO$_4$: 416.2; found: 416.0. $^1$H NMR shows a mixture of rotamers at room temperature. $^1$H NMR (300 MHz, CDCl$_3$) δ: 1.71 (s), 1.73 (s), 1.87 (m), 2.62 (m), 3.28 (m), 3.44 (m), 4.53 (s), 4.58 (s), 6.08 (s), 6.93–7.21 (overlapping m).

Compound 51

3-{(4-Fluoro-benzyl)-[3-(2-fluoro-phenyl)-propyl]-carbamoyl}-2-hydroxy-acrylic acid

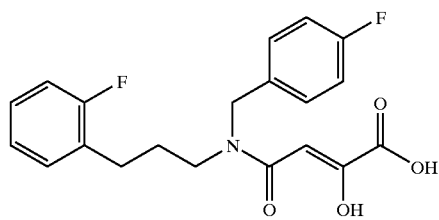

Compound 51 was prepared from Intermediate 51A using Method XVIII. MS (M–H) calcd for C$_{20}$H$_{18}$NO$_4$F$_2$: 372.12; found: 374.01. $^1$H NMR shows a mixture of rotamers at room temperature. $^1$H NMR (500 MHz, d$_6$-MeOD) δ: 1.86 (m), 2.65 (m), 3.34 (m), 3.47 (m), 3.72 (m), 4.61 (s), 4.63 (s), 6.21 (s), 6.29 (s), 6.98–7.26 (overlapping m).

EXAMPLE 52

Intermediate 52A 2-(2,2-Dimethyl-5-oxo[1,3]dioxolan-4-ylidene)-N-(4-fluoro-benzyl)-N-(2-phenyl-cyclopropylmethyl)-acetamide

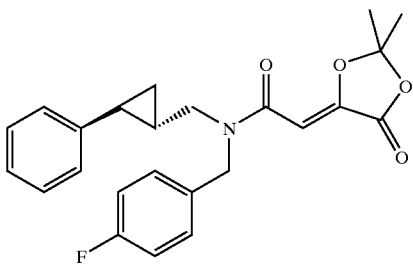

Intermediate 52A was prepared from (4-fluoro-benzyl)-(2-phenyl-cyclopropylmethyl)-amine hydrochloride using Method XIV. MS (M+H) calcd for $C_{24}H_{25}FNO_4$: 410.2; found: 410.1.

Compound 52

3-[(4-Fluoro-benzyl)-(2-phenyl-cyclopropylmethyl)-carbamoyl]-2-hydroxy-acrylic acid

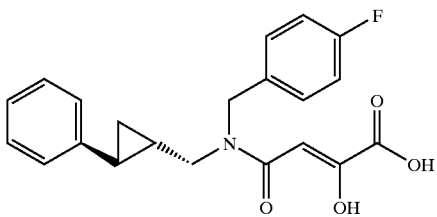

Compound 52 was prepared from Intermediate 52A using Method XVIII. MS (M−H) calcd for $C_{21}H_{19}NO_4F$: 368.13; found: 368.06. $^1$H NMR and $^{13}$C NMR show a mixture of rotamers at room temperature. $^1$H NMR (500 MHz, $d_6$-MeOD) δ: 0.92 (m), 1.28 (m), 1.85 (m), 3.39–3.65 (overlapping m), 4.73 (s), 6.25 (s), 6.46 (s), 6.92–7.29 (overlapping m). $^{13}$C NMR (125 MHz, $d_6$-MeOD) δ: 14.96, 15.19, 22.98, 23.11, 23.41, 23.53, 23.73, 49.73, 49.92, 51.29, 51.99, 52.35, 95.20, 95.24, 116.27, 116.45, 116.51, 116.63, 116.69, 126.64, 126.72, 126.81, 129.35, 129.39, 129.52, 129.58, 130.45, 130.52, 130.84, 130.91, 134.61, 143.28, 143.78, 160.78, 160.82, 162.89, 164.63, 165.51, 165.63, 172.42, 172.95.

EXAMPLE 53

Intermediate 53A 2-(2,2-Dimethyl-5-oxo[1,3]dioxolan-4-ylidene)-N-(4-fluoro-benzyl)-N-naphthalen-2-ylmethyl-acetamide

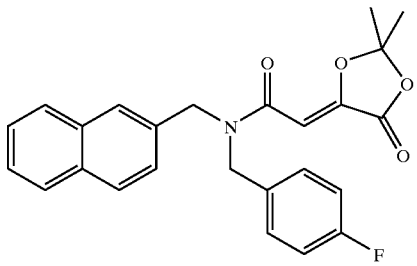

Intermediate 53A was prepared from (4-fluoro-benzyl)-naphthalen-2-ylmethyl-amine hydrochloride using Method XIV. $^1$H NMR shows a mixture of rotamers at room temperature. $^1$H NMR (500 MHz, CDCl$_3$) δ: 1.73 (s), 1.76 (s), 4.50 (s), 4.66 (s), 4.67 (s), 4.79 (s), 6.21 (s), 6.24 (s), 7.00–7.86 (overlapping m).

Compound 53

3-[(4-Fluoro-benzyl)-naphthalen-2-ylmethyl-carbamoyl]-2-hydroxy-acrylic acid

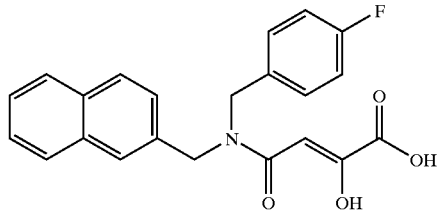

Compound 53 was prepared from Intermediate 53A using Method XVIII. $^1$H NMR shows a mixture of rotamers at room temperature. $^1$H NMR (500 MHz, $d_6$-MeOD) δ: 4.57 (s), 4.70 (s), 4.77 (s), 4.82 (s), 6.39 (s), 6.42 (s), 7.01–7.85 (overlapping m).

EXAMPLE 54

Intermediate 54A 2-(2,2-Dimethl-5-oxo-[1,3]dioxolan-4-ylidene)-N-methyl-N-naphthalen-2-ylmethyl-acetamide

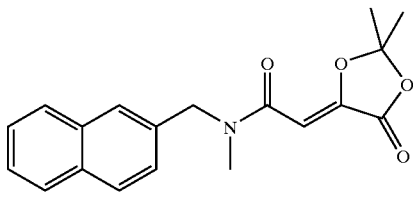

Intermediate 54A was prepared from methyl-naphthalen-2-ylmethyl-amine hydrochloride using Method XVII. $^1$H NMR shows mixture of rotamers at room temperature. $^1$H NMR (500 MHz, CDCl$_3$) δ: 1.69 (s), 1.76 (s), 3.03 (s), 3.05

(s), 4.75 (s), 4.82 (s), 6.21 (s), 6.22 (s), 7.28–7.85 (overlapping m).

Compound 54

2-Hydroxy-3-(methyl-naphthalen-2-ylmethyl-carbamoyl)-acrylic acid

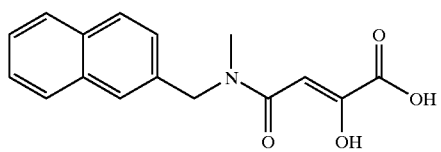

Compound 54 was prepared from Intermediate 54A using Method XVIII. MS (M–H) calcd $C_{16}H_{14}NO_5$: 284.09; found: 284.07. $^1$H NMR shows a mixture of rotamers at room temperature. $^1$H NMR (500 MHz, $d_6$-MeOD) δ: 3.33 (s), 3.34 (s), 4.82 (s), 6.40 (s), 6.44 (s), 7.33–7.88 (overlapping m).

EXAMPLE 55

Intermediate 55A

N-(4-Chloro-phenyl)-2-(2,2-deimethyl-5-oxo-[1,3]-4-ylidene)-N-naphthalen-2-ylmethyl-acetamide

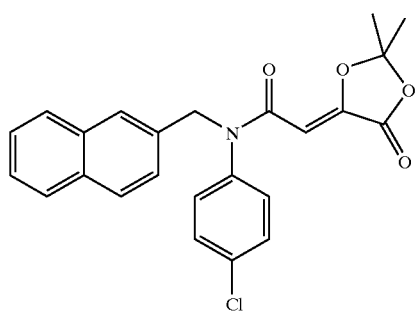

Intermediate 55A was prepared from (4-chloro-phenyl)-naphthalen-2-ylmethyl-amine hydrochloride using Method XVII. MS (M+H) calcd for $C_{24}H_{21}ClNO_4$: 422.1; found: 422.1. $^1$H NMR (500 MHz, $d_6$-MeOD) δ: 1.69 (s, 6), 5.15 (s, 2), 5.62 (s, 1), 7.11–7.82 (overlapping m, 11).

Compound 55

3-[(4-Chloro-phenyl)-naphthalen-2-ylmethyl-carbamoyl]-2-hydroxy-acrylic acid

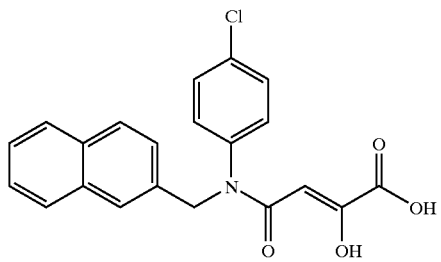

Compound 55 was prepared from Intermediate 55A using Method XVIII. MS (M–H) calcd for $C_{21}H_{15}NO_4Cl$: 380.07; found: 380.07. $^1$H NMR shows a mixture of rotamers at room temperature. $^1$H NMR (500 MHz, DMSO) δ: 5.04 (s), 5.14 (s), 5.59 (br s), 7.23–7.88 (overlapping m).

EXAMPLE 56

Intermediate 56A

N-(4-Chloro-phenyl)-2-(2,2-dimethyl-5-oxo-[1,3] dioxolan-4-ylidene)-N-(3-phenyl-propyl)-acetamide

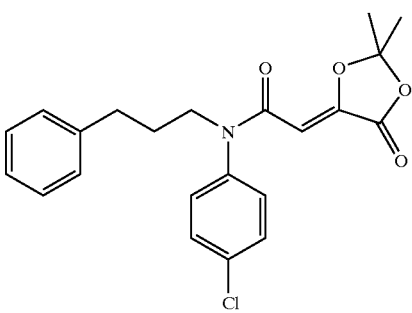

Intermediate 56A was prepared from (4-chloro-phenyl)-(3-phenyl-propyl)-amine hydrochloride using Method XVII. MS (M+H) calcd for $C_{22}H_{23}ClNO_4$: 400.1; found: 400.1.

Compound 56

3-[(4-Chloro-phenyl)-(3-phenyl-propyl)-carbamoyl]-2-hydroxy-acrylic acid

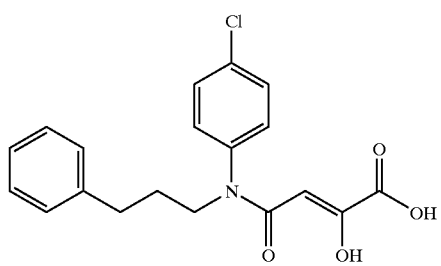

Compound 56 was prepared from Intermediate 56A using Method XVIII. MS (M–H) calcd for $C_{19}H_{17}NO_4Cl$: 358.08; found: 358.02.

EXAMPLE 57

Intermediate 57A

N,N-Bis(4-chloro-benzyl)-acetamide

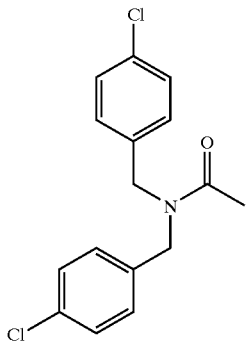

Intermediate 57A was prepared from 4-chlorobenzylamine and 4-chlorobenzylbromide using the same method as intermediate 43A. HRMS (M+H) calcd for $C_{16}H_{16}Cl_2NO$: 308.0609; found: 308.0611. $^1$H NMR (500 MHz, CDCl$_3$) δ: 2.20 (s, 3), 4.39 (s, 2), 4.52 (s, 2), 7.07 (d, 2, J=8), 7.14 (d, 2, J=8), 7.27 (d, 2, J=8), 7.34 (d, 2, J=8). $^{13}$C NMR (125 MHz, CDCl$_3$) δ: 21.70, 47.41, 50.31., 127.78, 128.83, 129.25, 129.72, 133.41, 133.66, 134.67, 135.63, 171.07.

Intermediate 57B

3-[Bis-(4-chloro-benzyl)-carbamoyl]-2-hydroxy-acrylic acid methyl ester

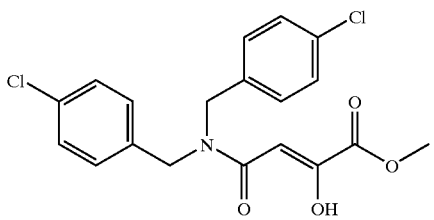

Intermediate 57B was prepared from Intermediate 57A using Method IX. HRMS (M+H) calcd for $C_{19}H_{18}NO4Cl_2$: 394.0613; found: 394.0602. $^1$H NMR (500 MHz, CDCl$_3$) δ: 3.87 (s, 3), 4.46 (s, 2), 4.58 (s, 2), 6.30 (s, 1), 7.08 (d, 2, J=8), 7.16 (d, 2, J=8), 7.31 (d, 2, J=8), 7.34 (d, 2, J=8). $^{13}$C NMR (125 MHz, CDCl$_3$) δ: 47.54, 49.50, 53.05, 93.21, 128.10, 129.04, 129.34, 129.65, 133.79, 133.66, 134.09, 134.58, 160.39, 163.04, 171.46.

Compound 57

3-[Bis-(4-chloro-benzyl)-carbamoyl]-2-hydroxy-acrylic acid

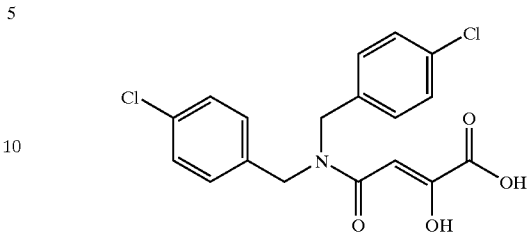

Compound 57 was prepared from Intermediate 57B using Method XVIII. HRMS (M−H) calcd for $C_{18}H_{14}NO_4Cl_2$: 378.0300; found: 378.0297. Anal calcd for $C_{18}H_{15}NO_4Cl_2$: C, 56.86; H, 3.97; N, 3.68. found: C, 57.04; H, 4.02; N, 3.60. H NMR (500 MHz, DMSO) δ: 4.62 (s, 2), 4.69 (s, 2), 6.23 (s, 1), 7.21–7.44 (overlapping m, 8). $^{13}$C NMR (125 MHz, DMSO) δ: 48.14, 49.65, 93.21, 128.31, 128.39, 128.63, 129.64, 131.90, 131.94, 135.68, 135.76, 160.39, 163.24, 171.36.

EXAMPLE 58

Intermediate 58A (3-Chloro-4-fluoro-benzyl)-methyl-amine

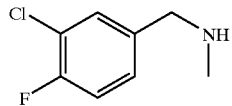

Intermediate 58A was formed from 4-fluoro-3-chloro-benzaldehyde using Method III. HRMS (M+H) calcd for $C_8H_{10}NClF$: 174.0486; found: 174.0481. $^1$H NMR (500 MHz, CDCl$_3$) δ: 2.43 (s, 3), 3.69 (s, 2), 7.07 (m, 1), 7.17 (m, 1), 7.37 (m, 1). $^{13}$C NMR (125 MHz, CDCl$_3$) δ: 35.96, 54.87, 116.27, 116.44, 120.68, 120.82, 127.70, 127.75, 130.19, 137.32, 137.35, 156.15, 158.11.

Intermediate 58B

N-(3-Chloro-4-fluoro-benzyl)-2-(2,2-dimethyl-5-oxo-[1,3]dioxolan-4-ylidene)-N-methyl-acetamide

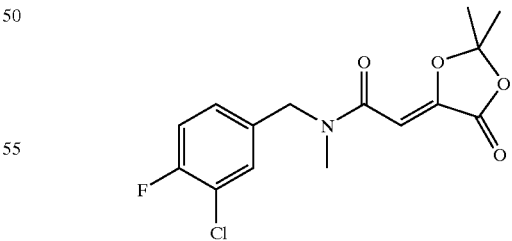

Intermediate 58B was prepared from Intermediate 58A using Method XVII. HRMS (M+H) calcd for $C_{15}H_{16}NO_4ClF$: 328.0752; found: 328.0755. $^1$H NMR and $^{13}$C NMR show a mixture of rotamers at room temperature. $^1$H NMR (500 MHz, CDCl$_3$) δ: 1.72 (s), 1.74 (s), 2.96 (s), 3.01 (s), 4.53 (s), 4.58 (s), 6.09 (s), 6.16 (s), 7.06–7.34 (overlapping m). $^{13}$C NMR (125 MHz, CDCl$_3$) δ: 26.78, 26.85, 33.28, 35.37, 49.71, 52.88, 96.68, 96.87, 113.89, 113.96, 116.65, 116.82, 117.03, 117,19, 121.11, 121.26, 121.67, 121.81, 126.33, 126.39, 127.95, 128.01, 128.77, 130.20, 133.99, 134.02, 144.85, 144.95, 156.55, 158.53, 162.31, 162.42, 164.08, 164.30.

Compound 58

3-[(3-Chloro-4-fluoro-benzyl)-methyl-carbamoyl]-2-hydroxy-acrylic acid

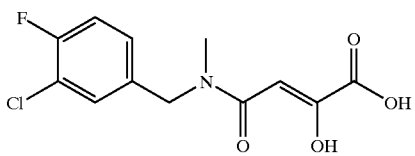

Compound 58 was prepared from Intermediate 58B using Method XVIII. HRMS (M–H) calcd for $C_{12}H_{10}NO_4ClF$: 286.0282; found: 286.0281. $^1H$ NMR and $^{13}C$ NMR show a mixture of rotamers at room temperature. $^1H$ NMR (500 MHz, CDCl$_3$) δ: 3.03 (s), 3.04 (s), 4.55 (s), 4.60 (s), 6.34 (s), 6.37 (s), 7.10–7.32 (overlapping m). $^{13}C$ NMR (125 MHz, CDCl$_3$) δ: 33.74, 35.03, 49.89, 52.32, 93.17, 93.63, 116.92, 117.08, 117.27, 117.44, 121.39, 121.53, 126.36, 126.42, 127.81, 127.87, 128.91, 130.22, 133.13, 133.16, 156.77, 158.75, 159.09, 159.27, 164.97, 170.95, 171.16.

EXAMPLE 59

Intermediate 59A (3,4-Difluoro-benzyl)-methyl-amine; hydrochloride

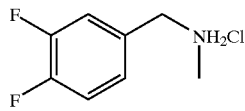

Intermediate 59A was prepared from 3,4-difluorobenzaldehyde using Method III. HRMS (M+H) calcd for $C_8H_{10}NF_2$ 158.0781; found: 158.0783. $^1H$ NMR (500 MHz, d$_6$-MeOD) δ: 1.18 (s, 3), 2.66 (s, 2), 5.82 (m, 2), 5.98 (m, 1). $^{13}C$ NMR (125 MHz, d$_6$-MeOD) δ: 31.74, 50.87, 117.67, 117.69, 117.80, 118.82, 118.93, 118.97, 126.71, 126.75, 126.80, 128.49, 128.54, 128.58, 149.07, 149.19, 149.80, 149.92, 151.06, 151.18, 151.80, 151.92.

Intermediate 59B

N-(3,4-Difluoro-benzyl)-2-(2,2-dimethyl-5-oxo-[1,3]dioxolan-4-ylidene)-N-methyl-acetamide

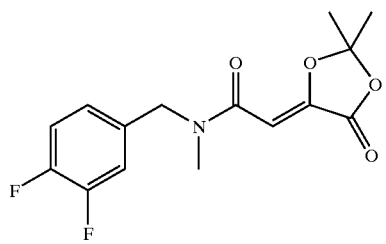

Intermediate 59B was prepared from Intermediate 59A using Method XVII. HRMS (M+H) calcd for $C_{15}H_{16}NO_4F_2$: 312.1048; found: 312.1042. $^1H$ NMR shows a mixture of rotamers at room temperature. $^1H$ NMR (500 MHz, CDCl$_3$) δ: 1.70 (s), 1.73 (s), 1.74 (s), 2.97 (s), 3.02 (s), 4.53 (s), 4.58 (s), 6.09 (s), 6.16 (s), 7.00–7.13 (overlapping m).

Compound 59

3-[(3,4-Difluoro-benzyl)-methyl-carbamoyl]-2-hydroxy-acrylic acid

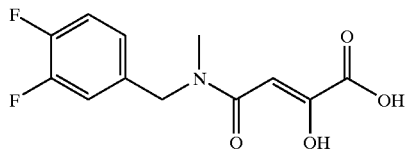

Compound 59 was prepared from Intermediate 59B using Method XVIII. HRMS (M–H) calcd for $C_{12}H_{10}NO_4F_2$: 270.0578; found: 270.0581. $^1H$ NMR shows a mixture of rotamers at room temperature. $^1H$ NMR (500 MHz, CDCl$_3$) δ: 3.04 (s), 4.55 (s), 4.61 (s), 6.34 (s), 6.37 (s), 6.90–7.19 (overlapping m).

EXAMPLE 60

Intermediate 60A (4-Fluoro-3-methoxy-benzyl)-methyl-amine

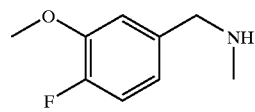

Intermediate 60A was prepared from 4-fluoro-3-methoxybenzaldehyde using Method III. HRMS (M+H) calcd for $C_9H_{13}NOF$: 170.0981; found: 170.0984. $^1H$ NMR (500 MHz, CDCl$_3$) δ: 2.44 (s, 3), 3.69 (s, 2), 3.88 (s, 3), 6.80 (m, 1), 6.95–7.01 (overlapping m, 2). $^{13}C$ NMR (125 MHz, CDCl$_3$) δ: 36.06, 55.76, 56.17, 113.17, 115.54, 115.69, 120.25, 120.30, 136.52, 136.55, 147.49, 147.57, 150.53, 152.47.

Intermediate 60B 2-(2,2-Dimethyl-5-oxo-[1,3]dioxolan-4-ylidene)-N-(4-fluoro-3-methoxy-benzyl)-N-methyl-acetamide

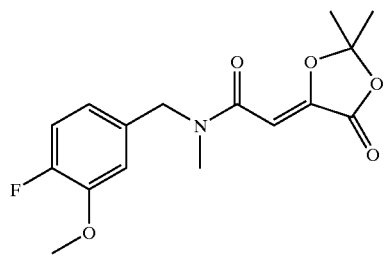

Intermediate 60B was prepared from Intermediate 60A using Method XVII. HRMS (M+H) calcd for $C_{16}H_{19}NO_5F$: 324.1247; found: 324.1239. $^1H$ NMR and $^{13}C$ NMR show a mixture of rotamers at room temperature. $^1H$ NMR (500 MHz, CDCl$_3$) δ: 1.69 (s), 1.72 (s), 2.97 (s), 2.99 (s), 3.85 (s), 3.86 (s), 4.52 (s), 4.58 (s), 6.13 (s), 6.16 (s), 6.79–7.04

(overlapping m). $^{13}$C NMR (125 MHz, CDCl$_3$) δ: 26.77, 26.84, 33.36, 35.12, 50.25, 53.50, 56.34, 96.99, 97.06, 111.69, 113.45, 113.79, 113.83, 115.82, 115.96, 116.33, 116.48, 118.78, 118.83, 120.61, 120.67, 132.43, 132.46, 133.22, 133.25, 144.74, 144.80, 147.81, 147.89, 148.14, 150.96, 152.92, 162.42, 162.51, 163.94, 164.31.

Compound 60

3-[(4-Fluoro-3-methoxy-benzyl)-methyl-carbamoyl]-2-hydroxy-acrylic acid

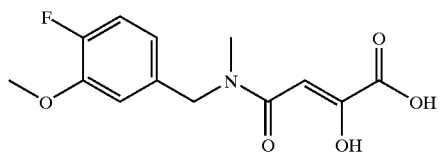

Compound 60 was prepared from Intermediate 60B using Method XVIII. HRMS (M−H) calcd for C$_{13}$H$_{13}$NO$_5$F: 282.0778; found: 282.0774. Anal calcd for C$_{13}$H$_{14}$NO$_5$F: C, 55.12; H, 4.98; N, 4.94. found: C, 55.15; H, 5.05; N, 4.81. $^1$H NMR and $^{13}$C NMR show a mixture of rotamers at room temperature. $^1$H NMR (500 MHz, DMSO) δ: 2.97 (s), 3.02 (s), 3.83 (s), 4.58 (s), 4.65 (s), 6.26 (s), 6.28 (s), 6.72–7.20 (overlapping m). $^{13}$C NMR (125 MHz, DMSO) δ: 33.48, 34.70, 49.36, 51.85, 55.77, 93.00, 93.10, 112.34, 113.26, 115.61, 115.75, 115.85, 115.99, 118.26, 118.31, 119.67, 119.73, 133.34, 146.94, 147.03, 147.09, 147.18, 149.78, 151.72, 160.00, 163.42, 170.61, 170.93.

EXAMPLE 61

Intermediate 61A (4-Fluoro-3-methyl-benzyl)-methyl-amine

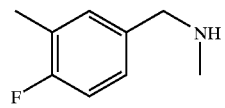

Intermediate 61A was prepared from 4-fluoro-3-methyl-benzylbromide using Method I. LC/MS (M+H) calcd for C$_9$H$_{13}$NF: 154.1; found: 154.1. $^1$H NMR (500 MHz, CDCl$_3$) δ: 2.25 (s, 3), 2.44 (s, 3), 3.67 (s, 2), 6.94 (m, 1), 7.08 (m, 1), 7.14 (m).

Intermediate 61B 2-(2,2-Dimethyl-5-oxo-[1,3]dioxolan-4-ylidene)-N-(4-fluoro-3-methyl-benzyl)-N-methyl-acetamide

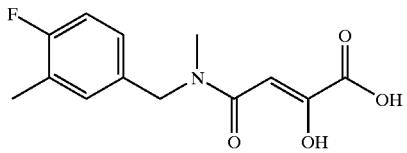

Intermediate 61B was prepared from Intermediate 61A using Method XVII. HRMS (M+H) calcd for C$_{16}$H$_{19}$NO$_4$F: 308.1298; found: 308.1302. $^1$H NMR and $^{13}$C NMR show a mixture of rotamers at room temperature. $^1$H NMR (500 MHz, CDCl$_3$) δ: 1.70 (s), 1.73 (s), 2.24 (s), 2.25 (s), 2.95 (s), 2.98 (s), 4.50 (s), 4.57 (s), 6.14 (s), 6.16 (s), 6.91–7.11 (overlapping m). $^{13}$C NMR (125 MHz, CDCl$_3$) δ: 14.52, 14.55, 14.60, 26.79, 26.86, 33.22, 35.12, 49.92, 53.26, 97.03, 97.28, 113.74, 113.84, 114.95, 115.13, 115.34, 115.52, 125.05, 125.18, 125.48, 125.55, 125.60, 127.16, 127.22, 129.59, 129.63, 131.32, 131.36, 131.45, 132.29, 144.68, 144.76, 159.83, 161.77, 162.47, 162.58, 163.88, 164.25.

Compound 61

3-[(4-Fluoro-3-methyl-benzyl)-methyl-carbamoyl]-2-hydroxy-acrylic acid

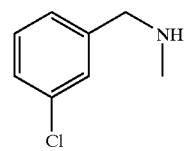

Compound 61 was prepared from Intermediate 61B using Method XVIII. HRMS (M−H) calcd for C$_{13}$H$_{13}$NO$_4$F: 266.0828; found: 266.0826. $^1$H NMR and $^{13}$C NMR show a mixture of rotamers at room temperature. $^1$H NMR (500 MHz, CDCl$_3$) δ: 2.26 (s), 3.01 (s), 4.52 (s), 4.59 (s), 6.36 (s), 6.39 (s), 6.98–7.29 (overlapping m). $^{13}$C NMR (125 Hz, CDCl$_3$) δ: 14.60, 33.64, 34.84, 50.17, 52.78, 93.47, 93.64, 115.23, 115.41, 115.55, 115.73, 125.37, 125.51, 125.69, 125.88, 127.05, 129.79, 130.64, 131.19, 131.37, 159.10, 160.03, 160.01, 165.16, 170.81, 171.06.

EXAMPLE 62

Intermediate 62A (3-Chlorobenzyl)-methylamine

Intermediate 62A was prepared from 3-chloro-benzylbromide using Method I. LC/MS (M+H) calcd for C$_8$H$_{11}$NCl; 156.1; found: 156.1. $^1$H NMR (500 MHz, CDCl$_3$) δ: 2.44 (s, 3), 3.72 (s, 2), 7.23 (m, 3), 7.32 (s, 1)

Intermediate 62B

N-(3-Chloro-benzyl)-2-(2,2-dimethyl-5-oxo-[1,3]dioxolan-4-ylidene)-N-methyl-acetamide

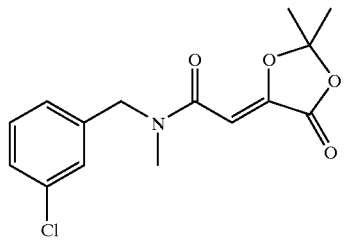

Intermediate 62B was prepared from Intermediate 62A using Method XVII. HRMS (M+H) calcd for $C_{15}H_{17}NO_4Cl$; 310.0846; found: 310.0845. $^1$H NMR and $^{13}$C NMR show a mixture of rotamers at room temperature. $^1$H NMR (500 MHz, CDCl$_3$) δ: 1.63 (s), 1.68 (s), 2.92 (s), 2.96 (s), 4.50 (s), 4.56 (s), 6.05 (s), 6.11 (s), 7.09–7.23 (overlapping m). $^{13}$C NMR (125 MHz, CDCl$_3$) δ: 27.03, 27.12, 33.63, 35.65, 50.42, 53.68, 97.15, 97.41, 114.07, 114.16, 125.04, 126.56, 126.94, 128.02, 128.30, 128.37, 130.23, 130.52, 134.84, 135.27, 138.56, 139.19, 144.94, 145.06, 162.61, 162.73, 164.35, 164.65.

Compound 62

3-[(3-Chloro-benzyl)-methyl-carbamoyl]-2-hydroxy-acrylic acid

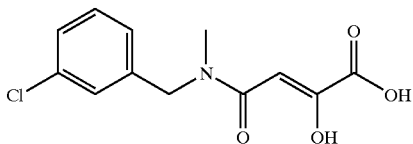

Compound 62 was prepared from Intermediate 62B using Method XVIII. HRMS (M−H) calcd for $C_{12}H_{11}NO_4Cl$; 268.0377; found: 268.0384. $^1$H NMR and $^{13}$C NMR show a mixture of rotamers at room temperature. $^1$H NMR (500 MHz, CDCl$_3$) δ: 3.04 (s), 4.57 (s), 4.63 (s), 6.35 (s), 6.37 (s), 7.14–7.32 (overlapping m). $^{13}$C NMR (125 MHz, CDCl$_3$) 33.83, 35.09, 50.37, 52.85, 93.26, 93.55, 124.75, 129.09, 126.77, 128.00, 128.13, 128.22, 128.39, 128.44, 130.19, 130.29, 130.47, 134.77, 135.13, 137.42, 138.06, 159.22, 164.93, 171.01, 171.24.

EXAMPLE 63

Intermediate 63A (4'-Fluoro-biphenyl-3-ylmethyl)-methyl-amine

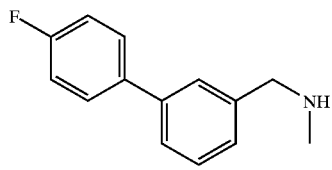

Intermediate 63A was prepared from 4'-fluoro-biphenyl-3-carbaldehyde using Method III. LC/MS (M+H) calcd $C_{14}H_{15}NF$; 216.1; found: 216.2. $^1$H NMR (500 MHz, CDCl$_3$) δ: 2.50 (s, 3), 3.82 (s, 2), 7.11 (m, 2), 7.30 (m, 1), 7.38–7.57 (overlapping m, 5). $^{13}$C NMR (125 MHz, CDCl$_3$) δ: 36.17, 56.13, 115.51, 115.68, 125.71, 126.88, 127.14, 128.71, 128.78, 128.91, 137.29, 140.41, 140.81.

Intermediate 63B 2-(2,2-Dimethyl-5-oxo-[1,3]dioxolan-4-ylidene)-N-(4'-fluoro-biphenyl-3-ylmethyl)-N-methyl-acetamide

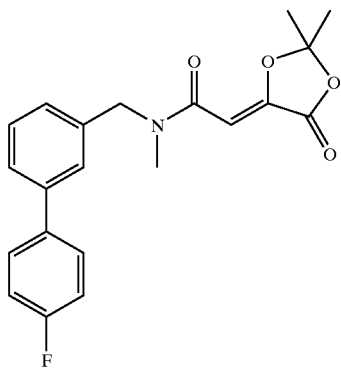

Intermediate 63B was prepared from Intermediate 63A using Method XVII. HRMS (M+H) calcd for $C_{21}H_{21}NO_4F$: 370.1455; found: 370.1450. $^1$H NMR and $^{13}$C NMR show a mixture of rotamers at room temperature. $^1$H NMR (500 MHz, CDCl$_3$) δ: 1.67 (s), 1.73 (s), 3.03 (s), 4.65 (s), 4.72 (s), 6.18 (s), 6.19 (s), 7.10–7.54 (overlapping m). $^{13}$C NMR (125 MHz, CDCl$_3$) δ: 26.75, 26.85, 33.49, 35.30, 50.60, 65.91, 97.11, 97.35, 113.75, 113.83, 115.56, 115.67, 115.73, 115.84, 125.10, 125.43, 126.29, 126.59, 126.79, 127.15, 128.77, 128.83, 129.18, 129.49, 136.83, 136.99, 137.51, 140.76, 141.11, 144.70, 162.56, 164.03, 164.45.

Compound 63

3-[(4'-Fluoro-biphenyl-3-ylmethyl)-methyl-carbamoyl]-2-hydroxy-acrylic acid

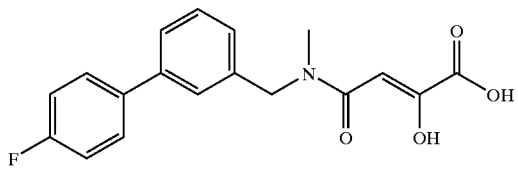

Compound 63 was prepared from Intermediate 63B using Method XVIII. HRMS (M−H) calcd for $C_{18}H_{15}NO_4F$; 328.0985; found: 328.0989. Anal. Calcd for $C_{18}H_{16}NO_4F$: C, 65.64; H, 4.89; N, 4.25. found: C, 65.39; H, 5.27; N, 4.00.

EXAMPLE 64

Intermediate 64A

Methyl-(3-phenoxy-benzyl)-amine

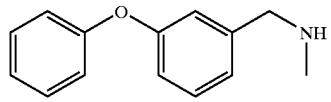

Intermediate 64A was prepared from 3-phenoxy-benzylbromide using Method I. LC/MS (M+H) calcd for $C_{14}H_{16}NO$: 214.1; found: 214.2. $^1$H NMR (500 MHz, CDCl$_3$) δ: 2.45 (s, 3), 3.74 (s, 2), 6.90 (m, 1), 7.00–7.35 (overlapping m, 8).

Intermediate 64B 2-(2,2-Dimethyl-5-oxo-[1,3]dioxolan-4-ylidene)-N-methyl-N-(3-phenoxy-benzyl)-acetamide

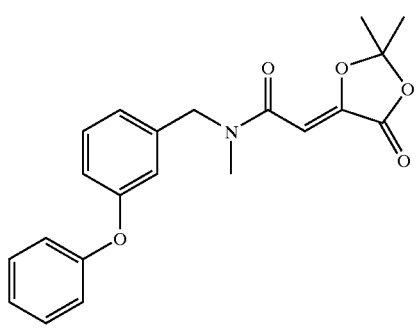

Intermediate 64B was prepared from Intermediate 64A using Method XVII. LC/MS (M+H) calcd $C_{21}H_{22}NO_5$: 368.1; found:368.2. HRMS calcd for $C_{21}H_{22}NO_5$: 368.1498; found: 368.1498. $^1$H NMR and $^{13}$C NMR show a mixture of rotamers at room temperature. $^1$H NMR (500 MHz, CDCl$_3$) δ: 1.69 (s), 1.72 (s), 2.99 (s), 3.01 (s), 4.55 (s), 4.64 (s), 6.13 (s), 6.17 (s), 6.85–7.36 (overlapping m). $^{13}$C NMR (125 MHz, CDCl$_3$) δ: 26.78, 26.84, 33.42, 39.32, 50.31, 53.66, 97.04, 97.28, 113.76, 113.83, 116.98, 117.80, 117.94, 118.59, 118.78, 119.03, 121.12, 122.92, 123.33, 123.61, 129.80, 129.88, 130.02, 130.31, 138.28, 138.91, 144.70, 156.78, 157.11, 157.48, 157.99, 162.55, 164.01, 164.35.

Compound 64

2-Hydroxy-3-[methyl-(3-phenoxy-benzyl)-carbamoyl]-acrylic acid

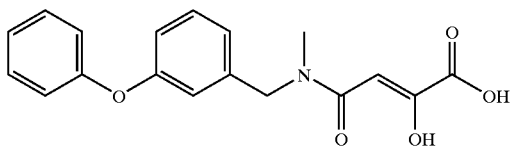

Compound 64 was prepared from Intermediate 64B using Method XVIII. LC/MS (M+H) calcd for $C_{18}H_{18}NO_5$: 328.1; found: 328.1. HRMS (M–H) calcd for $C_{18}H_{16}NO_5$: 326.1029; found: 326.1034. $^1$H NMR shows a mixture of rotamers at room temperature. $^1$H NMR (500 MHz, CDCl$_3$) δ: 3.02 (s), 3.03 (s), 4.55 (s), 4.63 (s), 6.35 (s), 6.80–7.37 (overlapping m).

EXAMPLE 65

Intermediate 65A (3,4-Dimethylbenzyl)-methylamine

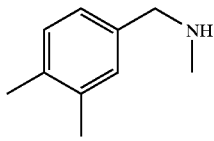

Intermediate 65A was prepared from 3,4-dimethylbenzaldehyde using Method III. HRMS (M+H) calcd for $C_{10}H_{16}N$; 150.1282; found: 150.1287. $^1$H NMR (500 MHz, CDCl$_3$) δ: 2.25 (s, 3), 2.27 (s, 3), 2.45 (s, 3), 3.69 (s, 2), 7.04–7.11 (m, 3). $^{13}$C NMR (125 MHz, CDCl$_3$) δ: 19.43, 19.74, 36.08, 55.88, 125.62, 129.59, 129.61, 135.18, 136.57, 137.63.

Intermediate 65B

N-(3,4-Dimethyl-benzyl)-2-(2,2-dimethyl-5-oxo-[1,3]dioxolan-4-ylidene)-N-methyl-acetamide

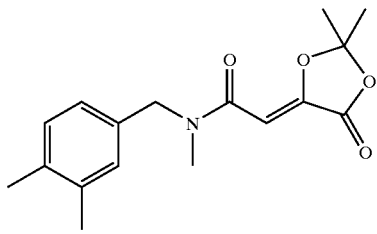

Intermediate 65B was prepared from Intermediate 65A using Method XVII. LC/MS (M+H) calcd for $C_{17}H_{22}NO_4$: 304.2; found: 304.3. HRMS (M+H) calcd for $C_{17}H_{22}NO_4$; 304.1549; found: 304.1552.

Compound 65

3-[(3,4-Dimethyl-benzyl)-methyl-carbamoyl]-2-hydroxy-acrylic acid

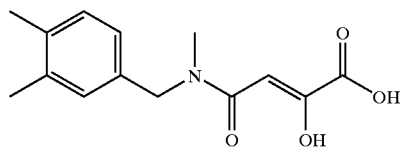

Compound 65 was prepared from Intermediate 65B using Method XVIII. LC/MS (M+H) calcd for $C_{14}H_{18}NO_4$; 264.1; found: 264.3.

EXAMPLE 66

Intermediate 66A (4-Methoxy-3-methylbenzyl)-methylamine

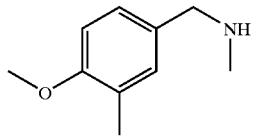

Intermediate 66A was prepared from 4-methoxy-3-methyl-benzaldehyde using Method III. HRMS (M+H) calcd for $C_{10}H_{16}NO$; 166.1232; found: 166.1235. $^1H$ NMR (500 MHz, CDCl$_3$) δ: 2.23 (s, 3), 2.46 (s, 3), 3.67 (s, 2), 3.82 (s, 3), 6.77 (m, 1), 7.10 (m, 2). $^{13}C$ NMR (125 MHz, CDCl$_3$) δ: 16.21, 35.97, 55.37, 55.59, 109.74, 126.53, 130.75, 131.84, 156.84.

Intermediate 66B 2-(2,2-Dimethyl-5-oxo-[1,3]dioxolan-4-ylidene)-N-(4-methoxy-3-methyl-benzyl)-N-methyl-acetamide

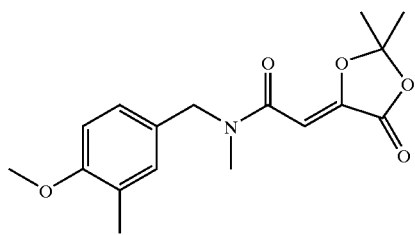

Intermediate 66B was prepared from Intermediate 66A using Method XVII. LC/MS (M+H) calcd for $C_{17}H_{22}NO_5$: 320.1; found: 320.1. HRMS (M+H) calcd for $C_{17}H_{22}NO_5$: 320.1498; found: 320.1490. $^1H$ NMR and $^{13}C$ NMR show a mixture of rotamers at room temperature. $^1H$ NMR (500 MHz, CDCl$_3$) δ: 1.70 (s), 1.73 (s), 2.19 (s), 2.95 (s), 2.98 (s), 3.80 (s), 3.81 (s), 4.48 (s), 4.55 (s), 6.16 (s), 6.19 (s), 6.75–7.08 (overlapping m). $^{13}C$ NMR (125 MHz, CDCl$_3$) δ: 16.20, 16.29, 26.80, 26.86, 33.11, 34.11, 34.94, 49.94, 53.42, 55.36, 55.41, 97.40, 97.71, 109.83, 110.06, 113.63, 113.74, 125.17, 126.93, 127.27, 127.46, 128.41, 129.02, 130.78, 144.43, 144.51, 157.26, 157.42, 162.55, 162.67, 163.77, 164.22.

Compound 66

2-Hydroxy-3-[(4-methoxy-3-methyl-benzyl)-methyl-carbamoyl]-acrylic acid

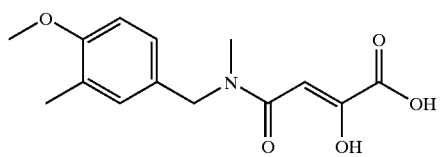

Compound 66 was prepared from Intermediate 66B using Method XVIII. LC/MS calcd for $C_{14}H_{18}NO_5$: 280.1; found: 280.3.

EXAMPLE 67

Intermediate 67A (4-Chloro-3-fluoro-benzyl)-methyl-amine

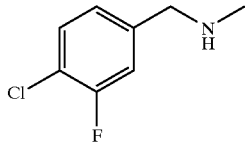

Intermediate 67A was prepared from 4-chloro-3-fluoro-benzaldehyde using Method III. LC/MS (M+H) calcd for $C_8H_{10}NClF$; 174.0; found: 174.1. $^1H$ NMR (500 MHz, CDCl$_3$) δ: 2.43 (s, 3), 3.72 (s, 2), 7.05 (m, 1), 7.15 (m, 1), 7.33 (m, 1). $^{13}C$ NMR (125 MHz, CDCl$_3$) δ: 35.92, 54.94, 116.08, 116.25, 119.13, 119.27, 124.35, 124.38, 130.39, 141.24, 141.29, 157.12, 159.10.

Intermediate 67B

N-(4-Chloro-3-fluoro-benzyl)-2-(2,2-dimethyl-5-oxo-[1,3]dioxolan-4-ylidene)-N-methyl-acetamide

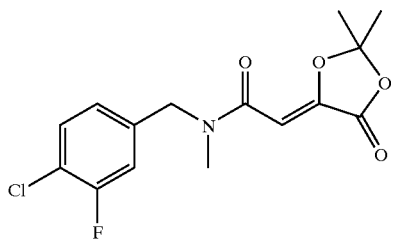

Intermediate 67B was prepared from Intermediate 67A using Method XVII. LC/MS (M+H) calcd for $C_{15}H_{16}NO_4ClF$: 328.1; found: 328.1. $^1H$ NMR and $^{13}C$ NMR show a mixture of rotamers at room temperature. $^1H$ NMR (500 MHz, CDCl$_3$) δ: 1.70 (s), 1.74 (s), 2.98 (s), 3.03 (s), 4.55 (s), 4.60 (s), 6.08 (s), 6.17 (s), 7.08 (overlapping m), 7.34 (overlapping m). $^{13}C$ NMR (125 MHz, CDCl$_3$) δ: 26.78, 26.85, 33.42, 35.46, 49.94, 53.04, 96.54, 96.74, 113.91, 113.98, 114.74, 114.91, 116.15, 116.32, 120.01, 120.15, 120.42, 120.55, 122.88, 122.91, 124.46, 124.49, 130.76, 131.20, 137.24, 137.88, 137.93, 144.95, 145.06, 157.22, 157.47, 159.20, 159.46, 162.29, 162.42, 164.10, 164.32.

Compound 67

3-[(4-Chloro-3-fluoro-benzyl)-methyl-carbamoyl]-2-hydroxy-acrylic acid

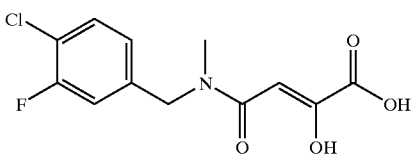

Compound 67 was prepared from Intermediate 67B using Method XVIII. LC/MS calcd for $C_{12}H_{12}NO_4FCl$: 288.0; found: 288.1.

EXAMPLE 68

Intermediate 68A

Benzo[1,3]dioxol-5-ylmethyl-methyl-amine

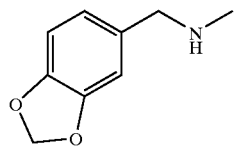

Intermediate 68A was prepared from benzo[1,3]dioxole-5-carbaldehyde using Method III. LC/MS (M+H) calcd for $C_9H_{12}NO_2$; 166.1; found: 166.1. $^1$H NMR (500 MHz, CDCl$_3$) δ: 2.42 (s, 3), 3.65 (s, 2), 5.95 (d, 2), 6.75–6.86 (overlapping m, 3).

Intermediate 68B

N-Benzo[1,3]dioxol-5-ylmethyl-2-(2,2-dimethyl-5-oxo-[1,3]dioxolan-4-ylidene)-N-methyl-acetamide

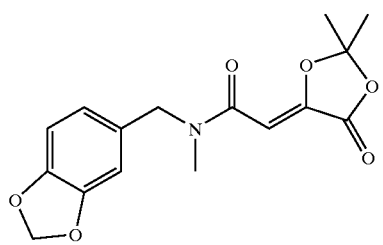

Intermediate 68B was prepared from Intermediate 68A using Method XVII. LC/MS (M+H) calcd for $C_{16}H_{18}NO_6$: 320.1; found: 320.1.

Compound 68

3-(Benzo[1,3]dioxol-5-ylmethyl-methyl-carbamoyl)-2-hydroxy-acrylic acid

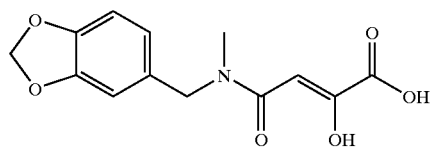

Compound 68 was prepared from Intermediate 68B using Method XVIII. LC/MS calcd for $C_{13}H_{14}NO_6$: 280.1; found: 280.1. $^1$H NMR and $^{13}$C NMR show a mixture of rotamers at room temperature. $^1$H NMR (500 MHz, CDCl$_3$) δ: 3.00 (s), 4.48 (s), 4.55 (s), 5.95 (s), 5.96 (s), 6.33 (s), 6.39 (s), 6.61–6.79 (overlapping m). $^{13}$C NMR (125 MHz, CDCl$_3$) δ: 33.51, 34.70, 50.58, 53.17, 93.31, 93.44, 101.20, 101.28, 101.35, 107.13, 108.36, 108.51, 108.66, 120.22, 121.59, 121.89, 129.04, 129.75, 147.35, 147.56, 148.15, 148.39, 159.28, 159.36, 164.85, 170.85, 171.10.

EXAMPLE 69

Intermediate 69A (2,2-Difluoro-benzo[1,3]dioxol-5-ylmethyl)-methyl-amine

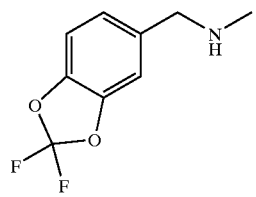

Intermediate 69A was prepared from 2,2-difluoro-benzo[1,3]dioxole-5-carbaldehyde using Method III. LC/MS (M+H) calcd for $C_9H_{10}NO_2F_2$: 202.1; found: 202.1. $^1$H NMR (500 MHz, CDCl$_3$) δ: 2.44 (s, 3), 3.73 (s, 2), 6.97–7.09 (overlapping m, 3). $^{13}$C NMR (125 MHz, CDCl$_3$) δ: 35.85, 55.59, 109.05, 109.42, 123.11, 129.63, 131.66, 133.68, 136.50, 142.71, 143.93.

Intermediate 69B

N-(2,2-Difluoro-benzo[1,3]dioxol-5-ylmethyl)-2-(2,2-dimethyl-5-oxo-[1,3]dioxolan-4-ylidene)-N-methyl-acetamide

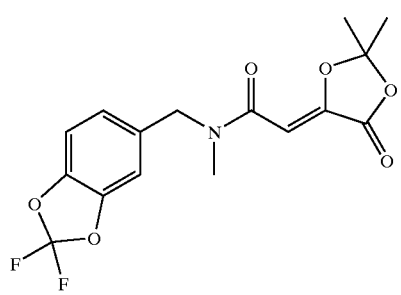

Intermediate 69B was prepared from Intermediate 69A using Method XVII. LC/MS (M+H) calcd for $C_{16}H_{16}NO_6F_2$: 356.1; found: 356.1. $^1$H NMR shows a mixture of rotamers at room temperature. $^1$H NMR (500 MHz, CDCl$_3$) δ: 1.70 (s), 1.74 (s), 2.97 (s), 3.01 (s), 4.56 (s), 4.60 (s), 6.11 (s), 6.15 (s), 6.90–7.06 (overlapping m).

Compound 69

3-[(2,2-Difluoro-benzo[1,3]dioxol-5-ylmethyl)-methyl-carbamoyl]-2-hydroxy-acrylic acid

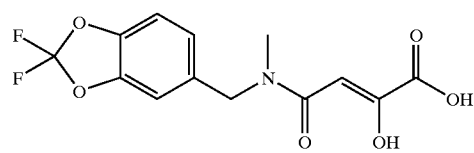

Compound 69 was prepared from Intermediate 69B using Method XVIII. LC/MS calcd for $C_{13}H_{12}NO_6F_2$: 316.1; found: 316.1. $^1$H NMR shows a mixture of rotamers at room temperature. $^1$H NMR (500 MHz, CDCl$_3$) δ: 3.02 (s), 4.57 (s), 4.62 (s), 6.34 (s), 6.89–7.06 (overlapping m).

EXAMPLE 70

Intermediate 70A (4-Chlorophenyl)-(4-fluorobenzyl)-amine

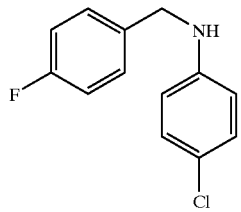

Intermediate 70A was prepared from N-(4-chlorophenyl)-4-fluorobenzamide using Method II, step 2. $^1$HNMR 400 MHz (CDCl$_3$) δ (ppm): 4.28 (2H, s, NCH$_2$), 6.54 (2H, d, J=9 Hz, aromatics), 7.03 (2H, broad t, aromatics), 7.12 (2H, d, J=9 Hz, aromatics), 7.31 (2H, m, aromatics). MS (ESI$^+$) (m/z) 236 (M+H$^+$).

Intermediate 70B

N-(4-Chloro-phenyl)-2-(2,2-dimethyl-5-oxo-[1,3] dioxolan-4-ylidene)-N-(4-fluoro-benzyl)-acetamide

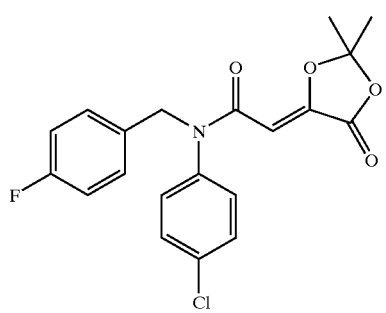

Intermediate 70B was prepared from Intermediate 70A using Method XIV. $^1$HNMR 400 MHz (CDCl$_3$) δ (ppm): 1.72 (6H, s, CH$_3$), 4.88 (2H, s, NCH$_2$), 5.63 (1H, s, CH), 6.94 (4H, m, aromatics), 7.19 (2H, m, aromatics), 7.32 (2H, m, aromatics). HRMS (MAB N$_2$) calculated for C$_{20}$H$_{17}$ClFNO$_4$ [M$^+$]: 389.083014: found: 389.084846. Anal. Calcd for C$_{20}$H$_{17}$ClFNO$_4$: C, 61.63; H, 4.40; N, 3.59. Found: C, 61.42; H, 4.45; N, 3.58.

Compound 70

3-[(4-Chloro-phenyl)-(4-fluoro-benzyl)-carbamoyl]-2-hydroxy-acrylic acid

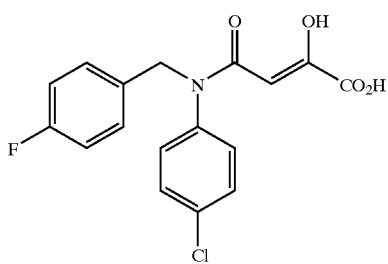

Compound 70 was prepared from Intermediate 70B using Method XVIII. $^1$HNMR 400 MHz (CDCl$_3$) δ (ppm): 4.89 (2H, s, NCH$_2$), 5.76 (1H, s, CH), 6.91 (2H, d, J=9 Hz, aromatics), 6.98 (2H, ~t, aromatics), 7.16 (2H, m, aromatics), 7.35 (2H, d, J=9 Hz, aromatics). HRMS (MAB N$_2$) calculated for C$_{17}$H$_{13}$ClFNO$_4$ [M$^+$]: 349.051714: found: 349.050812.

EXAMPLE 71

Intermediate 71A

N-(4-Chloro-phenyl)-2-(2,2-dimethyl-5-oxo-[1,3] dioxolan-4-ylidene)-N-(4-methyl-benzyl)-acetamide

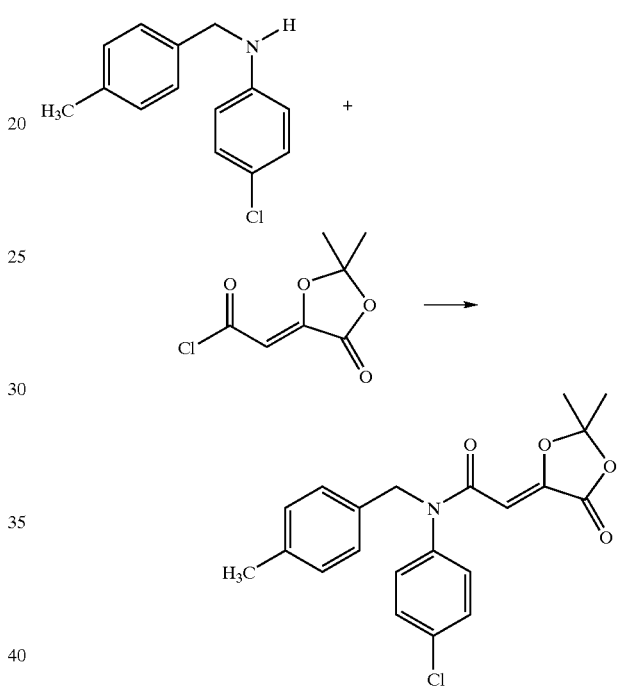

A solution of (Z)-2,2-dimethyl-5-(chlorocarbonylmethylene)-1,3-dioxolan-4-one (0.553 g, 2.90 mmol) in dry dichloromethane (5 ml) was added dropwise to a cold (0–5° C.) solution of (4-chlorophenyl)-(4-methylbenzyl)-amine (0.545 g, 2.35 mmol) (Ballistreri et al., J. Org. Chem., 41, 1976, 3364), pyridine (0.35 ml) and a small crystal of 4-N,N-dimethylaminopyridine in dry dichloromethane (10 ml). After 30 min, the cooling bath was removed and the resulting clear solution was stirred at 22° C. for another 30 min. The reaction mixture was then diluted wih ethyl acetate, washed with saturated sodium bicarbonate, brine and dried (magnesium sulfate). Evaporation of the solvent in vacuo, filtration of the residue on a short silica gel pad (elution-toluene ethyl acetate; 85:15) followed by crystallization from ethyl acetate-hexane gave 0.794 g (87%) of the title amide as white needles: mp 149° C. $^1$HNMR 400 MHz (CDCl$_3$) δ (ppm): 1.72 (6H, s, CH$_3$), 2.31 (3H, s, CH$_3$), 4.88 (2H, s, NCH$_2$), 5.64 (1H, s, CH), 6.93 (2H, d, J=8.5 Hz, aromatics), 7.08 (4H, m, aromatics), 7.3 (2H, d, J=8.5 Hz, aromatics). Anal. Calcd for C$_{21}$H$_{20}$ClNO$_4$: C, 65.37; H, 5.22; N, 3.63. Found: C, 65.22; H, 5.25; N, 3.52.

Compound 71

3-[(4-Chloro-phenyl)-(4-methyl-benzyl)-carbamoyl]-2-hydroxy-acrylic acid

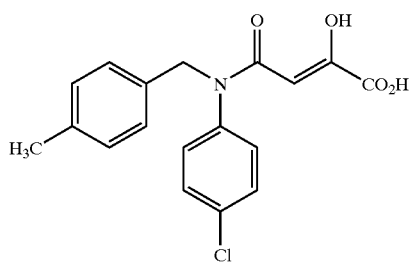

Compound 71 was prepared from Intermediate 71A using Method XVIII. $^1$HNMR 400 MHz (CDCl$_3$) δ (ppm): 2.32 (3H, s, CH$_3$), 4.88 (2H, s, NCH$_2$), 5.76 (1H, S, CH), 6.92 (2H, d, J=8.6 Hz, aromatics), 7.08 (4H, m, aromatics), 7.33 (2H, d, J=8.6 Hz, aromatics). HRMS (MAB N$_2$) calculated for C$_{18}$H$_{16}$ClNO$_4$ [M$^+$]: 345.076786: found: 345.078285.

EXAMPLE 72

Intermediate 72A 2-(2,2-Dimethyl-5-oxo-[1,3]dioxolan-4-ylidene)-N-(4-fluoro-benzyl)-N-(4-fluoro-phenyl)-acetamide

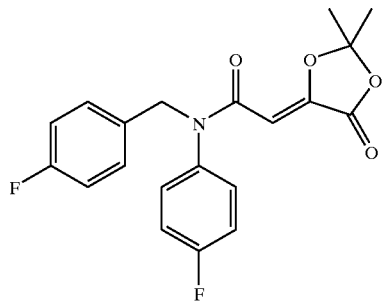

Acylation of (4-fluorobenzyl)-(4-fluorophenyl)-amine (Pombrik, S. I. et al., Izv. Akad. Nauk. SSSR Ser. Khim., 6, 1982, 1289–1294) with (Z)-2,2-dimethyl-5-(chlorocarbonylmethylene)-1,3-dioxolan-4-one as described in the preparation of Intermediate 71A gave the title amide as a syrup. $^1$HNMR 400 MHz (CDCl$_3$) δ (ppm): 1.72 (6H, s, CH$_3$), 4.88 (2H, s, NCH$_2$), 5.29 (1H, s, CH), 6.94 (4H, m, aromatics), 7.03 (2H, m, aromatics), 7.19 (2H, m, aromatics). HRMS (MAB N$_2$) calculated for C$_{20}$H$_{17}$F$_2$NO$_4$ [M$^+$]: 373.112565: found: 373.112320.

Compound 72

3-[(4-Fluoro-benzyl)-(4-fluoro-phenyl)-carbamoyl]-2-hydroxy-acrylic acid

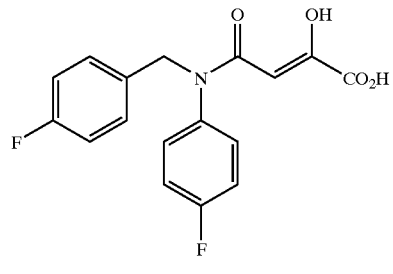

Compound 72 was prepared from Intermediate 72A using Method XVIII. $^1$HNMR 400 MHz (DMSO-d$_6$) δ (ppm): 4.93 (2H, s, NCH$_2$), 5.54 (1H, s, CH), 7.11 (2H, m, aromatics), 7.2–7.37 (6H, m, aromatics). HRMS (MAB N$_2$) calculated for C$_{17}$H$_{13}$F$_2$NO$_4$ [M$^+$]: 333.08127: found: 333.08220.

EXAMPLE 73

Intermediate 73A 2-(2,2-Dimethyl-5-oxo-[1,3]dioxolan-4-ylidene)-N-(4-fluoro-phenyl)-N-(4-methyl-benzyl)-acetamide

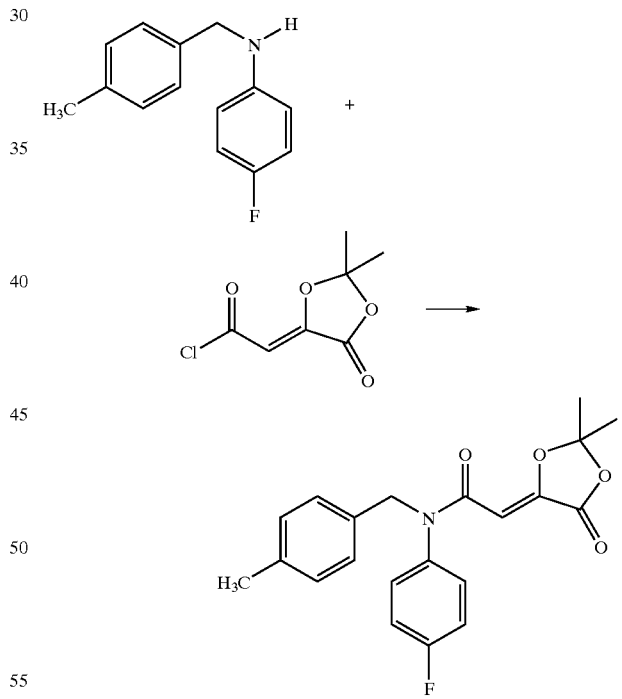

Acylation of (4-fluorophenyl)-(4-methylbenzyl)-amine (Pombrik, S. I. et al., Izv. Akad. Nauk. SSSR Ser. Khim., 10, 1981, 2406–2408) with (Z)-2,2-dimethyl-5-(chlorocarbonylmethylene)-1,3-dioxolan-4-one as described in the preparation of Intermediate 71A gave the title amide as a syrup. $^1$HNMR 400 MHz (CDCl$_3$) δ (ppm): 1.72 (6H, s, CH$_3$), 2.31 (3H, s, CH$_3$) 4.87 (2H, s, NCH$_2$), 5.63 (1H, s, CH), 6.93–7.11 (8H, m, aromatics). HRMS (MAB N$_2$) calculated for C$_{21}$H$_{20}$FNO$_4$ [M$^-$]: 369.137637: found: 369.137900.

Compound 73

3-[(4-Fluoro-phenyl)-(4-methyl-benzyl)-carbamoyl]-2-hydroxy-acrylic acid

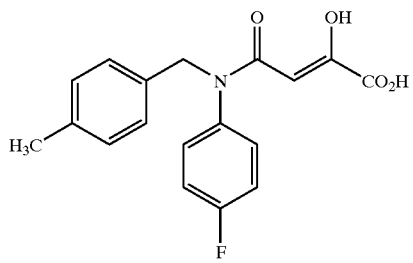

Compound 73 was prepared from Intermediate 73A using Method XVIII. $^1$HNMR 400 MHz δ (ppm): 2.32 (3H, s, CH$_3$), 4.87 (2H, s, NCH$_2$), 5.30 (1H, s, CH), 6.96 (2H, m, aromatics), 7.0–7.2 (6H, m, aromatics). HRMS (MAB N$_2$) calculated for C$_{18}$H$_{16}$FNO$_4$ [M$^+$]: 329.106336: found: 329.106590, δ −0.8 ppm.

EXAMPLE 74

Intermediate 74A

N-(4-Fluorobenzyl)-furfurylamine

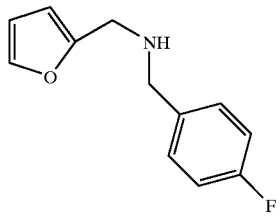

Intermediate 74A was prepared from 2-furoyl chloride and 4-fluorobenzylamine using Method II. $^1$HNMR 400 MHz (C$_6$D$_6$) δ (ppm): 3.49 (2H, s, NCH$_2$), 3.61 (2H, s, NCH$_2$), 6.08 (1H, broad s, CH furyl), 6.21 (1H, broad s, CH furyl), 6.92 (2H, broad t, aromatics), 7.11 (2H, m, aromatic), 7.23 (H, broad s, CH furyl). Anal. Calcd for C$_{12}$H$_{10}$FNO$_2$: C, 70.23; H, 5.89; N, 6.82. Found: C, 70.04; H, 6.03, N, 6.77.

Intermediate 74B 2-(2,2-Dimethyl-5-oxo-[1,3]dioxolan-4-ylidene)-N-(4-fluoro-benzyl)-N-furan-2-ylmethyl-acetamide

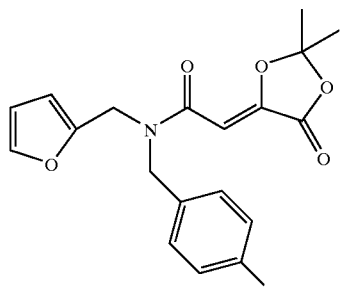

Intermediate 74B was prepared from Intermediate 74A using Method XIV. $^1$HNMR 400 MHz (CDCl$_3$) δ (ppm): mixture of rotamers; 1.74 and 1.77 (6H, 2 s, CH$_3$), 4.43, 4.61, 4.62 and 4.64 (4H, 4 s, 2×NCH$_2$), 6.14, 6.21, 6.29, 6.35 and 6.37 (3H, 5 broad s, CH and CH of furyl), 7.04 (2H, m, aromatics) 7.17 (2H, m, aromatics), 7.36 and 7.4 (1H, 2 s, CH of furyl). HRMS (MAB N$_2$) calculated for C$_{19}$H$_{18}$FNO$_5$ [M$^+$]: 359.116901: found: 359.117325. Anal. Calcd for C$_{19}$H$_{18}$FNO$_5$: C, 63.51; H, 5.05; N, 3.90. Found: C, 63.87; H, 5.17; N, 3.74.

Compound 74

3-[(4-Fluoro-benzyl)-furan-2-ylmethyl-carbamoyl]-2-hydroxy-acrylic acid

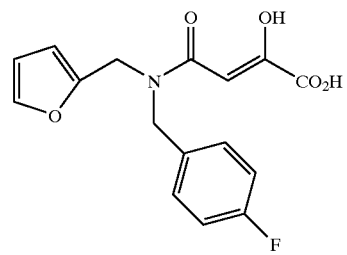

Compound 74 was prepared from Intermediate 74B using Method XVIII. $^1$HNMR 400 MHz (DMSO-d$_6$) δ (ppm): mixture of rotamers; 4.6, 4.64, 4.65 and 4.69 (4H, 4 s, 2×NCH$_2$), 6.18 and 6.48 (1H, 2 s, CH), 6.34–6.41 (2H, m, CH of furyl), 7.13–7.32 (4H, m, aromatics), 7.59 and 7.63 (1H, 2s, CH of furyl), 13.67 (1H, broad, OH), 14.24 and 14.32 (1H, 2 broad s, OH). Anal. Calcd for C$_{16}$H$_{14}$FNO$_5$: C, 60.19; H, 4.42; N, 4.39. Found: C, 60.15; H, 4.21; N, 4.30.

EXAMPLE 75

Intermediate 75A 2-(2,2-Dimethyl-5-oxo-[1,3]dioxolan-4-ylidene)-N-furan-2-ylmethyl-N-methyl-acetamide

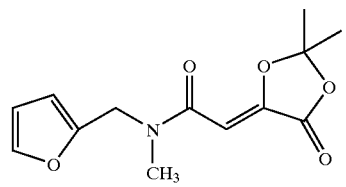

Intermediate 75A was prepared from N-ethylfurfurylamine using Method XIV. Solid: mp 83–86° C. (hexane). $^1$HNMR 400 MHz (CDCl$_3$) δ (ppm): mixture of rotamers 1.63 (6H, s, CH$_3$), 3.03 and 3.1 (3H, 2 s, NCH$_3$), 4.52 and 4.65 (2H, 2 s, NCH$_2$), 6.1–6.4 (3H, m, CH and furyl CH), 7.38 and 7.4 (1H, 2 s, furyl CH). MS (ESI$^+$) (m/z) 266 (M+H$^+$). Anal. Calcd for C$_{13}$H$_{15}$NO$_5$: C, 58.86; H, 5.69; N, 5.28. Found: C, 59.02; H, 5.52; N, 5.12.

Compound 75

3-(Furan-2-ylmethyl-methyl-carbamoyl)-2-hydroxy-acrylic acid

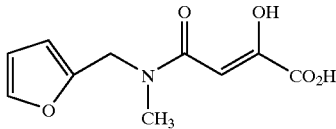

Compound 75 was prepared from Intermediate 75A using Method XVIII. $^1$HNMR 400 MHz (CDCl$_3$) δ (ppm): mixture of rotamers; 3.0 (3H, s, NCH$_3$), 4.5 and 4.7 (2H, 2 s, NCH$_2$), 6.3–6.6 (3H, m, CH and furyl CH), 7.41 (1H, s, furyl CH). MS (ES$^-$) (m/z) 224 (M−H)$^-$. Anal. Calcd for C$_{10}$H$_{11}$NO$_5$: C, 53.33; H, 4.92; N, 6.22. Found: C, 53.43; H, 5.0; N, 5.92.

EXAMPLE 76

Intermediate 76A

N-(4-Fluorobenzyl)-3-chloro-4-methoxy-benzylamine

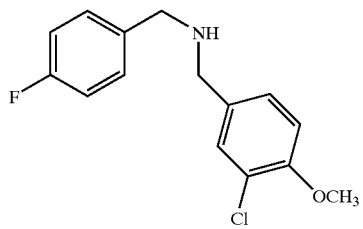

Intermediate 76A was prepared from 4-fluorobenzoyl chloride and 3-chloro-4-methoxy-benzylamine using Method II. $^1$HNMR 400 MHz (CDCl$_3$) δ (ppm): 3.71 (2H, s, NCH$_2$), 3.75 (2H, s, NCH$_2$), 3.89 (3H, s, OCH$_3$), 6.89 (1H, d, J=8.2 Hz, CH), 7.02 (2H, m, aromatics), 7.2 (1H, dd, J=2.1 Hz and J=8.2 Hz, aromatic), 7.31 (2H, m, aromatics), 7.36 (1H, d, J=2.1 Hz, aromatic). HRMS (MAB N$_2$) calculated for C$_{15}$H$_{15}$ClFNO [M$^+$]: 279.08262: found: 279.08157.

Intermediate 76B

N-(3-Chloro-4-methoxy-benzyl)-2-(2,2-dimethyl-5-oxo-[1,3]dioxolan-4-ylidene)-N-(4-fluoro-benzyl)-acetamide

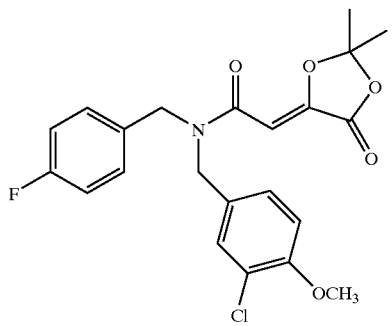

Intermediate 76B was prepared from Intermediate 76A using Method XIV. $^1$HNMR 400 MHz (CDCl$_3$) δ (ppm): mixture of rotamers; 1.74 (6H, s, CH$_3$), 3.89 and 3.90 (3H, 2 s, OCH$_3$), 4.40, 4.46, 4.51 and 4.58 (4H, 4 s, 2 ×NCH$_2$), 6.15 and 6.16 (1H, 2 s, CH), 6.84–7.27 (7H, m, aromatics). HRMS (ESI$^+$) calculated for C$_{22}$H$_{22}$ClFNO$_5$ [M+H$^+$] calculated for: 434.11707: found: 434.11820.

Compound 76

3-[(3-Chloro-4-methoxy-benzyl)-(4-fluoro-benzyl)-carbamoyl]-2-hydroxy-acrylic acid

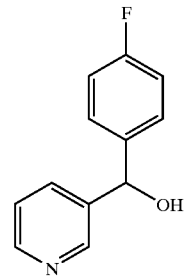

Compound 76 was prepared from Intermediate 76B using Method XVIII. $^1$HNMR 400 MHz (CDCl$_3$) δ (ppm): mixture of rotamers; 3.90 and 3.91 (3H, 2 s, OCH$_3$), 4.41, 4.47, 4.53 and 4.59 (4H, 4 s, 2×NCH$_2$), 6.39 (1H, broad s, CH), 6.87–7.25 (7H, m, aromatics). HRMS (MAB N$_2$) calculated for C$_{19}$H$_{17}$ClFNO$_5$ [M$^+$]: 393.07794: found: 393.07000.

EXAMPLE 77

Intermediate 77A (4-Fluorophenyl)-(3-pyridyl)-methanol

A solution of 3-pyridinecarboxaldehyde (5.32 g, 49.7 mmol) in tetrahydrofuran (100 ml) was cooled to −78° C. and treated dropwise with 25 ml (50 mmol) of a 2 M solution of 4-fluorophenyl magnesium bromide in ether. The reaction mixture was then slowly warmed up to 0° C. over 1 h and then quenched by the addition of saturated aqueous sodium bicarbonate and ethyl acetate. The organic phase was washed with brine, dried (magnesium sulfate) and concentrated under reduced pressure. Filtration of the residue on a short silica gel pad (elution ethyl acetate) followed by distillation in vacuo gave 9.42 g (93%) of the title material as a clear oil which crystallized upon standing. bp 120–130° C./0.2 torr (bulb to bulb distillation, air bath temperature), mp 45–47° C. $^1$HNMR 400 MHz (CDCl$_3$) δ (ppm): 5.88 (1H, s, CH benzhydryl), 7.05 (2H, m, aromatics), 7.25–7.36 (3H, m, aromatics), 7.73 (1H, d, J=7.9 Hz, aromatic), 8.44 (1H, d, J=5.2 Hz, aromatic), 8.55 (1H, s, aromatic). Anal. Calcd for C$_{12}$H$_{10}$FNO: C, 70.92; H, 4.96; N, 6.89. Found: C, 70.61; H, 4.86; N, 6.71.

Intermediate 77B (4-Fluorophenyl)-(3-pyridyl)-N-methyl-methylamine

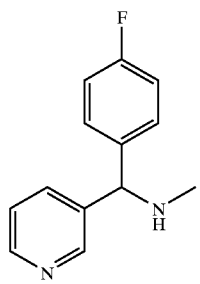

A solution of Intermediate 77A (2.0 g, 9.84 mmol) in dry benzene was treated with thionyl chloride (1.7 ml) and heated under reflux for 1 h. The solvent and excess reagent were evaporated under reduce pressure. The residue was then dissolved in 60 ml of a 1.85 M solution of methylamine in tetrahydrofuran and the resulting mixture was heated at 125° C. in a pressure vessel for 72 h. The reaction mixture was then diluted with ethyl acetate, washed with water, brine and dried (magnesium sulfate). Evaporation of the solvent under reduce pressure and filtration of the residue on a short silica gel pad (elution ethyl acetate-methanol 0–20%) followed by distillation in vacuo gave 1.38 g (64%) of the title amine as a clear oil: bp 90–100° C./0.2 torr (bulb to bulb distillation, air bath temperature). $^1$HNMR 400 MHz (CDCl$_3$) δ (ppm): 2.33 (3H, s, CH$_3$), 4.65 (1H, s, CH benzhydryl), 6.93 (2H, m, aromatics), 7.16 (1H, dd, J=4.8 Hz and J=7.8 Hz, aromatic), 7.29 (2H, m, aromatics), 7.61 (1H, m, aromatic), 8.41 (1H. broad d, aromatic), 8.56 (1H, d, J=2.1 Hz, aromatic). Anal. Calcd for C$_{12}$H$_{10}$FNO. 0.2H$_2$O: C, 71.02; H, 6.14; N, 12.74. Found: C, 71.19; H, 5.98; N, 12.75.

Intermediate 77B 2-(2,2-Dimethyl-5-oxo-[1,3]dioxolan-4-ylidene)-N-[(4-fluoro-phenyl)-pyridin-3-yl-methyl]-N-methyl-acetamide

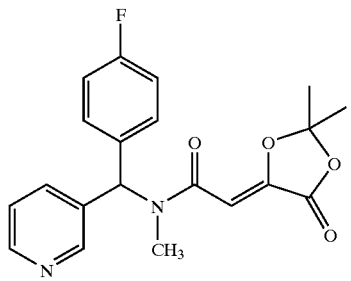

Intermediate 77C was prepared from Intermediate 77B using Method XIV. $^1$HNMR 400 MHz (CDCl$_3$) δ (ppm): mixture of rotamers; 1.56, 1.59 and 1.69 (6H, 3 s, CH$_3$), 2.71 and 2.84 (3H, 2 s, NCH$_3$), 6.08 and 6.14 (1H, 2 s, CH), 6.93–7.45 and 8.4–8.55 (8H, m, CH and aromatic). HRMS (MAB N$_2$) calculated for C$_{20}$H$_{19}$FN$_2$O$_4$ [M$^+$]: 370.13288: found: 370.13248.

Compound 77

3-{[(4-Fluoro-phenyl)-pyridin-3-yl-methyl]-methyl-carbamoyl}-2-hydroxy-acrylic acid

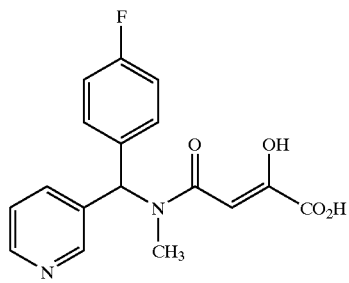

Compound 77 was prepared from Intermediate 77B using Method XVIII. $^1$HNMR 400 MHz (DMSO-d$_6$) δ (ppm): mixture of rotamers of keto (minor)-enol forms; 2.72 and 2.88 (3H, 2 s, NCH$_3$), 6.28 and 6.43 (1H, 2 s, CH), 6.94 and 6.99 (1H, 2 s, CH), 7.25 (4H, m, aromatics), 7.42 (1H, m, aromatic), 7.60 (1H, m aromatic), 8.41 (1H, broad s, aromatic), and 8.55 (1H, m, aromatic). HRMS (MAB N$_2$) calculated for C$_{27}$H$_{15}$FN$_2$O$_4$ [M$^+$]: 330.10158: found: 330.10009.

EXAMPLE 78

Intermediate 78A 1,2-Bis-(4-fluorophenyl)-N-methyl-ethylamine

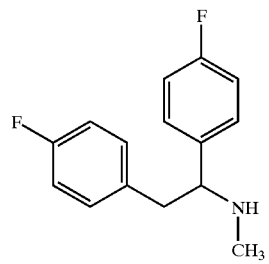

Intermediate 78A was prepared from 4,4'-difluro-deoxybenzoin using Method III. Anal. Calcd for C$_{15}$H$_{15}$F$_2$N: C, 72.86; H, 6.11; N, 5.66. Found: C, 72.48; H, 6.27; N, 5.75. The hydrochloride salt was obtained as a white solid; mp 155–157° C. $^1$HNMR 400 MHz (DMSO-d$_6$) δ (ppm): 2.39 (3H, broad s, NCH$_3$), 3.14 (1H, dd, J=11.0 Hz and J=13.2 Hz. CH), 3.51 (1H, dd, J=4.58 Hz and J=13.2 Hz. CH), 4.49 (1H, broad. CH), 7.03 (4H, m, aromatics), 7.22 (2H, m, aromatics), 7.50 (2H, m, aromatics).

Intermediate 78B

N-[1,2-Bis-(4-fluoro-phenyl)-ethyl]-2-(2,2-dimethyl-5-oxo-[1,3]dioxolan-4-ylidene)-N-methyl-acetamide

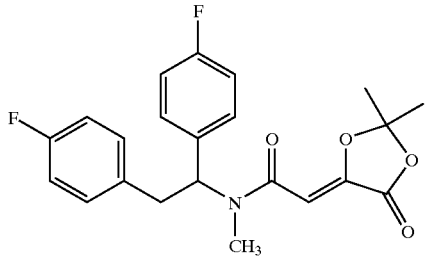

Intermediate 78B was prepared from Intermediate 78A using Method XIV. MS (ESI⁺) (m/z): 402 (M+H)⁺

Compound 78

3-{[1,2-Bis-(4-fluoro-phenyl)-ethyl]-methyl-carbamoyl}-2-hydroxy-acrylic acid

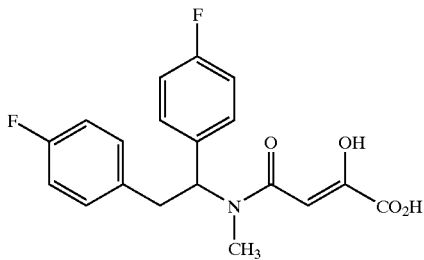

Compound 78 was prepared from Intermediate 78B using Method XVIII. MS(ESI⁻) (m/z): 360 (M−H).

EXAMPLE 79

Intermediate 79A

4-Fluoro-3'-(N-methylcarbamoyl)-benzophenone

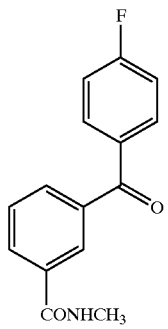

A solution of 3-{1-hydroxy-1-(4-fluorophenyl)-methyl}-N-methyl-benzamide (0.91 g, 3.51 mmol) in dichloromethane (75 ml) was treated with 1,1,1-triacetoxy-1,1-dihydro-1,2-benziodoxol-3(1H)-one (Dess-Martin periodinane) (5.9 g, 13.9 mmol) and the resulting mixture was stirred at 25° C. for 18 h. The solution was then diluted with ethyl acetate, washed with 5% aqueous sodium thiosulfate, sodium bicarbonate, brine and dried (magnesium sulfate). Evaporation of the solvent under reduce pressure and chromatography of the residue on silica gel (elution toluene-ethyl acetate, 1:1) gave 0.854 g (94%) of the title material as a white solid: mp 118–119° C. (ethyl acetate-hexane). $^1$HNMR 400 MHz (CDCl$_3$) δ (ppm): 3.05 (3H, d, J=4.7 Hz, NCH$_3$), 6.29 (1H, broad, NH), 7.20 (2H, m, aromatics), 7.59 (1H, t, J=8.0 Hz, aromatic), 7.84–7.3 (3H, m, aromatics), 8.05 (1H, m, aromatic), 8.14 (1H broad s, aromatic). Anal. Calcd for C$_{15}$H$_{12}$FNO$_2$: C, 70.03; H, 4.70; N, 5.44. Found: C, 70.04; H, 4.59, N, 5.36.

Intermediate 79B

4-Fluoro-3'-(N-methylcarbamoyl)-benzhydrylmethylamine

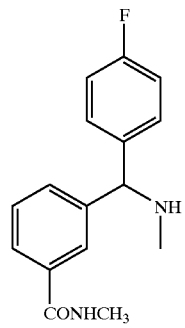

Intermediate 79B was prepared using Method III from Intermediate 79A. $^1$HNMR 400 MHz (CDCl$_3$) δ (ppm): 2.36 (3H, s, NCH$_3$), 2.95 and 2.97 (3H, 2 s, NCH$_3$), 4.7 (1H, s. CH), 6.38 (1H, broad, NH), 6.95 (2H, m, aromatics), 7.32 (3H, m, aromatics), 7.47 (1H, broad d, aromatic), 7.60 (1H, broad d, aromatic), 7.79 (1H, broad s, aromatic). MS (ESI⁺) (m/z): 273 (M+H).

Intermediate 79C

3-[{[2-(2,2-Dimethyl-5-oxo-[1,3]dioxolan-4-ylidene)-acetyl]-methyl-amino}-(4-fluoro-phenyl)-methyl]-N-methyl-benzamide

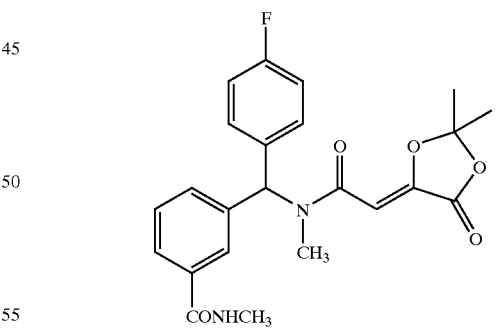

Intermediate 79C was prepared from Intermediate 79B using Method XIV. $^1$HNMR 400 MHz (DMSO-d$_6$) δ (ppm): mixture of rotamers; 1.48, 1.52 and 1.69 (6H, 3 s, CH$_3$), 2.63 and 2.82 (3H, 2 s, NCH$_3$), 2.76 (2H, d, J=4.56 Hz, CH$_3$), 6.19 (1H, broad s, CH benzhydryl), 6.58 and 6.96 (1H, 2 s, CH), 7.21 (4H, m, aromatics), 7.27 (1H, d, J=8.2 Hz, aromatic), 7.47 (1H, t, J=7.9 Hz, aromatic), 7.64 (1H, broad s, aromatic), 7.79 (1H, d, J=8.0 Hz, aromatic) and 8.49 (1H, s, NH). HRMS (ESI⁺) calculated for C$_{23}$H$_{24}$FN$_2$O$_5$ [M+H⁺]: 427.16693: found: 427.16840.

Compound 79

3-{[(4-Fluoro-phenyl)-(3-methylcarbamoyl-phenyl)-methyl]-methyl-carbamoyl}-2-hydroxy-acrylic acid

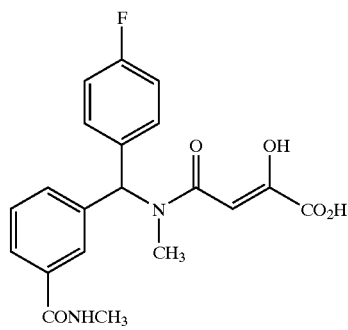

Compound 79 was prepared from Intermediate 79C using Method XVIII. $^1$HNMR 400 MHz (DMSO-$d_6$) δ (ppm): mixture of rotamers; 2.70 and 2.87 (3H, 2 s, NCH$_3$), 2.76 (2H, d, J=4.5 Hz, NCH$_3$), 6.31 and 6.41 (1H, 2 s, CH benzhydryl), 6.76 and 6.99 (1H, 2 s, CH), 7.21 (4H, m, aromatics), 7.19–7.81 (8H, m, aromatics). HRMS (MAB N$_2$) calculated for $C_{20}H_{19}FN_2O_5$ [M$^+$]: 386.12780: found: 386.12843.

EXAMPLE 80

Intermediate 80A 3,3-bis-(4-fluorophenyl)-propionic acid ethyl ester

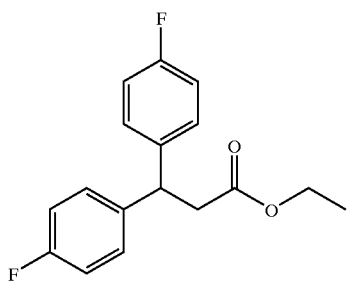

A suspension of zinc (5.7 g, 87.2 mmol) in dichloromethane (20 ml) was treated with iodine (0.1 g) and heated under reflux. A solution of ethyl bromoacetate (10.0 g, 59.8 mmol) in dichloromethane was then added dropwise over 15 min and the resulting mixture was heated for another 15 min. The thick paste was then cooled to 0–5° C. and treated dropwise with a solution of 4,4'-difluorobenzhydryl chloride (11.93 g, 50.0 mmol) in dichloromethane (20 ml). The cooling bath was then removed and the mixture was stirred at 22° C. for another 2 h. The reaction mixture was quenched by the addition of 1N hydrochloric acid and ethyl acetate. The organic phase was washed with water, saturated sodium bicarbonate, brine and dried (magnesium sulfate). Evaporation of the solvent under reduce pressure and distillation of the residue in vacuo gave 11.6 g (80%) of the title material as a clear oil: bp 95–100° C./0.1 torr (bulb to bulb distillation, air bath temperature). $^1$HNMR 400 MHz (CDCl$_3$) δ (ppm): 1.14 (3H, t, J=7.1 Hz, CH$_3$), 3.01 (2H, d, J=8.1 Hz, CH$_2$), 4.06 (2H, q, J=7.1 Hz, CH$_2$), 4.54 (1H, t, J=8.1 Hz, CH),7.0 (4H, m, aromatics), 7.2 (4H, m, aromatics). Anal. Calcd for $C_{17}H_{16}F_2O_2$: C, 70.34; H, 5.56. Found: C, 70.44; H, 5.50.

Intermediate 80B 3,3-bis-(4-fluorophenyl)-propionic acid

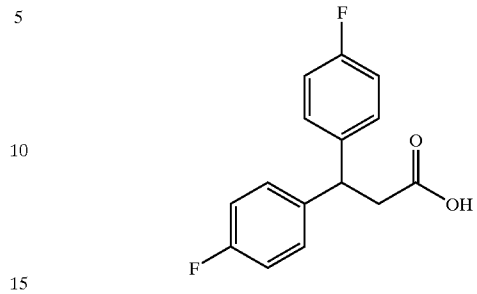

Saponification of Intermediate 80A as described in the preparation of Intermediate 1B gave the title acid as white needles: mp 106–107° C. (benzene-hexane). $^1$HNMR 400 MHz (CDCl$_3$) δ (ppm): 3.05 (2H, d, J=8.1 Hz, CH$_2$), 4.51 (1H, t, J=8.1 Hz, CH), 7.0 (4H, m, aromatics), 7.18 (4H, m, aromatics). Anal. Calcd for $C_{15}H_{12}F_2O_2$: C, 68.69; H, 4.61. Found: C, 68.71; H, 4.63.

Intermediate 80C 3,3-bis-(4-Fluorophenyl)-N-methyl-propylamine

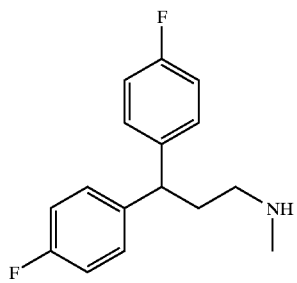

Intermediate 80C was prepared from Intermediate 80B using Method II. $^1$HNMR 400 MHz (CDCl$_3$) δ (ppm: 2.18 (2H, m, CH$_2$), 2.39 (3H, s, NCH$_3$), 2.51 (2H, t, J=7.3 Hz, CH$_2$), 3.99 (1H, t, J=8.0 Hz, CH), 6.96 (4H, m, aromatics), 7.16 (4H, m, aromatics). MS (ESI$^+$) (m/z): 262 (M+H).

Intermediate 80D

N-[3,3-Bis-(4-fluoro-phenyl)-propyl]-2-(2,2-dimethyl-5-oxo-[1,3]dioxolan-4-ylidene)-N-methyl-acetamide

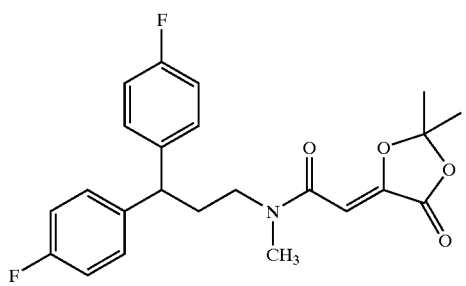

Intermediate 80D was prepared from Intermediate 80C using Method XIV. $^1$HNMR 400 MHz (CDCl$_3$) δ (ppm):

mixture of rotamers; 1.67 and 1.72 (6H, 2 s, CH₃), 2.29 (2H, m, CH₂), 2.97 and 3.01 (3H, 2 s, NCH₃), 3.27 and 3.35 (2H, 2 m, NCH₂), 3.87 and 3.92 (1H, 2 t, J=7.98 and J=7.83 Hz, CH), 5.85 and 6.07 (1H, 2 s, CH), 6.98 (4H, m, aromatics) and 7.17 (4H, m, aromatics). HRMS (ESI⁺) calculated for $C_{23}H_{24}F_2NO_4$ [M+H⁺]: 416.16733: found: 416.16850.

Compound 80

3-{[3,3-Bis-(4-fluoro-phenyl)-propyl]-methyl-carbamoyl}-2-hydroxy-acrylic acid

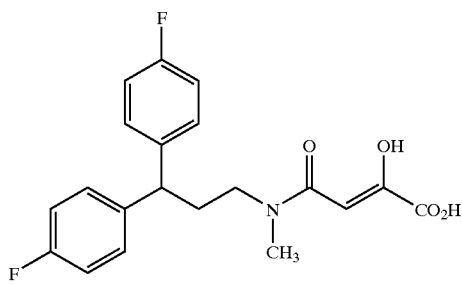

Compound 80 was prepared from Intermediate 80D using Method XVIII. ¹HNMR 400 MHz (CDCl₃) δ (ppm): mixture of rotamers; 2.29 (2H, m, CH₂), 3.0 (3H, s, NCH₃), 3.29 and 3.39 (2H, 2 m, NCH₂), 3.88 and 3.91 (1H, 2 t, J 7.7 and J=8.2 Hz, CH), 6.01 and 6.24 (1H, 2 s, CH), 7.08 (4H, m, aromatics) and 7.19 (4H, m, aromatics). HRMS (MAB N₂) calculated for $C_{20}H_{19}F_2NO_4$ [M⁺]: 375.12821: found: 375.12874.

EXAMPLE 81

Intermediate 81A

2-{1-Hydroxy-1-(4-fluorophenyl)-methyl}-N-methyl-benzamide

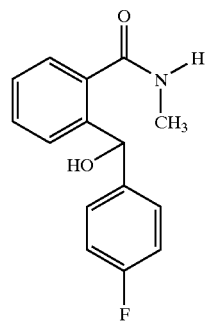

Reaction of 2-bromo-N-methylbenzamide with 4-fluorobenzaldehyde as described in the preparation of Intermediate 2A gave the title material as a white solid: mp: 133–134° C. ¹HNMR 400 MHz (CDCl₃) δ (ppm): 2.81 (3H, d, J=5.1 Hz, NCH₃), 5.89 (2H, broad s, CH and NH), 7.01 (2H, m, aromatics), 7.28–7.45 (6H, m, aromatics). Anal. Calcd for $C_{15}H_{14}FNO_2$: C, 69.49; H, 5.44; N, 5.40. Found: C, 69.46; H, 5.44; N, 5.41.

Intermediate 81B 2-(4-Fluorobenzyl)-N-methyl-benzamide

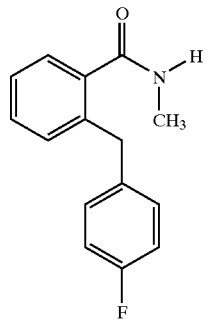

Hydrogenolysis of Intermediate 81A, as described in the preparation of Intermediate 2B, gave the title amide as white needles: mp 129–130° C. ¹HNMR 400 MHz (CDCl₃) δ (ppm): 2.9 (3H, d, J=4.5 Hz, NCH₃), 4.16 (2H, s, CH₂), 5.61 (1H, broad, NH), 6.96 (2H, m, aromatics), 6.99–7.38 (6H, m, aromatics). Anal. Calcd for $C_{15}H_{14}FNO$: C, 74.06; H, 5.80; N, 5.76. Found: C, 74.08; H, 5.86; N, 5.69.

Intermediate 81D 2-(4-Fluorobenzyl)-N-methyl-benzylamine

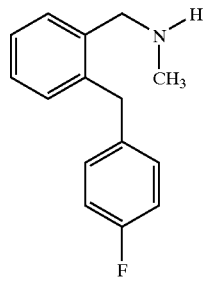

Reduction of Intermediate 81C, as described in the preparation of Intermediate 8B, gave the title amine as an oil: bp 85–90° C./0.1 torr (bulb to bulb distillation, air bath temperature). ¹HNMR 400 MHz (C₆D₆) δ (ppm): 2.26 (3H, s, NCH₃), 3.54 (2H, s, CH₂), 4.0 (2H, s, CH₂), 6.87 (2H, m, aromatics), 6.94 (2H, m, aromatics), 7.07 (1H, d, aromatic), 7.23 (2H,m aromatics),7.4 (1H, d, aromatic). MS (ESI⁺) (m/z): 230 (M+H). Anal. Calcd for $C_{15}H_{16}FN$: C, 78.57; H, 7.03; N, 6.10. Found: C, 78.37; H, 7.00; N, 6.16.

127
Intermediate 81E 2-(2,2-Dimethyl-5-oxo-[1,3]dioxolan-4-ylidene)-N-[2-(4-fluoro-benzyl)-benzyl]-N-methyl-acetamide

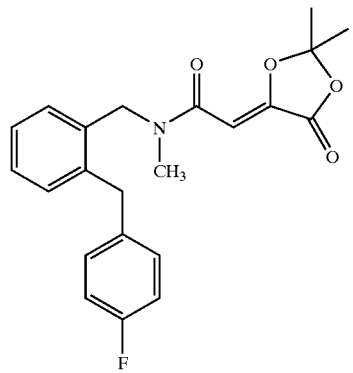

Intermediate 81E was prepared from Intermediate 81D using Method XIV. $^1$HNMR 400 MHz (CDCl$_3$) δ (ppm: mixture of rotamers; 1.59 and 1.72 (6H, 2 s, CH$_3$), 2.81 and 2.92 (3H, 2 s, NCH$_3$), 3.96 and 3.99 (2H, 2 s, CH$_2$), 4.43 and 4.64 (2H, 2 s, NCH$_2$), 5.88 and 6.03 (H, 2 s, CH), 6.91–7.3 (8H, m, aromatics). HRMS (MAB N$_2$) calculated for C$_{22}$H$_{22}$FNO$_4$ [M$^+$]: 383.15329: found: 383.15425.

Compound 81

3-{[2-(4-Fluoro-benzyl)-benzyl]-methyl-carbamoyl}-2-hydroxy-acrylic acid

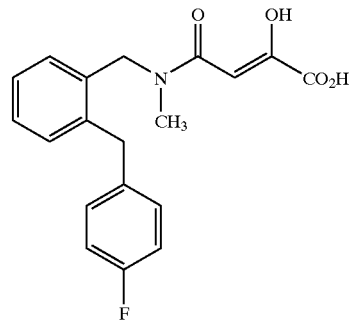

Compound 81 was prepared from Intermediate 81E using Method XVIII. $^1$HNMR 400 MHz (CDCl$_3$) δ (ppm): mixture of rotamers; 2.80 and 2.94 (3H, 2 s, NCH$_3$), 3.98 and 3.99 (2H, 2 s, CH$_2$), 4.44 and 4.64 (2H, 2 s, NCH$_2$), 6.06 and 6.19 (H, 2 s, CH), 6.90–7.36 (8H, m, aromatics). HRMS (MAB N$_2$) calculated for C$_{19}$H$_{18}$FNO4 [M$^+$]: 343.12199: found: 343.12171.

128
EXAMPLE 82

Intermediate 82A 2-(4-Fluorobenzyloxy)-N-methyl-benzylamine

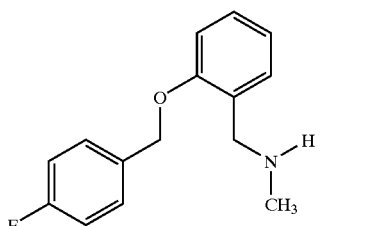

Intermediate 82A was prepared from 2-(4-fluorobenzyloxy)-benzaldehyde (Hellwinkle et al using Method III. Synthesis 1995, 1135.). $^1$HNMR 400 MHz (C$_6$D$_6$) δ (ppm): 1.90 (3H, s, NCH$_3$), 3.56 (2H, s, NCH$_2$), 4.77 (2H, s, OCH$_2$), 6.50 (1H, d, J=7.6 Hz, aromatic), 6.73 (1H, broad t, aromatic), 6.83 (2H, m, aromatics), 6.95 (1H, broad t, aromatic), 7.28 (2H, m, aromatics), 7.47 (1H, d, J=7.7 Hz, aromatic). HRMS (MAB N$_2$) calculated for C$_{15}$H$_{16}$FNO [M$^+$]: 245.12159: found: 245.12192, δ −1.3 ppm.

Intermediate 82B 2-(2,2-Dimethyl-5-oxo-[1,3]dioxolan-4-ylidene)-N-[2-(4-fluoro-benzyloxy)-benzyl]-N-methyl-acetamide

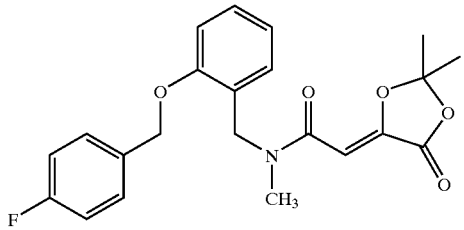

Intermediate 82B was prepared from Intermediate 82A using Method XIV. $^1$HNMR 400 MHz (CDCl$_3$) δ (ppm): mixture of rotamers; 1.67 and 1.73 (6H, 2 s, CH$_3$), 2.98 and 3.01 (3H, 2 s, NCH$_3$), 4.57 and 4.72 (2H, 2 s, NCH$_2$), 5.04 (2H, s, OCH$_2$), 6.1 and 6.16 (H, 2 s, CH), 6.91–7.41 (8H, m, aromatics). HRMS (MAB N$_2$) calculated for C$_{22}$H$_{22}$FNO$_5$ [M$^+$]: 399.1482: found: 399.1499.

Compound 82

3-{[2-(4-Fluoro-benzyloxy)-benzyl]-methyl-carbamoyl}-2-hydroxy-acrylic acid

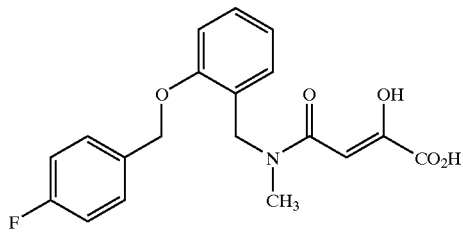

Compound 82 was prepared from Intermediate 82B using Method XVIII. $^1$HNMR 400 MHz (CDCl$_3$) δ (ppm): mixture of rotamers; 3.0 and 3.01 (3H, 2 s, NCH$_3$), 4.58 and 4.72 (2H, 2 s, NCH$_2$), 5.03 (2H, s, OCH$_2$), 6.30 and 6.32 (H, 2 s, CH), 6.95–7.52 (8H, m, aromatics). HRMS (MAB N$_2$) calculated for C$_{19}$H$_{18}$FNO$_5$ [M$^+$]: 359.1169: found: 359.1165.

EXAMPLE 83

Intermediate 83A (4-chlorobenzyl)-(3,4-dichlorobenzyl)-amine

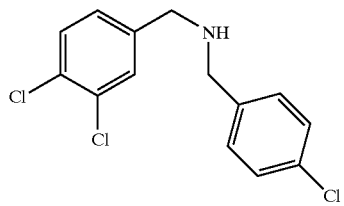

Intermediate 83A was prepared from N-(4-chlorobenzyl)-3,4-dichlorobenzamide (Borgma et al. *Farmaco Ed. Sci.* 1977, 32, 813) using Method II, step 2. $^1$HNMR 400 MHz (C$_6$D$_6$) δ (ppm): 3.22 (2H, s, NCH$_2$), 3.31 (2H, s, NCH$_2$), 6.78 (1H, d, J=8.5 Hz, aromatic), 6.99 (2H, d, J=8.1 Hz, aromatics), 7.15 (2H, d, J=8.1 Hz, aromatics), 7.24–7.31 (3H, m, aromatics).

Intermediate 83B

N-(4-Chloro-benzyl)—N-(3,4-dichloro-benzyl)-2-(2,2-dimethyl-5-oxo-[1, 3]dioxolan-4-ylidene)-acetamide

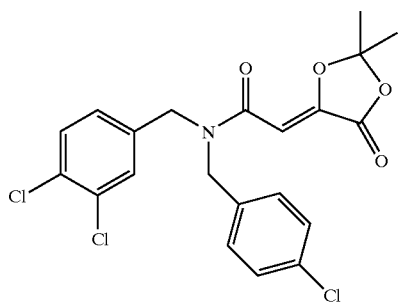

Intermediate 83B was prepared from Intermediate 83A using Method XIV. $^1$HNMR 400 MHz (CDCl$_3$) δ (ppm): mixture of rotamers; 1.77 (6H, s, CH$_3$), 4.47, 4.51, 4.57 and 4.6 (4H, 4 s, 2×NCH$_2$), 6.12 and 6.17 (1H, 2 s, CH), 7.02–7.47 (7H, m, aromatics). HRMS (FAB) calculated for C$_{21}$H$_{19}$Cl$_3$NO$_4$ [M+H$^+$]: 454.03796 found: 454.03740.

Compound 83

3-[(4-Chloro-benzyl)-(3,4-dichloro-benzyl)-carbamoyl]-2-hydroxy-acrylic acid

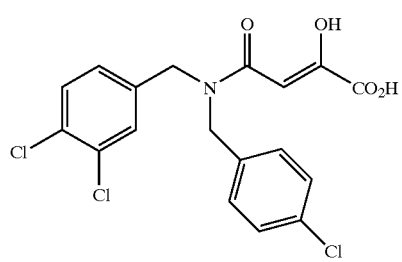

Compound 83 was prepared from Intermediate 83B using Method XVIII. Solid: mp 152° C. (dec. (hexane). $^1$HNMR 400 MHz (CDCl$_3$) δ (ppm): mixture of rotamers; 4.48, 4.51, 4.59 and 4.63 (4H, 4 s, 2×NCH$_2$), 6.35 and 6.41 (1H, 2 s, CH), 7.08–7.48 (7H, m, aromatics). HRMS (FAB) calculated for C$_{18}$H$_{15}$Cl$_3$NO$_4$ [M+H$^+$]: 414.00665: found: 414.00820.

EXAMPLE 84

Intermediate 84A

2-Benzyl-N-methyl-benzylamine

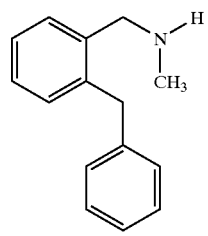

Intermediate 84A was prepared using Method II, step 2 from Intermediate 81B. $^1$HNMR 400 MHz (C$_6$D$_6$) δ (ppm):

2.27 (3H, s, NCH₃), 3.6 (2H, s, CH₂), 4.13 (2H, s, CH₂), 7.14–7.45 (8H, m, aromatics). MS (ESI⁺) (m/z): 212 (M+H). Hydrochloride salt: Anal. Calcd for C₁₅H₁₆FN.HCl: C, 72.72; H, 7.32; N, 5.65. Found: C, 72.71, H, 7.26, N, 5.64.

Intermediate 84B

N-(2-Benzyl-benzyl)-2-(2,2-dimethyl-5-oxo-[1,3]dioxolan-4-ylidene)-N-methyl-acetamide

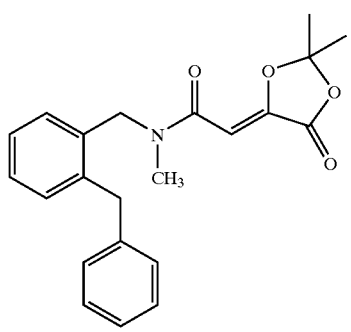

Intermediate 84B was prepared from Intermediate 84A using Method XIV. ¹HNMR 400 MHz (CDCl₃) δ (ppm): mixture of rotamers; 1.67 and 1.74 (6H, 2 s, CH₃), 2.78 and 2.93 (3H, 2 s, NCH₃), 4.03 and 4.06 (2H, 2 s, CH₂), 4.47 and 4.69 (2H, 2 s, NCH₂), 5.93 and 5.99 (H, 2 s, CH), 7.09–7.34 (8H, m, aromatics). MS (ESI⁺) (m/z) 366 (M+H⁺).

Compound 84

3-[(2-Benzyl-benzyl)-methyl-carbamoyl]-2-hydroxy-acrylic acid

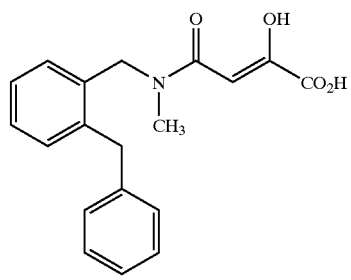

Compound 84 was prepared from Intermediate 84B using Method XVIII. ¹HNMR 400 MHz (CDCl₃) δ (ppm): mixture of rotamers; 2.78 and 2.94 (3H, 2 s, NCH₃), 4.05 and 4.06 (2H, 2 s, CH₂), 4.48 and 4.68 (2H, 2 s, NCH₂), 6.11 and 6.18 (H, 2 s, CH), 7.04–7.37 (8H, m, aromatics). HRMS (MAB N₂) calculated for C₁₉H₁₉NO₄ [M⁺]: 325.131408: found: 325.130098.

EXAMPLE 85

Intermediate 85A

N-(3-Biphenyl-4-yl-propyl)-N-(4-fluoro-benzyl)-acetamide

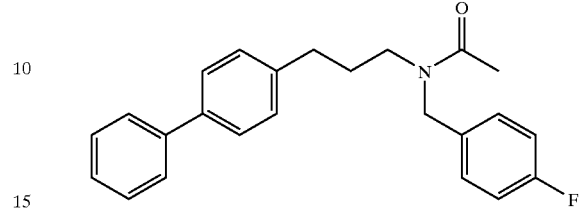

Intermediate 85A was prepared from (3-biphenyl-4-ylpropyl)-(4-fluorobenzyl)-amine hydrochloride using Method IV. ¹H NMR shows a mixture of rotamers at room temperature. ¹H NMR (CDCl₃) δ: 1.90 (m), 2.10 (s), 2.11 (s), 2.65 (m), 3.21 (m), 3.42 (m), 4.46 (s), 4.54 (s), 6.95–7.60 (overlapping m).

Compound 85

3-[(3-Biphenyl-4-yl-propyl)-(4-fluoro-benzyl)-carbamoyl]-2-hydroxy-acrylic acid

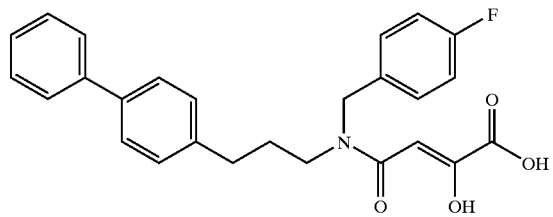

Compound 85 was prepared from Intermediate 85A using Method XII. MS (M–H) calcd for C₂₆H₂₃NO₄F: 432.16; found: 432.11. ¹H NMR shows a mixture of rotamers at room temperature. ¹H NMR (500 MHz, CDCl₃) δ: 1.99 (m), 2.66 (m), 3.26 (m), 3.47 (m), 3.76 (m), 4.48 (s), 4.57 (s), 6.30 (s), 6.33 (s), 6.96–7.61 (overlapping m).

EXAMPLE 86

Intermediate 86A

N-(4-Fluoro-benzyl)-N-(2-pyridin-4-yl-ethyl)-acetamide

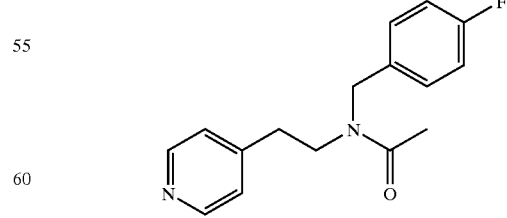

Intermediate 86A was prepared from N-(2-pyridin-4-yl-ethyl)-acetamide and 4-fluorobenzylbromide using Method VII. ¹H NMR shows a mixture of rotamers at room temperature. ¹H NMR (500 MHz, d₆-MeOD) δ: 2.03 (s), 2.12

(s), 2.87 (t, J=8), 2.93 (t, J=8), 3.59 (m), 4.56 (s), 4.60 (s), 7.06 (m), 7.23–7.31 (overlapping m), 8.40 (m), 8.44 (m).

Compound 86

3-[(4-Fluoro-benzyl)-(2-pyridin-4-yl-ethyl)-carbamoyl]-2-hydroxy-acrylic acid

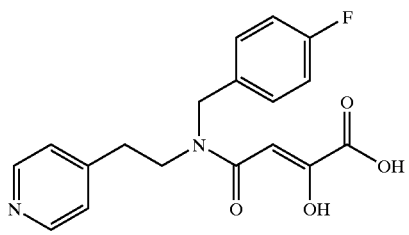

Compound 86 was prepared from Intermediate 86A using Method XII. MS (M−H) calcd for $C_{18}H_{16}N_2O_4F$: 343.11; found:343.06. $^1$H NMR shows a mixture of rotamers at room temperature. $^1$H NMR (500 MHz, d$_6$-MeOD) δ: 3.19 (m), 3.83 (m), 4.71 (s), 6.08 (s), 6.30 (s), 7.05 (m), 7.29 (m), 7.35 (m), 7.95 (m), 8.72 (m).

EXAMPLE 87

Intermediate 87A

N-[3-(2-Chloro-phenyl)-propyl]-N-(4-fluoro-benzyl)-acetamide

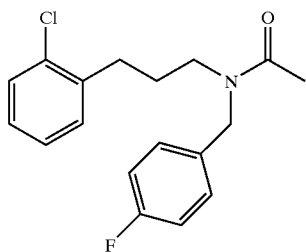

Intermediate 87A was prepared from [3-(2-chloro-phenyl)-propyl]-(4-fluoro-benzyl)-amine hydrochloride using Method IV. $^1$H NMR shows a mixture of rotamers at room temperature. $^1$H NMR (500 MHz, CDCl$_3$) δ: 1.86 (m), 2.12 (s), 2.70 (m), 3.23 (m), 3.42 (m), 4.48 (s), 4.54 (s), 6.95–7.36 (overlapping m).

Compound 87

3-[[3-(2-Chloro-phenyl)-propyl]-(4-fluoro-benzyl)-carbamoyl]-2-hydroxy-acrylic acid

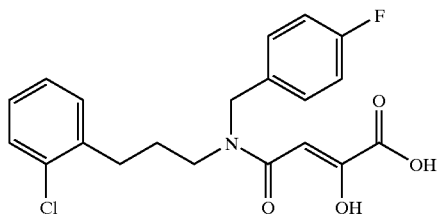

Compound 87 was prepared from Intermediate 87A using Method XII. MS (M−H) calcd for $C_{20}H_{18}NO_4ClF$: 390.04; found: 390.07. $^1$H NMR shows a mixture of rotamers at room temperature. $^1$H NMR (300 MHz, d$_6$-MeOD) δ: 1.87 (m), 2.72 (m), 3.36 (m), 3.50 (m), 4.63 (s), 6.25 (s), 6.31 (s), 6.92–7.36 (overlapping m).

EXAMPLE 88

Intermediate 88A

N-(4-Fluoro-benzyl)-N-[2-(4-fluoro-benzyloxy)-phenyl]-acetamide

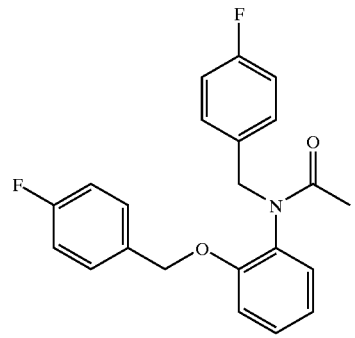

Intermediate 88A was prepared from 2-(4-fluoro-benzyloxy)-phenylamine and 4-fluorobenzylbromide the same method used for Intermediate 43A. $^1$H NMR (500 MHz, CDCl$_3$) δ: 1.83 (s, 3), 4.46 (d, 1, J=14), 4.90 (dd, 2, J=12, 60), 5.01 (d, 1, J=14). 6.59–7.25 (overlapping m, 12).

Intermediate 88B

3-{(4-Fluoro-benzyl)-[2-(4-fluoro-benzyloxy)-phenyl]-carbamoyl}-2-hydroxy-acrylic acid methyl ester

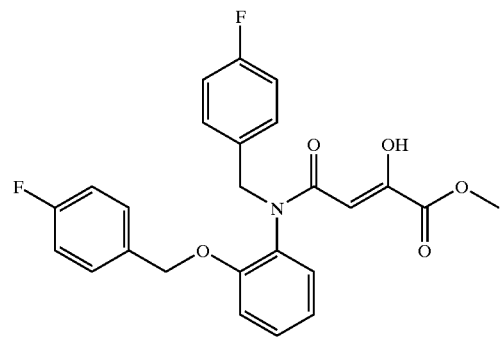

Intermediate 88B was prepared from intermediate 88A using Method IX. MS (M−H) calcd for $C_{25}H_{19}F_3NO_5$: 470.1; found: 470.1 $^1$H NMR (500 MHz, CDCl$_3$) δ: 3.80 (s, 3), 4.48 (d, 1, J=14), 4.93 (dd, 2, J=12, 33), 5.12 (d, 1, J=14), 5.64 (s, 1), 6.60–7.22 (overlapping m, 12).

Compound 88

3-{(4-Fluoro-benzyl)-[4-fluoro-2-(4-fluoro-benzyloxy)-phenyl]-carbamoyl}-2-hydroxy-acrylic acid

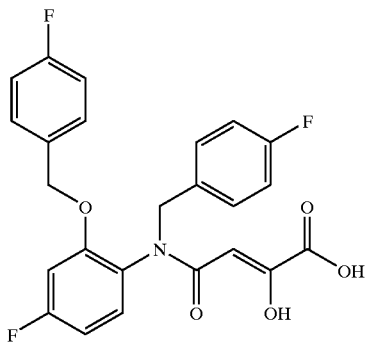

Compound 88 was prepared from Intermediate 88B using Method XII. MS (M–H) calcd for $C_{24}H_{17}NO_4F_3$: 456.11; found: 456.00. $^1$H NMR (500 MHz, CDCl$_3$) δ: 4.50 (d, J=14), 4.89 (d, J=12), 4.95 (d, J=12), 5.09 (d, J=14), 5.73 (s), 6.61–7.21 (m).

EXAMPLE 89

Intermediate 89A

N-(3,5-dichloro-benzyl)-2-(2,2-dimethyl-5-oxo-[1,3]dioxolan-4-ylidene)N-methylacetamide

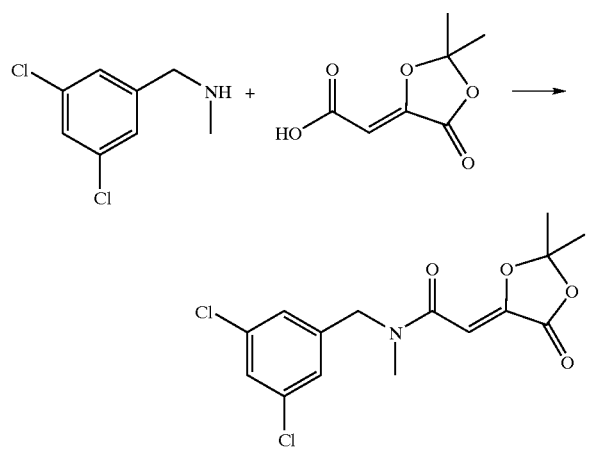

Coupling of (Z)-2,2-dimethyl-5-(carboxymethylene)-1,3-dioxolan-4-one with N-methyl-3,5-dichlorobenzylamine (Meindl, W. R. et al., *J. Med. Chem.*, 27, 1984, 1111–1118) as described in Method XIV gave the title material as a syrup. $^1$HNMR 400 MHz (CDCl$_3$) δ (ppm): mixture of rotamers; 1.71 and 1.75 (6H, 2 s, CH$_3$)$_1$ 2.98 and 3.04 (3H, 2 s, NCH$_3$), 4.54 and 4.60 (2H, 2 s, NCH$_2$), 6.08 and 6.18 (1H, 2 s, CH), 7.07–7.31 (3H, m, aromatics). HRMS (MAB N$_2$) calculated for $C_{15}H_{15}Cl_2NO_4$ [M$^+$]: 343.037814: found: 343.038563.

Compound 89

3-[(3,5-dichloro-benzyl)-methyl-carbamoyl]-2-hydroxy-acrylic acid

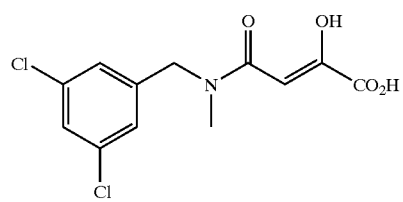

Saponification of Intermediate 89A carried out using Method XVIII yielded the title acid as a white solid. $^1$HNMR 400 MHz (DMSO-d$_6$) δ (ppm): mixture of rotamers; 3.06 (3H, s, NCH$_3$), 4.55 and 4.61 (2H, 2 s, NCH$_2$), 6.31 and 6.39 (1H, 2 s, CH), 7.05–7.34 (3H, m, aromatics). HRMS (MAB N$_2$) calculated for $C_{12}H_{11}Cl_2NO_4$ [M$^+$]: 303.006513: found: 303.007587.

EXAMPLE 90

Intermediate 90A

N-(3,4-Dichlorophenyl)-4-fluorobenzamide

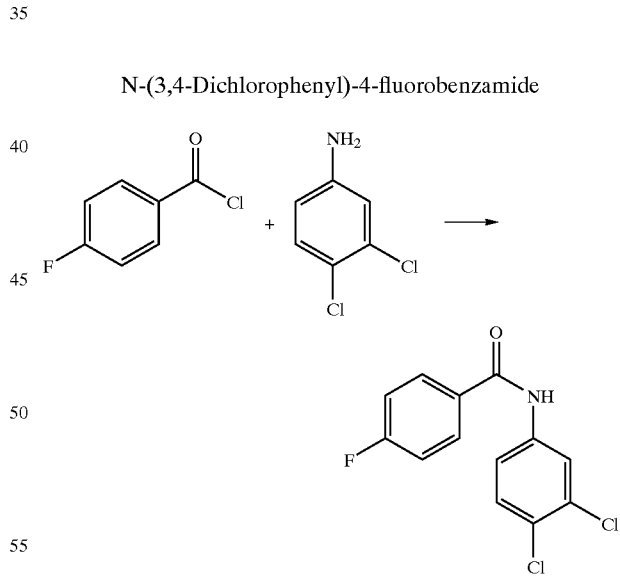

Reaction of 4-fluorobenzoyl chloride with 3,4-dichloroaniline using Method II, step 1, gave the title amide as crystals: mp 160–161° C. (ethyl acetate-hexane). $^1$HNMR 400 MHz (CDCl$_3$) δ (ppm): 7.19 (2H, m, aromatics), 7.44 (2H, m, aromatics), 7.70 (1H, broad, NH), 7.88 (3H, m, aromatics). Anal. Calcd for $C_{13}H_{18}Cl_2FNO$: C, 54.96; H, 2.84; N, 4.93. Found: C, 54.96; H, 2.87; N, 4.90.

Intermediate 90B (3,4-Dichlorophenyl)-(4-fluorobenzyl)-amine

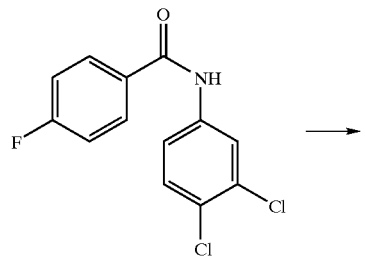

Reduction of Intermediate 90A using Method II step 2, gave the title amine. The hydrochloride salt was obtained as a white solid. ¹HNMR 400 MHz (DMSO-d$_6$) δ (ppm): 4.25 (2H, s, NCH$_2$), 6.56 (1H, dd, J=2.6 Hz and J=8.7 Hz, aromatic), 6.73 (1H, d, J=2.6 Hz, aromatic), 7.15 (2H, m, aromatics), 7.22 (1H, d, J=8.7 Hz, aromatic), 7.36 (2H, m, aromatics).

Intermediate 90C

N-(3,4-dichloro-phenyl)-2-(2,2-dimethyl-5-oxo-[1,3]dioxolan-4-ylidene)-N-(4-fluoro-benzyl)-acetamide

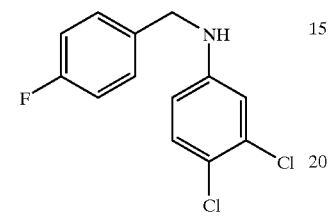

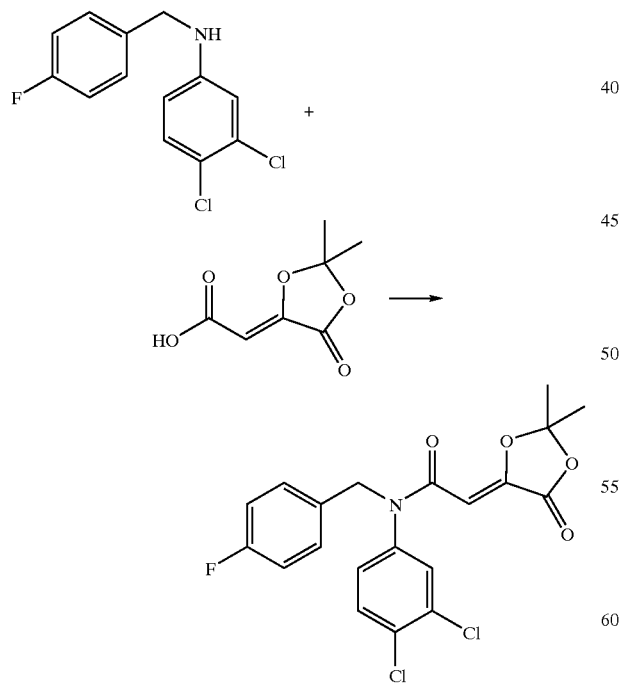

Acylation of Intermediate 90B with (Z)-2,2-dimethyl-5-(chlorocarbonylmethylene)-1,3-dioxolan-4-one as described in Method XIV gave the title amide as a foam. ¹HNMR 400 MHz (CDCl$_3$) δ (ppm): 1.73 (6H, s, CH$_3$), 4.88 (2H, s, NCH$_2$), 5.63 (1H, s, CH), 6.81 (1H, dd, J=2.7 Hz and J=8.5 Hz, aromatic), 6.97 (2H, m, aromatics), 7.15 (1H, d, J=2.7 Hz, aromatics), 7.19 (2H, m, aromatics), 7.41 (1H, d, J=8.5 Hz, aromatic). HRMS (FAB) calculated for C$_{20}$H$_{17}$Cl$_2$FNO$_4$ [M+H$^+$]: 424.05188: found: 424.05120.

Compound 90

3-[(3,4-dichloro-phenyl)-(4-fluoro-benzyl)-carbamoyl]-2-hydroxy-acrylic acid

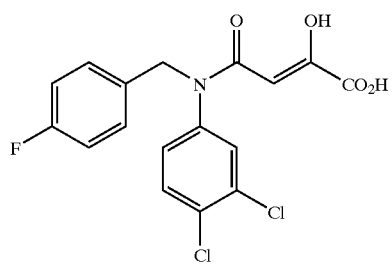

Saponification of Intermediate 90C carried out using Method XVIII yielded the title acid as a white solid. ¹HNMR 400 MHz (DMSO-d$_6$) δ (ppm): 4.97 (2H, s, NCH$_2$), 5.75 (1H, broad s, CH), 7.12 (2H, m, aromatics), 7.2 (1H, dd, aromatic), 7.27 (2H, m, aromatics), 7.69 (1H, d, J=8.6 Hz, aromatic), 7.71 (1H, d, J=2.4 Hz, aromatic). HRMS (MAB N$_2$) calculated for C$_{17}$H$_{12}$Cl$_2$FNO$_4$ [M$^+$]: 383.012742: found: 383.012742.

EXAMPLE 91

Intermediate 91A 2-(2,2-Dimethyl-5-oxo-[1,3]dioxolan-4-ylidene)-N-(3-fluoro-4-methyl-benzyl)-acetamide

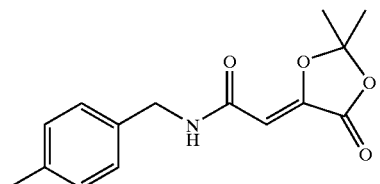

Intermediate 91A was prepared 3-fluoro-4-methyl-benzyl-amine hydrochloride using Method XVII HRMS (M+H) calcd for C$_{15}$H$_{17}$NO$_4$F: 294.1142; found: 294.1146. ¹H NMR (500 MHz, CDCl$_3$) δ: 1.73 (s, 6), 2.25 (s, 3), 4.49 (s, 1), 4.50 (s, 1) 5.90 (s, 1), 6.69 (br s, 1), 6.96 (m, 2), 7.13 (m, 1). ¹³C NMR (125 MHz, CDCl$_3$) δ: 14.29, 26.86, 29.52, 42.84, 67.10, 101.21, 107.65, 113.97, 114.05, 114.23, 122.90, 122.93, 123.94, 124.07, 131.65, 131.69, 137.77, 143.05, 160.41, 161.66, 162.35, 163.07.

Compound 91

3-(3-Fluoro-4-methyl-benzylcarbamoyl)-2-hydroxy-acrylic acid

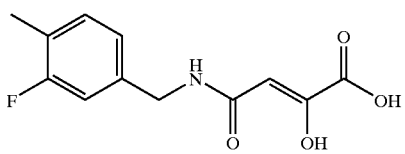

Compound 91 was prepared from Intermediate 91A using Method XVIII. HRMS (M–H) calcd for $C_{12}H_{11}NO_4F$: 252.0672; found: 252.0676. $^1$H NMR (500 MHz, DMSO) δ: 2.20 (s, 3), 4.36 (m, 2), 6.04 (s, 1), 7.03 (m, 2), 7.25 (m, 1), 9.01 (m, 1). $^{13}$C NMR (125 MHz, DMSO) δ: 13.72, 13.74, 41.17, 97.80, 113.63, 113.81, 122.65, 122.77, 123.01, 131.47, 131.51, 138.31, 138.37, 157.52, 159.50, 161.43, 163.31, 170.32.

EXAMPLE 92

Intermediate 92A

N-[Bis-(4-chloro-phenyl)-methyl]-2-(2,2-dimethyl-5-oxo-[1,3]dioxolan-4-ylidene)-acetamide

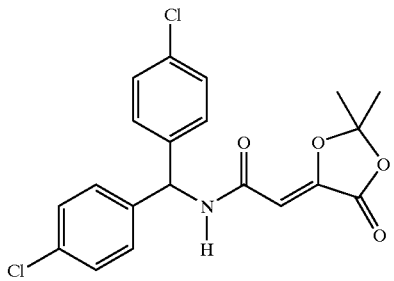

Intermediate 92A was prepared from Bis-(4-chlorophenyl)-methyl-amine hydrochloride using Method XIV.

$^1$HNMR 400 MHz (CDCl$_3$) δ (ppm): 1.75, (6H, s, CH$_3$), 5.93 (1H, s, CH), 6.29 (1H, d, J=8.2 Hz, CH benzhydryl), 6.75 (1H, broad d, NH), 7.18 (4H, broad d, aromatics), 7.34 (4H, broad d, aromatics). HRMS (MAB N$_2$) calculated for $C_{20}H_{17}Cl_2NO_4$ [M$^{30}$]: 405.05364: found: 405.05432.

Compound 92

3-{[Bis-(4-chloro-phenyl)-methyl]-carbamoyl}-2-hydroxy-acrylic acid

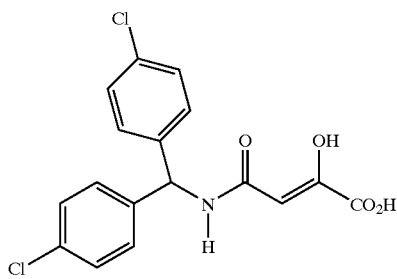

Compound 92 was prepared from Intermediate 92A using Method XVIII. $^1$HNMR 400 MHz (DMSO-d$_6$) δ (ppm): 6.16 (1H, s, CH), 6.23 (1H, d, J=8.7 Hz, CH benzhydryl), 7.32 (4H, broad d, aromatics), 7.44 (4H, broad d, aromatics), 9.44 (1H, d, J=8.7 Hz, NH). HRMS (MAB N$_2$) calculated for $C_{17}H_{13}Cl_2NO_4$ [M$^+$]: 365.02216: found: 365.02317.

Chemical intermediates of the present invention, having the following formula, were prepared according to Method XV.

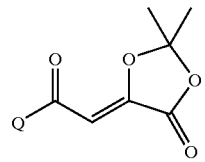

| Intermediate Number | Q | HPLC Retention time (min) | Formula | MS Data (M + H)$^+$ |
|---|---|---|---|---|
| 93A | 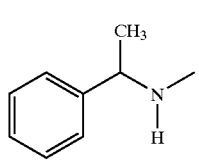 | 1.86 | $C_{15}H_{17}NO_4$ | 276 |

-continued
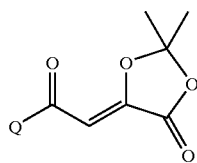
| Intermediate Number | Q | HPLC Retention time (min) | Formula | MS Data (M + H)+ |
|---|---|---|---|---|
| 94A | 2-OCH₃-C₆H₄-CH₂-N(H)-CH₃ | 1.83 | $C_{15}H_{17}NO_5$ | 292 |
| 95A | 2-CH₃-C₆H₄-CH₂-N(H)-CH₃ | 1.88 | $C_{15}H_{17}NO_4$ | 276 |
| 96A | 3-CH₃O-C₆H₄-CH₂-N(H)-CH₃ | 1.76 | $C_{15}H_{17}NO_5$ | 292 |
| 97A | 3-CH₃-C₆H₄-CH₂-N(H)-CH₃ | 1.92 | $C_{15}H_{17}NO_4$ | 276 |
| 98A | 4-F-C₆H₄-CH₂-N(H)-CH₃ | 1.81 | $C_{14}H_{14}FNO_4$ | 280 |
| 99A | 4-Cl-C₆H₄-CH₂-N(H)-CH₃ | 1.99 | $C_{14}H_{14}ClNO_4$ | 296 |
| 100A | 4-CH₃O-C₆H₄-CH₂-N(H)-CH₃ | 1.74 | $C_{15}H_{17}NO_5$ | 292 |
| 101A | 4-CH₃-C₆H₄-CH₂-N(H)-CH₃ | 1.93 | $C_{15}H_{17}NO_4$ | 276 |
| 102A | 4-CF₃-C₆H₄-CH₂-N(H)-CH₃ | 2.12 | $C_{15}H_{14}F_3NO_4$ | 330 |
| 103A | 4-O₂N-C₆H₄-CH₂-N(H)-CH₃ | 1.77 | $C_{14}H_{14}N_2O_6$ | 307 |

-continued
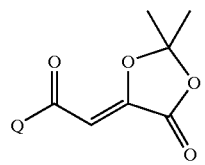
| Intermediate Number | Q | HPLC Retention time (min) | Formula | MS Data $(M + H)^+$ |
|---|---|---|---|---|
| 104A | 3-Cl-C6H4-CH2-NH-CH3 | 1.98 | $C_{14}H_{14}ClNO_4$ | 296 |
| 105A | 4-t-Bu-C6H4-CH2-NH-CH3 | 2.34 | $C_{18}H_{23}NO_4$ | 318 |
| 106A | 4-F-C6H4-CH(CH3)-NH-CH3 | 1.91 | $C_{15}H_{16}FNO_4$ | 294 |
| 107A | 2,3-Cl2-C6H3-CH2-NH-CH3 | 2.12 | $C_{14}H_{13}Cl_2NO_4$ | 330 |
| 108A | 2,4-(OCH3)2-C6H3-CH2-NH-CH3 | 1.84 | $C_{16}H_{19}NO_6$ | 322 |
| 109A | 3,5-F2-C6H3-CH2-NH-CH3 | 1.91 | $C_{14}H_{13}F_2NO_4$ | 298 |
| 110A | (R)-C6H5-CH(CH3)-NH-CH3 | 1.85 | $C_{15}H_{17}NO_4$ | 276 |
| 111A | (S)-C6H5-CH(CH3)-NH-CH3 | 1.85 | $C_{15}H_{17}NO_4$ | 276 |

-continued
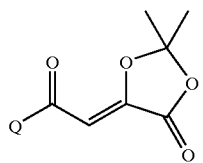
| Intermediate Number | Q | HPLC Retention time (min) | Formula | MS Data (M + H)+ |
|---|---|---|---|---|
| 112A | (N-benzyl-N-methyl-anilino) | 1.86 | C20H19NO4 | 338 |
| 113A | (N-benzyl-N-methyl-benzylamino) | 1.91 | C21H21NO4 | 352 |
| 114A | (N-ethyl-N-methyl-benzylamino) | 1.99 | C16H19NO4 | 290 |
| 115A | (N-butyl-N-methyl-benzylamino) | 1.88 | C18H23NO4 | 318 |
| 116A | (3,4-dichloro-N,N-dimethyl-benzylamino) | 1.82 | C15H15Cl2NO4 | 344 |
| 117A | (N-benzyl-N-methyl-α-methylbenzylamino) | 1.95 | C22H23NO4 | 366 |
| 118A | (2-(4-chlorophenoxy)-N,N-dimethyl-ethylamino) | 1.77 | C16H18ClNO5 | 340 |

-continued

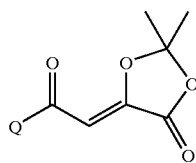

| Intermediate Number | Q | HPLC Retention time (min) | Formula | MS Data (M + H)+ |
|---|---|---|---|---|
| 119A | (S)-α-methylbenzyl-N,N-dimethylamine group | 1.64 | $C_{16}H_{19}NO_4$ | 290 |
| 120A | N-benzyl-N-methyl-(4-methylbenzyl)amine group | 2.09 | $C_{23}H_{25}NO_4$ | 380 |
| 121A | (R)-α-methylbenzyl-N,N-dimethylamine group | 1.64 | $C_{16}H_{19}NO_4$ | 290 |
| 122A | 4,4-bis(4-chlorophenyl)-N-methylbutylamine group | 2.18 | $C_{24}H_{25}Cl_2NO_4$ | 462 |
| 123A | N-(4-fluorobenzyl)-N-methyl-(4-methylbenzyl)amine group | 2.01 | $C_{22}H_{22}FNO_4$ | 384 |
| 124A | 3-(4-isopropylphenoxy)-N,N-dimethylpropylamine group | 1.95 | $C_{20}H_{27}NO_5$ | 362 |

-continued
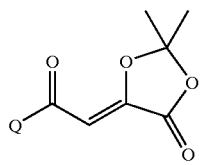
| Intermediate Number | Q | HPLC Retention time (min) | Formula | MS Data $(M + H)^+$ |
|---|---|---|---|---|
| 125A | 4-chloro-2-benzylphenoxy ethyl N,N-dimethylamine | 2.06 | $C_{23}H_{24}ClNO_5$ | 430 |
| 126A | 4-carbamoylphenoxy-2-hydroxy-3-(N-isopropyl-N-methylamino)propyl | 1.53 | $C_{21}H_{28}N_2O_7$ | 421 |
| 127A | 1,2-diphenyl-1-hydroxy-2-(N-isopropyl-N-methylamino)ethyl | 2.71 | $C_{24}H_{27}NO_5$ | 410 |
| 128A | (R)-1-phenylethyl-N-methyl-3,4-dimethoxybenzyl amine | 2.29 | $C_{24}H_{27}NO_6$ | 426 |
| 129A | N-methyl-N-phenethylamine | 1.95 | $C_{16}H_{19}NO_4$ | 290 |

-continued
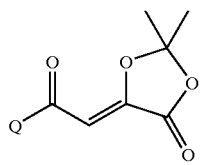
| Intermediate Number | Q | HPLC Retention time (min) | Formula | MS Data (M + H)+ |
|---|---|---|---|---|
| 130A | | 2.53 | $C_{21}H_{30}N_2O_4$ | 375 |
| 131A | | 1.47 | $C_{15}H_{18}N_2O_4$ | 291 |
| 132A | | 1.71 | $C_{18}H_{23}NO_6$ | 350 |
| 133A | | 2.39 | $C_{23}H_{27}NO_6$ | 414 |
| 134A | | 2.15 | $C_{18}H_{23}NO_5$ | 334 |
| 135A | | 2.46 | $C_{22}H_{29}NO_6$ | 404 |
| 136A | | 2.62 | $C_{26}H_{27}NO_4$ | 418 |

-continued

| Intermediate Number | Q | HPLC Retention time (min) | Formula | MS Data (M + H)+ |
|---|---|---|---|---|
| 137A | (2-methyl-1-phenylpropan-2-yl)dimethylamine group | 2.36 | $C_{18}H_{23}NO_4$ | 318 |
| 138A | N-(2-methylphenyl)-2-(N-methyl-N-propylamino)propanamide group | 2.15 | $C_{20}H_{26}N_2O_5$ | 375 |
| 139A | (naphthalen-1-ylmethyl)dimethylamine group | 2.22 | $C_{19}H_{19}NO_4$ | 326 |
| 140A | 1-(4-hydroxyphenyl)-2-(N-butyl-N-methylamino)ethanol group | 1.74 | $C_{19}H_{25}NO_6$ | 364 |
| 141A | 3-(10,11-dihydro-5H-dibenzo[a,d]cyclohepten-5-yl)-N,N-dimethylpropylamine group | 2.63 | $C_{25}H_{28}N_2O_4$ | 421 |
| 142A | N-methyl-N-(1-phenylethyl)-3,3-diphenylpropylamine group | 2.89 | $C_{30}H_{31}NO_4$ | 470 |

-continued

| Intermediate Number | Q | HPLC Retention time (min) | Formula | MS Data (M + H)⁺ |
|---|---|---|---|---|
| 143A | [structure: 4-fluorophenyl and 3-(N-methyl-N-methylaminomethyl)phenyl groups on CH attached to n-butyl chain with H₃C terminus] | 3.9 | $C_{26}H_{30}FNO_4$ | 440 |

Compounds of the present invention, as shown in the following formula, were prepared according to Method XIX.

| Compound Number | Q | Formula | MS Data (M − H)⁻ |
|---|---|---|---|
| 93 | [1-phenylethyl-N(H)-CH₃] | $C_{12}H_{13}NO_4$ | 234 |
| 94 | [2-methoxybenzyl-N(H)-CH₃] | $C_{12}H_{13}NO_5$ | 250 |
| 95 | [2-methylbenzyl-N(H)-CH₃] | $C_{12}H_{13}NO_4$ | 234 |
| 96 | [3-methoxybenzyl-N(H)-CH₃] | $C_{12}H_{13}NO_5$ | 250 |
| 97 | [3-methylbenzyl-N(H)-CH₃] | $C_{12}H_{13}NO_4$ | 234 |

-continued
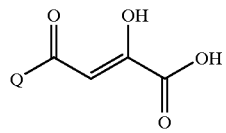
| Compound Number | Q | Formula | MS Data (M − H)⁻ |
|---|---|---|---|
| 98 | 4-F-C₆H₄-CH₂-NH- | C₁₁H₁₀FNO₄ | 238 |
| 99 | 4-Cl-C₆H₄-CH₂-NH- | C₁₁H₁₀ClNO₄ | 254 |
| 100 | 4-H₃CO-C₆H₄-CH₂-NH- | C₁₂H₁₃NO₅ | 250 |
| 101 | 4-H₃C-C₆H₄-CH₂-NH- | C₁₂H₁₃NO₄ | 234 |
| 102 | 4-F₃C-C₆H₄-CH₂-NH- | C₁₂H₁₀F₃NO₄ | 288 |
| 103 | 4-O₂N-C₆H₄-CH₂-NH- | C₁₁H₁₀N₂O₆ | 265 |
| 104 | 3-Cl-C₆H₄-CH₂-NH- | C₁₁H₁₀ClNO₄ | 254 |
| 105 | 4-t-Bu-C₆H₄-CH₂-NH- | C₁₅H₁₉NO₄ | 276 |
| 106 | 4-F-C₆H₄-CH(CH₃)-NH- | C₁₂H₁₂FNO₄ | 252 |
| 107 | 2,3-Cl₂-C₆H₃-CH₂-NH- | C₁₁H₉Cl₂NO₄ | 288 |

-continued
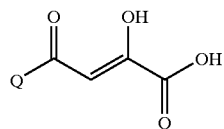
| Compound Number | Q | Formula | MS Data $(M - H)^-$ |
|---|---|---|---|
| 108 | 2,4-dimethoxybenzyl-N(H)-methyl | $C_{13}H_{15}NO_6$ | 280 |
| 109 | 3,5-difluorobenzyl-N(H)-methyl | $C_{11}H_9F_2NO_4$ | 256 |
| 110 | (R)-α-methylbenzyl-N(H)-methyl | $C_{12}H_{13}NO_4$ | 234 |
| 111 | (S)-α-methylbenzyl-N(H)-methyl | $C_{12}H_{13}NO_4$ | 234 |
| 112 | N-benzyl-N-phenyl-methyl | $C_{17}H_{15}NO_4$ | 296 |
| 113 | N,N-dibenzyl-methyl | $C_{18}H_{17}NO_4$ | 310 |
| 114 | N-benzyl-N-ethyl-methyl | $C_{13}H_{15}NO_4$ | 248 |

-continued
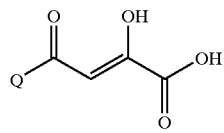
| Compound Number | Q | Formula | MS Data (M − H)⁻ |
|---|---|---|---|
| 115 | H₃C—CH₂CH₂CH₂—N(CH₃)—CH₂—C₆H₅ | $C_{15}H_{19}NO_4$ | 276 |
| 116 | 3,4-dichlorobenzyl-N(CH₃)₂ | $C_{12}H_{11}Cl_2NO_4$ | 302 |
| 117 | (α-methylbenzyl)(benzyl)(methyl)amine | $C_{19}H_{19}NO_4$ | 324 |
| 118 | 4-ClC₆H₄—O—CH₂CH₂—N(CH₃)₂ | $C_{13}H_{14}ClNO_5$ | 298 |
| 119 | (S)-α-methylbenzyl-N(CH₃)₂ | $C_{13}H_{15}NO_4$ | 248 |
| 120 | (4-methylbenzyl)(4-methylbenzyl)(methyl)amine | $C_{20}H_{21}NO_4$ | 338 |
| 121 | (R)-α-methylbenzyl-N(CH₃)₂ | $C_{13}H_{15}NO_4$ | 248 |

-continued
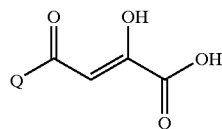
| Compound Number | Q | Formula | MS Data (M − H)⁻ |
|---|---|---|---|
| 122 | 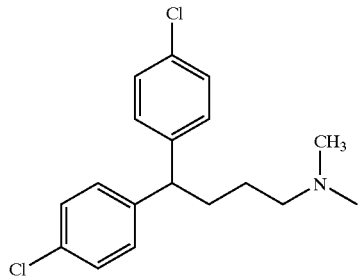 | $C_{21}H_{21}Cl_2NO_4$ | 420 |
| 123 | 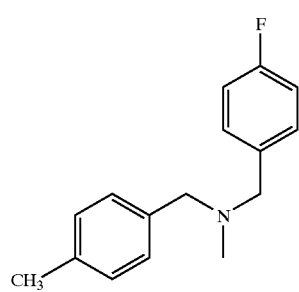 | $C_{19}H_{18}FNO_4$ | 342 |
| 124 | 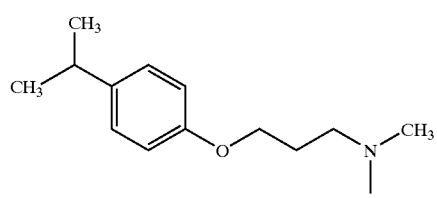 | $C_{17}H_{23}NO_5$ | 320 |
| 125 | 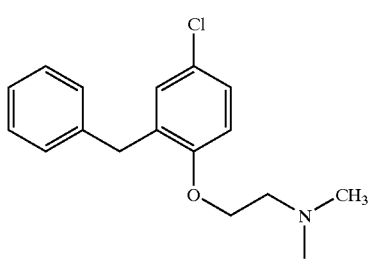 | $C_{20}H_{20}ClNO_5$ | 388 |
| 126 | 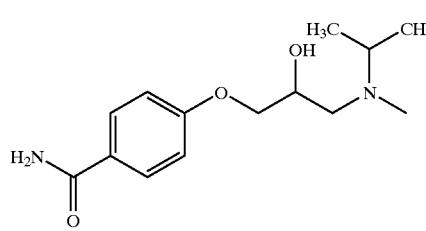 | $C_{18}H_{24}N_2O_7$ | 379 |

-continued
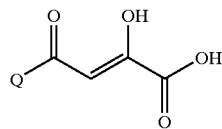
| Compound Number | Q | Formula | MS Data (M − H)⁻ |
|---|---|---|---|
| 127 | | $C_{21}H_{23}NO_5$ | 368 |
| 128 | | $C_{21}H_{23}NO_6$ | 384 |
| 129 | | $C_{13}H_{15}NO_4$ | 248 |
| 130 | | $C_{18}H_{26}N_2O_4$ | 333 |
| 131 | | $C_{12}H_{14}N_2O_4$ | 249 |
| 132 | | $C_{15}H_{19}NO_6$ | 308 |
| 133 | | $C_{20}H_{23}NO_6$ | 372 |

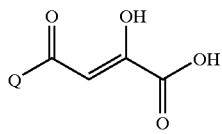

-continued

| Compound Number | Q | Formula | MS Data (M − H)⁻ |
|---|---|---|---|
| 134 | 2-methoxy-N,N-dimethylamphetamine structure | $C_{15}H_{19}NO_5$ | 292 |
| 135 | 1-(2-allylphenoxy)-3-(isopropyl(methyl)amino)propan-2-ol structure | $C_{19}H_{25}NO_6$ | 362 |
| 136 | amitriptyline-like structure | $C_{23}H_{23}NO_4$ | 376 |
| 137 | N,N,α,α-tetramethylphenethylamine structure | $C_{15}H_{19}NO_4$ | 276 |
| 138 | N-(2-methylphenyl)-2-(methyl(propyl)amino)propanamide structure | $C_{17}H_{22}N_2O_5$ | 333 |
| 139 | N,N-dimethyl-1-naphthalenemethylamine structure | $C_{16}H_{15}NO_4$ | 284 |
| 140 | 1-(4-hydroxyphenyl)-2-(butyl(methyl)amino)ethanol structure | $C_{16}H_{21}NO_6$ | 322 |

-continued

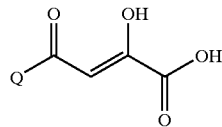

| Compound Number | Q | Formula | MS Data (M − H)− |
|---|---|---|---|
| 141 | | C22H24N2O4 | 379 |
| 142 | | C27H27NO4 | 428 |
| 143 | | C23H26NO4 | 398 |

EXAMPLE 144

Compound 144

2-Hydroxy-but-2-enedioic acid 4-[bis-(4-fluoro-benzyl)-amide] 1-propylamide

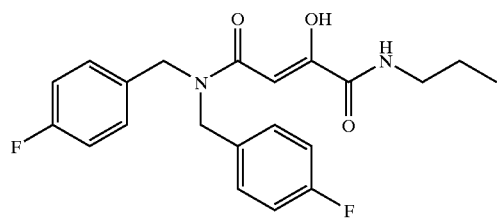

Compound 144 was prepared from Compound 11 using Method XX. MS (M−H) calcd for $C_{21}H_{21}N_2O_3F_2$: 387.15; found: 387.11. $^1$H NMR (500 MHz, $d_6$-MeOD) δ: 0.92 (t, 3, J=7), 1.58 (sextet, 2, J=7), 3.24 (q, 2, J=7), 4.59 (s, 2), 4.63 (s, 2), 6.32 (s, 1), 7.05 (m, 4), 7.20 (m, 2), 7.28 (m, 2).

EXAMPLE 145

Compound 145

{3-[Bis-(4-fluoro-benzyl)-carbamoyl]-2-hydroxy-acryloylamino}-acetic acid

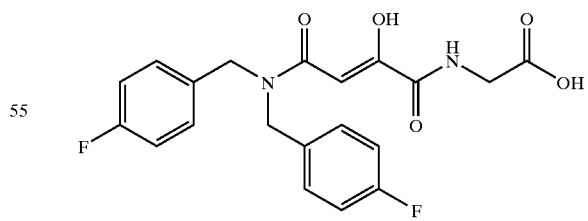

Compound 145 was prepared from Compound 11 using Method XX. MS (M−H) calcd for $C_{20}H_{17}N_2O_5F_2$: 403.11; found: 403.12. $^1$H NMR (500 MHz, $d_6$-MeOD) δ: 4.00 (s, 2), 4.60 (s, 20, 4.64 (s, 2), 6.36 (s, 1), 7.05 (m, 4), 7.20 (m, 2), 7.29 (m, 2).

EXAMPLE 146

Compound 146

2-Hydroxy-but-2-enedioic acid 1-[(6-benzenesulfonylamino-6-oxo-hexyl)-amide] 4-[bis-(4-fluoro-benzyl)-amide]

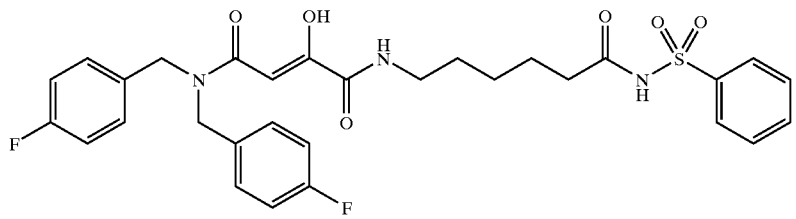

Compound 146 was prepared from Compound 11 using Method XX. MS (M−H) calcd for $C_{30}H_{30}N_3O_6SF_2$: 598.18; found: 598.05. $^1$H NMR (500 MHz, DMSO) δ: 1.07 (m, 2), 1.36 (m, 4), 2.18 (t, 2, J=7), 3.06 (m,2), 4.62 (s, 2), 4.66 (s, 2), 6.15 (s), 7.12–8.506 (overlapping m).

EXAMPLE 147

Compound 147

2-Hydroxy-but-2-enedioic acid 1-[(6-benzenesulfonylamino-6-oxo-hexyl)-amide] 4-[[3-(2-chloro-phenyl)-propyl]-(4-fluoro-benzyl)-amide]

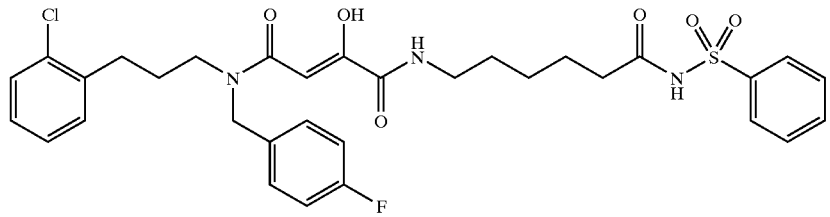

Compound 147 was prepared from Compound 87 using Method XX. MS (M−H) calcd for $C_{32}H_{34}N_3O_6SClF$: 642.18; found: 642.08. $^1$H NMR shows a mixture of rotamers at room temperature. $^1$H NMR (500 MHz, CDCl$_3$) δ: 1.27 (m), 1.50 (m), 1.61 (m), 1.89 (m), 2.27 (m), 2.72 (m), 3.26–3.46 (overlapping m), 4.60 (s), 6.40 (s), 6.43 (s), 6.96–8.05 (overlapping m).

Biological Activity

The in vitro activities, against integrase, of compounds of the present invention were measured by one of the following three methods.

Method A:

In Method A, the in vitro activity against integrase was measured in a manner which was similar to previously disclosed methods (cf. Hazuda, D. J.; Felock, P.; Witmer, M.; Wolfe, A.; Stillmock, K.; Grobler, J. A.; Espeseth, A.; Gabryelski, L.; Schleif, W.; Blau, C.; Miller, M. D. Science, 2000, 287, 646) Purified recombinant HIV-1 integrase was incubated with immobilized precleaved substrate DNA in a 96 well plate for 20 min at 37° C. After the integration complex was formed, compounds at desired concentrations were added to the wells followed by a 10 min incubation at 37° C. Biotinyted Target DNA was then added and the reaction was carried out for an additional 1 hour at 37° C. Wells were then washed thoroughly to remove any free DNA and integration activity was measured by using a commercial kit to quantitate the amount of biotinyted target DNA integrated into the substrate.

Method B (SPA Assay):

In Method B, the in vitro activity against integrase was measured by binding, for each reaction, 5 pmole of biotin labeled substrate DNA to 100 ug of Streptavidin coated PVT SPA beads (Amersham Pharmacia Biotech). 0.26 ng of recombinant integrase was then incubated with the beads for 90 min at 37° C. Unbound enzyme was removed by washing the complex followed by addition of inhibitors and 0.1 fmol of P33 labeled target DNA. Reaction was stopped by adding EDTA to a final concentration of 10 mM. Samples were counted in TopCountNXT (Packard) and the CPM was used as a measure of integration. Reaction condition was as described in A. Engelman and R. Craigie, J. Virol. 69, 5908–5911 (1995). The sequences of substrate and target DNA were described in Nucleic Acid Research 22, 1121–1122 (1994).

Method C (Electroluminesence Assay):

The ECL assay of Method C is essentially the same as the SPA assay of Method B, except that 0.5 μg of Streptavidin coated magnetic beads and 0.5 pmol Ru labeled target DNA were used for each reaction instead of SPA beads and P33 labeled DNA. The samples were read in a M8 analyzer (IGEN International, Inc).

| Compound Number | Percent inhibition of HIV Integrase at 70 uM | Assay Method |
|---|---|---|
| 1 | 40 | A |
| 2 | 88 | A |
| 3 | 99 | A |
| 4 | 90 | A |
| 5 | 65 | A |
| 6 | 75 | A |
| 7 | 32 | A |
| 10 | 79 | A |
| 11 | 97 | B |
| 12 | 85 | A |
| 13 | 94 | A |

| Compound Number | Percent inhibition of HIV Integrase at 70 uM | Assay Method |
|---|---|---|
| 14 | 94.5 | B |
| 15 | 97 | A |
| 16 | 97 | B |
| 17 | 89.5 | A |
| 18 | 89.5 | A |
| 19 | 96.5 | A |
| 20 | 97.5 | A |
| 21 | 98 | A |
| 22 | 75 | A |
| 23 | 55 | A |
| 24 | 90 | A |
| 25 | 96.5 | A |
| 26 | 97 | A |
| 27 | 33.5 | A |
| 28 | 96.5 | A |
| 29 | 38 | A |
| 30 | 84 | A |
| 31 | 82 | A |
| 32 | 93 | A |
| 33 | 90 | A |
| 34 | 85 | A |
| 35 | 95.5 | A |
| 36 | 30 | A |
| 37 | 82.5 | A |
| 38 | 70 | A |
| 39 | 85 | A |
| 40 | 90 | A |
| 41 | 95 | A |
| 42 | 91 | A |
| 43 | 93.5 | A |
| 44 | 95.5 | C |
| 45 | 99 | C |
| 46 | 99 | C |
| 47 | 99 | C |
| 48 | 99 | C |
| 49 | 99 | C |
| 50 | 99 | C |
| 51 | 100 | C |
| 52 | 99 | C |
| 53 | 99 | B |
| 54 | 99 | B |
| 55 | 99 | B |
| 56 | 88 | B |
| 57 | 99 | B |
| 58 | 99 | B |
| 59 | 98 | B |
| 60 | 99 | B |
| 61 | 99 | B |
| 62 | 99 | B |
| 63 | 98 | B |
| 64 | 95 | B |
| 70 | 92 | B |
| 71 | 99 | B |
| 72 | 99 | B |
| 73 | 99 | B |
| 74 | 98 | B |
| 75 | 91 | C |
| 76 | 99 | B |
| 77 | 60 | A |
| 78 | 75 | C |
| 79 | 90 | C |
| 80 | 90 | B |
| 81 | 95 | B |
| 82 | 80 | A |
| 84 | 88 | B |
| 85 | 94 | C |
| 86 | 97 | C |
| 87 | 99 | C |
| 88 | 90 | A |
| 91 | 99 | B |
| 92 | 94 | B |
| 94 | 55 | B |
| 95 | 45 | B |
| 96 | 65 | B |
| 97 | 70 | B |
| 98 | 80 | B |
| 99 | 80 | B |
| 100 | 70 | B |
| 101 | 80 | B |
| 102 | 60 | B |
| 103 | 80 | B |
| 104 | 83 | B |
| 105 | 35 | B |
| 106 | 40 | B |
| 107 | 80 | B |
| 108 | 65 | B |
| 109 | 60 | B |
| 111 | 25 | B |
| 112 | 99 | B |
| 114 | 97 | B |
| 115 | 97 | B |
| 116 | 100 | B |
| 117 | 68 | B |
| 118 | 85 | B |
| 119 | 40 | B |
| 120 | 97 | B |
| 121 | 95 | B |
| 123 | 98 | B |
| 125 | 75 | B |
| 144 | 83 | C |
| 145 | 95 | A |
| 146 | 98 | B |
| 147 | 98 | C |

We claim:

1. A compound of the formula

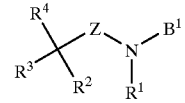

wherein:

a) $R^1$ is $C_1$–$C_4$ alkyl, carbocyclic radical, aryl-$C_1$–$C_3$ alkylene, aryloxy-$C_1$–$C_2$ alkylene, alkoxy-$C_1$–$C_2$ alkylene, wherein $R^1$ is optionally substituted from 1–3 times with halo, $C_1$–$C_2$ alkyl or $C_1$–$C_2$ alkoxy, or $R^1$ is H;

b) $R^2$ is H or $C_1$–$C_4$ alkyl;

c) $R^3$ is H, $C_1$–$C_4$ alkyl or phenyl-$C_0$–$C_2$ alkylene which is optionally substituted with 1–3 $R^5$;

d) $R^4$ is aryl-$C_1$–$C_4$ alkylene, carbocylic radical, heterocyclic radical, selected from the group consisting of furanyl, pyridiyl, and benzothienyl; aryloxy, arylcyclopropylene, aryl-NHC(O)—, wherein $R^4$ is optionally substituted with 1–3 $R^5$, provided that, when $R^1$, $R^2$ and $R^3$ are each H, $R^4$ is not unsubstituted phenyl, o-methoxyphenyl or naphthalen-1-yl;

e) each $R^5$ is independently selected from H, halo, $C_1$–$C_4$ alkyl, $C_1$–$C_4$ alkenyl, $C_1$–$C_4$ haloalkyl, $C_1$–$C_4$ alkoxy, $R^6$-phenyl, $R^6$-phenoxy, $R^6$-benzyl, $R^6$-benzyloxy, $NH_2C(O)$—, alkyl-NHC(O)—;

f) $R^6$ is H, halo;

g) Z is a bond or a substituted or unsubstituted $C_1$–$C_4$ alkylene group;

h) $B^1$ is selected from the group consisting of

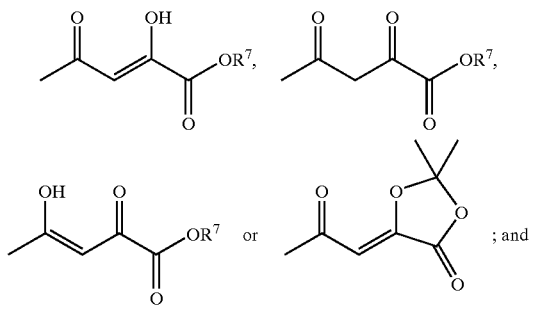

i) $R^7$ is H or $C_1$–$C_4$ alkyl, or a pharmaceutically acceptable salt or solvate thereof.

2. A compound of the formula

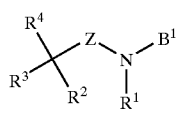

wherein:

a) $R^1$ is $C_1$–$C_4$ alkyl, carbocyclic radical, aryl-$C_1$–$C_3$ alkylene, aryloxy-$C_1$–$C_2$ alkylene, alkoxy-$C_1$–$C_2$ alkylene, wherein $R^1$ is optionally substituted from 1–3 times with halo, $C_1$–$C_2$ alkyl or $C_1$–$C_2$ alkoxy, or $R^1$ is H;

b) $R^2$ is H or $C_1$–$C_4$ alkyl;

c) $R^3$ is H, $C_1$–$C_4$ alkyl or phenyl-$C_0$–$C_2$ alkylene which is optionally substituted with 1–3 $R^5$;

d) $R^4$ is aryl-$C_1$–$C_4$ alkylene, carbocyclic radical, heterocyclic radical selected from the group consisting of furanyl, puridiyl, and benzothienyl; aryloxy, aryl-cyclopropylene, aryl-NHC(O)—, wherein $R^4$ is optionally substituted with 1–3 $R^5$, provided that, when $R^1$, $R^2$ and $R^3$ are each H, $R^4$ is not unsubstituted phenyl, o-methoxyphenyl or naphthalen-1-yl;

e) each $R^5$ is independently selected from H, halo, $C_1$–$C_4$ alkyl, $C_1$–$C_4$ alkenyl, $C_1$–$C_4$ haloalkyl, $C_1$–$C_4$ alkoxy, $R^6$-phenyl, $R^6$-phenoxy, $R^6$-benzyl, $R^6$-benzyloxy, $NH_2C(O)$—, alkyl-NHC(O)—;

f) $R^6$ is H, halo;

g) Z is a bond or a substituted or unsubstituted $C_1$–$C_4$ alkylene group;

h) $B^1$ is selected from the group consisting of

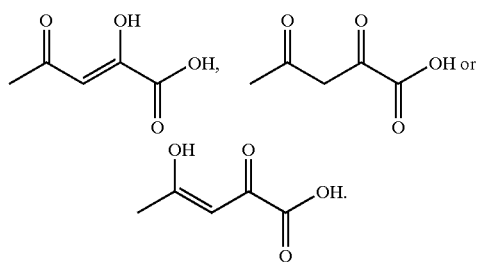

i) $R^7$ is H or $C_1$–$C_4$ alkyl, or a pharmaceutically acceptable salt, solvate or prodrug thereof.

3. A prodrug of claim 2 having the formula

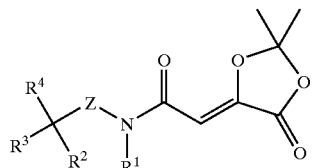

wherein:

a) R1 is $C_1$–$C_4$ alkyl, carbocyclic radical, aryl-$C_1$–$C_3$ alkylene, aryloxy-$C_1$–$C_2$ alkylene, alkoxy-$C_1$–$C_2$ alkylene, wherein $R^1$ is optionally substituted from 1–3 times with halo, $C_1$–$C_2$ alkyl or $C_1$–$C_2$ alkoxy, or $R^1$ is H;

b) $R^2$ is H or $C_1$–$C_4$ alkyl;

c) $R^3$ is H, $C_1$–$C_4$ alkyl or phenyl-$C_0$–$C_2$ alkylene which is optionally substituted with 1–3 $R^5$;

d) $R^4$ is aryl-$C_1$–$C_4$ alkylene, carbocyclic radical, heterocyclic radical selected from the group consisting of furanyl, puridiyl, and benzothienyl; aryloxy, aryl-cyclopropylene, aryl-NHC(O)—, wherein $R^4$ is optionally substituted with 1–3 $R^5$, provided that, when $R^1$, $R^2$ and $R^3$ are each H, $R^4$ is not unsubstituted phenyl, o-methoxyphenyl or naphthalen-1-yl;

e) each $R^5$ is independently selected from H, halo, $C_1$–$C_4$ alkyl, $C_1$–$C_4$ alkenyl, $C_1$–$C_4$ haloalkyl, $C_1$–$C_4$ alkoxy, $R^6$-phenyl, $R^6$-phenoxy, $R^6$-benzyl, $R^6$-benzyloxy, $NH_2C(O)$—, alkyl-NHC(O)—;

f) $R^6$ is H, halo; and g) Z is a bond or a substituted or unsubstituted $C_1$–$C_4$ alkylene group.

4. A compound of the formula

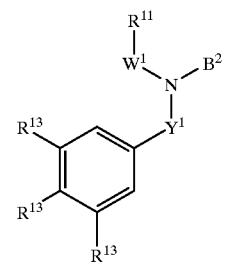

wherein:

a) $W^1$ is a bond or a $C_1$–$C_4$ alkylene group;

b) $R^{11}$ is aryl, aryloxy, aryl-cyclopropylene, heteroaryl selected from the group consisting of furanyl, pyridyl, and benzothienyl; wherein $R^{11}$ is optionally substituted from 1–3 times with halo, $C_1$–$C_2$ alkyl or $C_1$–$C_2$ alkoxy, or $C_1$–$C_2$ alkoxy, or wherein $R^{11}$ is H;

c) $Y^1$ is a bond, $C_1$–$C_3$ alkylene or —O—$C_1$–$C_2$ alkylene;

d) each $R^{13}$ is independently selected from H, halo, nitro, $C_1$–$C_4$ alkyl, $C_1$–$C_2$ alkoxy, $C_1$–$C_2$ haloalkyl, phenyl, phenoxy, benzyl, benzyloxy, p-halophenyl, p-halobenzyl, p-halophenoxy and p-halobenzyloxy; and e) $B^2$ is selected from

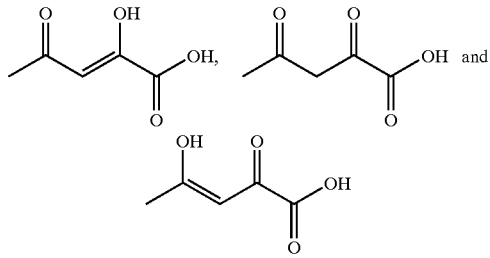

or a pharmaceutically acceptable salt, solvate or prodrug thereof.

5. A compound of the formula

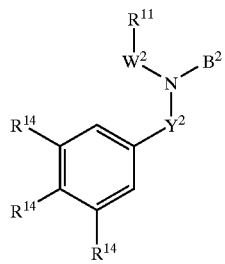

wherein:

a) $W^1$ is $C_1$–$C_3$ alkylene;

b) $R^{11}$ is aryl, aryloxy, aryl-cyclopropylene, heteroaryl selected from the group consisting of furanyl, pyridyl, and benzothienyl; wherein $R^{11}$ is optionally substituted from 1–3 times with halo, $C_1$–$C_2$ alkyl or $C_1$–$C_2$ alkoxy, or $R^{11}$ is H;

c) $y^2$ is a bond, $C_1$–$C_3$ alkylene;

d) each $R^{14}$ is independently selected from H, halo, $C_1$–$C_2$ alkyl $C_1$–$C_2$ alkoxy, and $C_1$–$C_2$ haloalkyl;

e) $B^2$ is selected from

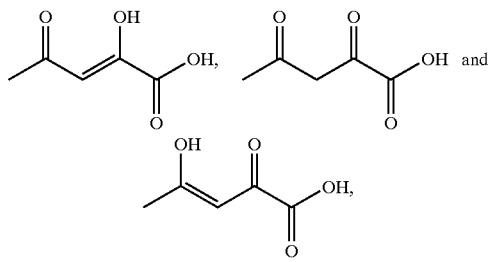

or a pharmaceutically acceptable salt, solvate or prodrug thereof.

6. A compound of the formula

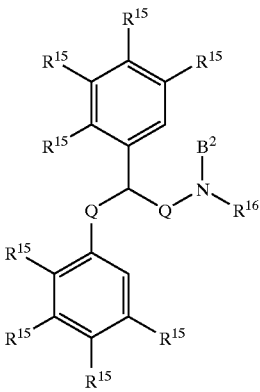

wherein:

a) independently, each Q is a bond or a methylene group;

b) each $R^{15}$ is independently selected from H, halo, nitro, $C_1$–$C_4$ alkyl, $C_1$–$C_2$ alkoxy, $C_1$–$C_2$ haloalkyl and CON-HCH$_3$; $R^{16}$ is H or $C_1$–$C_2$ alkyl; and c) $B^2$ is selected from

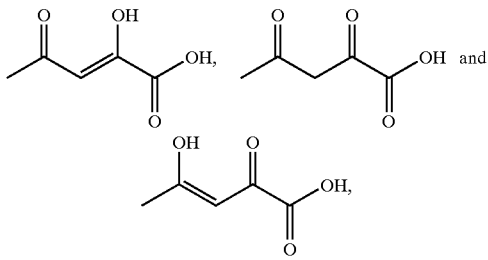

or a pharmaceutically acceptable salt, solvate or prodrug thereof.

7. A compound of the formula

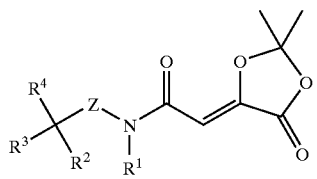

wherein:

a) $R^1$ is $C_1$–$C_4$ alkyl, carbocyclic radical, aryl-$C_1$–$C_3$ alkylene, aryloxy-$C_1$–$C_2$ alkylene, alkoxy-$C_1$–$C_2$ alkylene, wherein $R^1$ is optionally substituted from 1–3 times with halo, $C_1$–$C_2$ alkyl or $C_1$–$C_2$ alkoxy, or $R^1$ is H;

b) $R^2$ is H or $C_1$–$C_4$ alkyl;

c) $R^3$ is H, $C_1$–$C_4$ alkyl or phenyl-$C_0$–$C_2$ alkylene which is optionally substituted with 1–3 $R^5$;

d) $R^4$ is carbocyclic radical, heterocyclic radical selected from the group consisting of furanyl, pyridyl, and benzothienyl; aryloxy, aryl-$C_1$–$C_4$ alkylene, aryl-cyclopropylene, aryl-NHC(O)—, wherein $R^4$ is optionally substituted with 1–3 $R^5$ e) each $R^5$ is independently selected from H, halo, $C_1$–$C_4$ alkyl, $C_1$–$C_4$ alkenyl, $C_1$–$C_4$ haloalkyl, $C_1$–$C_4$ alkoxy, $R^6$-phenyl, $R^6$-phenoxy, $R^6$-benzyl, $R^6$-benzyloxy, $NH_2C(O)$—, alkyl-NHC(O)—;

f) $R^6$ is H, halo; and g) z is a bond or a substituted or unsubstituted $C_1$–$C_4$ alkylene group.

8. A pharmaceutical composition, comprising therapeutic amount of a compound of claim 1 or a pharmaceutically acceptable salt, solvate or prodrug thereof and a pharmaceutically acceptable carrier.

\* \* \* \* \*

UNITED STATES PATENT AND TRADEMARK OFFICE
CERTIFICATE OF CORRECTION

PATENT NO.    : 6,803,378 B2
DATED         : October 12, 2004
INVENTOR(S)   : Michael A. Walker, Timothy D. Johnson and Nicholas A. Meanwell It is certified that error appears in the above-identified patent and that said Letters Patent is hereby corrected as shown below:

Title page,
Item [75], Inventors, "Jacque" should be -- Jacques --.

Signed and Sealed this

Fifteenth Day of February, 2005

JON W. DUDAS
*Director of the United States Patent and Trademark Office*